(12) United States Patent
Stockmann et al.

(10) Patent No.: US 12,152,107 B2
(45) Date of Patent: Nov. 26, 2024

(54) ISOMER-ENRICHED 3-CARANLACTAMS AND POLYAMIDES BASED THEREON WITH HIGH OPTICAL PURITY AND ADJUSTABLE CRYSTALLINITY FOR HIGH-PERFORMANCE APPLICATIONS

(71) Applicant: Fraunhofer-Gesellschaft zur Förderung der angewandten Forschung e.V., Munich (DE)

(72) Inventors: Paul Stockmann, Stuttgart (DE); Harald Strittmatter, Stuttgart (DE); Volker Sieber, Stuttgart (DE); Claudia Falcke, Stuttgart (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 1119 days.

(21) Appl. No.: 16/978,523

(22) PCT Filed: Mar. 1, 2019

(86) PCT No.: PCT/EP2019/055124
§ 371 (c)(1),
(2) Date: Sep. 4, 2020

(87) PCT Pub. No.: WO2019/170538
PCT Pub. Date: Sep. 12, 2019

(65) Prior Publication Data
US 2021/0017332 A1    Jan. 21, 2021

(30) Foreign Application Priority Data

Mar. 9, 2018   (DE) ..................... 10 2018 203 631.4

(51) Int. Cl.
*C08G 69/14*    (2006.01)
*C07C 225/10*    (2006.01)
(Continued)

(52) U.S. Cl.
CPC ............ *C08G 69/14* (2013.01); *C07C 225/10* (2013.01); *C07C 251/44* (2013.01); *C07D 223/32* (2013.01)

(58) Field of Classification Search
CPC ..... C08G 69/14; C07C 225/10; C07C 251/44; C07D 223/32
(Continued)

(56) References Cited

U.S. PATENT DOCUMENTS 3,560,571 A    2/1971   Kropp
3,686,097 A    8/1972   Kropp

FOREIGN PATENT DOCUMENTS

DE    102014221061 A1 *    4/2016    ........... C07C 209/48

OTHER PUBLICATIONS

International Search Report and Written Opinion for PCT/EP2019/0555124 dated Jun. 12, 2019, with English translation of ISR, 16 pages.
(Continued)

*Primary Examiner* — Ling Siu Cho
*Assistant Examiner* — Ronald Grinsted
(74) *Attorney, Agent, or Firm* — Sheppard Mullin Richter & Hampton LLP

(57) ABSTRACT

The present invention relates to a process for the preparation of an isomer-enriched mixture of 3S- and 3R-caranone from 3-carane epoxide, a 3S-caranone obtained therefrom, a process for the production of 3S-caranlactam from 3-carene, a process for the production of 3R-caranlactam from 3-carene, a 3S-caranoxime, a 3S-caranlactam, a 3S-polycaranamide, a 3R-polycaranamide, a 3S/3R-co-polycaranamide, a 3S-caranlactam-laurolactam co-polycaranamide, a 3R-caranlactam-laurolactam co-polycaranamide, a 3S-caranlactam-3R-caranlactam-laurolactam co-polycaranamide, a 3S-caranlactam-caprolactam co-polycaranamide, a 3R-car-
(Continued)

anlactam-caprolactam co-polycaranamide, as well as a 3S/3R-caranlactam-caprolactam co-polycaranamide.

6 Claims, 83 Drawing Sheets

(51) Int. Cl.
    *C07C 251/44* (2006.01)
    *C07D 223/32* (2006.01)
(58) Field of Classification Search
    USPC .......................................................... 528/325
    See application file for complete search history.

(56) References Cited

OTHER PUBLICATIONS

Winnacker et al., "Sustainable, Stereoregular, and Optically Active Polyamides via Cationic Polymerization of epsilon-Lactams Derived from the Terpene Beta-Pinene", Macromolecular Rapid Communications, 2917, 38, 1600787, 7 pages.
Lochynski et al., "Stereochemistry of terpene derivatives. Part 2: Synthesis of new chiral amino acids with potential neuroactivity", Tetrahedron: Asymmetry, 11: 1295-1302, 2000.
Arata, "Isomerization of 2- and 3-Carene Oxides over Solid Acids and Bases", American Chemical Society, 1978, 5 pages.
Beyer, "Organische Chemie", 25. Auflage, 2016, 137,250, 3 pages.
Sasai et al., "Efficient Synthesis of c10 Chiron by Lewis Acid Catalyzed Rearrangement of (+)-alpha-3,4-Epoxycarane", J. Org. Chem., 1995, 60, 465-467.
International Preliminary Report on Patentability for PCT/EP2019/055124 dated Sep. 24, 2020, 12 pages.
Polovinka, et al. Terpenes in Superacids: Synthetic Aspect. Chemistry for Sustainable Development. Jan. 1, 2011;19(6):575-588.
Polovinka, et al. Molecular rearrangements of α-(trans)-and β-(cis)-3,4-epoxycaranes in acid media. Journal of Organic Chemistry, vol. 34, No. 9, 1998, p. 1342-1349.

* cited by examiner

Figure 1:
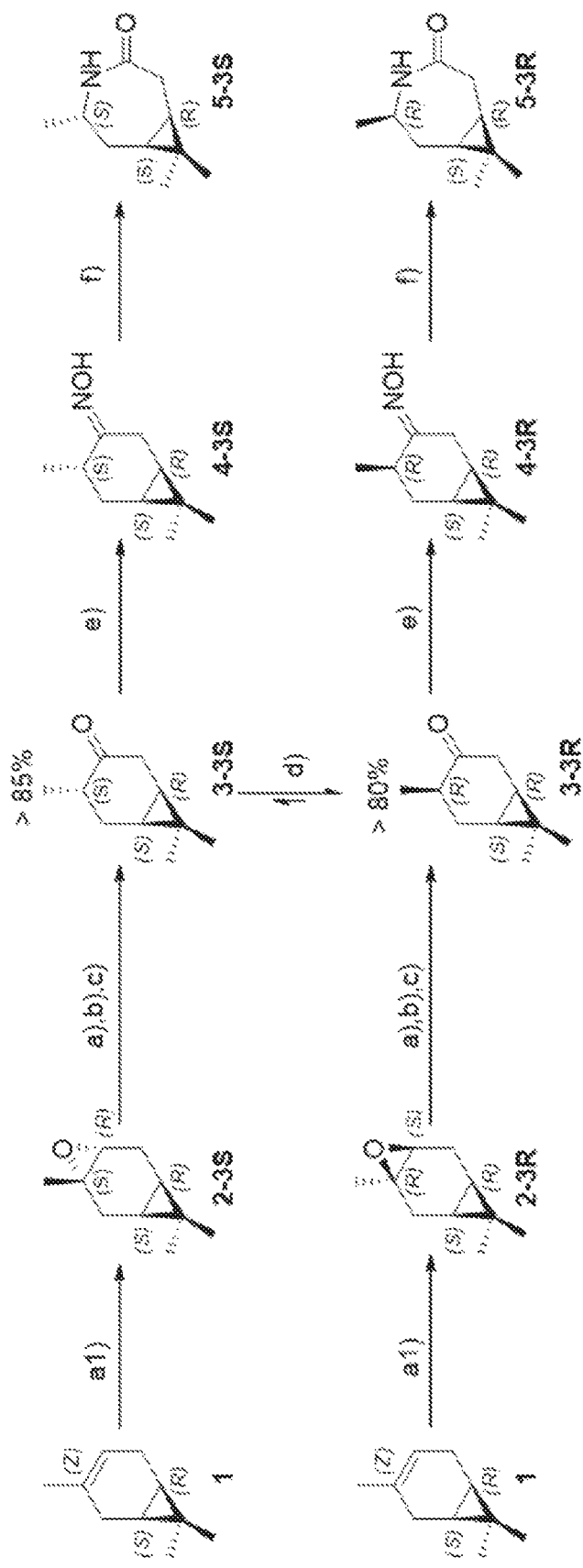

Figure 1. Overview of process steps a1) to f)

Figure 2:
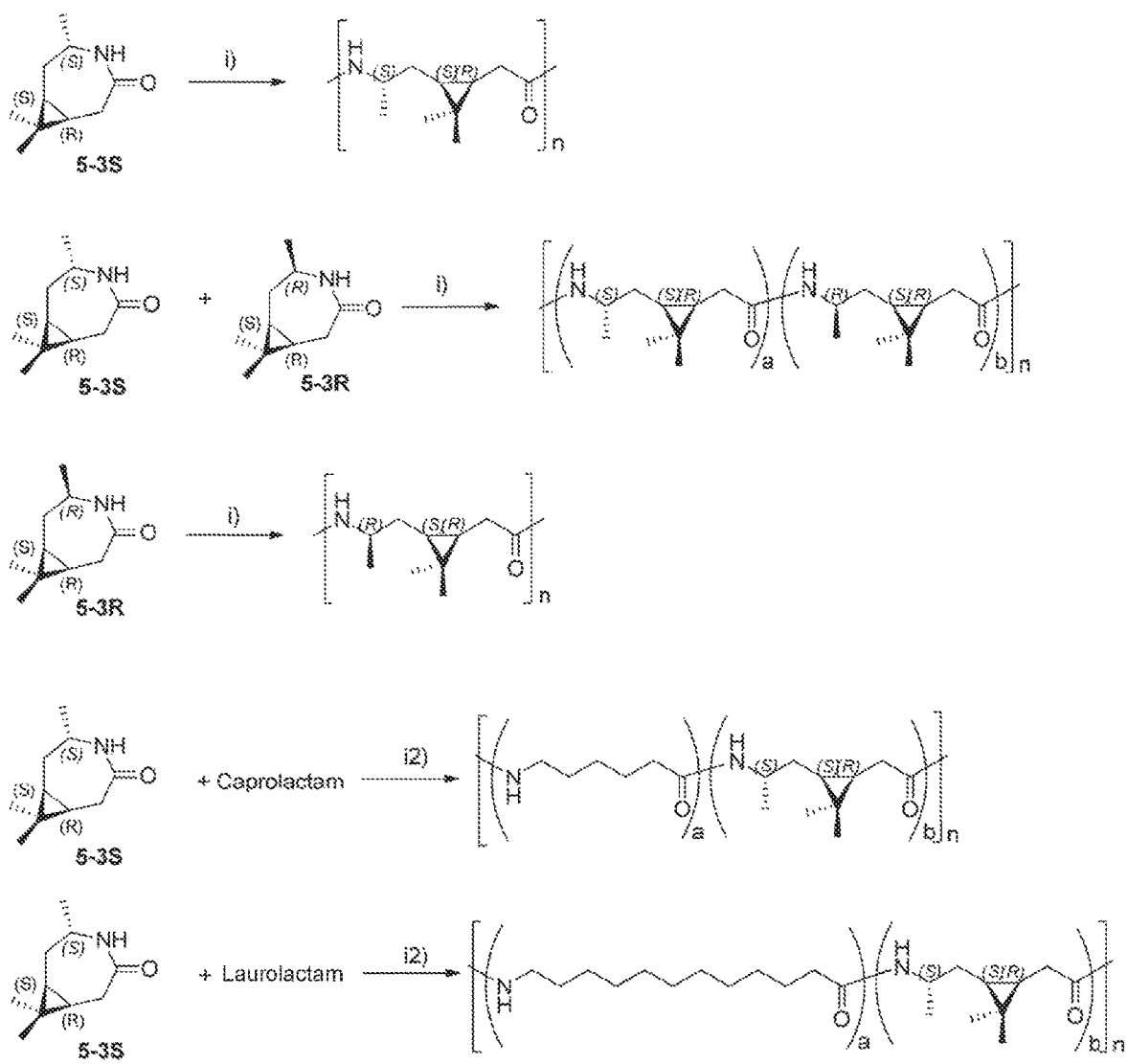

Figure 2. Overview of the individual process steps i) to i2)

Figure 5:
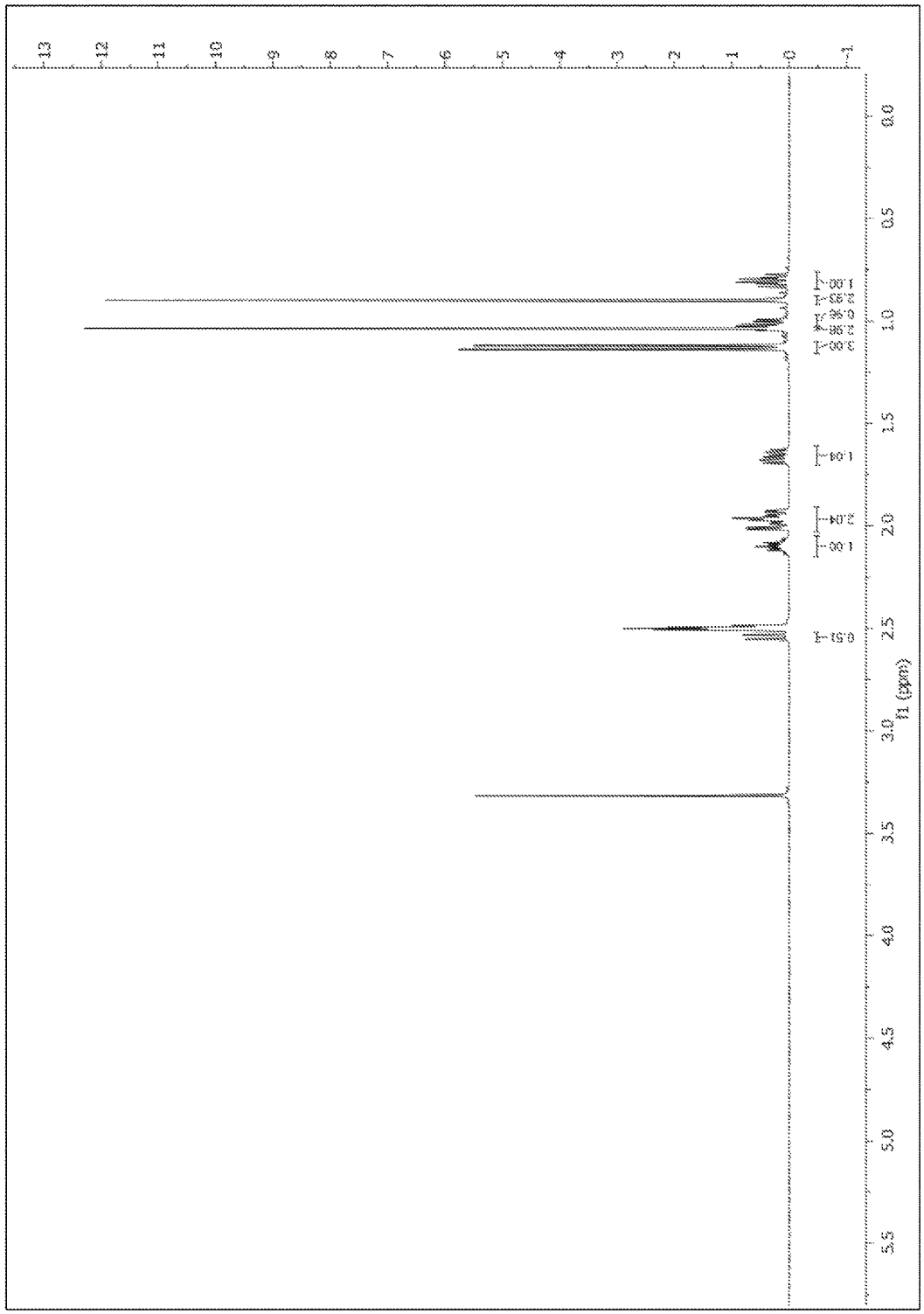

Figure 5. ¹H-NMR spectrum of 3S-caranone (3-3S)

Figure 11:
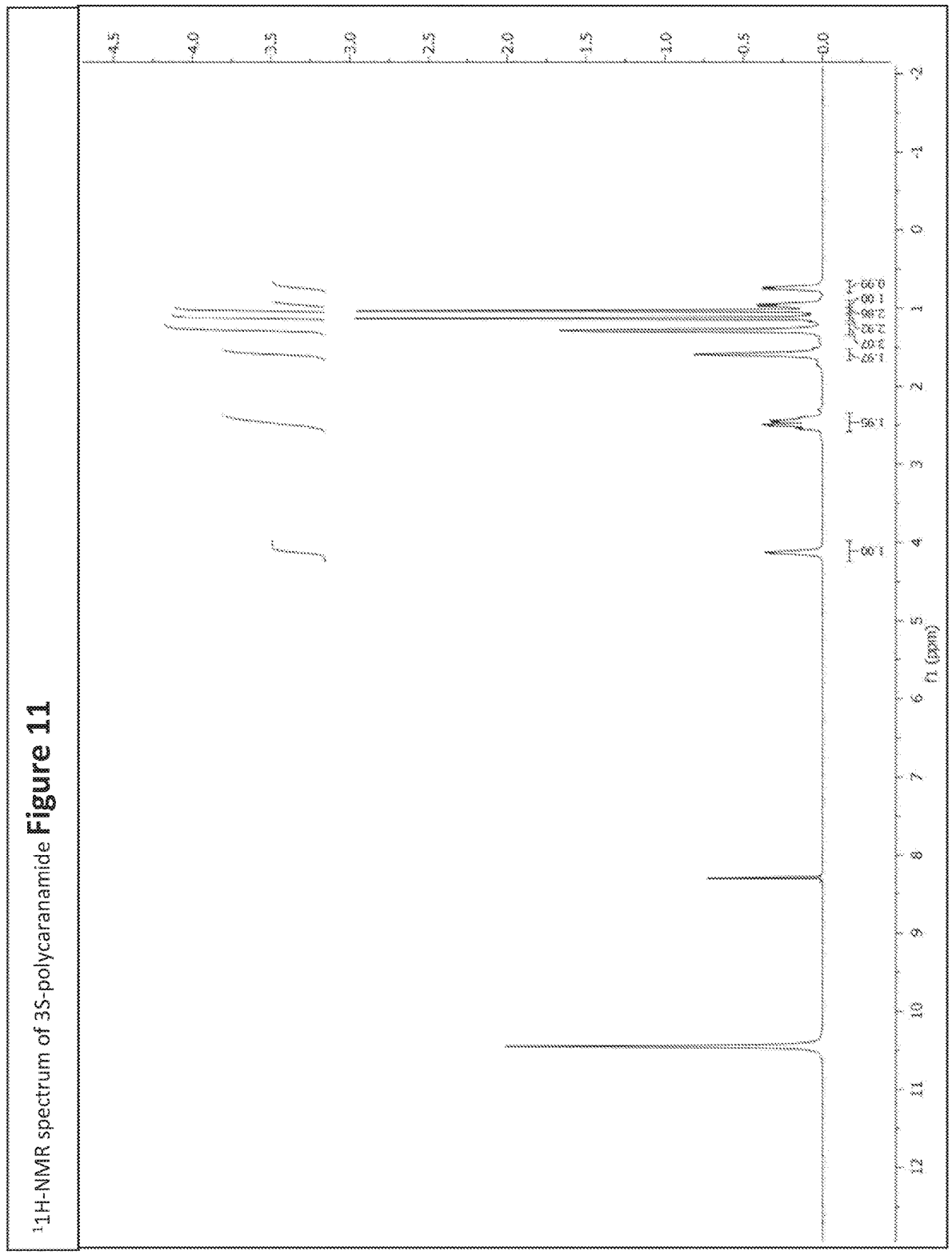

Figure 11 1H-NMR spectrum of 3S-polycaranamide

Figure 1A HSQC spectrum of 3S-polycaranamide

Figure 16:
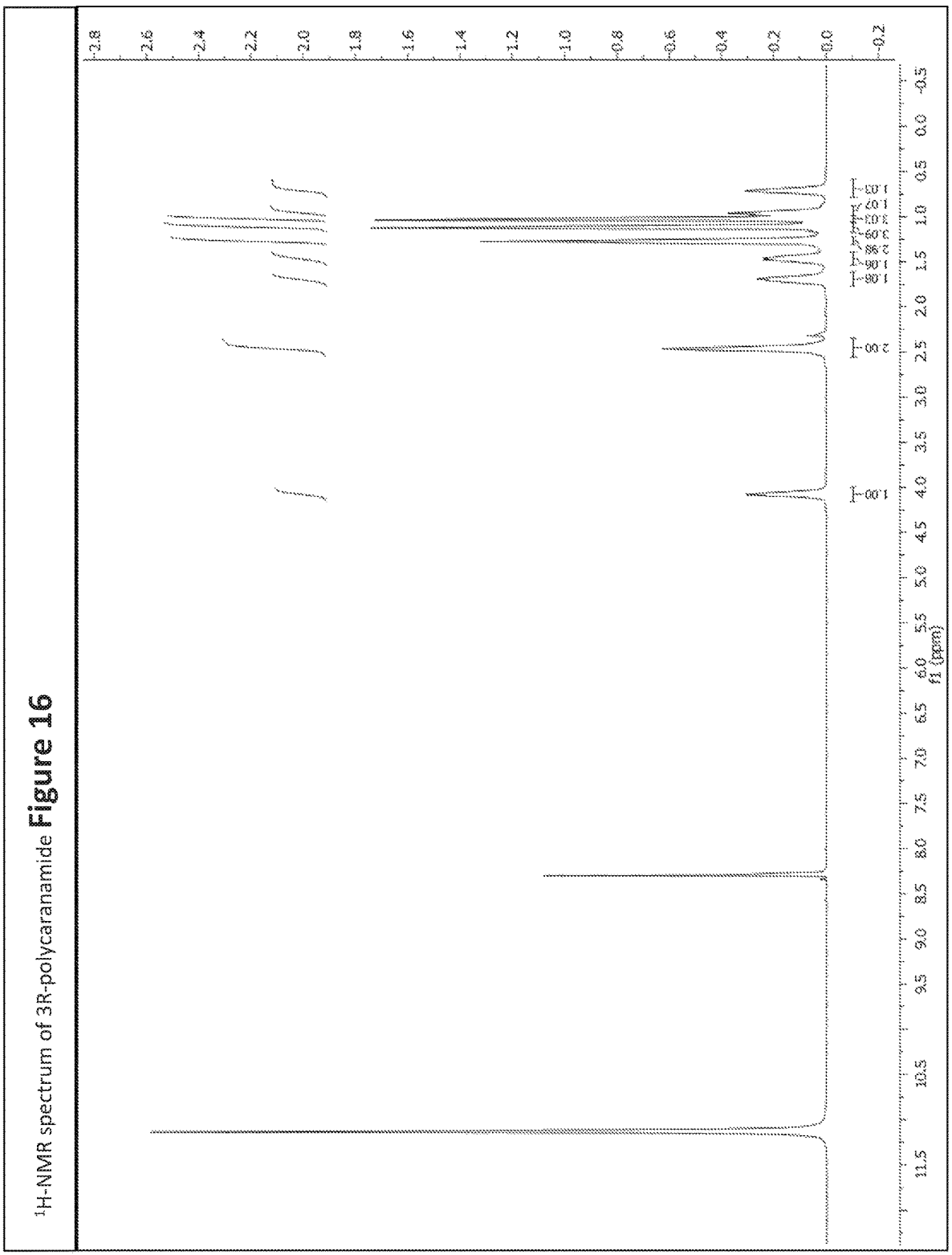

Figure 16. $^1$H-NMR spectrum of 3R-polycaranamide

Figure 21:
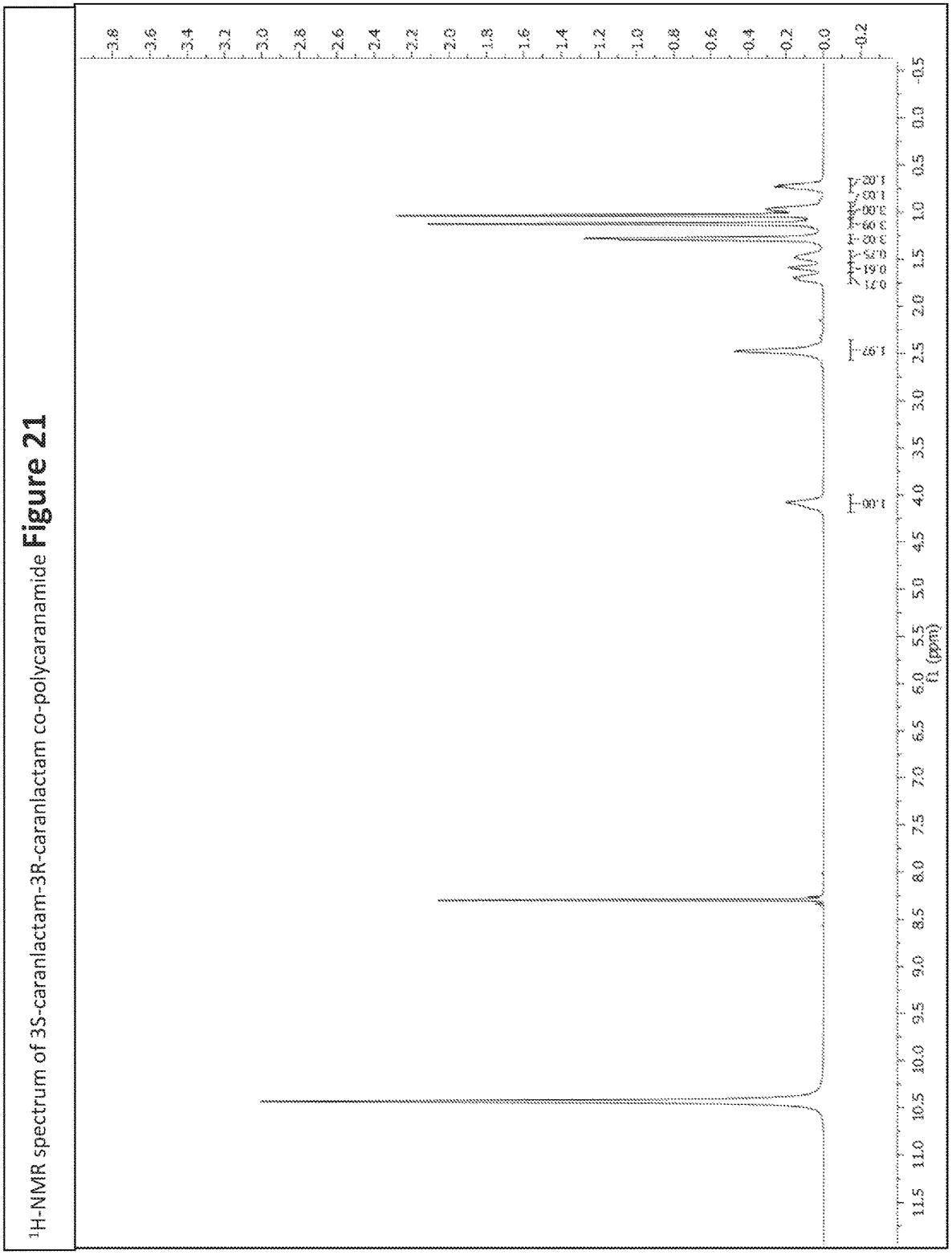

Figure 21. $^1$H-NMR spectrum of 3S-caranlactam-3R-caranlactam co-polycaranamide Figure 24 ¹H-NMR spectrum of 3S-caranlactam-caprolactam co-polycaranamide Figure 28 DSC of poly-3S-caranamide DSC of poly-3S-caranamide Figure 29

Figure 36:
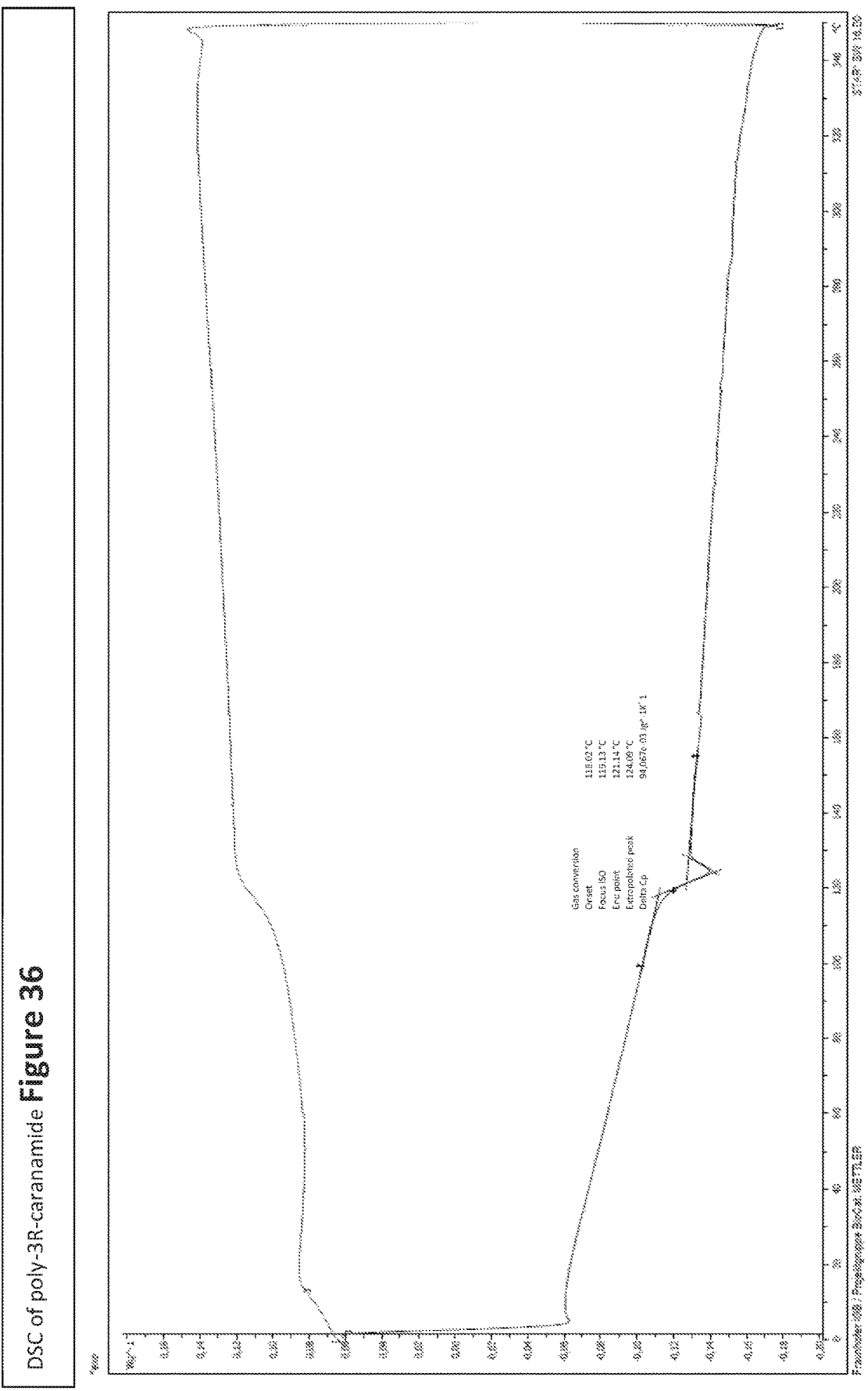

Figure 36 DSC of poly-3R-caranamide

Figure 37:
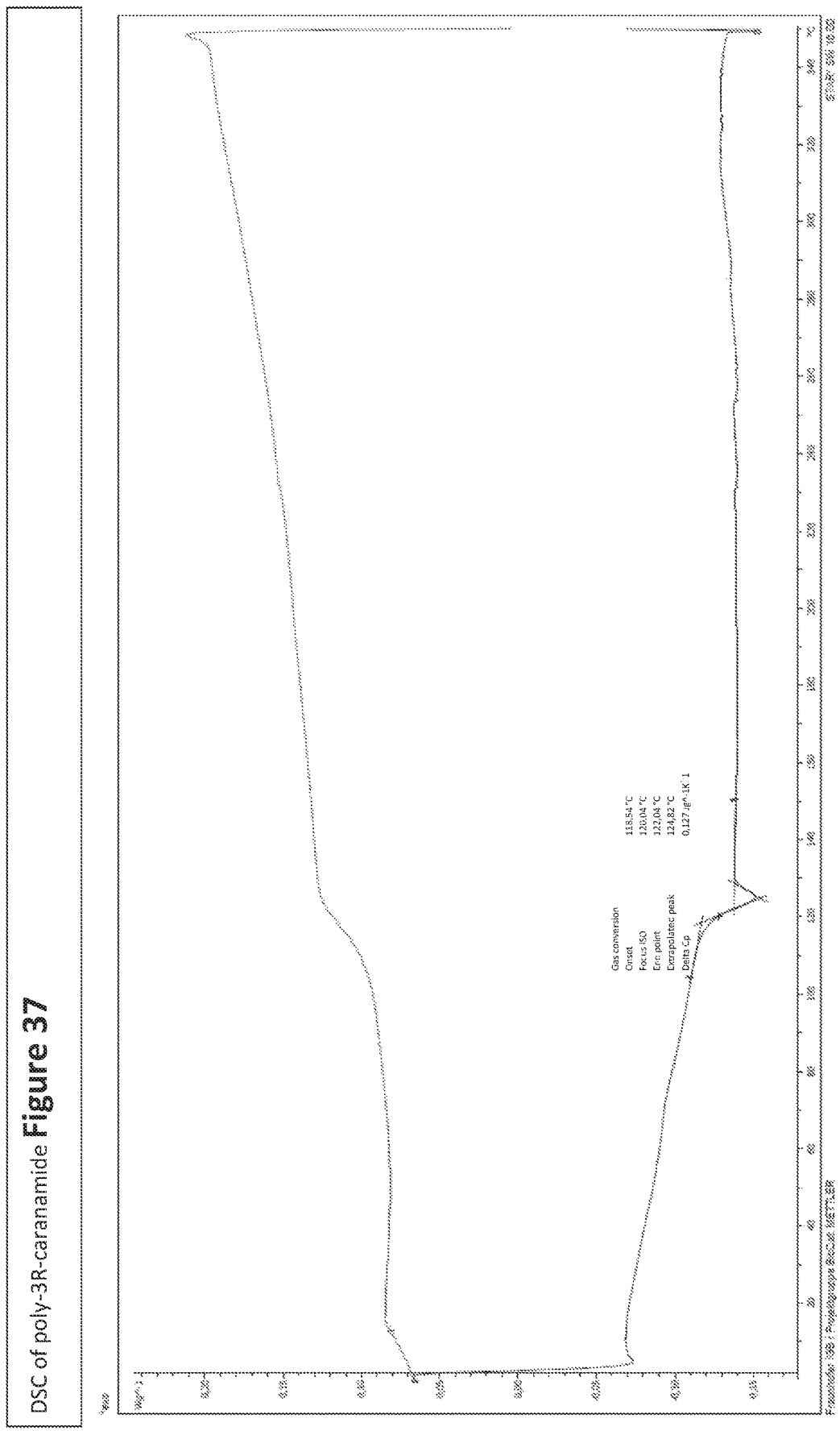

Figure 37 DSC of poly-3R-caranamide

Figure 38:

DSC of poly-3R-caranamide Figure 38

Figure 42:
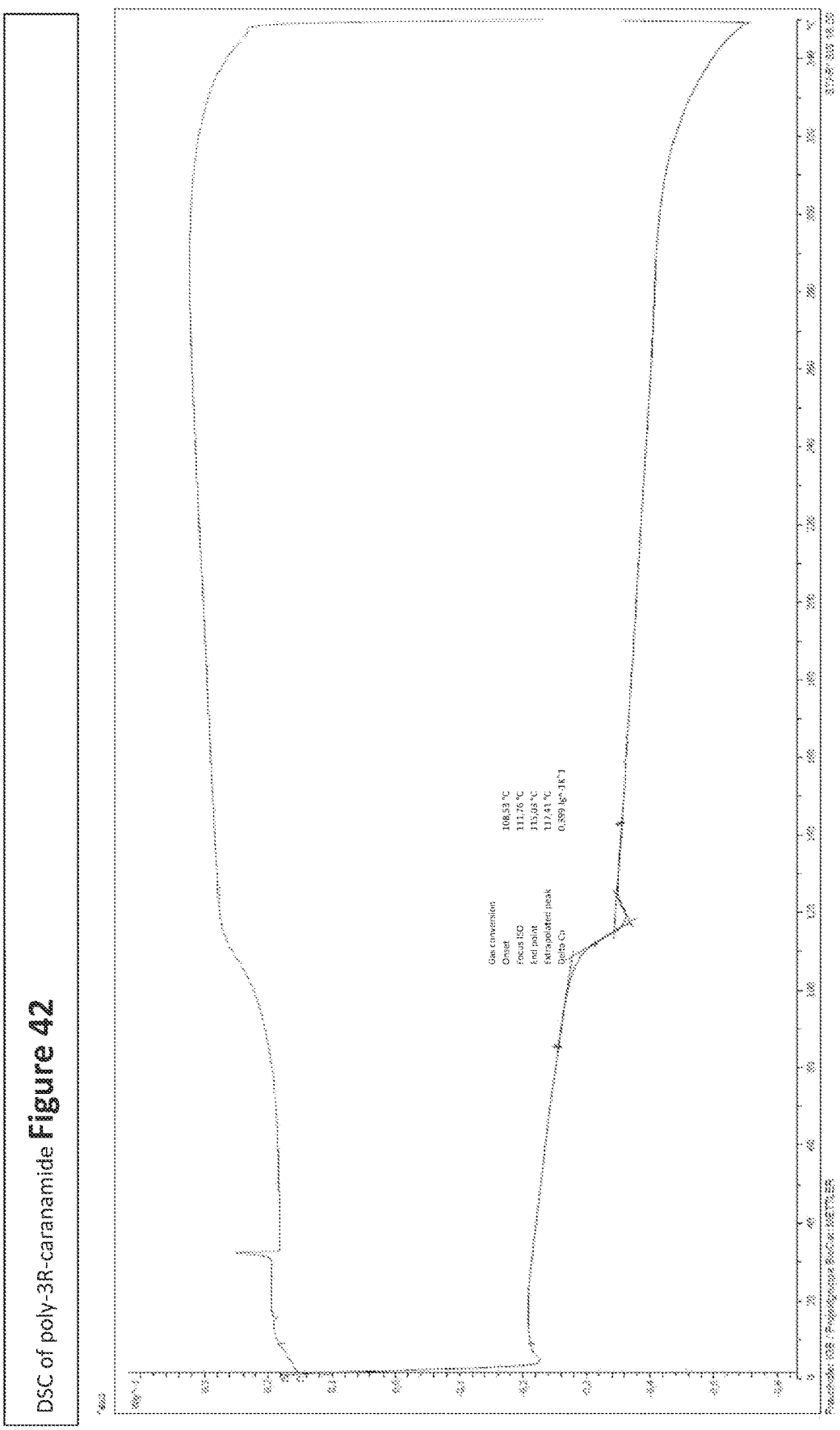

Figure 42 — DSC of poly-3R-caranamide

Figure 44:
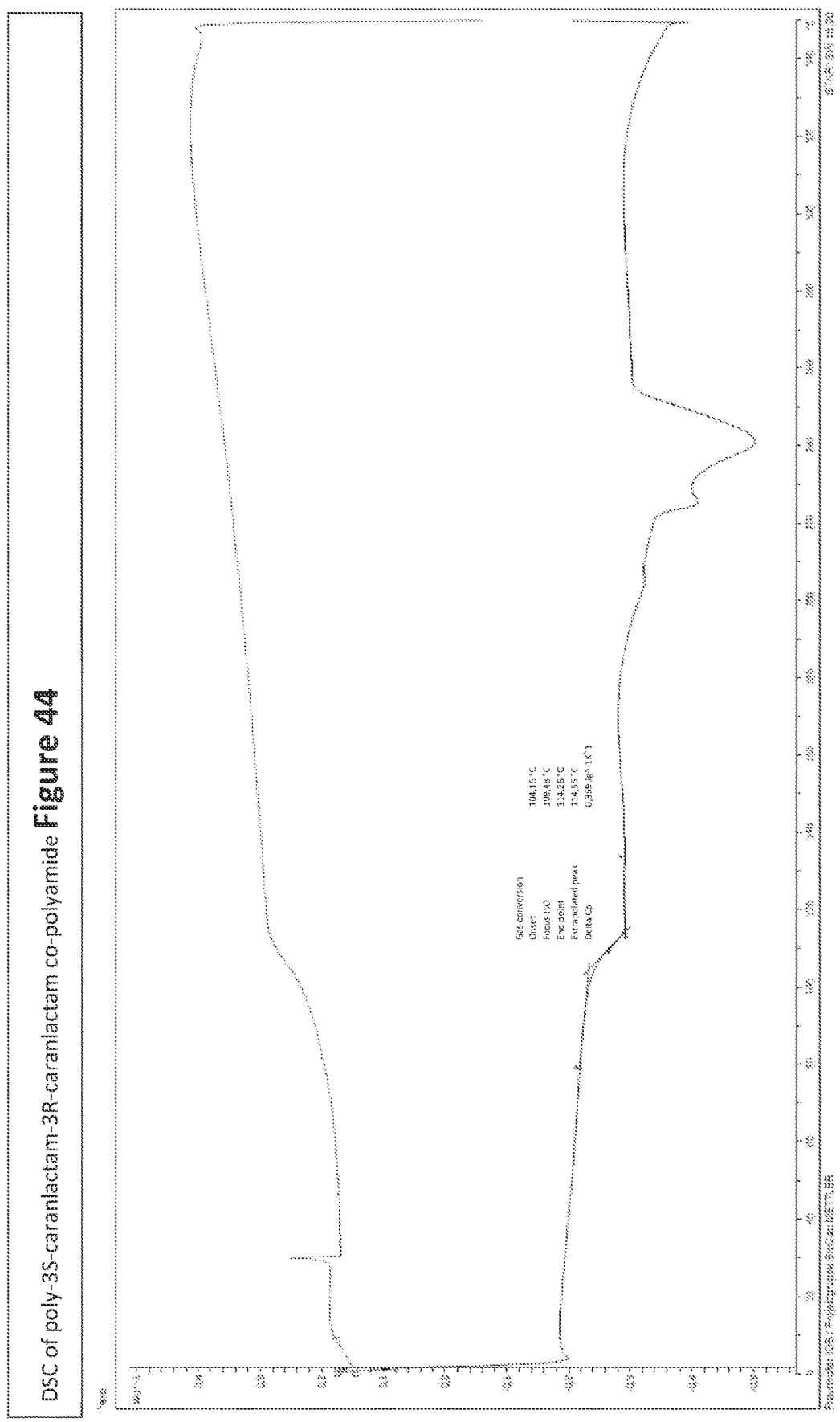

Figure 44. DSC of poly-3S-caranlactam-3R-caranlactam co-polyamide

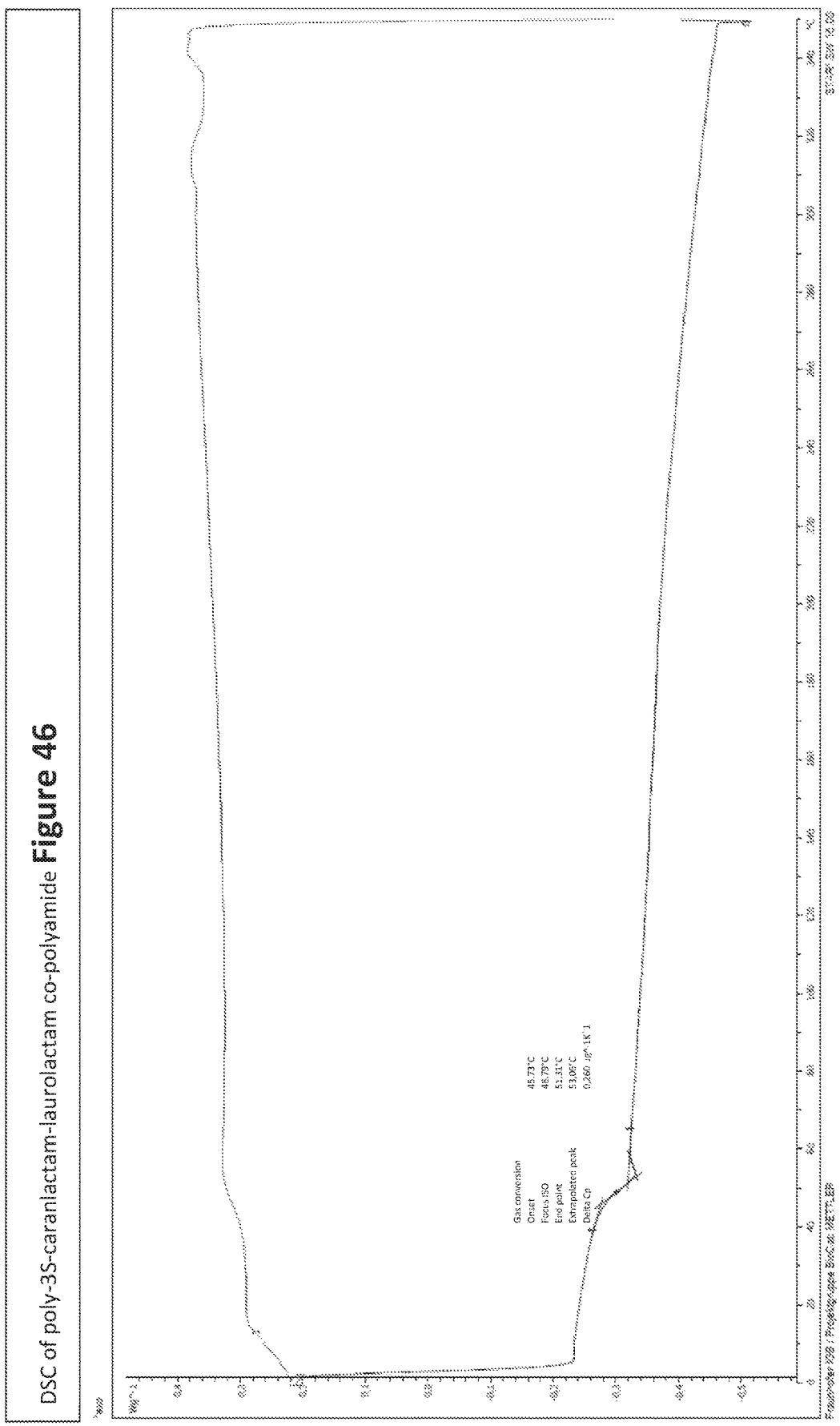
Figure 46. DSC of poly-3S-caranlactam-laurolactam co-polyamide

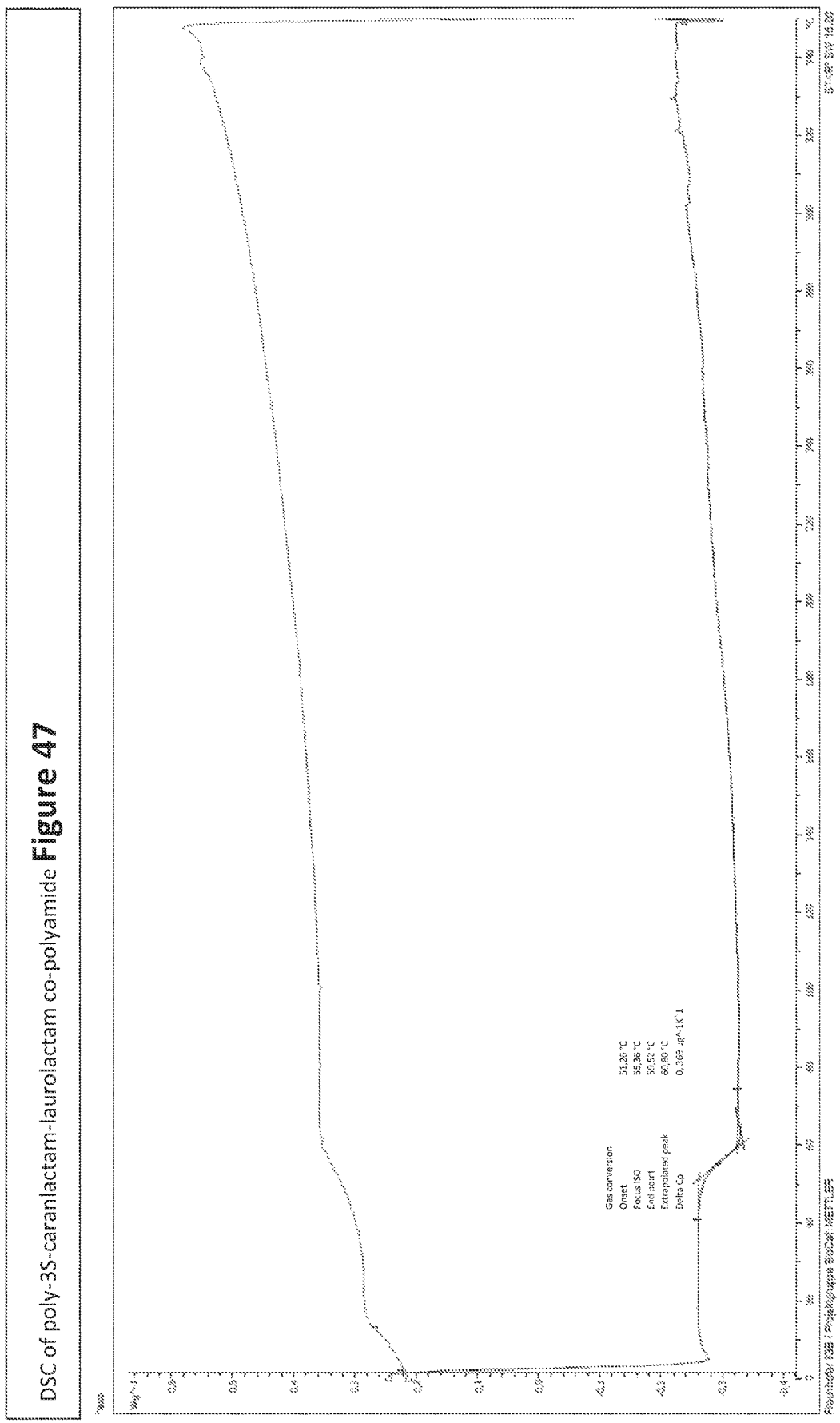
Figure 47 DSC of poly-3S-caranlactam-laurolactam co-polyamide

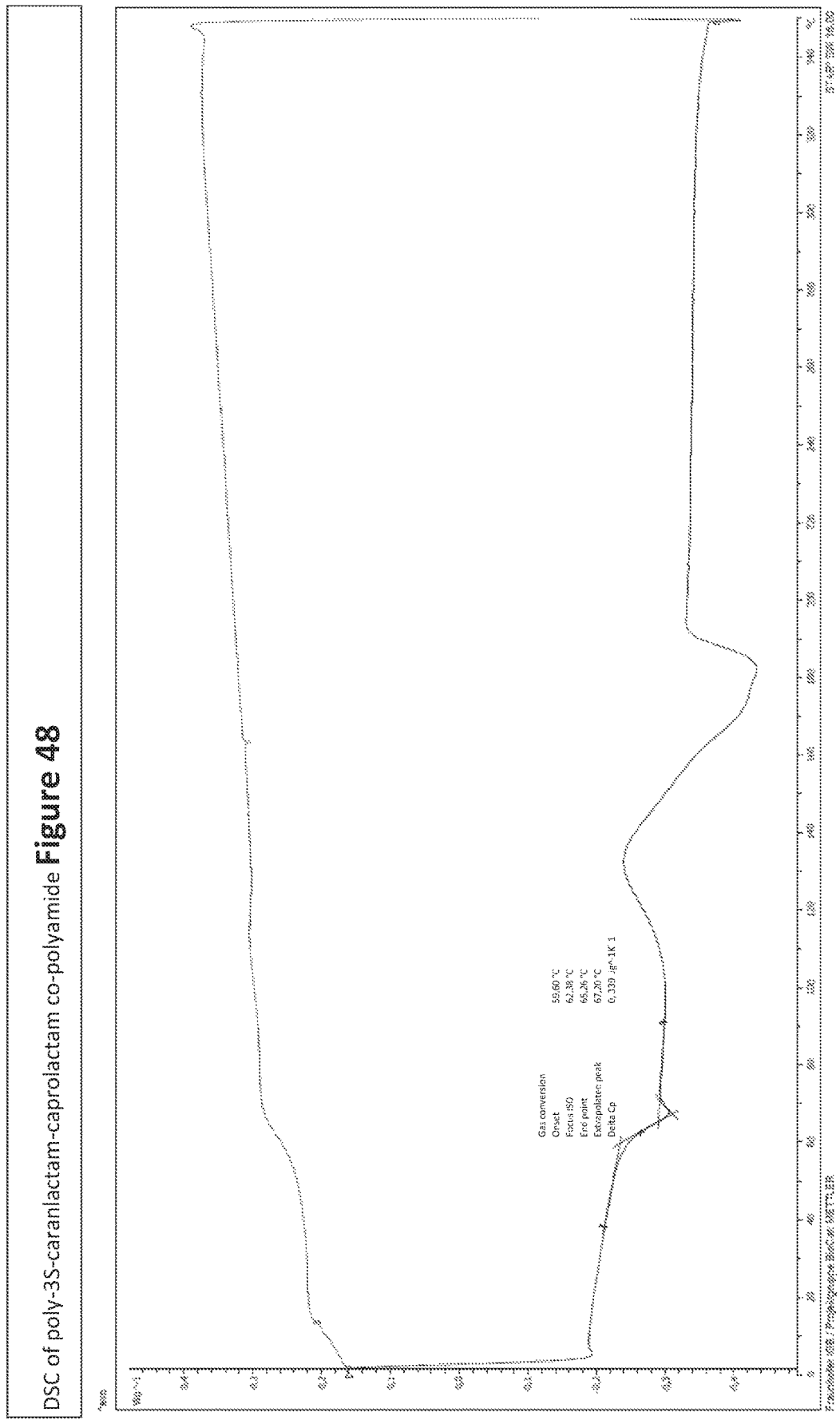
Figure 48 DSC of poly-3S-caranlactam-caprolactam co-polyamide

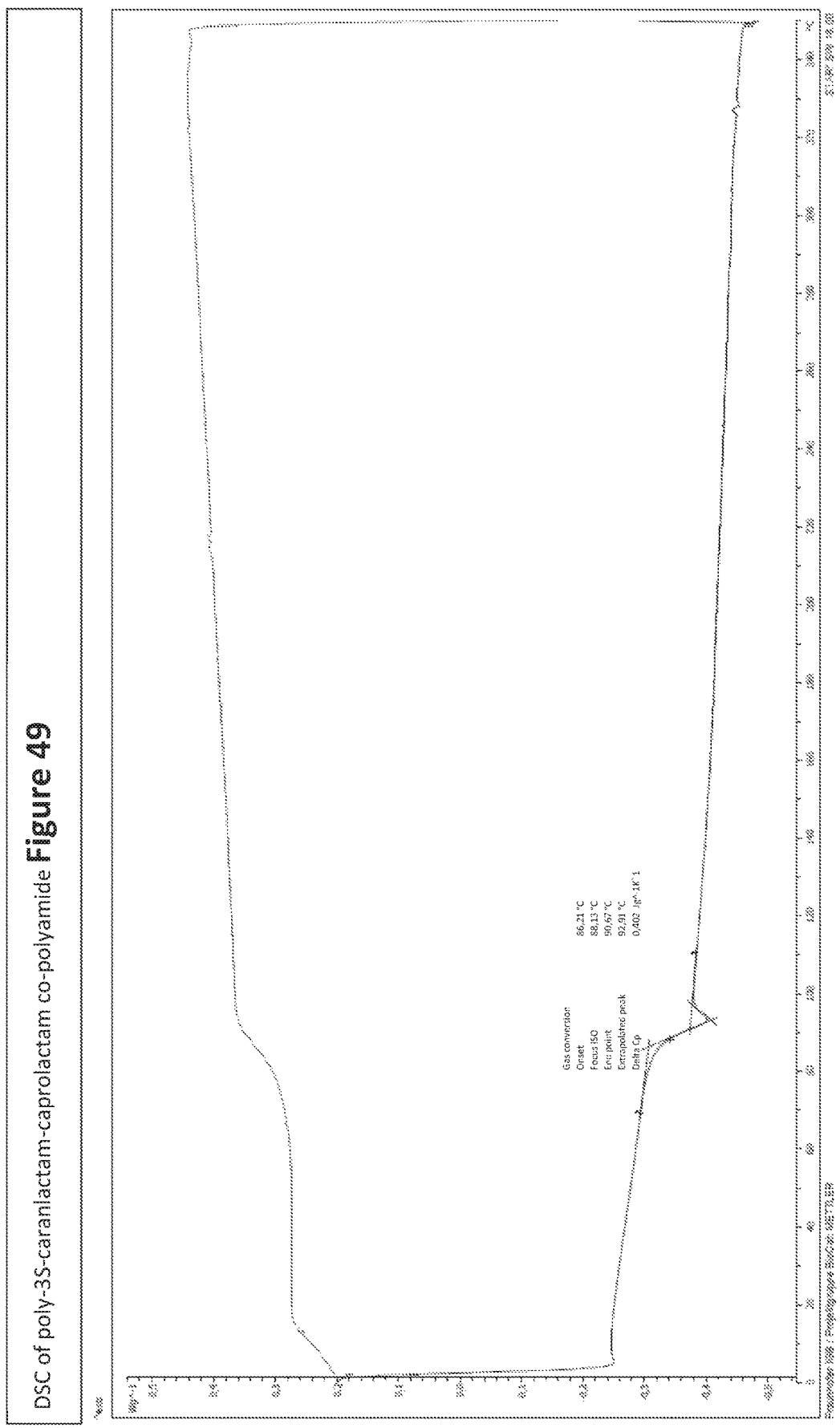
Figure 49 DSC of poly-3S-caranlactam-caprolactam co-polyamide

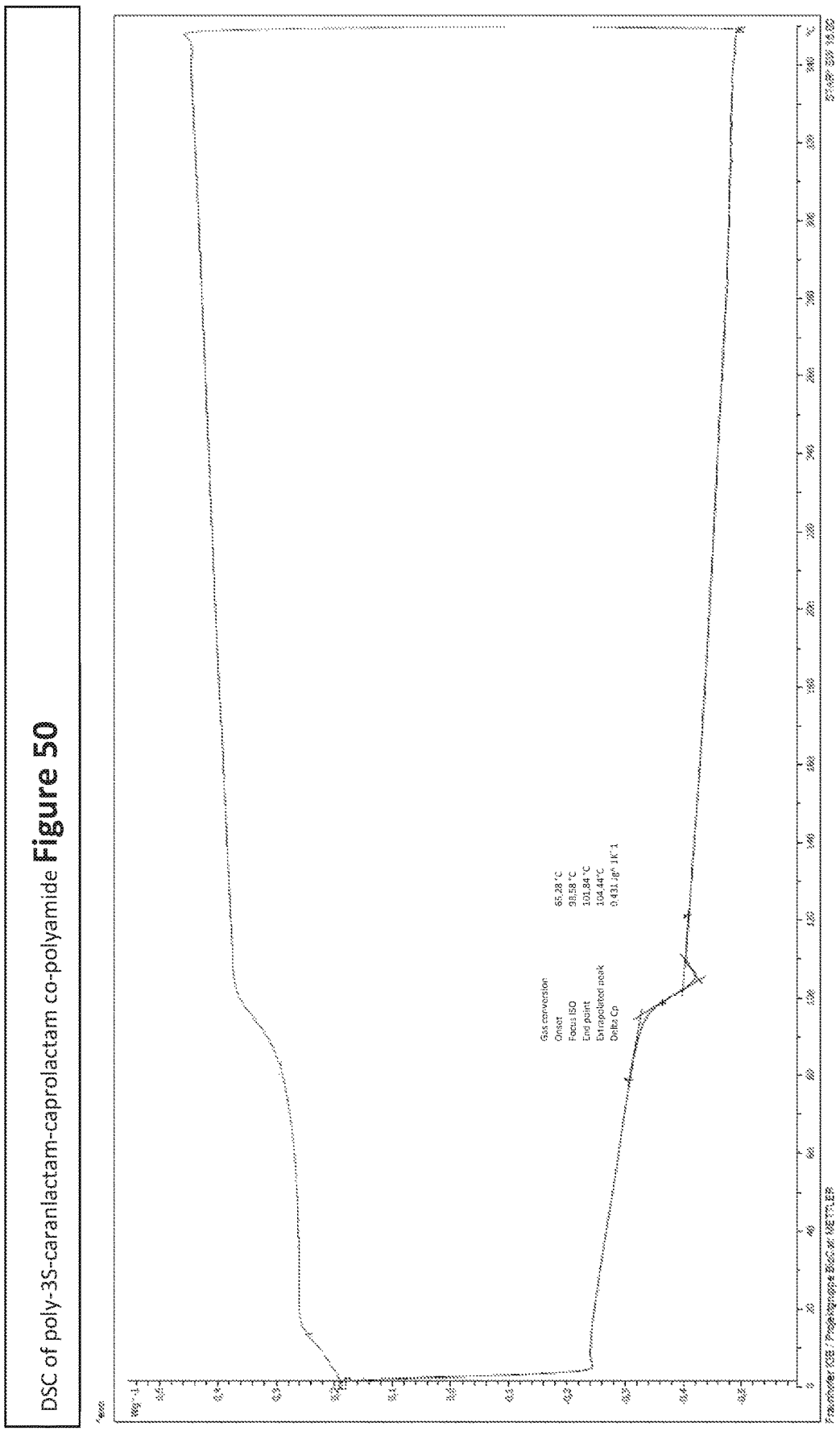

FIGURE 51 (GPC of poly-3S-caranamide)
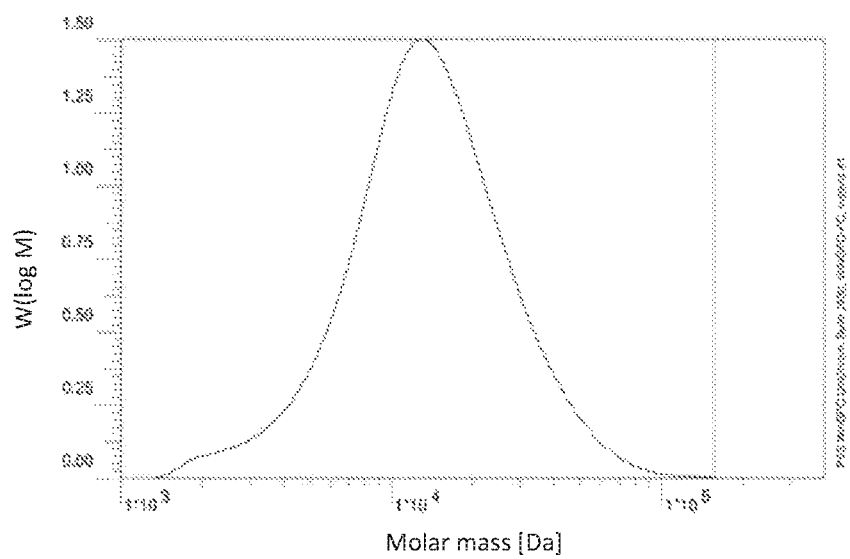

Figure 52 (GPC of poly-3S-caranamide)
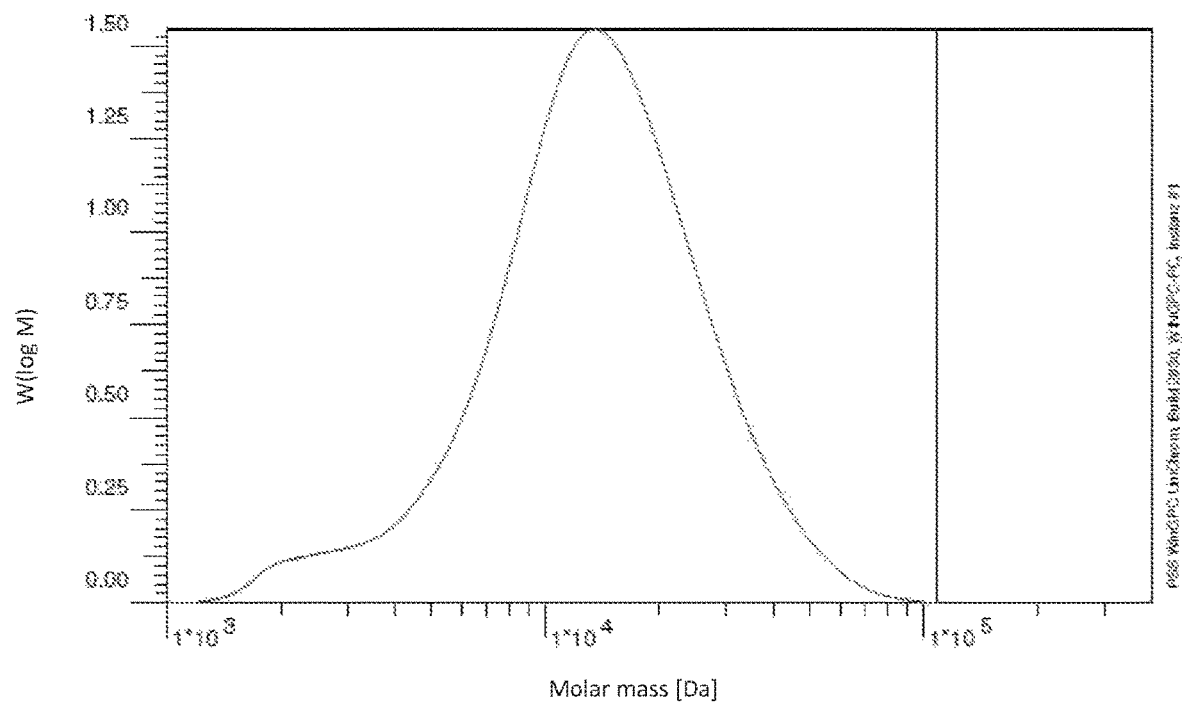

Figure 53 (GPC of poly-3S-caranamide)
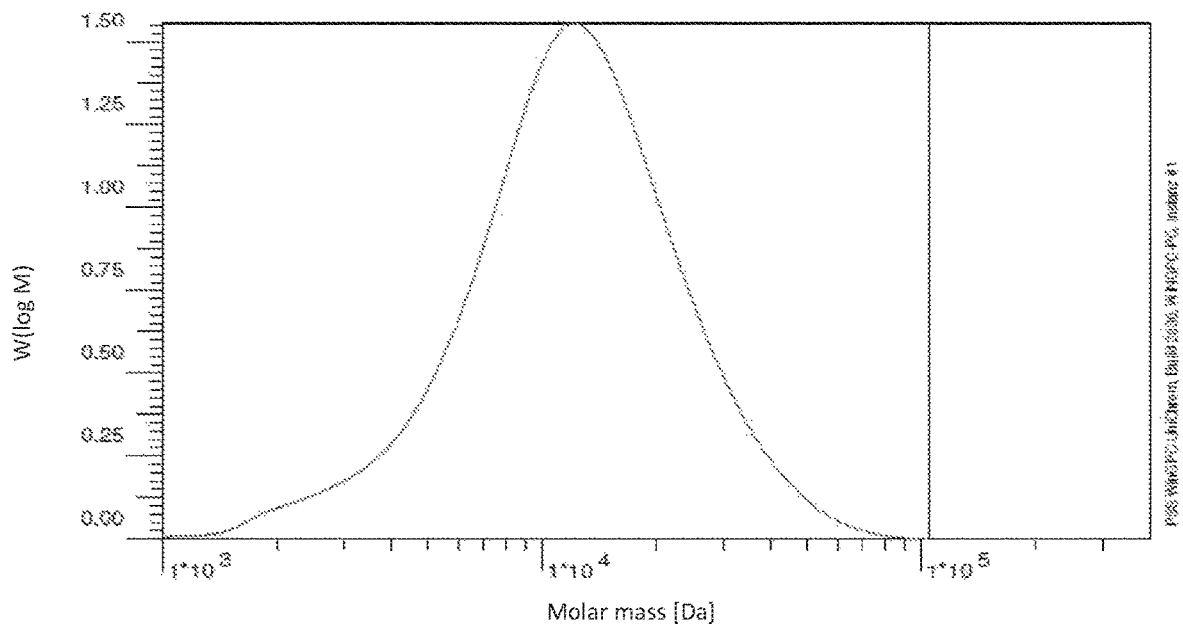

Figure 54 (GPC of poly-3S-caranamide)
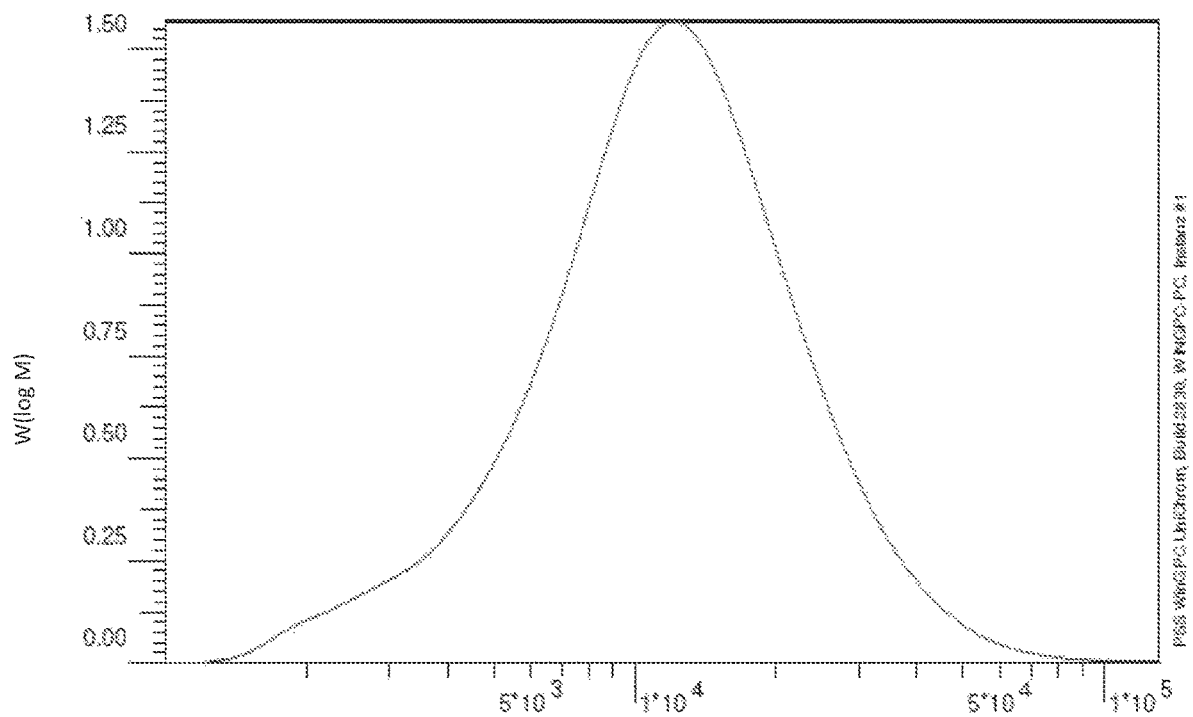

Figure 55 (GPC of poly-3S-caranamide)
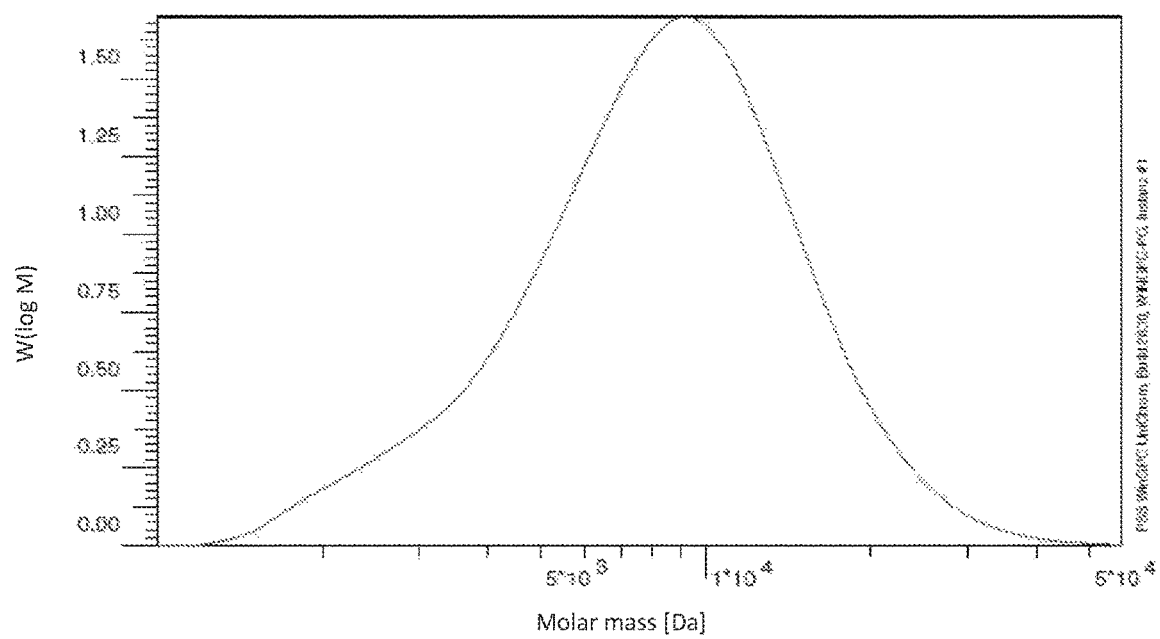

Figure 56 (GPC of poly-3S-caranamide)
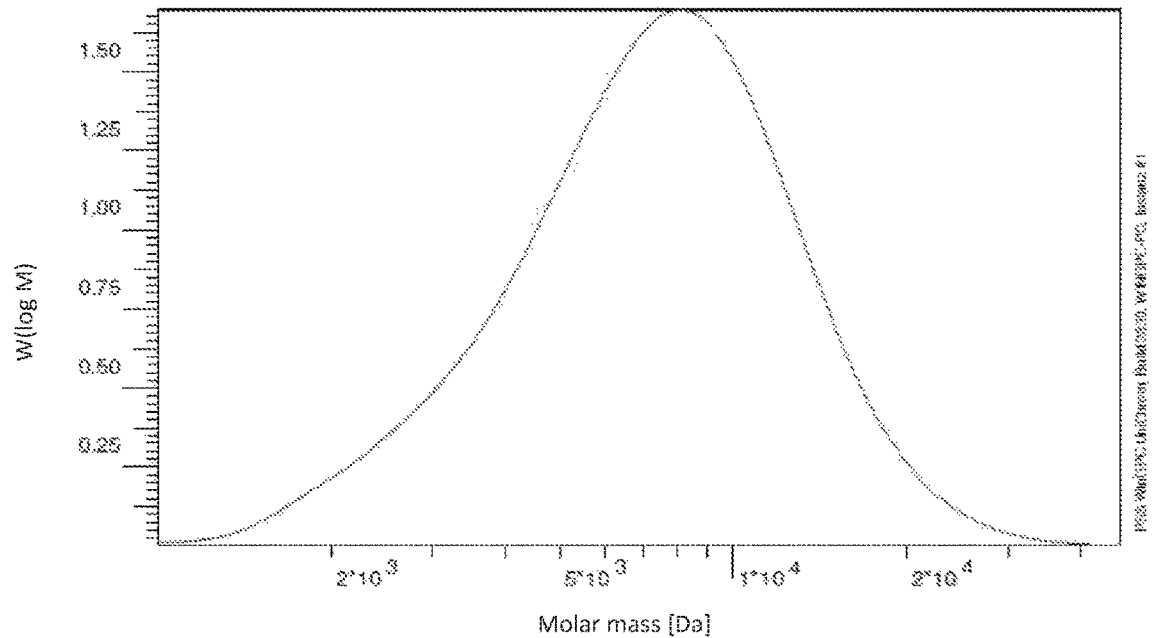

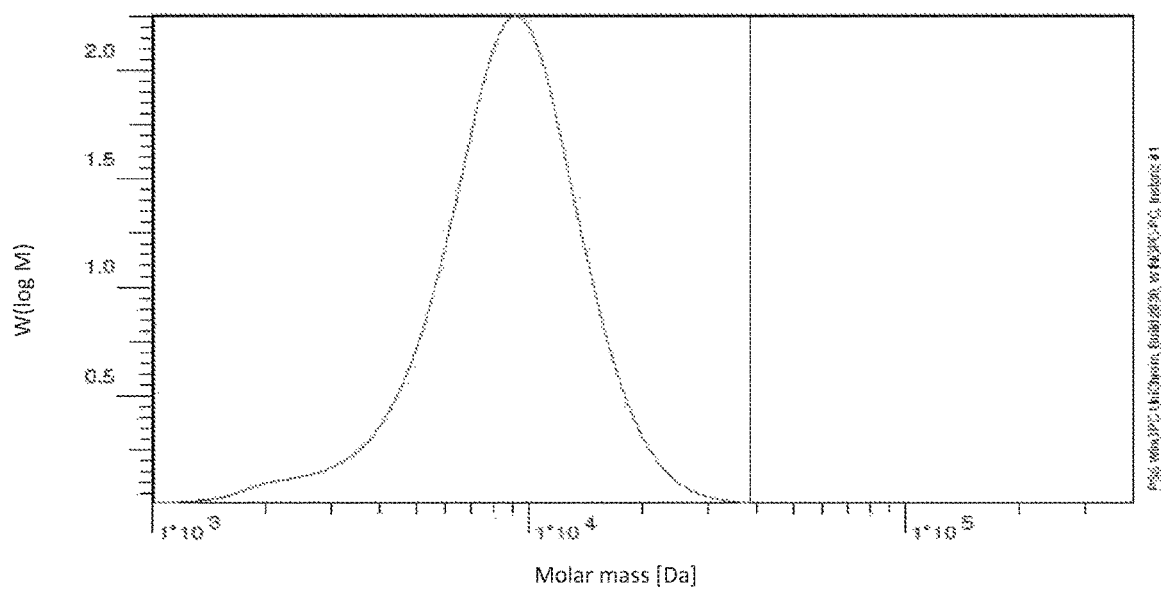
Figure 57 (GPC of poly-3S-caranamide)

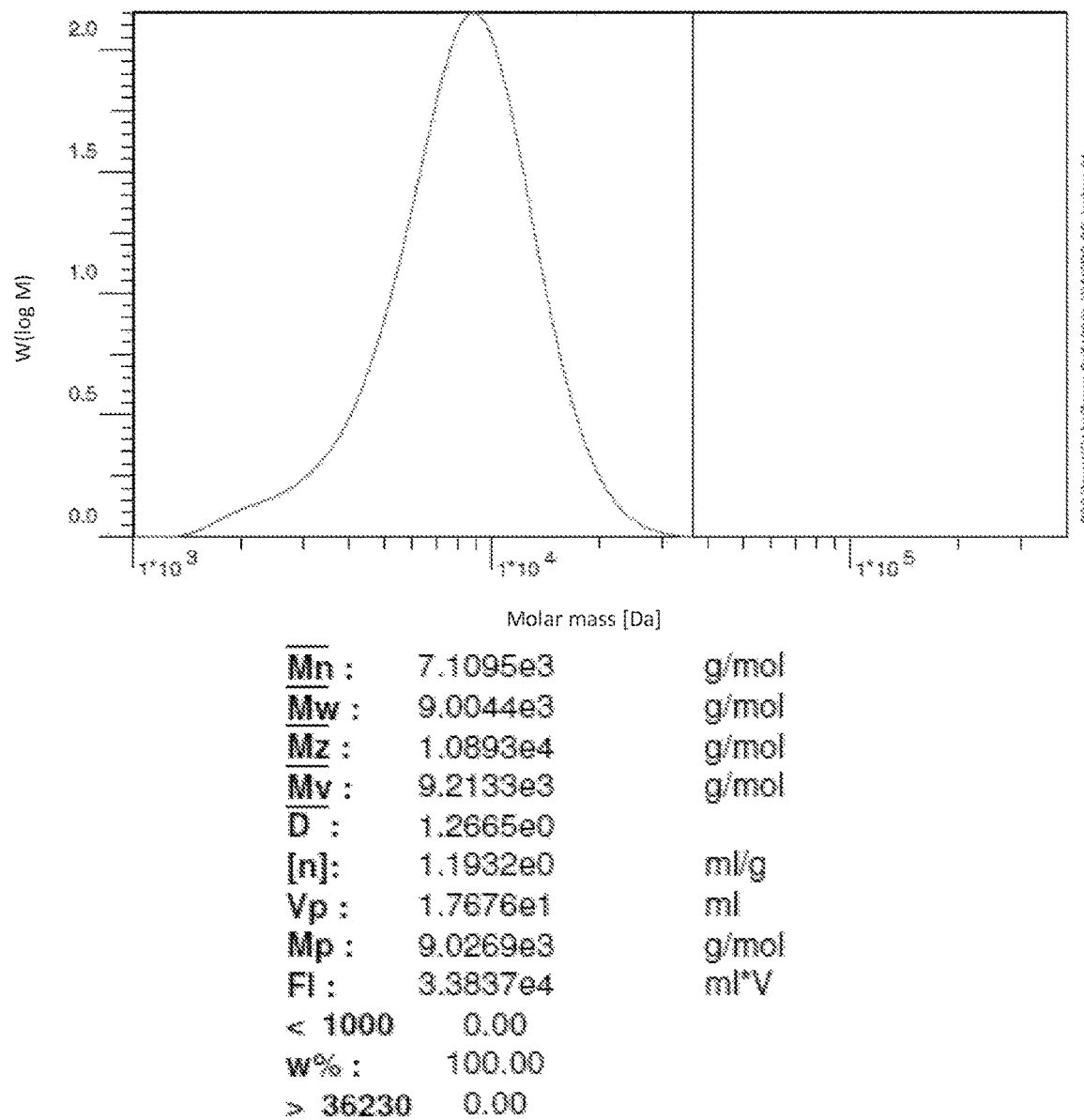
Figure 58 (GPC of poly-3S-caranamide)

Figure 59 (GPC of poly-3S-caranamide)
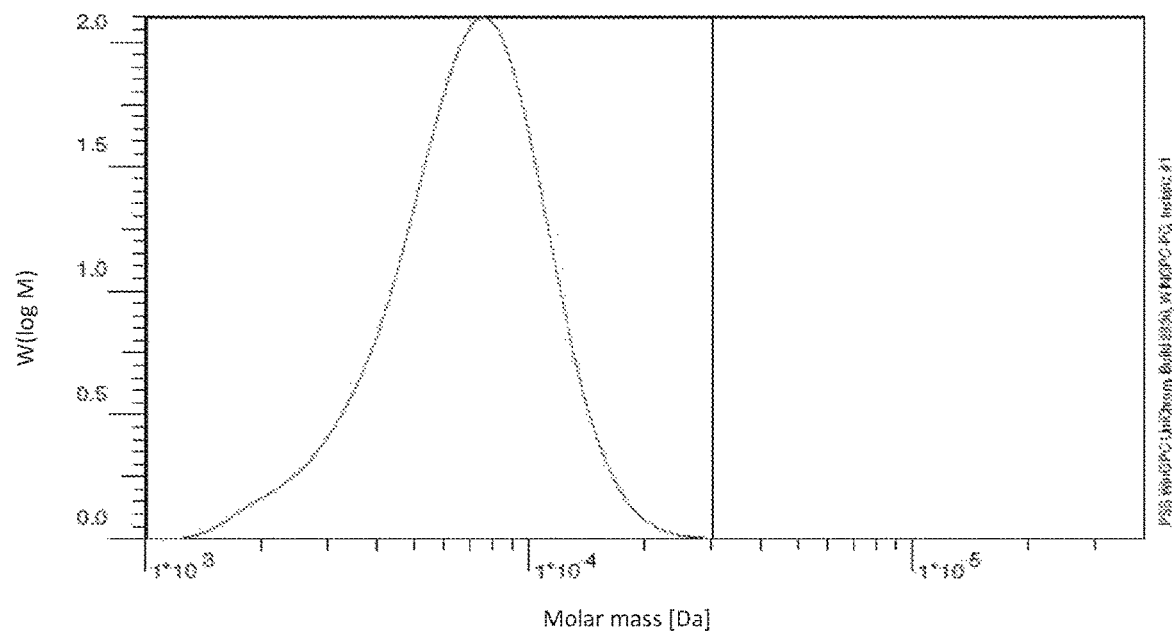

Figure 60 (GPC of poly-3S-caranamide)
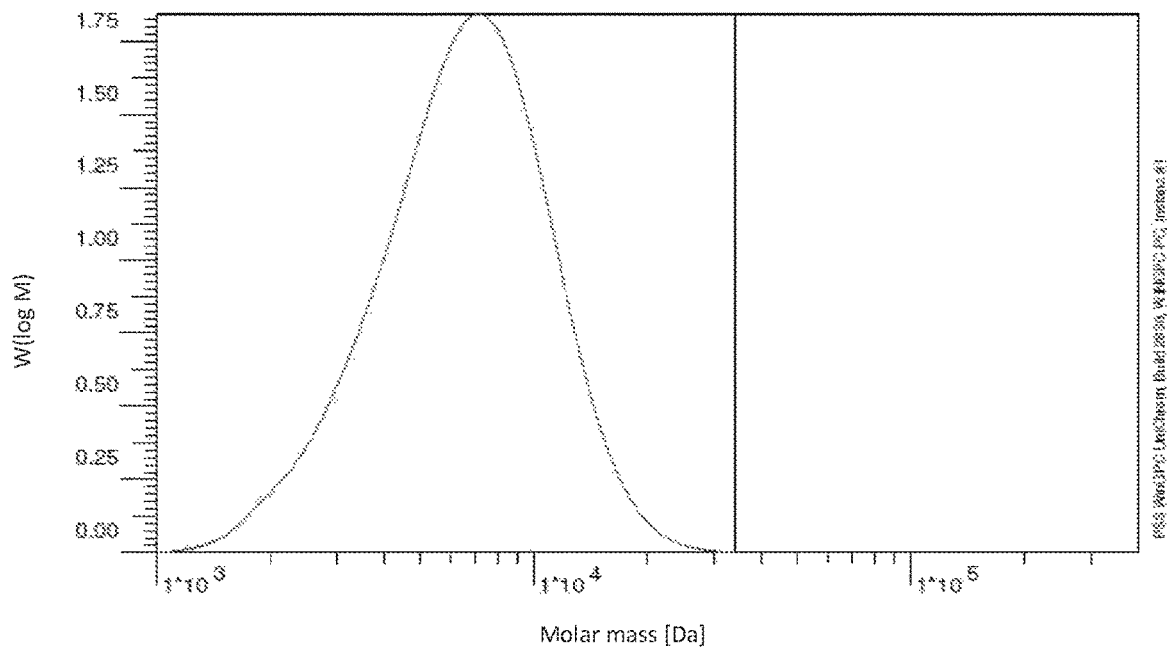

Figure 61 (GPC of poly-3S-caranamide)
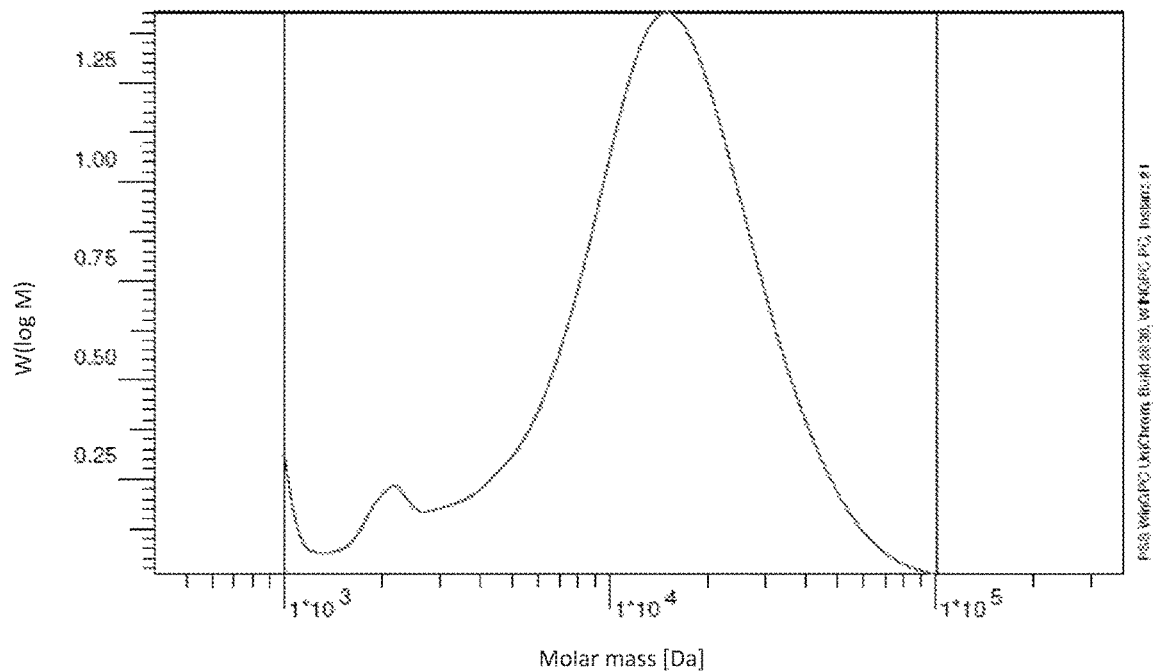

Figure 62 (GPC of poly-3R-caranamide)
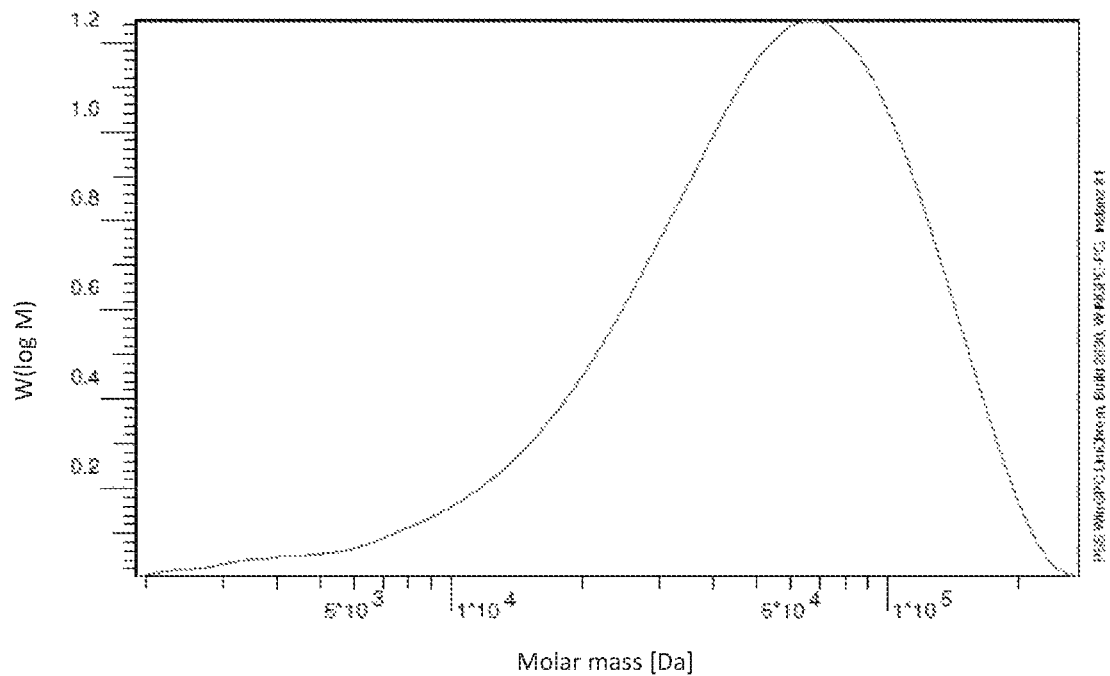

Figure 63 (GPC of poly-3R-caranamide)
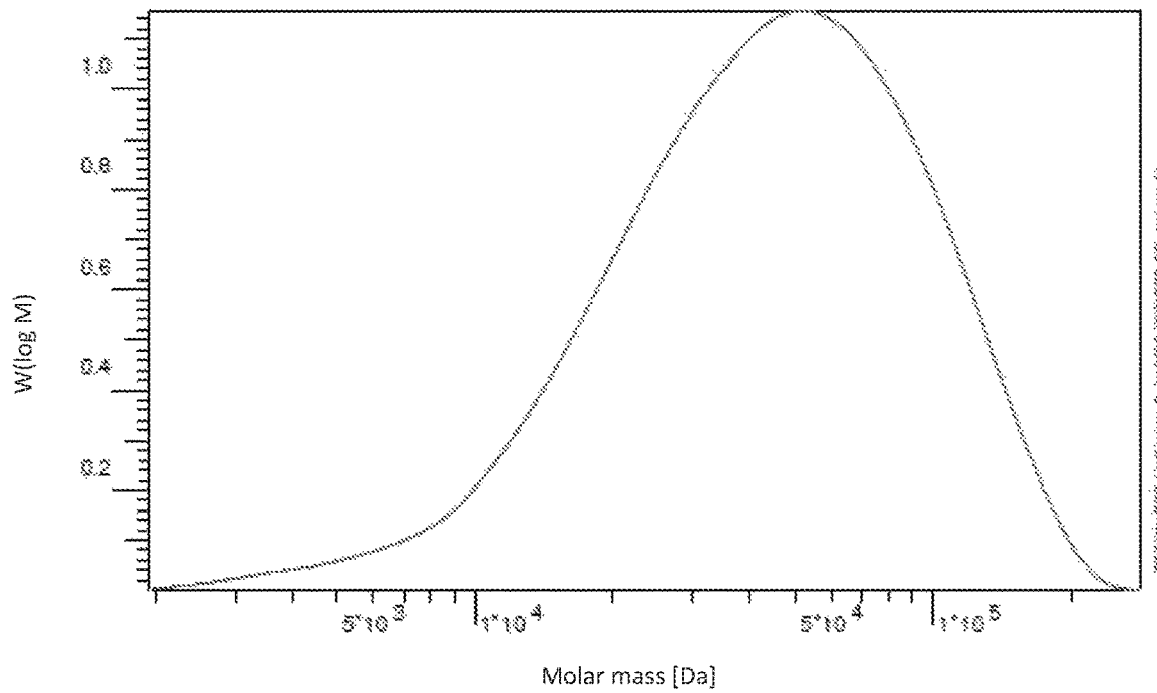

Figure 64 (GPC of poly-3R-caranamide)
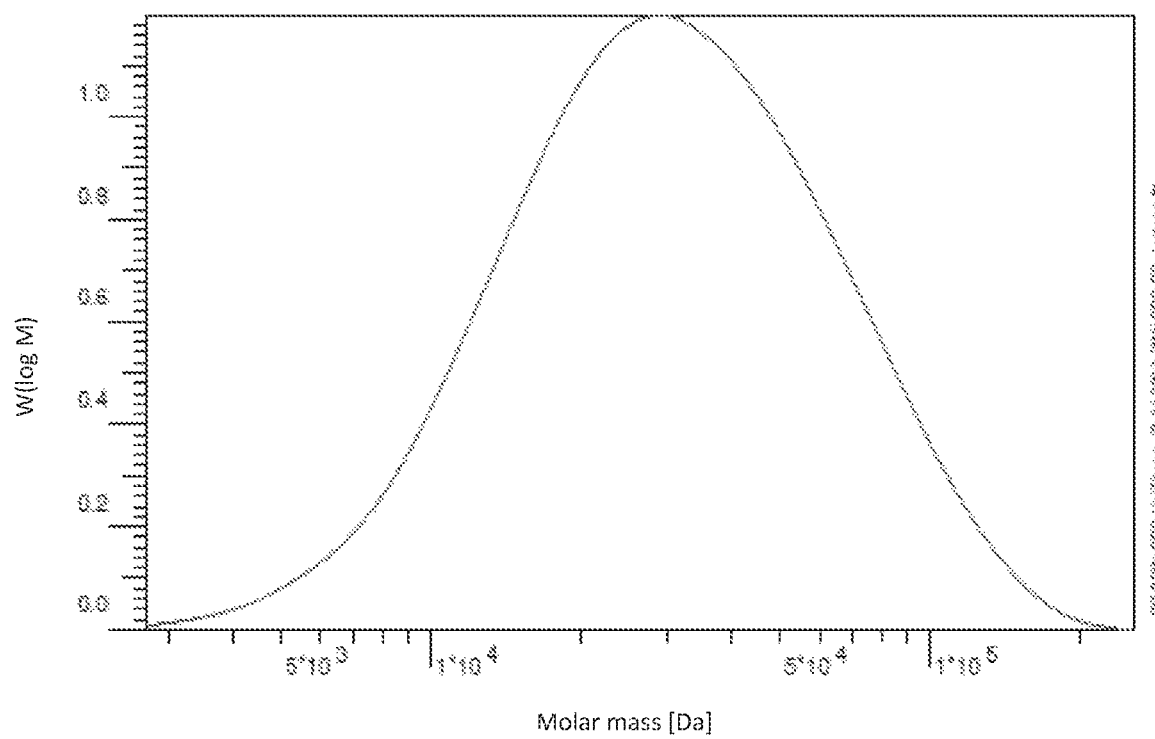

Figure 65 (GPC of poly-3R-caranamide)
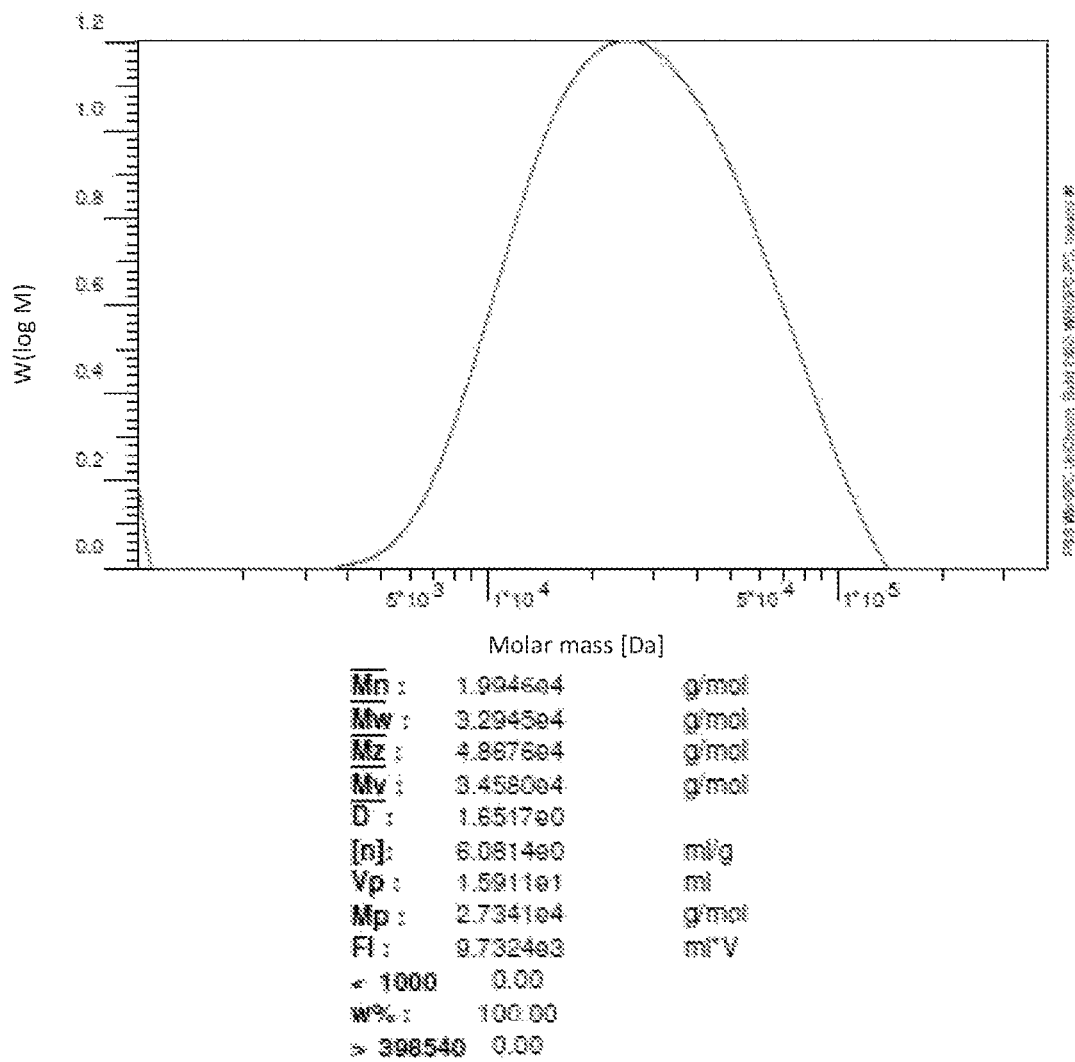

Figure 66 (GPC of poly-3R-caranamide)
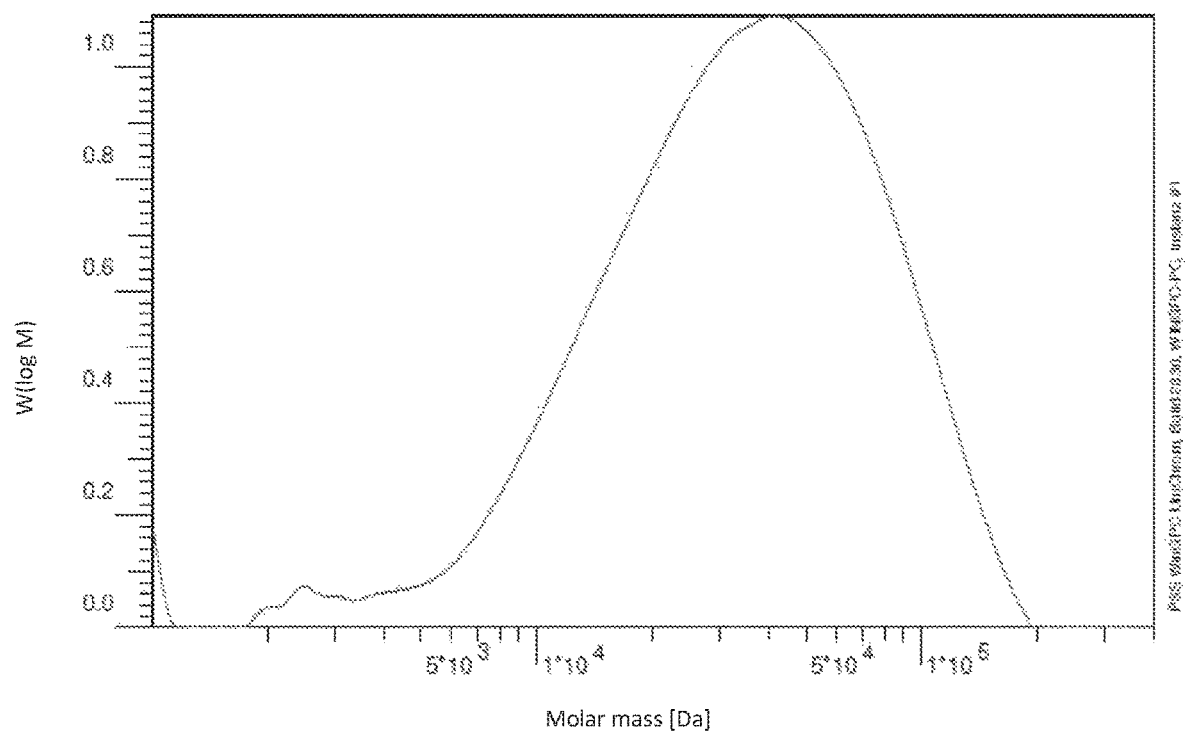

Figure 67 (GPC of poly-3R-caranamide)
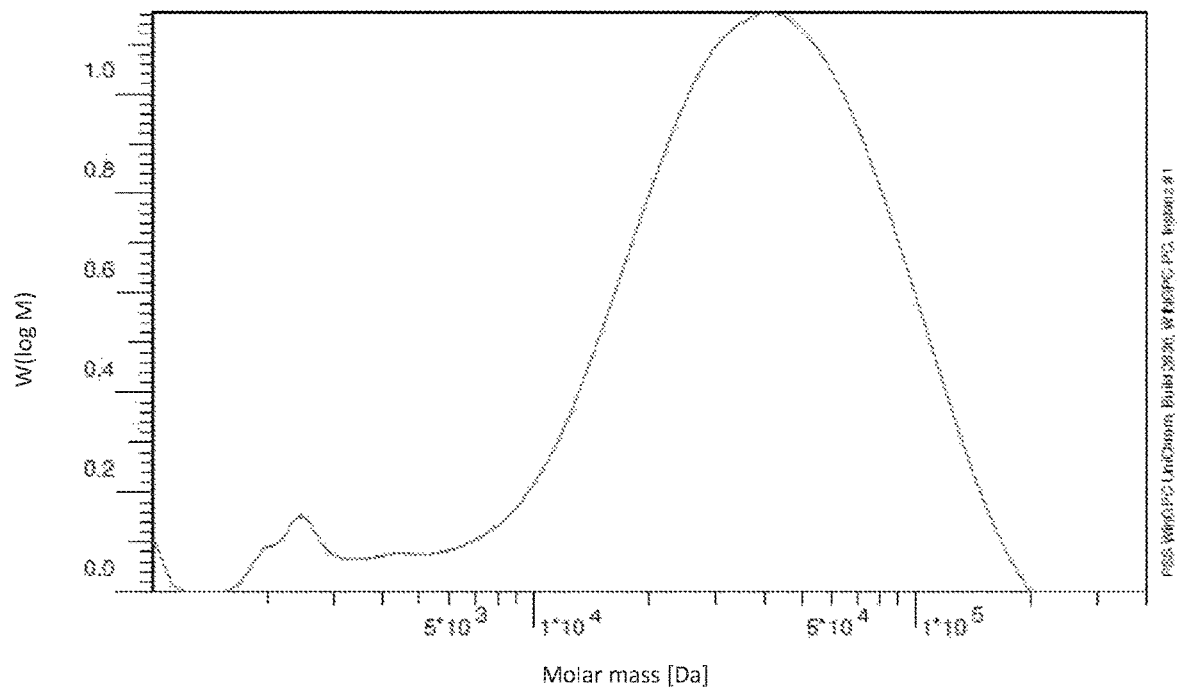

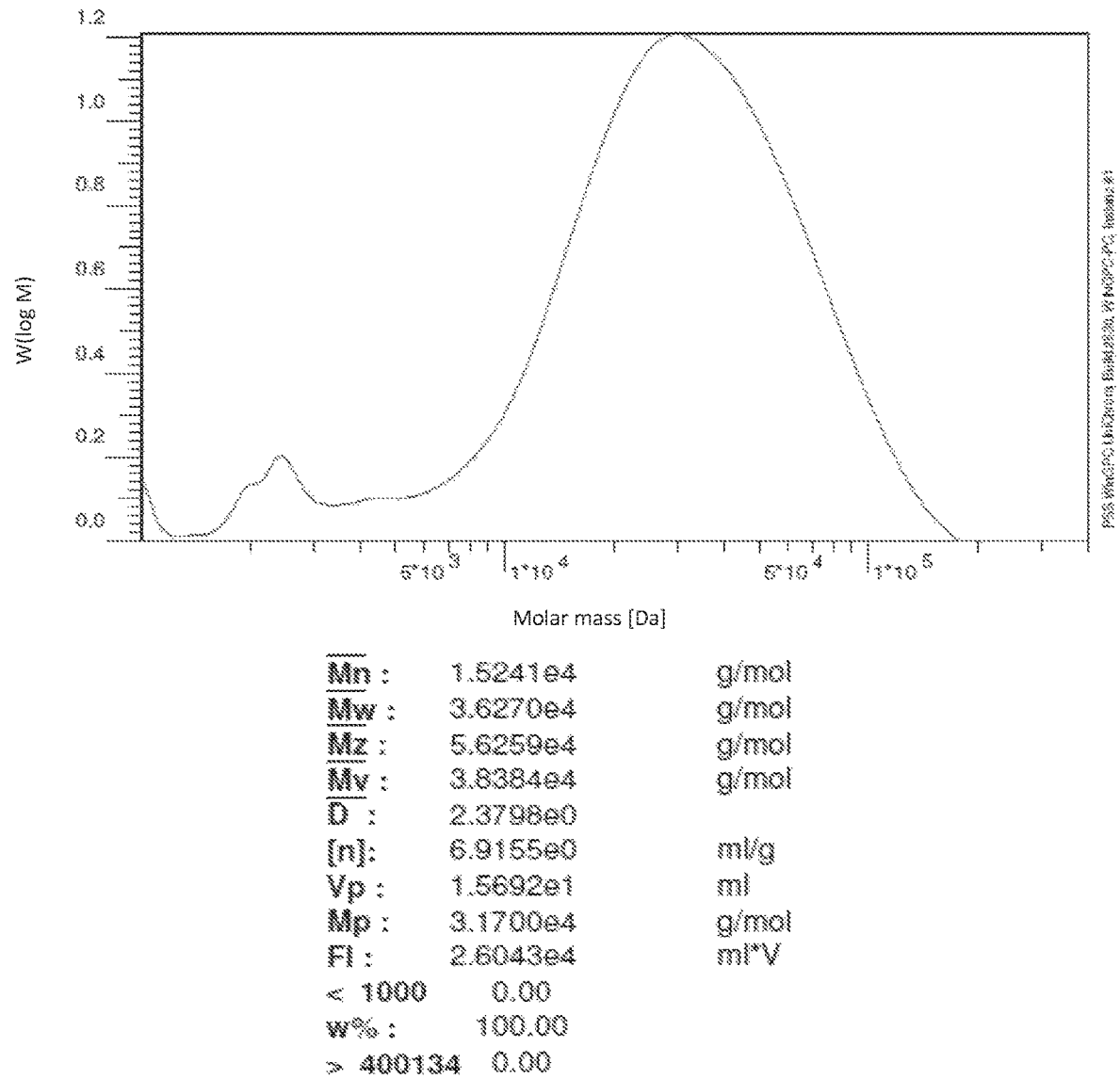
Figure 68 (GPC of poly-3R-caranamide)

Figure 69 (GPC of poly-3R-caranamide)
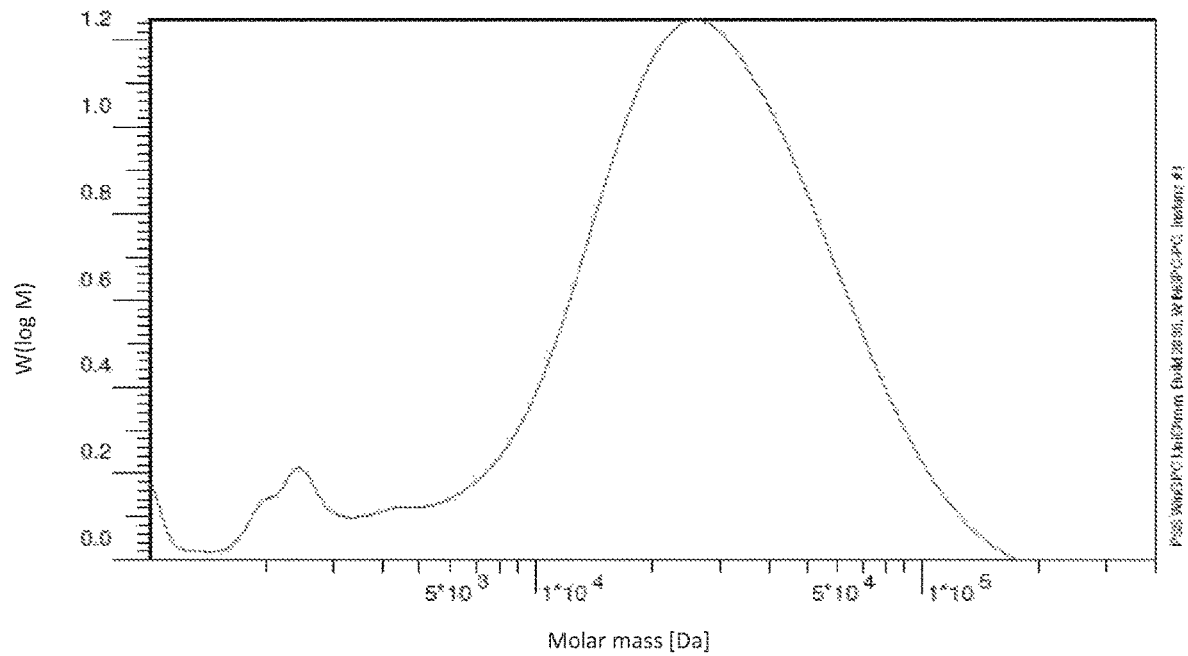

Figure 70 (GPC of poly-3R-caranamide)
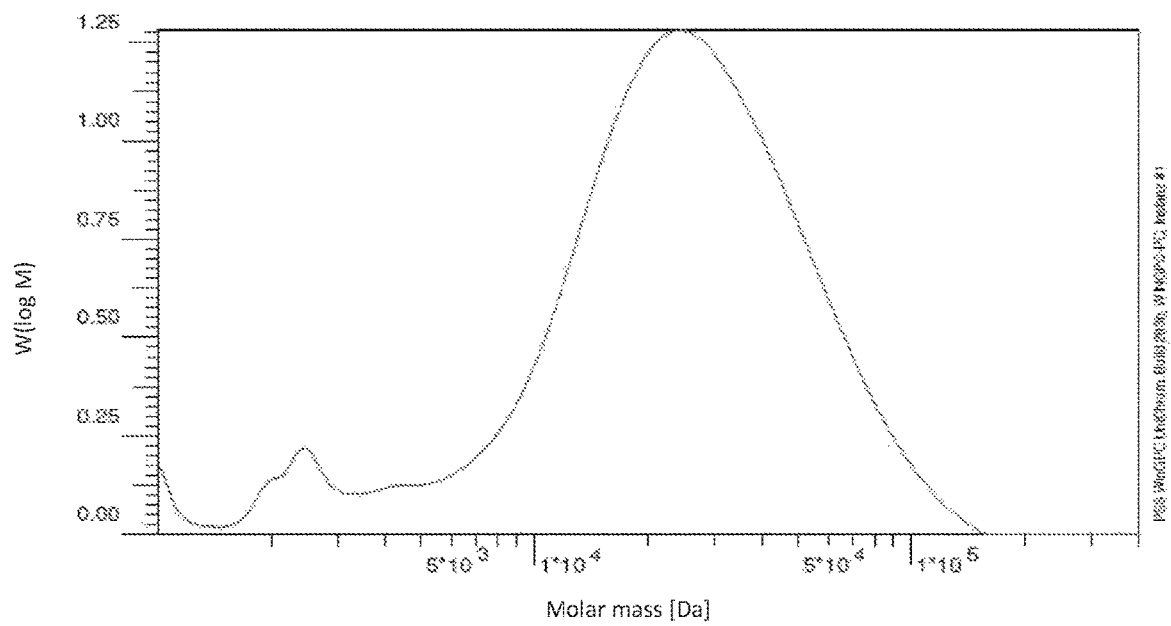

Figure 71 (GPC of poly-3R-caranamide)
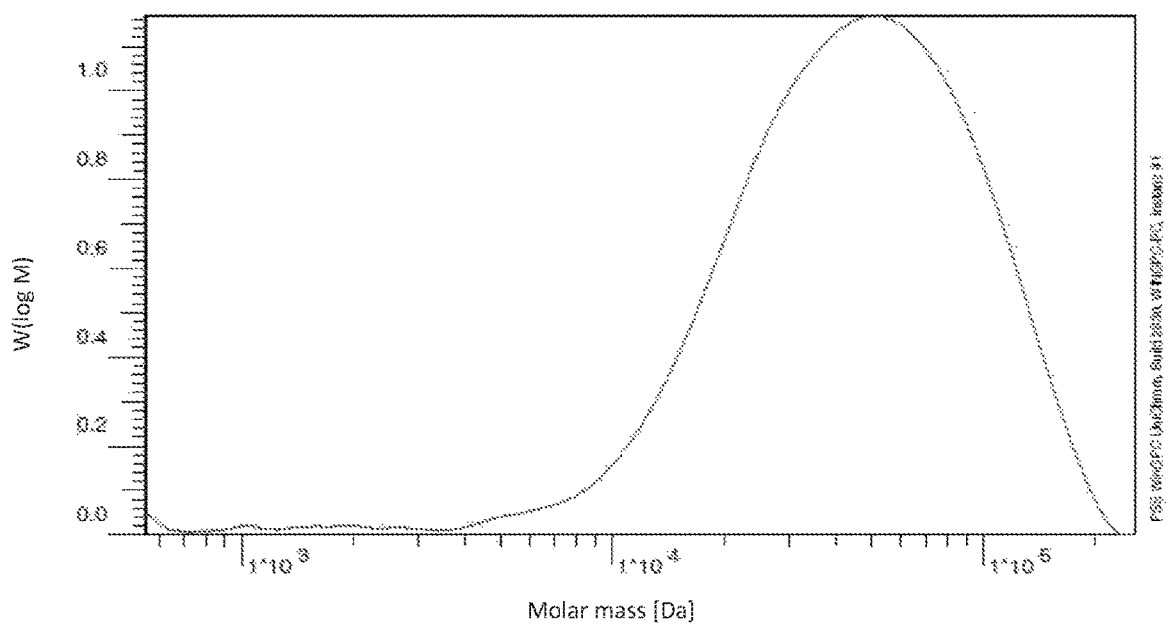

Figure 72 (GPC of 3S-caranlactam-3R-caranlactam co-polycaranamide)
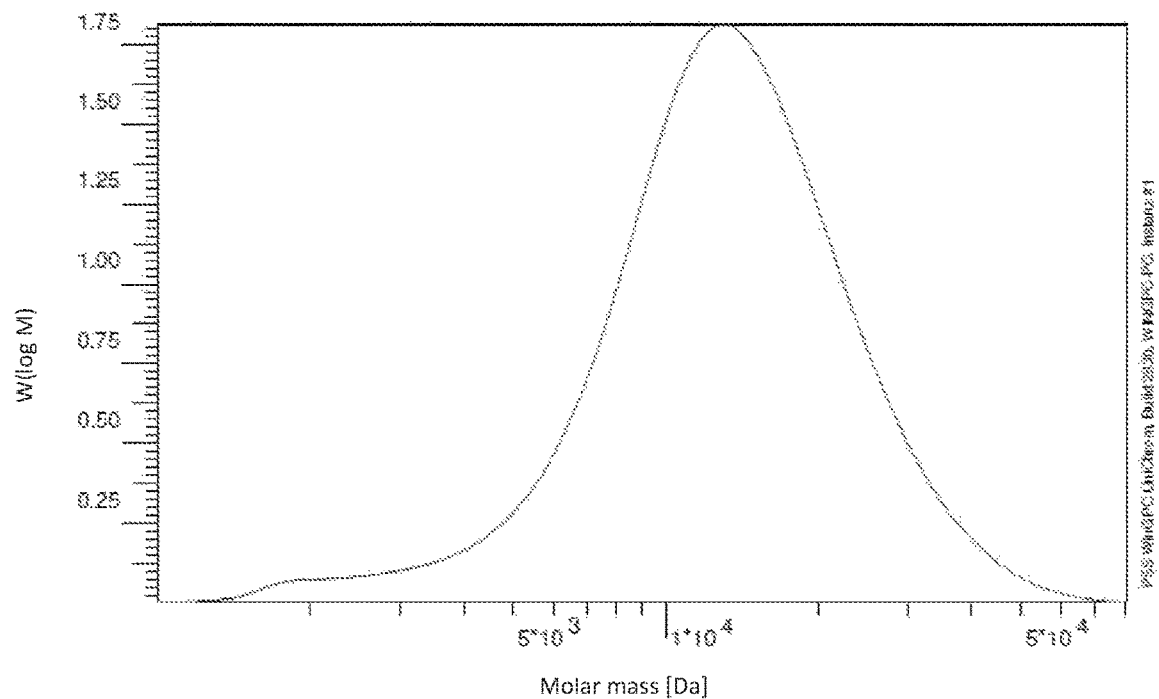

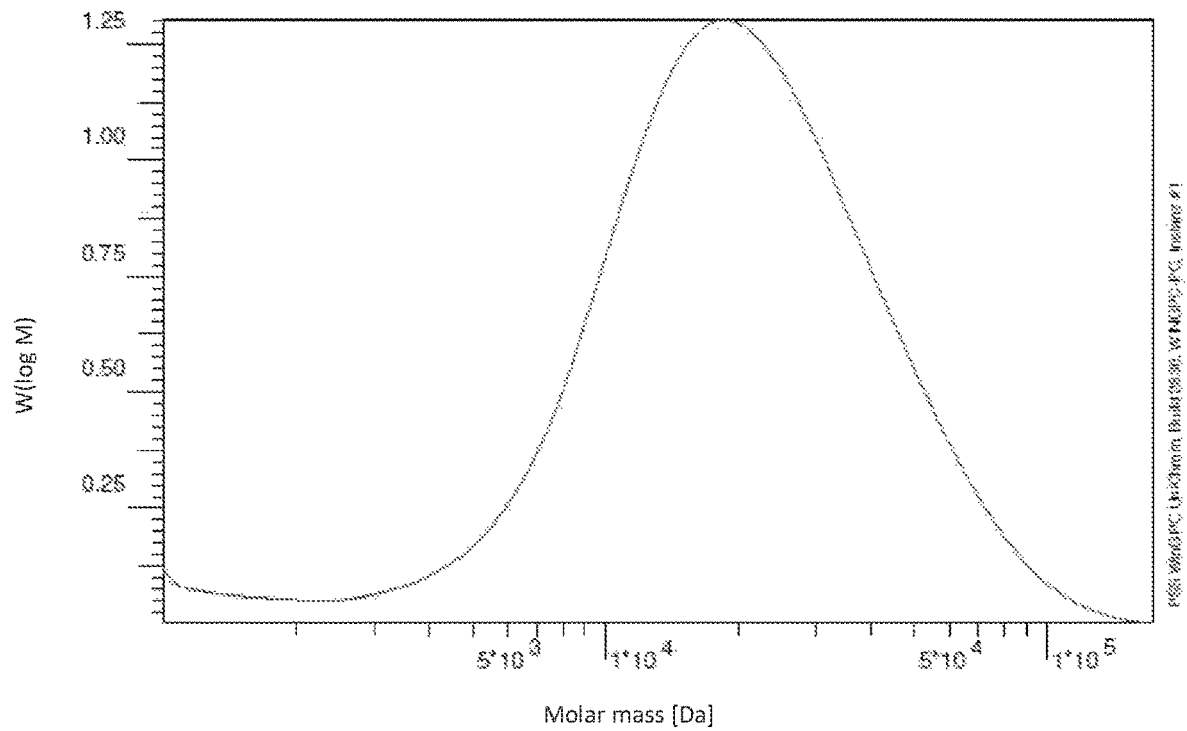
Figure 73 (GPC of 3S-caranlactam-laurolactam co-polycaranamide)

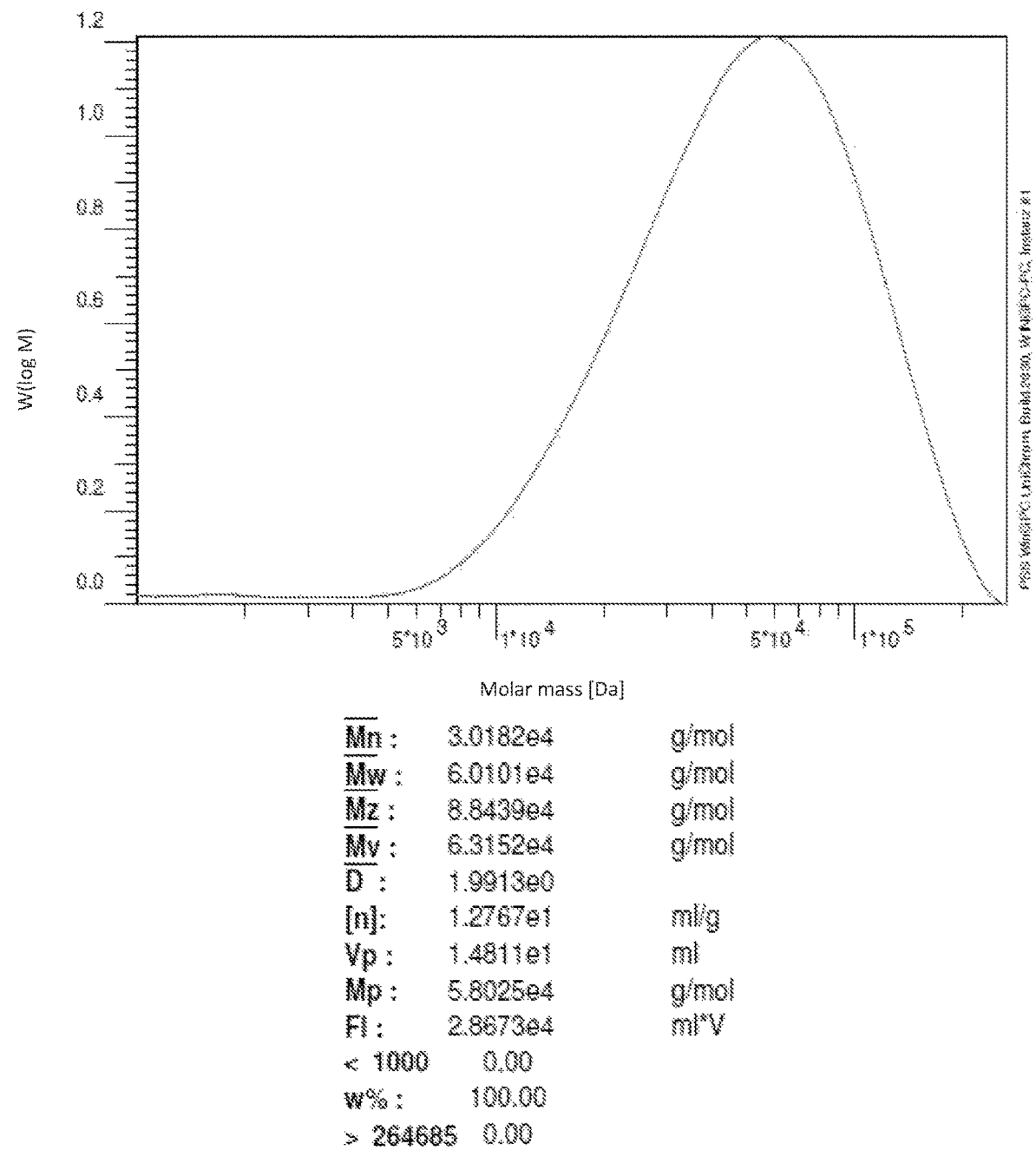
Figure 74 (GPC of 3S-caranlactam-laurolactam co-polycaranamide)

Figure 75 (GPC of 3S-caranlactam-laurolactam co-polycaranamide)
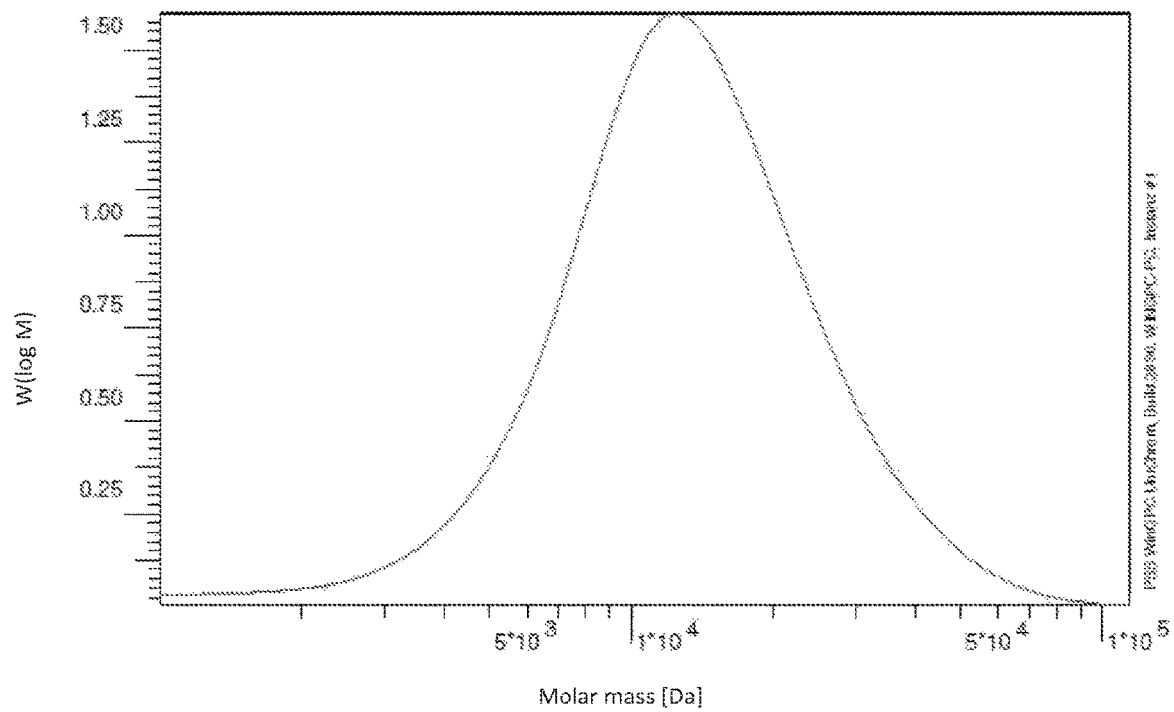

Figure 76 (GPC of 3S-caranlactam-caprolactam co-polycaranamide)
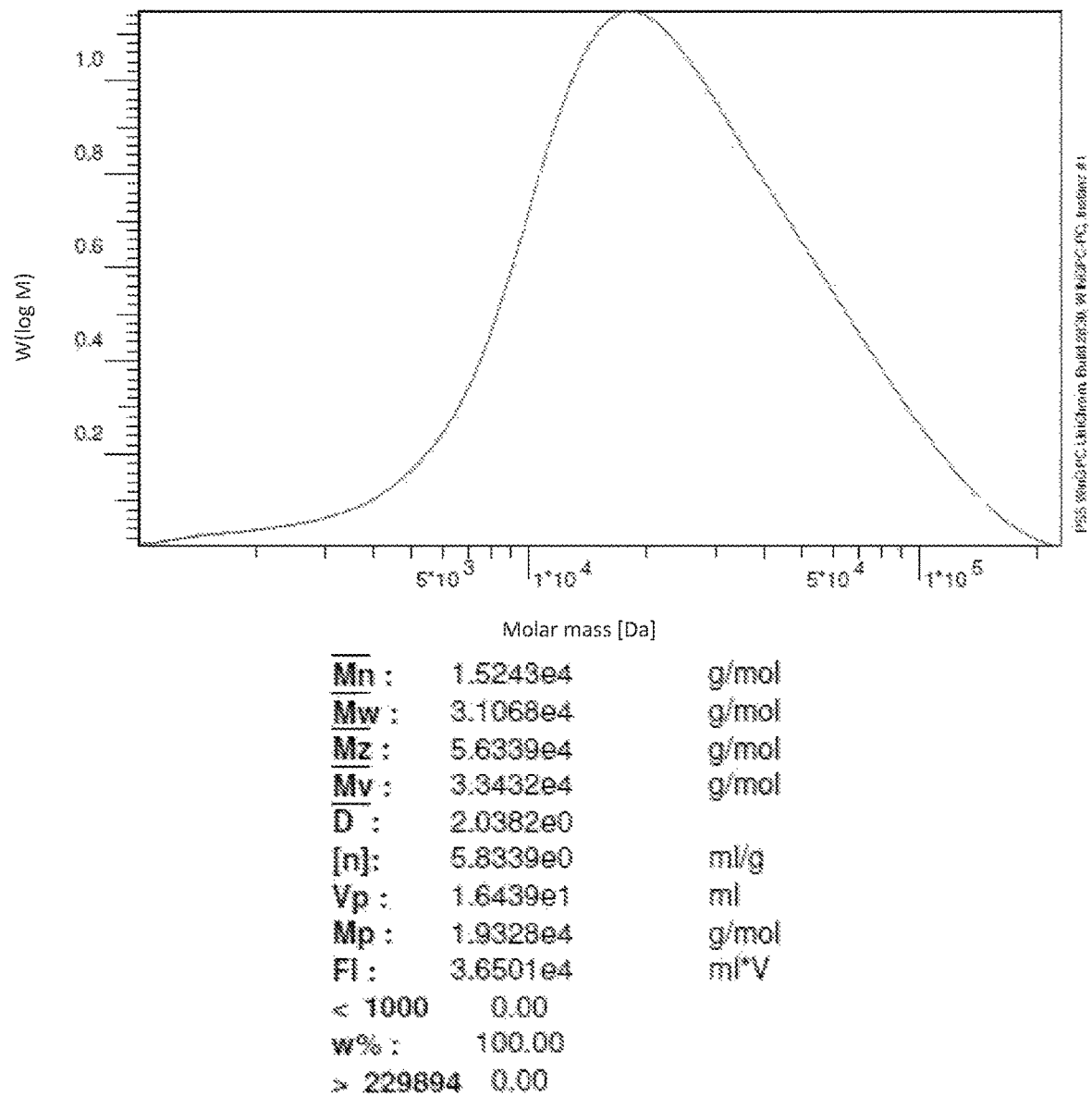

Figure 77 (GPC of 3S-caranlactam-caprolactam co-polycaranamide)
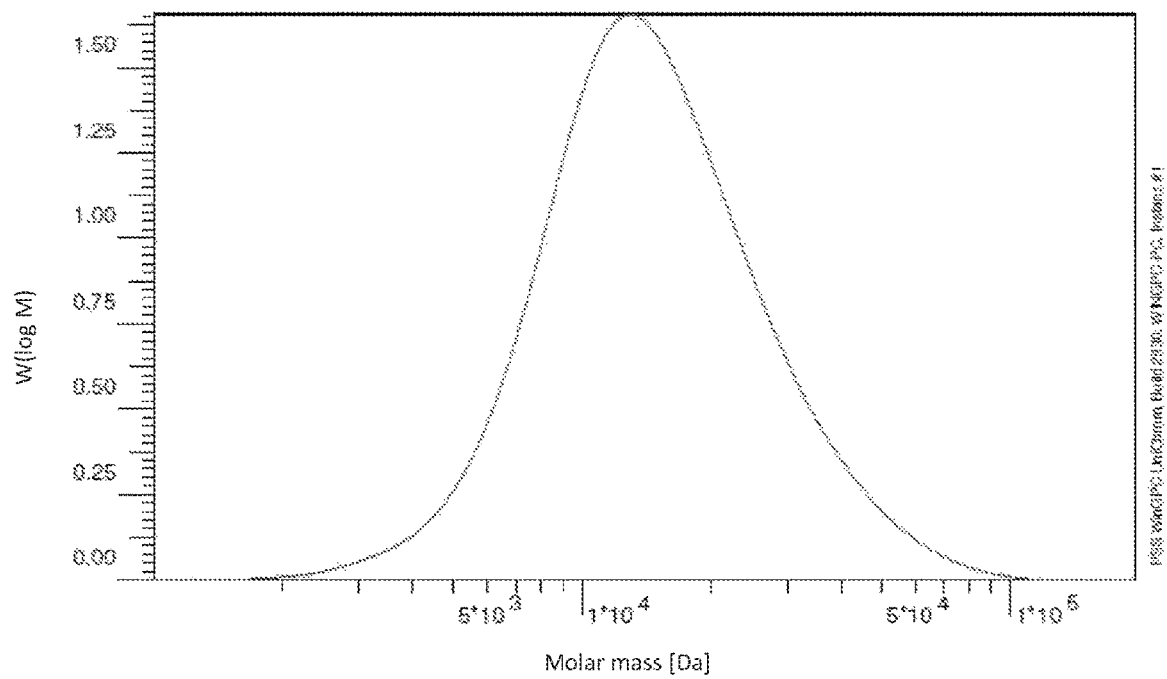

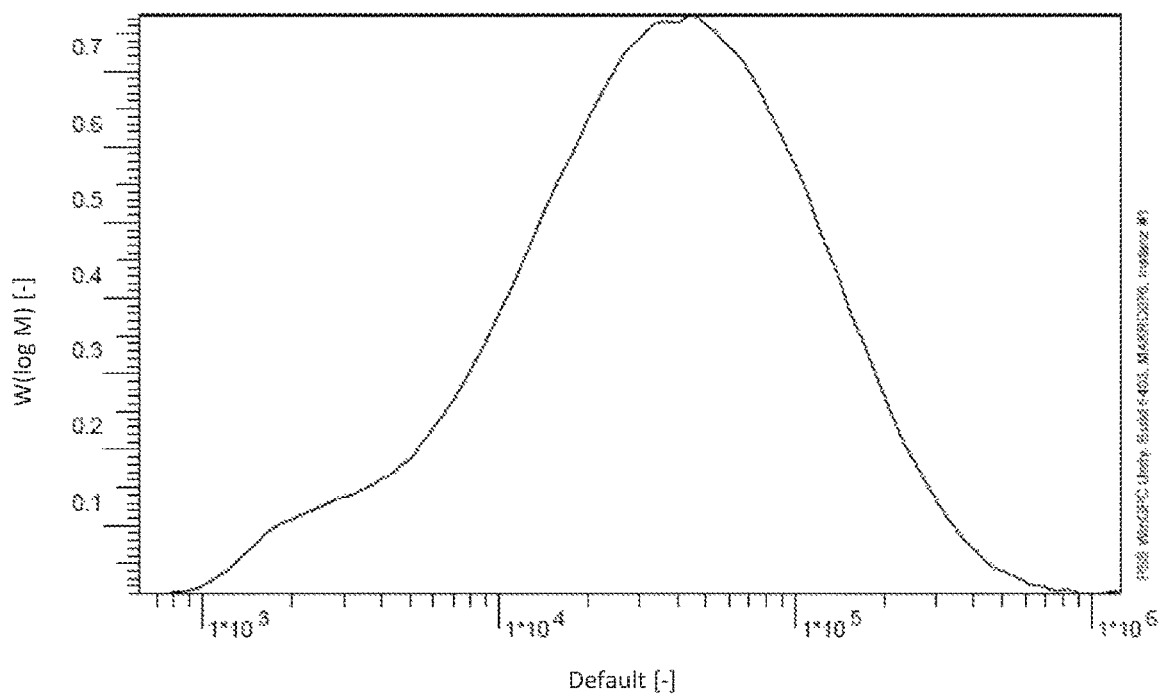
Figure 78 (GPC 3S-polycaranamide according to GPC method 4.1)

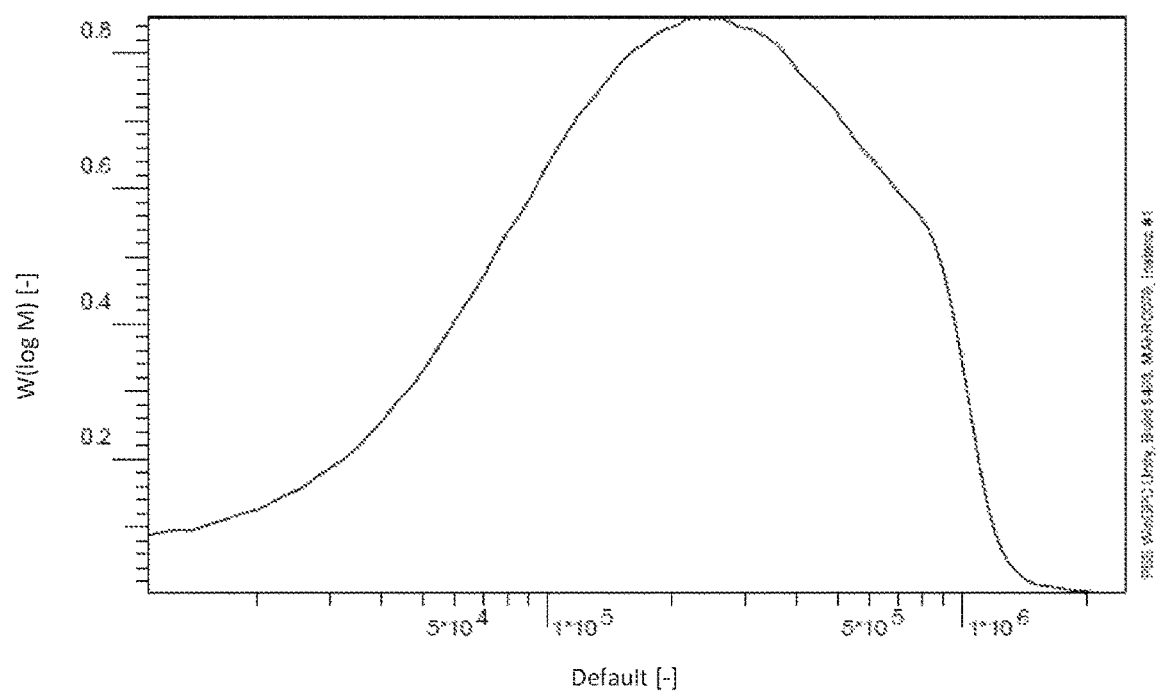
Figure 79 (GPC 3S-polycaranamide according to GPC method 4.1)

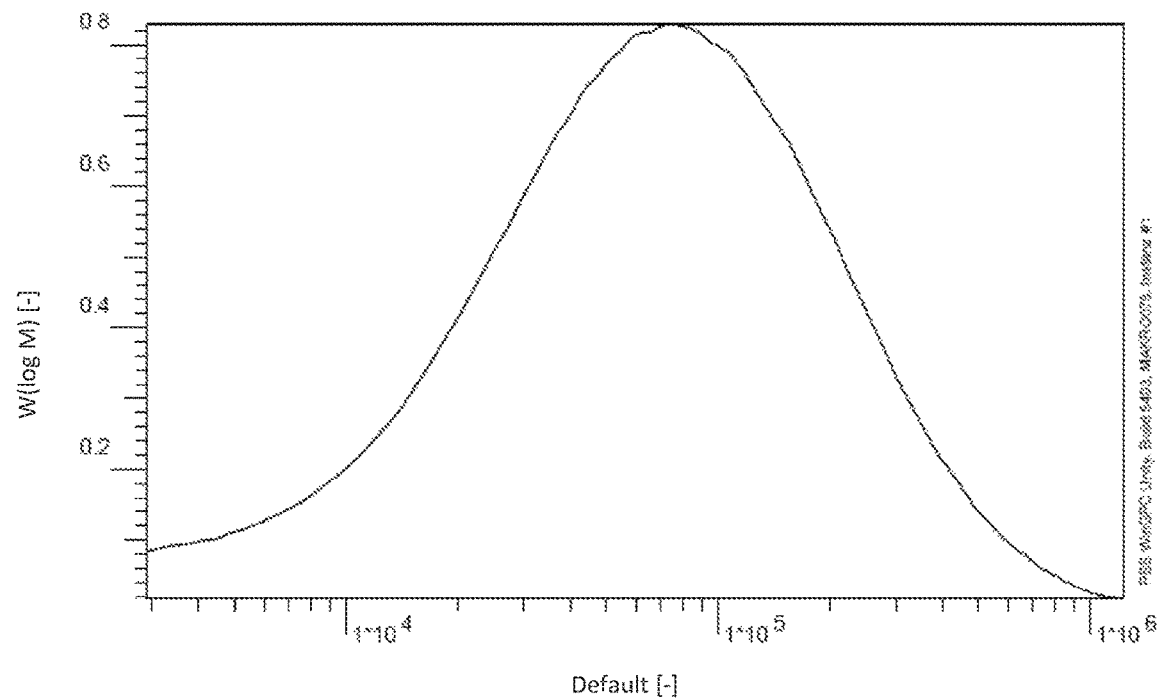
Figure 80 (GPC 3S-caranlactam-3R-caranlactam co-polycaranamide according to GPC method 4.1)

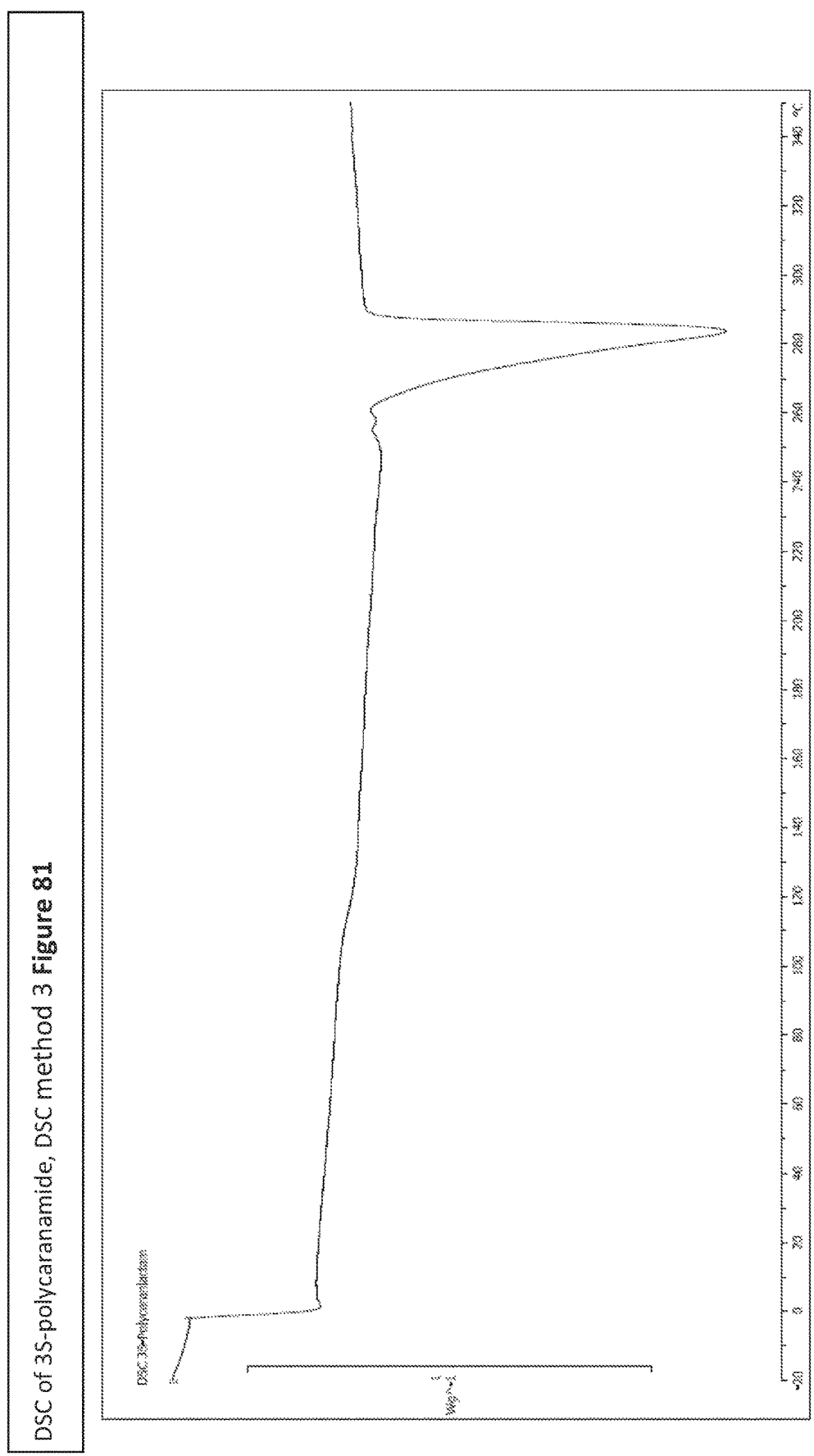

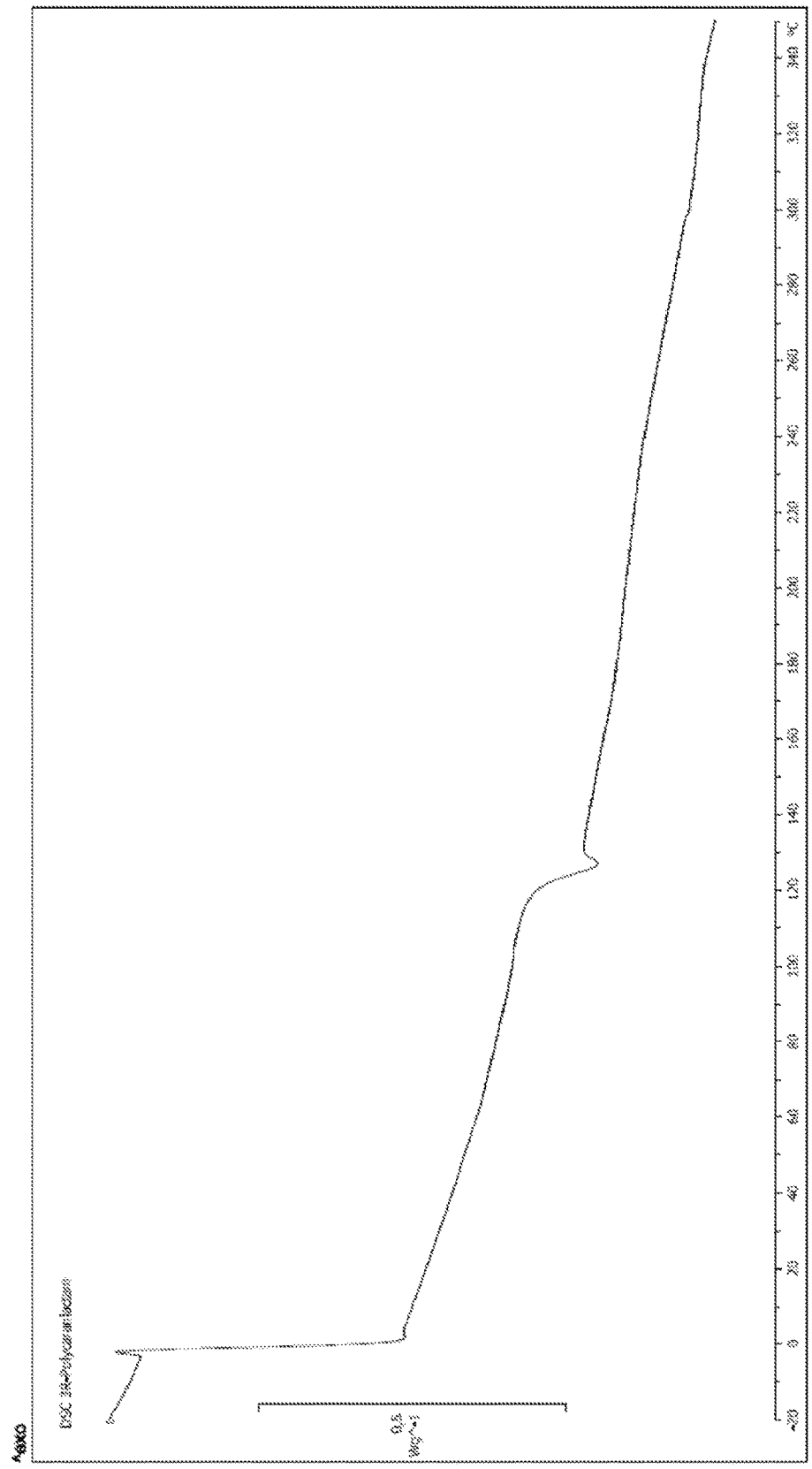

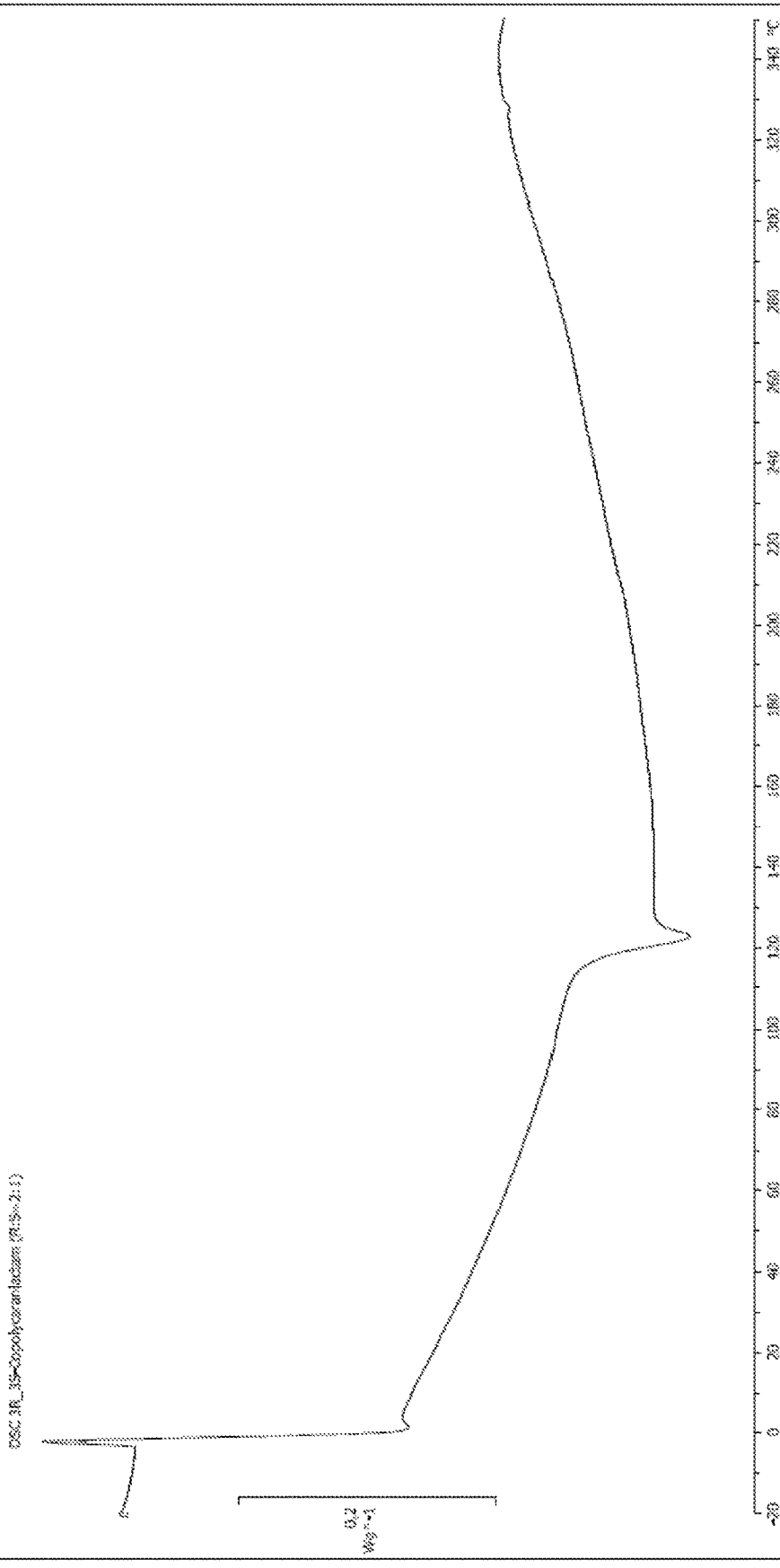
DSC of 3S-caranlactam-3R-caranlactam co-polycaranamide, DSC method 3 Figure 83

ISOMER-ENRICHED 3-CARANLACTAMS AND POLYAMIDES BASED THEREON WITH HIGH OPTICAL PURITY AND ADJUSTABLE CRYSTALLINITY FOR HIGH-PERFORMANCE APPLICATIONS

CROSS REFERENCE TO RELATED APPLICATIONS

This application is a U.S. National Stage Application under 35 U.S.C. 371 of International Application No. PCT/EP2019/055124, filed Mar. 1, 2019, which claims priority to German Patent Application 10 2018 203 631.4, filed Mar. 9, 2018. The contents of each of the aforementioned are hereby incorporated by reference in their entirety into the present disclosure.

The present invention relates to a process for the preparation of an isomer-enriched mixture of 3S- and 3R-caranone (IUPAC: (1R,4S,6S)-4,7,7-trimethylbicyclo[4.1.0]heptan-3-one and (1R,4R,6S)-4,7,7-trimethylbicyclo[4.1.0]heptan-3-one) from 3S-carane epoxide (IUPAC: (1S,3S,5R,7R)-3,8,8-trimethyl-4-oxatricyclo[5.1.0.03,5]octane), a 3S-caranone obtained therefrom, a process for the preparation of 3S-caranlactam (IUPAC: (1R,5S,7S)-5,8,8-trimethyl-4-azabicyclo[5.1.0]octan-3-one) from (+)-3-carene ((1S,6R)-3,7,7-trimethylbicyclo[4.1.0]hept-3-ene), a process for the preparation of 3R-caranlactam (IUPAC: (1R,5R,7S)-5,8,8-trimethyl-4-azabicyclo[5.1.0]octan-3-one) from (+)-3-carene, a 3S-caranoxime (IUPAC: (1R,4S,6S)-4,7,7-trimethylbicyclo[4.1.0]heptan-3-one oxime), a 3S-caranlactam, a 3S-polycaranamide, a 3R-polycaranamide and a 3S/3R-co-polycaranamide, particularly a 3S-caranlactam-3R-caranlactam co-polycaranamide, a 3S-caranlactam-laurolactam co-polycaranamide, a 3S-caranlactam-caprolactam co-polycaranamide, a 3R-caranlactam-laurolactam co-polycaranamide, a 3R-caranlactam-caprolactam co-polycaranamide.

So as to conserve fossil resources and reduce greenhouse gas emissions, there is great interest in replacing conventional plastics, such as fossil-based polyamides, with those that can be produced from renewable raw materials. Polyamides are formed by linking bi-functional monomers with amino-groups and with, preferably activated, carboxyl-groups. In this case, diamines can be reacted with dicarboxylic acids, and also amino acids can be reacted with amino acids. In the latter, both functional groups required for the linking—the amino-group and the carboxyl-group—are present in the same molecule. Among other things, lactams, such as ε-caprolactam, can be used to produce polyamides, for example by ring-opening polymerization.

Two industrially important lactams based on fossil raw materials that are used for polymerization are ε-caprolactam for the production of polyamide-6 (PA6) and laurolactam for the production of polyamide-12. ε-caprolactam is manufactured industrially from cyclohexanone and laurolactam is manufactured from cyclododecanone. The ketone in this case is first converted to the oxime and this oxime is then converted to the lactam, i.e. the monomer for the polyamide production, by a Beckmann rearrangement.

Bio-based polyamides available in industrial quantities have so far mainly been produced proceeding from castor oil. The monomers made from fatty acids lead to linear, partially crystalline polymer chains (PA11, PA410, PA610, PA1010, PA10.12) with properties comparable to fossil-based polyamides.

The glass transition point (Tg) of the commercial fatty acid-based polyamides is generally below 60° C. The polyamide described by Winnacker (M. Winnacker, J. Sag, A. Tischner, B. Rieger, Macromol. Rapid Commun. 2017, 38, 1600787), based on B-pinene, has a Tg of 160° C. and a melting point (Tm) of 264° C.; however, only molar masses of approx. 24 kDa are achieved. So far, menthone lactam can only be converted into oligomers. Previously known terpene and fatty acid-based polyamides are partially crystalline. Furthermore, terpene- and fatty acid-based polyamides have hitherto been produced either predominantly with low molar masses or with a low glass transition point and thus a restricted field of application. The syntheses of the respective monomers are usually not feasible on an industrial scale (terpene-based).

It is advantageous if the renewable raw material that is used for the production of the monomer, on the one hand, does not compete with food production and, on the other hand, does not itself have to be cultivated specifically for this application. It would be particularly advantageous if the renewable raw material is obtained as a residual/waste material in the production of other products from renewable raw materials. For example, large quantities of terpenes are produced in the production of cellulose, in particular as a waste product in cellulose production from wood. In this connection, reference is made to DE 10 2014 221 061 A1.

Another disadvantage of previously known processes for the production of polyamides from renewable raw materials is that the monomers, or the intermediates used for the production of the polyamides along the synthesis pathway for these monomers, often cannot be obtained in a chemically pure form and/or are not free of isomers. Another disadvantage is that the temperatures at which the polyamides can be used are often unsuitable for a large number of applications, and the molar masses which can be achieved are also low. It may also be disadvantageous that the optical purity, that is to say the tacticity and the crystallinity of the polyamides, cannot be adjusted in a targeted manner.

In principle, cleaning processes, for example chromatographic separations, are available in chemistry to separate isomers, in particular isomeric intermediates for the production of the monomers or the isomeric monomers themselves, but these processes are often very complex and expensive. The corresponding polyamides can therefore be very expensive compared to polyamides made from fossil raw materials.

It is therefore an object of the present invention to provide processes for the production of polyamides from renewable raw materials or residues and processes for the production of the monomers and intermediates required for the production of the polyamides along the synthesis pathway for these monomers, wherein the disadvantages known from the prior art are avoided. In particular, it should be particularly possible to produce polyamides using the processes provided which have improved product properties, preferably improved transparency and/or strength and/or toughness and/or stereoregularity, in particular for stereo- or enantioselective applications, compared to known polyamides made from non-renewable or petroleum-based raw materials.

The object of the present invention is achieved in particular by the teaching of claim 1 and by the further independent claims.

The present invention solves the present technical problem in particular also by providing polycaranamide, wherein the polycaranamide is 3S-polycaranamide according to the formula (with n repeat units):

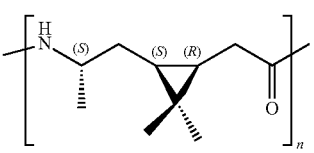

or 3R-polycaranamide with the formula (with n repeat units):

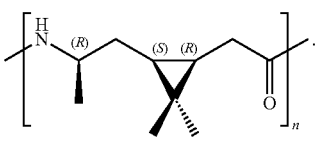

The invention also relates to 3S-3R co-polycaranamides according to the formula (with a, b and n repeat units):

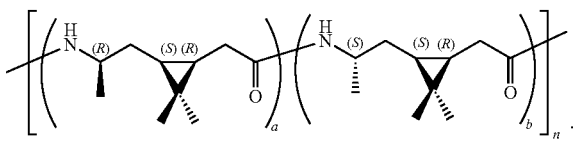

In a preferred embodiment, the polycaranamides mentioned can be prepared by the processes according to the present invention, in particular using processes according to the invention, which obtain the polycaranamides according to the invention from 3-carene, preferably 3-carane epoxide, and in particular isomer-enriched mixtures of 3S-caranone and 3R-caranone obtained therefrom. An essential contribution of the present invention is to provide the precursors for co-polycaranamide synthesis, in particular 3S-caranone for the provision of 3S-polycaranamide, from 3-carene or 3-carane epoxide via the process according to the invention. An advantageous embodiment of the invention provides for the provision of 3S-caranone-enriched mixtures, in particular a 3S-caranone-enriched mixture, from which 3S-caranoxime and 3S-caranlactam can be advantageously obtained as precursors for the 3S-polycaranamide or a 3S-co-polycaranamide.

The present invention also relates to a process for the preparation of an isomer-enriched mixture of 3S-caranone and 3R-caranone from 3-carane epoxide, comprising the following process steps: a) providing a reaction mixture containing 3-carane epoxide and at least one acid catalyst, b) reacting the 3-carane epoxide in the reaction mixture at a temperature of −40° C. to 140° C., with rearrangement, and c) obtaining the isomer-enriched mixture with an isomer ratio of at least 80% 3S-caranone or 3R-caranone (based on the total material quantity of caranone).

It is preferably provided according to the invention that the reaction mixture provided in process step a) additionally contains a first organic solvent.

The present invention relates in particular to a process for the preparation of an isomer-enriched mixture of 3S-caranone and 3R-caranone from 3-carane epoxide, comprising the following process steps: a) providing a reaction mixture containing 3-carane epoxide, at least one acid catalyst and at least one first organic solvent, b) reacting the 3-carane epoxide in the reaction mixture at a temperature of −40° C. to 140° C. with rearrangement, and c) obtaining the isomer-enriched mixture with an isomer ratio of at least 80% 3S-caranone or 3R-caranone (based on the total material quantity of 3S- and 3R-caranone). The provision according to the invention of a reaction mixture comprising 3-carane epoxide, at least one acid catalyst and, in a preferred embodiment, at least one first organic solvent preferably corresponds to a mixing of 3-carane epoxide, at least one acid catalyst and, optionally, at least one first organic solvent. According to process step b), the reaction mixture thus obtained includes the reaction according to the invention of 3-carane epoxide to give the isomer-enriched mixture obtained in process step c), with an isomer ratio of at least 80% 3S-caranone or at least 80% 3R-caranone (in each case based on the total material quantity of 3S- and 3R-caranon together, hereinafter also referred to as "caranone" for short), wherein the 3-carane epoxide is rearranged to 3S-caranone and 3R-caranone. The mixture containing isomers can preferably be purified or isolated.

The at least one acid catalyst is preferably a Lewis acid, particularly preferably a metal salt of very strong acids, in particular a metal salt of acids stronger than trifluoroacetic acids with a pKa of 0.23, preferably with metals of the third to fifth period, in particular of groups 4 to 13, in particular groups 7 to 12, in particular with an oxidation state of 2 to 3.

The at least one first organic solvent is preferably an aliphatic or aromatic solvent, in particular a solvent consisting only of hydrocarbons without heteroatoms, in particular a solvent with 4-10 carbons, in particular 5-7 carbons, and a boiling point between 30° C. and 126° C., preferably 60° C. to 81° C., in particular with a relative polarity lower than 0.164 (dioxanes).

It is preferably provided according to the invention that the conversion of the 3-carane epoxide in process step b) to the isomer-enriched mixture of S- and R-caranone proceeds at a temperature of 0° C. to 100° C., preferably 20° C. to 80° C., preferably of 40° C. to 65° C., in particular 45° C. to 60° C., in particular 48° C. to 53° C., in particular 50° C. to 60° C., in particular at 50° C., or at 60° C.

Furthermore, it is preferably provided according to the invention that the conversion of the 3-carane epoxide in process step b) takes place with a Meinwald rearrangement. In particular, it is envisaged that the Meinwald rearrangement occurs via a concerted mechanism without intermediates or via a mechanism with intermediates, in particular via the intermediates (1R,6S)-7,7-dimethyl-4-methylenebicyclo[4.1.0]heptane-3-ol and (1R,6S)-4,7,7-trimethylbicyclo[4.1.0]hept-3-ene-3-ol. A theory, without being bound to this, for the stereoselective Meinwald rearrangement of 3S-carane epoxide in process step b) to obtain an at least 80% 3S-caranone, based on the total material quantity of caranone, isomer-enriched mixture in process step c), is that the reaction proceeds preferentially via a concerted mechanism.

It is preferably provided according to the invention that the isomer-enriched mixture obtained in process step c) has an isomer ratio of at least 85%, at least 90%, or at least 95% 3S-caranone or 3R-caranone (based on the total material quantity of caranone).

The process according to the invention for producing an isomer-enriched mixture of 3S-caranone and 3R-caranone advantageously enables the production of intermediates, in particular isomers of 3-caranone, from which the monomers according to the invention required for polyamide production can be obtained. According to the invention, the reaction can be controlled in a preferred embodiment in such a way that the correspondingly desired intermediate product is present in a high proportion in the isomer-enriched mixture obtained—i.e., either 3S-caranone or 3R-caranone. The monomers required for the preparation of the polyamides according to the invention can be prepared cheaply, quickly and efficiently from this isomer-enriched mixture of 3S-caranone and 3R-caranone via the further intermediates 3-caranoxime and 3-caranolactam.

The terpene-based thermoplastic polyamides according to the invention which can be produced therefrom meet high thermal requirements and have high molar masses. In addition, the performance of the production process for the polymers according to the invention is potentially comparable to the commercially used production processes for fossil-based polyamides. The production process according to the invention, also referred to here as a synthesis pathway, can preferably be controlled in such a way that either a partially crystalline or a completely amorphous polyamide is formed. The production process according to the invention enables 3-carene-based lactams—i.e., the monomers of the polyamides according to the invention, to be produced separately in two diastereomers, which in the polyamide either lead to complete amorphicity or to partial crystallinity and thus meet different application requirements. A 3S-caranlactam polyamide is partially crystalline and a 3R-caranlactam polyamide is amorphous. Both polyamides can achieve molar masses above 50 kDa and/or 100 kDa, respectively, preferably above 10 kDa and/or 33 kDa. The polyamides provided according to the invention preferably have a high optical purity, are transparent in a preferred embodiment and preferably have stereoregularity which can be used advantageously in particular for stereo and enantioselective applications, for example for chiral stationary phases in HPLC or chiral membranes. In a preferred embodiment, the polyamides provided according to the invention are isotactic in the form of their homopolymers.

In the context of the present invention, the term 3-carene means both (1S,6R)-(+)-3-carene and the isomer (1R,6S)-(−)-3-carene. The preferred 3-carene used is (1S,6R)-(+)-3-carene. The substances and products produced from the 3-carene according to the invention accordingly have either the stereoisomeric (1S,6R)-(+) configuration or the (1R,6S)-(−) configuration, preferably the (1S,6R)-(+) configuration.

In the context of the present invention, the term "amorphous polymer" is understood to mean a polymer in which in the thermal analysis by means of differential scanning calorimetry (DSC) according to method (3) given below, a glass transition point alone but no melting point is observed up to the decomposition temperature or, according to process (3.1) and (3.2) given below, a glass transition point but no melting point can be observed up to a temperature of 320° C. (process 3.1) or up to the decomposition temperature (process 3.2).

In the context of the present invention, the term "partially crystalline polymer" is understood to mean a polymer in which, in thermal analysis by means of differential scanning calorimetry (DSC) according to method (3) or methods (3.1) or (3.2) given below, both a glass transition point and a melting point can be observed before the decomposition temperature.

The number average (Mn) and weight average (Mw) are preferably determined according to the invention by methods (4.1) or (4.2) below, in particular by method (4.2).

In the context of the present invention, polydispersity means the quotient of the weight average (Mw) (also referred to here as mass average) divided by the number average (Mn) (Mw/Mn), where (Mn) and (Mw) are determined according to method (4.1) or (4.2), in particular according to method (4.2).

In the context of the present invention, the term "water absorption" is understood to mean a reduction in the mass increase of a polyamide sample after conditioning with water compared to the dry state in a qualitative comparison to PA6 (polyamide 6), which can be determined for PA6 in a qualitative comparison according to the method (5) given below.

In the context of the present invention, a polyamide is "transparent" if, in accordance with method (6) given below, a colorless-transparent to opaque film can be produced in qualitative comparison with PA6 and PA12.

In the context of the present invention, the term "intermediate product" is understood to mean a compound which is obtained from a starting compound, in the present case in particular 3-carene or 3-carane epoxide, after carrying out a first process step, and which, in at least one second process step, for example also several process steps, is converted into an end product, in the present case in particular 3-caranlactam or its polyamide. In the context of the present invention, an intermediate product is in particular 3-caranone and 3-caranoxime, that is to say precursors for the production of 3-carane epoxide to form the monomer 3-caranlactam.

Furthermore, in the context of the present invention, the term "isomer-enriched mixture" is understood to mean a mixture of two diastereomeric compounds, one of the diastereomeric compounds occurring more frequently in the mixture than the other compound. An isomer in the context of the present invention is preferably a diastereomeric compound.

In particular, in a preferred embodiment of the present invention, an "isomer-enriched mixture" of the present invention comprises at least 80, at least 85, at least 90, at least 95, at least 98, at least 99% (in each case based on the amount of all isomers) of an isomer, in particular one of the diastereomeric compounds.

The expression "isomer-enriched mixture of 3S-caranone and 3R-caranone" (in relation to a specified enrichment, also referred to as a 3S- or 3R-caranone-enriched mixture or isomer mixture) is understood to mean that the isomer-enriched mixture comprises—and particularly predominantly comprises—the aforementioned diastereomeric compounds, and in particularly is comprised of more than 50, in particular more than 60, in particular more than 70, in particular more than 80, in particular more than 90, in particular more than 95, in particular more than 99% (based on the dry mass of the diastereomeric compounds relative to the bulk dry substance of the mixture), and in particular consists of, the diastereomeric compounds. With respect to the other isomer-enriched mixtures provided in the present invention, in particular 3S- and 3R-caranoxime and 3S- and 3R-caranlactam, it is also true that the term "enriched mixture of" means that the isomers indicated in each case predominate in the mixture, preferably as more than 50, in particular make up more than 60, in particular more than 70, in particular more than 80, in particular more than 90, in particular more than 95, in particular more than 99 wt. % (in each case based on the dry mass of the diastereomeric compounds relative to the dry substance of the mixture), and the mixture in particular consists of the diastereomeric compounds mentioned.

By means of the process according to the invention for producing an isomer-enriched mixture of 3S-caranone and 3R-caranone, the desired isomer can be obtained in high yield and high purity of at least 80%, in particular at least 85%, preferably at least 90%, in particular at least 95%, and in particular at least 91% of an isomer is obtained (in each case based on the amount of substance of both isomers), in particular without a significant proportion of by-products, in particular by-products which cannot be converted or isomerized into the desired isomer.

It is furthermore advantageous in the process according to the invention that the 3S-caranone-enriched isomer mixture can be obtained in only one reaction step, starting from the epoxide, without the need for intermediate steps.

In addition to an increased amorphous fraction, the polyamides according to the invention synthesized from 3-carene also have a significantly higher glass transition point Tg of 100 to 130° C., in particular 105 to 125° C., in particular 105 to 115° C., 110 to 120° C., in particular approximately 115° C., instead of about 60° C. as with most commercial polyamides made from renewable raw materials. Without being bound by theory, the values observed for the polyamides and co-polyamides according to the invention could possibly be explained by the fact that the polyamides prepared from the lactams—i.e., the monomers according to the invention, the bridged terpene 3-carene—lead to a snagging of the chains because of the rings remaining in the polymer chain, and to a softening that only occurs at higher temperatures (glass transition point). This enables an extended temperature range in which the polymers can be used.

Due to the molecular structure of 3-carene, two different diastereomers potentially arise from reaction forming the lactam. According to the invention, it is possible in special embodiments to synthesize both isomers with high selectivity at the stereo center in an economically interesting process.

The 3R-polycaranamide according to the invention (also referred to as 3R-polyamide), which can preferably be produced selectively from R-caranlactam, is amorphous, preferably completely amorphous, and has a glass transition point Tg of approximately 100 to 130° C., in particular 105 to 125° C., in particular 110 to 120° C. The material thus exhibits behavior that has not previously been known for commercially interesting bio-based polyamides.

The 3S-polycaranamide according to the invention, preferably likewise selectively producible from 3S-caranlactam—with the new stereo center rotated—is partially crystalline with a melting point Tm in the range from 230 to 290° C., in particular 240 to 285° C., in particular 260° C. to 290° C., the glass transition point likewise being in the range from 100 to 130° C., in particular 105 to 125° C., in particular 110 to 120° C. The crystalline structures present in addition to the amorphous areas in the molecule enable use at further elevated temperatures.

The 3S-caranlactam according to the invention is further characterized in a preferred embodiment in that the 3S-caranlactam can be co-polymerized with other lactams, preferably caprolactam (CL) or laurolactam (LL). 3S-caranlactam is preferably incorporated into the co-polycaranamide as at least 1%, in particular at least 10%, in particular at least 50%, in particular at least 70%, in particular at least 80% and up to 100% of the maximum value determined by the quantitative ratio of the monomers at the start of the polymerization. The invention therefore also relates to 3S-co-polycaranamides which is prepared or can be prepared from 3S-caranlactam and at least one other lactam, preferably 3R-caranlactam, caprolactam and/or laurolactam.

In a preferred embodiment, 3S-caranlactam-laurolactam co-polycaranamides according to the invention are characterized in that amorphous phases become pronounced with increasing incorporation of 3S-caranlactam. This enables adjusting the crystallinity. Furthermore, in a preferred embodiment, 3S-caranlactam-laurolactam co-polycaranamides are characterized in that higher $T_g$s can be achieved with increasing incorporation of 3S-caranlactam. This enables use at higher temperatures than PA12 (polyamide 12).

3S-caranlactam-caprolactam co-polycaranamides according to the invention are preferably characterized in that amorphous phases become pronounced with increasing incorporation of 3S-caranlactam. This enables adjusting the crystallinity. Furthermore, in a preferred embodiment, 3S-caranlactam-laurolactam co-polycaranamides are characterized in that higher $T_g$s can be achieved with increasing incorporation of 3S-caranlactam. This enables use at higher temperatures than PA6.

In a preferred embodiment, the 3R-caranlactam according to the invention is further characterized in that the 3R-caranlactam can be co-polymerized with other lactams, preferably caprolactam or laurolactam. 3R-caranlactam is preferably incorporated into the co-polycaranamide as at least 1.0%, in particular at least 10%, in particular at least 50%, in particular at least 70%, in particular at least 80% and up to 100% of the maximum value determined by the quantitative ratio of the monomers at the start of the polymerization. The present invention therefore also relates to 3R-co-polycaranamides which are produced or can be produced from 3R-caranlactam and at least one other lactam, preferably 3S-caranlactam, caprolactam and/or laurolactam.

In a preferred embodiment, 3R-caranlactam-laurolactam co-polycaranamides according to the invention are characterized in that amorphous phases become pronounced with increasing incorporation of 3R-caranlactam. This enables adjusting the crystallinity. Furthermore, in a preferred embodiment, 3S-caranlactam-laurolactam co-polycaranamides are characterized in that higher $T_g$s can be achieved with increasing incorporation of 3R-caranlactam. This enables the use of higher temperatures compared to PA12.

In a preferred embodiment, 3R-caranlactam-caprolactam co-polycaranamides according to the invention are characterized in that amorphous phases become pronounced with increasing incorporation of 3R-caranlactam. This enables adjusting the crystallinity. Furthermore, 3R-caranlactam-laurolactam co-polycaranamides are characterized in a preferred embodiment in that higher $T_g$s can be achieved with increasing incorporation of 3R-caranlactam. This enables use at higher temperatures than PA6.

The following tables 1a) and 1b) disclose preferred properties of the 3R- and 3S-polycaranamides according to the invention, as well as of their copolymers, and copolymers with laurolactam and caprolactam.

TABLE 1a

Properties of a 3S-polycaranamide, a 3R-polycaranamide, a 3S-caranlactam-3R-caranlactam co-polycaranamide, a 3S-caranlactam-laurolactam co-polycaranamide and a 3S-caranlactam-caprolactam co-polycaranamide of the present invention (according to methods (3.1), (3.2) and (4.2)).

| Polymer | $T_g$ (range, ° C.) | $T_m$ (range, ° C.) | $M_w$ [kDa] | $M_n$ [kDa] |
|---|---|---|---|---|
| 3S-polycaranamide (semi-crystalline) | 105-120 | 230-290, particularly 260-290 | 16.2 | 10.2 |

TABLE 1a-continued

Properties of a 3S-polycaranamide, a 3R-polycaranamide, a 3S-caranlactam-3R-caranlactam co-polycaranamide, a 3S-caranlactam-laurolactam co-polycaranamide and a 3S-caranlactam-caprolactam co-polycaranamide of the present invention (according to methods (3.1), (3.2) and (4.2)).

| Polymer | $T_g$ (range, °C.) | $T_m$ (range, °C.) | $M_w$ [kDa] | $M_n$ [kDa] |
|---|---|---|---|---|
| 3R-polycaranamide (amorphous) | 105-120 | none | 64.7 | 33.0 |
| 3R-/3S-co-polycaranamide (R:S = 1:3) | 105-120 | 210-250 | 15.0 | 10.4 |
| 3S-caranlactam-laurolactam co-polycaranamide (Incorporation 3S/LL = 1:1.4) | 45-65 | none | 15.6 | 10.0 |
| 3S-caranlactam-caprolactam co-polycaranamide (Incorporation 3S/CL = 1:1.1) | 50-100, particularly 50-70 | none | 17.3 | 12.1 |

A further characterization of the polyamides according to the invention can be found in the respective GPC curves for 3S-polycaranamide (FIG. 78), for 3R-polycaranamide (FIG. 79) and for 3R/3S-co-polycaranamide (FIG. 80).

TABLE 1b

Properties of a 3S-polycaranamide, a 3R-polycaranamide and a 3S-caranlactam-3R-caranlactam co-polycaranamide according to the present invention (according to methods (3) and (4.1)).

| Polymer | $T_g$ (range, °C.) | $T_m$ (range, °C.) | $M_w$ [g/mol] | $M_n$ [g/mol] |
|---|---|---|---|---|
| 3S-polycaranamide (semi-crystalline) | 110-120 | 260-290 | $6.5 \cdot 10^4$ | $1.4 \cdot 10^4$ |
| 3R-polycaranamide (amorphous) | 110-120 | none | $3.0 \cdot 10^5$ | $1.1 \cdot 10^5$ |
| 3S/3R-co-polycaranamide (R:S = 2:1) | 110-120 | none | $1.1 \cdot 10^5$ | $3.2 \cdot 10^4$ |

A further characterization of the polyamides according to the invention can be found in the respective GPC curves for 3S-polycaranamide (FIGS. 51-60), for 3R-polycaranamide (FIGS. 62-71) and for 3S/3R-co-polycaranamide (FIG. 72), for 3S-caranlactam-laurolactam co-polycaranamide (FIGS. 73-75) and for 3S-caranlactam-caranlactam co-polycaranamide (FIGS. 76-77).

In a preferred embodiment, the 3S-polycaranamide according to the invention (also referred to as 3S-polyamide) is characterized in that the 3S-polycaranamide has a glass transition point or glass transition range (Tg) from 100° C. to 130° C., in particular 105° C. to 125° C., in particular 110° C. to 120° C., a melting temperature or melting range (Tm) from 230 to 300° C., in particular 230 to 290° C., in particular 250° C. to 300° C., in particular 255° C. to 295° C., in particular 260° C. to 290° C., and, in a preferred embodiment, a number average molecular weight (Mn) of $5.5 \cdot 10^4$ g/mol to $7.5 \cdot 10^4$ g/mol, in particular $6.5 \cdot 10^4$ g/mol, and, in a preferred embodiment, a weight average molecular weight (Mw) of $0.4 \cdot 10^4$ g/mol to $2.4 \cdot 10^4$ g/mol, in particular $1.4 \cdot 10^4$ g/mol, (Mn and Mw measured according to method (4.1)).

The 3S-polycaranamide according to the invention (also referred to as 3S-polyamide) is preferably characterized in that the 3S-polycaranamide has a glass transition point or glass transition range (T_g) from 100° C. to 130° C., in particular 105° C. to 125° C., in particular 110° C. to 120° C., a melting temperature or melting range (Tm) from 230 to 300° C., in particular 230 to 290° C., in particular 250° C. to 300° C., in particular 255° C. to 295° C., in particular 260° C. to 290° C., and, in a preferred embodiment, a number average molecular weight (Mn) of 1.0 kDa to 100 kDa, in particular 5 to 50 kDa, in particular 5 to 25 kDa, in particular 10 kDa to 70 kDa, and, in a preferred embodiment, has a weight average (Mw) of the molecular weight of 1.0 kDa to 200 kDa, in particular 5 to 50 kDa, in particular 5 to 25 kDa, in particular 15 kDa to 110 kDa (Mn and Mw measured according to method (4.2)).

The 3S-polycaranamide according to the invention can preferably be prepared according to one of the processes of the present invention. Furthermore, in a preferred embodiment, the 3S-polycaranamide according to the invention—in a preferred embodiment after polymerization by anionic ring opening polymerization, in particular according to embodiment 7.1.1-7.1.11—has a polydispersity (PD) of 1.0 to 10, in particular 1.0 to 5, in particular 1.0 to 2.5, in particular 1.0 to 1.3.

The 3R-polycaranamide according to the invention is preferably characterized in that the 3R-polycaranamide has a glass transition point (Tg) of 100° C. to 130° C., in particular 105° C. to 125° C., in particular 110° C. to 120° C., and, in a preferred embodiment, a number average molecular weight (Mn) of $2.0 \cdot 10^5$ g/mol to $4.0 \cdot 10^5$ g/mol, in particular $3.0 \cdot 10^5$ g/mol, and, in a preferred embodiment, a weight average molecular weight (Mw) of $0.1 \cdot 10^5$ g/mol to $2.1 \cdot 10^5$ g/mol, in particular $1.1 \cdot 10^5$ g/mol, (Mn and Mw measured according to method (4.1)).

The 3R-polycaranamide according to the invention is preferably characterized in that the 3R-polycaranamide has a glass transition point (Tg) of 100° C. to 130° C., in particular 105° C. to 125° C., in particular 110° C. to 120° C., and, in a preferred embodiment, a number average molecular weight (Mn) of 1.0 kDa to 100 kDa, in particular 10 kDa to 70 kDa and, in a preferred embodiment, a weight average molecular weight (Mw) of 1.0 kDa to 200 kDa, in particular 15 kDa to 110 kDa (Mn and Mw measured according to method (4.2)).

The 3R-polycaranamide according to the invention can preferably be prepared according to one of the processes of the present invention. Furthermore, in a preferred embodiment, the 3R-polycaranamide according to the invention—in a preferred embodiment after polymerization by anionic ring opening polymerization, in particular according to embodiment 7.2.1-7.2.10—has a polydispersity (PD) of 1.0 to 10, in particular 1.0 to 5, in particular 1.0 to 2.5, in particular 1.0 to 1.3.

The 3S/3R-co-polyamide according to the invention, also referred to as 3S-caranlactam-3R-caranlactam co-polycaranamide, is preferably characterized in that the 3S/3R-polyamide has a glass transition point (Tg) of 100° C. to 130° C., in particular 105° C. to 125° C., in particular 110° C. to 120° C., has a melting range of 250° C. to 300° C., in particular 255° C. to 295° C., in particular 260° C. to 290° C., and, in a preferred embodiment, a number average molecular weight (Mn) of $2.2 \cdot 10^4$ g/mol to $4.2 \cdot 10^4$ g/mol, in particular $3.2 \cdot 10^4$ g/mol, and, in a preferred embodiment, a weight average molecular weight of $0.1 \cdot 10^5$ g/mol to $2.1 \cdot 10^5$ g/mol, in particular $1.1 \cdot 10^5$ g/mol, (Mn and Mw measured according to method (4.1)).

The 3S/3R-co-polyamide according to the invention, also referred to as 3S-caranlactam-3R-caranlactam co-polycaranamide, is preferably characterized in that the 3S/3R- polyamide has a glass transition point (Tg) of 100° C. to 130° C., in particular 105° C. to 125° C., in particular 110° C. to 120° C., has a melting range of 250° C. to 300° C., in particular 255° C. to 295° C., in particular 260° C. to 290° C., and, in a preferred embodiment, a number average molecular weight (Mn) of 1.0 kDa to 100 kDa, in particular 10 kDa to 70 kDa and, in a preferred embodiment, a weight average molecular weight (Mw) of 1.0 kDa to 200 kDa, in particular 15 kDa to 110 kDa (Mn and Mw measured according to method (4.2)).

The 3S-caranlactam-3R-caranlactam co-polycaranamide according to the invention can preferably be prepared according to one of the processes of the present invention. Furthermore, in a preferred embodiment, the 3S-caranlactam-3R-caranlactam co-polycaranamide according to the invention—in a preferred embodiment after polymerization by anionic ring opening polymerization, in particular according to embodiment 7.3.2—has a polydispersity (PD) of 1.0 to 10, in particular 1.0 to 5, in particular 1.0 to 2.5, in particular 1.0 to 1.3.

The 3S-caranlactam-laurolactam co-polycaranamide according to the invention is preferably characterized in that the glass transition point ($T_g$), for a ratio of 3S-caranlactam:laurolactam=1:1.4 in the 3S-caranlactam-laurolactam co-polycaranamide is 45° C. to 65° C., in particular 50° C. to 60° C., it has no melting point according to DSC method (3.2) and, in a preferred embodiment, it has a number average molecular weight (Mn) of 1.0 kDa to 100 kDa, in particular 10 kDa to 70 kDa and, in a preferred embodiment, has a weight average molecular weight from 1.0 kDa to 200 kDa, in particular 15 kDa to 110 kDa (Mn and Mw measured by method (4.2)), and preferably it can be produced according to one of the processes of the present invention.

The 3S-caranlactam-laurolactam co-polycaranamide according to the invention is preferably characterized in that the glass transition point ($T_g$) for a ratio of 3S-caranlactam:laurolactam=1:2 in the 3S-caranlactam-laurolactam co-polycaranamide is 35° C. to 55° C., in particular 40° C. to 50° C., it has no melting point according to DSC method (3.2) and, in a preferred embodiment, a number average molecular weight (Mn) from 1.0 kDa to 100 kDa, in particular 10 kDa to 70 kDa and, in a preferred embodiment, has a weight average molecular weight of 1.0 kDa to 200 kDa, in particular 15 kDa to 110 kDa (Mn and Mw measured according to method (4.2)), and preferably it can be produced according to one of the processes of the present invention.

Furthermore, in a preferred embodiment, a 3S-caranlactam-laurolactam co-polycaranamide according to the invention—in a preferred embodiment, after polymerization by anionic ring opening polymerization, in particular according to embodiment 8.1.1-8.1.3—has a polydispersity (PD) of 1.0 to 10, in particular 1.0 to 5, in particular 1.0 to 2.5, in particular 1.0 to 1.3.

The 3S-caranlactam-caprolactam co-polycaranamide according to the invention is preferably characterized in that the glass transition point ($T_g$) for a ratio of 3S-caranlactam:caprolactam=1:4.6 in the 3S-caranlactam-laurolactam co-polycaranamide is 50° C. to 100° C., in particular 50° C. to 75° C., in particular 50° C. to 70° C., in particular 58° C. to 68° C., it has a melting range of 140° C. to 220° C., in particular 155° C. to 200° C. and, in a preferred embodiment, it has a number average molecular weight (Mn) of 1.0 kDa to 100 kDa, in particular 10 kDa, according to DSC method (3.2) up to 70 kDa and, in a preferred embodiment, a weight average molecular weight of 1.0 kDa to 200 kDa, in particular 15 kDa to 110 kDa (Mn and Mw measured according to method (4.2)), and preferably it can be prepared according to one of the processes of the present invention.

The 3S-caranlactam-caprolactam co-polycaranamide according to the invention is preferably characterized in that the glass transition point ($T_g$) for a ratio of 3S-caranlactam:caprolactam=1:1.2 in the 3S-caranlactam-laurolactam co-polycaranamide is 70° C. to 100° C., in particular 80° C. to 93° C., it has no melting point according to DSC method (3.2) and, in a preferred embodiment, it has a number average molecular weight (Mn) of 1.0 kDa to 100 kDa, in particular 10 kDa to 70 kDa and, in a preferred embodiment, has a weight average molecular weight from 1.0 kDa to 200 kDa, in particular 15 kDa to 110 kDa (Mn and Mw measured by method (4.2)), and preferably it can be produced according to one of the processes of the present invention.

Furthermore, in a preferred embodiment, a 3S-caranlactam-capro co-polycaranamide according to the invention—in a preferred embodiment, after polymerization by anionic ring opening polymerization, in particular according to embodiment 8.1.1-8.1.3—has a polydispersity (PD) of 1.0 to 10, in particular 1.0 to 5, in particular 1.0 to 2.5, in particular 1.0 to 1.3.

By a suitable choice of the reaction conditions, it is possible, starting from one and the same starting compound, particularly preferably the natural product 3-carene, with high selectivity, to synthesize a first isomer of the lactam according to the invention, which due to its stereochemistry can be converted into a predominantly amorphous polyamide, and a second isomer of the lactam according to the invention, the polyamide of which is partially crystalline, both polyamides having glass transition points in the range from 100° C. to 130° C., in particular 110° C., wherein the 3S-caranlactam can be reacted to form a partially crystalline polyamide and the 3R-caranlactam can be reacted to form an amorphous polyamide. The approach according to the invention makes it possible to adjust the crystallinity of polyamides in a targeted manner and to provide isomer-enriched 3-caranlactam and polyamides based thereon having high optical purity.

With the polyamides according to the invention, the area of application of the polymer class of the polyamides, which is valuable due to its chemical stability, can be further increased. Analogously to PA66, mechanically and thermally stressed components such as coil formers, drilling machine housings, motor vehicle oil sumps, etc. can be realized; in addition, due to the higher temperature stability, applications over 100° C. are possible over the long term. The completely amorphous polyamide also offers applications in the area of transparent plastics. Combinations of the mentioned fields of application are also possible, whereby the field of use of the previously known bio-based polyamides can be significantly expanded in this regard by the polyamides according to the invention.

The invention accordingly provides polyamides which are in particular in the form of 3S-polycaranamide, 3R-polycaranamide, 3S/3R-co-polycaranamide or which are made up of at least one of the caranlactams according to the invention and at least one other lactam as a co-polycaranamide.

In the context of the present invention, polyamides according to the invention which contain monomers according to the invention can accordingly also be present as co-polycaranamides (abbreviated as: co-polyamides).

The invention therefore also relates to plastic parts which can be produced or are produced from polyamides according to the invention, in particular those which consist of or contain the polyamides according to the invention, in particular contain substantial proportions of the polyamides, for example in each case more than 5%, 10%, 15%, 20%, 30%, 40%, 50%, 60%, 70%, 80%, 90%, or 95% (based on the total weight of the plastic part).

It is preferably provided according to the invention that the 3-carane epoxide 3S-carane epoxide used in process step a) and the isomer-enriched mixture obtained in process step c) is a 3S-caranone-enriched mixture with an isomer ratio of at least 80%, in particular at least 85%, at least 90% or at least 95% of 3S-caranone (based on the total material quantity of caranone, i.e. 3R- and 3S-caranone).

It is further preferred that the 3-carane epoxide 3R-carane epoxide used in process step a) and the isomer-enriched mixture obtained in process step c) are a 3R-caranone-enriched mixture with an isomer ratio of at least 80%, in particular at least 85%, at least 90% or at least 95% of 3R-caranone (based on the total material quantity of caranone).

In a preferred embodiment, it is provided that the acid catalyst is a Lewis acid or a Brønsted acid or a mixture of the Lewis acid and Brønsted acid.

In a further preferred embodiment it is provided that the acid catalyst is a strong Brønsted acid or a Brønsted acid with a pKa of at most 0.7.

It is also preferably provided that the acid catalyst is a Brønsted acid with a pKa of at most 0.7, such as sulfonic acids, in particular para-toluenesulfonic acid (PTSA), methanesulfonic acid or trifluoromethanesulfonic acid.

Preferably the acid catalyst is a sulfonic acid.

Furthermore, it is preferably provided that the acid catalyst is a Lewis acid with an anion of a strong acid, in particular sulfonic acid, or an anion such as chlorate, trifluoromethanesulfonate(OTf) or perchlorate ($ClO_4^-$).

Furthermore, it is preferably provided that the acid catalyst is an iron Lewis acid, a nickel Lewis acid, a copper Lewis acid, a cobalt Lewis acid or a zinc Lewis acid, preferably an iron Lewis acid.

Furthermore, it is preferably provided that the acid catalyst is a Lewis acid with an anion of an—in particular, strong-acid or a—in particular, strong-Brønsted acid or a—in particular, strong-Brønsted acid with a pKa of at most 0.7.

Furthermore, it is preferably provided that anions of—in particular, strong-acids, such as sulfonic acids, are used as the anion of the Lewis acids or that an anion such as chlorate or perchlorate is used.

It is further preferably provided that the anion used for the Lewis acids, in particular for the iron, nickel, cobalt, copper or zinc Lewis acids, is chlorate and/or perchlorate and/or sulfonate.

Preferably used as the Lewis acid are $Fe(CO_4)_2 \cdot H_2O$, $Ni(ClO_4)_2$, $C(CO_4)_2$, $Cu(ClO_4)_2$ or their corresponding hydrates.

In a preferred embodiment, the acid catalyst is a Lewis acid, in particular an iron, copper, cobalt, nickel or zinc Lewis acid, preferably an iron Lewis acid, with an anion of an, in particular strong, acid, preferably a trifluoromethanesulfonate or perchlorate, or a strong Brønsted acid with a pKa of at most 0.7, such as sulfonic acids, in particular para-toluenesulfonic acid, methanesulfonic acid, trifluoromethanesulfonic acid, or a mixture of the aforementioned Lewis acids and Brønsted acids.

It is further preferably provided that the acid catalyst is a mixture of the aforementioned Lewis acids and Brønsted acids.

Furthermore, it is preferably provided that a zeolite, in particular ZSM-5, is used as the acid catalyst. This also has the advantage that the zeolite can be added to the reaction mixture as a separable solid and can thus be separated out by filtration.

Furthermore, it is preferably provided that an acidic heterogeneous catalyst is used as the acid catalyst in a gas phase rearrangement.

In a further preferred embodiment it is provided that the first organic solvent provided in a preferred embodiment is a non-polar solvent or a solvent with a relative polarity of at most 0.310, in particular at most 0.200, preferably at most 0.100.

In a further preferred embodiment it is provided that the first organic solvent is a, in particular non-polar, solvent such as aliphatic or aromatic hydrocarbons, preferably xylene, toluene, cyclohexane, pentane, hexane or heptane.

In a further preferred embodiment it is provided that the first organic solvent is 2-methyl-tetrahydrofuran, tetrahydrofuran, ethyl acetate, chloroform or dichloromethane.

In a further preferred embodiment it is provided that the first organic solvent is a solvent with a relative polarity of at most 0.310, in particular at most 0.200, preferably at most 0.100.

In the context of the present invention, the term "relative polarity" is understood to mean a polarity as described in the document "Solvents and Solvent Effects in Organic Chemistry," Christian Reichards, Wiley-VCH Publishers, 3rd ed., 2003. The relative polarities for cyclohexane, hexane, heptane and toluene can be found in the table from Embodiment 1.1. For further relative polarities of other solvents, reference is made to the Reichards document mentioned.

Furthermore, it is preferably provided that the 3-carane epoxide in the reaction mixture according to process steps a) and b) is used at a concentration of at least 0.1 M, preferably from 0.25M to 5 M, in particular 0.3 to 3 M, particularly preferably from 0.5M to 2 M, in particular from 0.75 to 1.5 M, in particular 1 M. This has the advantage that, at low concentrations, both the overall selectivity and the isomer selectivity can be positively influenced.

In a preferred embodiment, it is provided that the process has a selectivity, based on the total material quantity of a mixture of 3R-caranone and 3S-caranone, of at least 50%, in particular at least 70%, with at least 80% conversion of 3S-carane epoxide, and this mixture of 3R-caranone and 3S-caranone has at least 80%, preferably at least 85%, 3S-caranone.

Furthermore, it is preferably provided that the acid catalyst is used in the reaction mixture according to process steps a) and b) at a concentration of 0.01 mol % to 2.0 mol % with respect to the 3-carane epoxide used.

Furthermore, it is preferably provided that the acid catalyst in the reaction mixture according to process steps a) and b) is used at a concentration of 0.01 mol % to 2.0 mol %, in particular 0.05 mol % to 1.0 mol %, in particular from 0.1 mol % to 0.5 mol %, in particular from 0.15 mol % to 0.25 mol %, particularly preferably from 0.2 mol %, with respect to the 3-carane epoxide used.

The reaction time for process step b) is preferably 2 minutes to 25 hours, in particular 5 hours to 24 hours, in particular 5 hours to 20 hours, in particular 30 minutes to 1 hour, in particular 10 minutes to 40 minutes.

In a preferred embodiment, the invention relates to a process for the preparation of an isomer-enriched mixture of 3S-caranone and 3R-caranone from 3S-carane epoxide, comprising the following process steps:
 a) Providing a reaction mixture containing 3S-carane epoxide, at least one acid catalyst and a first organic solvent, the acid catalyst being a sulfonic acid or a Lewis acid selected from the group consisting of $Fe(ClO_4)_2 \cdot H2O$, $Ni(ClO_4)_2$, $Co(ClO_4)_2$, $Ni(ClO_4)_2$ or $Cu(ClO_4)_2$ or a mixture of the aforementioned acids, and wherein the first organic solvent is selected from the group consisting of toluene, cyclohexane, pentane, hexane, heptane, 2-methyl-tetrahydrofuran, tetrahydrofuran, ethyl acetate and dichloromethane, b) Reacting the 3S-carane epoxide in the reaction mixture at a temperature of −40° C. to 140° C., with rearrangement, and c) Obtaining the isomer-enriched mixture having an isomer ratio of at least 80% 3S-caranone (based on the total material quantity of caranone).

The invention also relates to an aforementioned process for producing an isomer-enriched mixture of 3S-caranone and 3R-caranone from 3S-carane epoxide, the acid catalyst being a sulfonic acid selected from the group consisting of para-toluenesulfonic acid (PTSA), methanesulfonic acid and trifluoromethanesulfonic acid.

In a particularly preferred embodiment, the 3-carane epoxide used in process step a) is obtained in a process step a1) by epoxidation of 3-carene.

In a further preferred embodiment it is provided that the starting compound used in process step a) is 3S-carane epoxide, and is obtained in a process step a1a) by epoxidation of 3-carene in the presence of a) a peroxide acid, for example dilute peracetic acid, or b) a peroxide, for example $H_2O_2$, and an enzyme.

In a preferred embodiment, the enzyme can be, for example, a lipase, for example lipase B, in particular from *Candida* spec., in particular from *Candida antarctica*.

In a further preferred embodiment, it is provided that the starting compound used in process step a) is 3R-carane epoxide, and is obtained in process step a1b) by epoxidation of 3-carene in the presence of N-bromosuccinimide (NBS), optionally additionally in the presence of a base.

In a particularly preferred embodiment, it is provided that the isomer-enriched mixture obtained in process step c) is purified, in particular is obtained in isolated form, in particular the acid catalyst and/or the first solvent are separated off, and/or the mixture is optionally further processed, for example by drying.

If, according to the invention, an at least 80% 3S-caranone-enriched mixture has been obtained from 3S-carane epoxide, this can, if desired, be converted into a 3R-caranone-enriched mixture, in order to be able to produce 3R-caranlactam, preferably 3R-polycaranamide, in the further process steps according to the invention. In a preferred embodiment, it is provided that the 3S-caranone-enriched mixture preferably obtained in process step c) from 3S-carane epoxide is isomerized in at least one second solvent in the presence of a base or a Brønsted acid in a process step d) to produce a 3R-caranone-enriched mixture having an isomer content of at least 50%, in particular at least 60%, in particular at least 70%, in particular at least 80%, in particular at least 85%, in particular at least 90% or in particular at least 95% 3R-caranone (based on the total material quantity of caranone).

It is preferably provided that the base is potassium hydroxide, sodium hydroxide, or another strong base.

It is further preferably provided that the base is an alcoholate, in particular a methanolate.

It is preferably provided that the Brønsted acid is a Brønsted acid with a pKa of at most 0.7.

It is further preferably provided that the Brønsted acid is a strong Brønsted acid. The Brønsted acid is preferably aqueous hydrogen chloride, also referred to as aqueous HCl or hydrochloric acid, or sulfuric acid.

The Brønsted acid is preferably a sulfonic acid.

Furthermore, it is preferably provided that the second solvent is an aprotic polar solvent with a relative polarity of at least 0.200 or a protic polar solvent with a relative polarity of at least 0.200.

Furthermore, it is preferably provided that the aprotic polar solvent with a relative polarity of at least 0.200 is a solvent such as tetrahydrofuran, ethyl acetate, chloroform, dichloromethane, acetone or acetonitrile, in particular acetone or acetonitrile.

It is further preferably provided that the protic polar solvent with a relative polarity of at least 0.200 is a solvent such as water, alcohol, amine, carboxylic acid or amide.

Furthermore, it is preferably provided that the protic polar solvent with a relative polarity of at least 0.200 is an alcohol such as methanol, ethanol, propanol or butanol.

The reaction time for process step d) is preferably 2 to 80 hours, in particular 5 to 68 hours, preferably 4 to 12 hours, in particular 4 to 10 hours.

In a preferred embodiment, it is provided that the 3S-caranone-enriched mixture preferably obtained in process step c) from 3S-carane epoxide is isomerized in at least one second solvent in the presence of a, in particular strong, base or a, in particular strong, Brønsted acid with a pKa of at most 0.7 in a process step d) to produce a 3R-caranone-enriched mixture with an isomer fraction of at least 50%, in particular at least 60%, in particular at least 70%, in particular at least 80%, in particular at least 85%, in particular at least 90% or in particular at least 95% 3R-caranone (based on the total material quantity of caranone), the second solvent being an aprotic polar solvent with a relative polarity of at least 0.200 or a protic polar solvent with a relative polarity of at least 0.200.

In a particularly preferred embodiment it is provided that the 3S-caranone-enriched mixture preferably obtained in process step c) from 3S-carane epoxide is isomerized in at least one second solvent in the presence of a, in particular strong, base or a, in particular strong, Brønsted acid with a pKa of at most 0.7, preferably a sulfonic acid solution or a hydrochloric acid solution, preferably a 6% hydrochloric acid solution, in a process step d) to produce a 3R-caranone-enriched mixture with an isomer fraction of at least 50%, in particular at least 60%, in particular at least 70%, in particular at least 80%, in particular at least 85%, in particular at least 90% or in particular at least 95% 3R-caranone (based on the total material quantity of caranone), the second solvent being an aprotic polar solvent with a relative polarity of at least 0.200, selected from the group consisting of tetrahydrofuran, ethyl acetate, chloroform, dichloromethane, acetone and acetonitrile, or a protic polar solvent with a relative polarity of at least 0.200, selected from the group consisting of water, alcohol, in particular methanol, ethanol, propanol, butanol, amine, carboxylic acid and amide.

These embodiments have the advantage that the 3R-caranone can be obtained without a significant proportion of by-product—i.e., with great overall selectivity. Furthermore, if a sulfonic acid is used as the acid catalyst in process step a), it is advantageous that for a rearrangement to 3R-caranone in process step d) this sulfonic acid can be used as a catalyst after the solvent has been separated off.

According to the invention, it is particularly preferred in a process for the preparation of an isomer-enriched mixture of 3R-caranone and 3S-caranone that an acid, in particular a sulfonic acid or a Lewis acid, is used as the acid catalyst in process step a). This embodiment has the advantage that after the solvent has been separated off by distillation, no further acid has to be added for the catalysis of the rearrangement to the 3R-caranone.

In a further preferred embodiment it is provided that the isomer-enriched mixture obtained in process step d) and subjected to the isomerization process is purified, in particular is obtained in isolated form, in particular the second solvent and/or the acid or base are separated off and/or the mixture is optionally subjected to further process steps, for example drying.

In a further embodiment, it is provided that the isomer-enriched mixture of 3S- and 3R-caranone obtained in process step c) or d) is reacted in a further process step e) in the presence of at least one third organic solvent, a base and a hydroxylamine, preferably hydroxylamine hydrochloride (HONH$_2$·HCl) to produce a 3-caranoxime-enriched mixture with an isomer ratio of at least 80%, in particular at least 85%, at least 90% or at least 95% 3S- or 3R-caranoxime (based on the total material quantity of caranoxime, i.e. 3R- and 3S-caranoxime).

If a 3R-caranone-enriched mixture is used in process step e) starting from process step c) or d), a 3R-caranoxime-enriched mixture is obtained. If a 3S-caranone-enriched mixture obtained according to process step c) is used in process step e), a 3S-caranone oxime-enriched mixture is obtained.

It is preferably provided that the third organic solvent is an organic solvent such as an ether, nitrile, alcohol, or an aqueous-organic solvent comprising water and one of the aforementioned third organic solvents.

Furthermore, it is preferably provided that the ether is tetrahydrofuran or 2-methyl-tetrahydrofuran.

It is further preferably provided that the nitrile is acetonitrile.

Furthermore, it is preferably provided that the alcohol is methanol, ethanol or isopropanol.

In a preferred embodiment, the base is sodium acetate (NaOAc).

In a preferred embodiment, it is provided that the isomer-enriched mixture of 3S- and 3R-caranone obtained in process step c) or d) is reacted in a further process step e) in the presence of at least one third organic solvent selected from the group consisting of ether, in particular tetrahydrofuran, 2-methyl-tetrahydrofuran, nitrile, in particular acetonitrile, alcohol, in particular methanol, ethanol and isopropanol, or an aqueous-organic solvent, comprising water and one of the aforementioned third organic solvents, a base and a hydroxylamine, preferably hydroxylamine hydrochloride (HONH$_2$·HCl), to produce a 3-caranoxime-enriched mixture with an isomer ratio of at least 80%, in particular at least 85%, at least 90% or at least 95% 3S or 3R-caranoxime (based on the total material quantity of caranoxime).

The 3-caranoxime-enriched mixture obtained from this process offers the advantage that a large proportion of the desired isomer is present in the mixture, so that, starting from the starting material, a predominant fraction of the starting material can be preserved in the desired product, that is to say in the desired intermediate for the desired monomer, in high yields.

In a particularly preferred embodiment it is provided that the 3-caranoxime-enriched mixture obtained in process step e) is purified, in particular obtained in isolated form, in particular the third solvent and/or the base and/or hydroxylamine are separated off, and/or the mixture is optionally subjected to further process steps, for example drying.

In a further embodiment it is provided that the 3-caranoxime-enriched mixture obtained in process step e), preferably without prior purification, in a further process step f) is reacted with rearrangement, to produce a 3-caranlactam-enriched mixture with an isomer ratio of at least 80% 3S- or 3R-caranlactam (based on the total material quantity of caranlactam—i.e., 3R- and 3S-caranlactam).

Proceeding from process step e), if a 3S-caranoxime-enriched mixture is used in process step f), a 3S-caranlactam-enriched mixture, in particular 3S-caranlactam, is obtained. If a 3R-caranoxime-enriched mixture obtained according to process step e) is used in process step f), a 3R-caranlactam-enriched mixture, in particular 3R-caranlactam, is obtained.

In a preferred embodiment, it is provided that the 3-caranoxime-enriched mixture obtained in process step e) is brought to a predetermined temperature in a further process step f1) and is reacted, with the addition of a base and para-toluenesulfonic acid chloride, with rearrangement, to produce a 3-caranlactam-enriched mixture with an isomer ratio of at least 80%, in particular at least 85%, at least 90% or at least 95% 3S- or 3R-caranlactam (based on the total material quantity of caranlactam).

It is also preferably provided that the temperature specified in process step f1) is 0° C. to 50° C., preferably 10 to 40° C., preferably 5° C. to 20° C., in particular 10° C. to 18° C.

Furthermore, it is preferably provided that the base is an aqueous base.

It is further preferred that the base is a potassium hydroxide or sodium hydroxide solution.

It is also preferably provided that the rearrangement is a Beckmann rearrangement.

In a preferred embodiment, it is provided that the 3-caranoxime-enriched mixture obtained in process step e) is brought in a further process step f) to a temperature of −10° C. to 50° C., in particular 5° C. to 20° C., in particular from 10° C. to 18° C., and is reacted, with the addition of a base, in particular an aqueous base, preferably a potassium hydroxide or sodium hydroxide solution, and para-toluenesulfonic acid chloride, with Beckmann rearrangement, to produce a 3-caranlactam-enriched mixture with an isomer ratio of at least 80%, in particular at least 85%, at least 90% or at least 95% 3S- or 3R-caranlactam (based on the total material quantity of caranlactam).

This has the advantage that the conversion of the 3-caranone via the 3-caranoxime to the 3-caranlactam can take place without intermediate purification steps or solvent changes, except in the case of alcohols as solvents, in a one-pot process of process steps e) and f), for example using acetonitrile as solvent, hydroxylamine hydrochloride, NaOH and tosyl chloride, so that this process is particularly fast, efficient and economical. Yields are obtained in this case which are comparable to those obtained with a process in which process steps are carried out one after the other with solvent changes.

It is further preferably provided that the 3-caranoxime-enriched mixture obtained in process step e) is brought to a predetermined temperature in a further process step f2) and is reacted, with the addition of a, in particular strong, Lewis acid, with rearrangement, to produce a 3-caranlactam-enriched mixture with an isomer ratio of at least 80%, in particular at least 85%, at least 90% or at least 95% 3S- or 3R-caranlactam (based on the total material quantity of caranlactam).

Furthermore, it is preferably provided that the temperature specified in process step f2) is 15° C. to 100° C., preferably 77° C. to 87° C., particularly preferably 82° C.

It is further preferably provided that the mixture is brought to the boiling temperature of a solvent, the solvent being the solvent in which the 3-caranoxime-enriched mixture obtained in process step e) is dissolved or is present.

It is preferably provided that a solvent in which the 3-caranoxime-enriched mixture obtained in process step e) is dissolved or is present is acetonitrile.

Furthermore, it is preferably provided that the Lewis acid is a strong Lewis acid.

It is also preferably provided that the Lewis acid is $In(ClO_4)_3 \cdot nH_2O$ (indium perchlorate n-hydrate) and/or $Zn(ClO_4)_2 \cdot nH_2O$ (zinc perchlorate n-hydrate).

Furthermore, it is preferably provided that the Lewis acid is $In(CF_3SO_3)_3$ (indium trifluoromethanesulfonate) and/or $Zn(CF_3SO_3)_2$ (zinc trifluoromethanesulfonate).

It is also preferably provided that the rearrangement is a Beckmann rearrangement.

It is preferably provided that the 3-caranoxime-enriched mixture obtained in process step e) is heated in a further process step f2) to a temperature of 77° C. to 87° C., in particular 82° C., and is reacted, with the addition of a, in particular strong, Lewis acid, such as $In(ClO_4)_3 \cdot nH_2O$ and/or $Zn(ClO_4)_2 \cdot nH_2O$, with rearrangement, to produce to produce a 3-caranlactam-enriched mixture with an isomer ratio of at least 80%, in particular at least 85%, at least 90% or at least 95% 3S- or 3R-caranlactam (based on the total material quantity of caranlactam), wherein preferably the 3-caranoxime-enriched mixture obtained from process step e) is dissolved or is present in acetonitrile.

In a particularly preferred embodiment, it is provided that the 3-caranlactam-enriched mixture obtained in process step f) is further purified, in particular obtained in isolated form, in particular the base and/or para-toluenesulfonic acid chloride are removed, and/or the mixture is optionally subjected to further process steps, for example drying.

In a preferred embodiment, it is provided that from the 3S-caranlactam-enriched mixture obtained in process step f), preferably without upstream purification, 3S-caranlactam is obtained in a process step g) by crystallization, for example by distillation, in particular fractional distillation.

Furthermore, it is preferably provided that 3R-caranlactam is obtained from the 3-caranlactam-enriched mixture obtained in process step f) after separation of 3S-caranlactam, in particular according to process step g), preferably by crystallization, for example by distillation, especially fractional distillation.

In a preferred embodiment of the present invention it is provided that in a process step i) the obtained 3S-caranlactam, 3R-caranlactam, or a mixture of 3R- and 3S-caranlactam are polymerized to form 3S-polycaranamide, 3R-polycaranamide, or 3S/3R-co-polycaranamide, preferably by anionic ring opening polymerization, cationic ring opening polymerization, hydrolytic polymerization or polycondensation.

According to the invention, the present invention also relates to a process for the preparation of a 3-caranoxime-enriched mixture, comprising process steps a), b), c) according to the invention, in a preferred embodiment including process steps a1), d) or a1) and d), wherein the isomer-enriched mixture of 3S- and 3R-caranone obtained in process step c) or d) is reacted in a further process step e) in the presence of at least a third organic solvent, a base and a hydroxylamine, preferably hydroxylamine hydrochloride ($HONH_2 \cdot HCl$) to produce a 3-caranoxime-enriched mixture with an isomer ratio of at least 80%, in particular at least 85%, at least 90% or at least 95% 3S- or 3R-caranoxime (based on the total material quantity of caranoxime).

It is further preferably provided that the third organic solvent is an organic solvent such as an ether, nitrile, alcohol, or an aqueous-organic solvent, comprising water and one of the aforementioned third organic solvents.

Furthermore, it is preferably provided that the ether is tetrahydrofuran or 2-methyl-tetrahydrofuran.

It is further preferably provided that the nitrile is acetonitrile.

Furthermore, it is preferably provided that the alcohol is methanol, ethanol or isopropanol.

In a preferred embodiment, the base is sodium acetate (NaOAc).

According to the invention, the present invention also relates to a process for the preparation of a 3-caranoxime-enriched mixture, comprising process steps a), b), c) according to the invention, in a preferred embodiment including process steps a1), d) or a1) and d), wherein the isomer-enriched mixture of 3S- and 3R-caranone obtained in process step c) or d) is reacted in a further process step e) in the presence of at least one third organic solvent selected from the group consisting of ether, in particular tetrahydrofuran, 2-methyl-tetrahydrofuran, nitrile, in particular acetonitrile, alcohol, in particular methanol, ethanol and isopropanol, or an aqueous-organic solvent, comprising water and one of the aforementioned third organic solvents, a base, and a hydroxylamine, preferably hydroxylamine hydrochloride ($HONH_2 \cdot HCl$) to produce a 3-caranoxime-enriched mixture with an isomer ratio of at least 80%, in particular at least 85%, at least 90% or at least 95% 3S- or 3R-caranoxime (based on the total material quantity of caranoxime).

According to the invention, the present invention also relates to a process for the preparation of a 3-caranlactam-enriched mixture, comprising process steps a), b), c), e) according to the invention, and in a preferred embodiment including process steps a1), d) or a1) and d), wherein the 3-caranoxime-enriched mixture obtained in process step e) is reacted in a further process step f), with rearrangement, to produce a 3-caranlactam-enriched mixture with an isomer ratio of at least 80% 3S- or 3R-caranlactam (based on the total material quantity of caranlactam).

Furthermore, it is preferably provided that in the process for producing a 3-caranlactam-enriched mixture, the 3-caranoxime-enriched mixture obtained in process step e) is brought to a predetermined temperature in a further process step f1) and reacted, with the addition of a base and para-toluenesulfonic acid chloride, with rearrangement, to produce a 3-caranlactam-enriched mixture with an isomer ratio of at least 80%, in particular at least 85%, at least 90% or at least 95% 3S- or 3R-caranlactam (based on the total material quantity of caranlactam).

Furthermore, it is preferably provided that the temperature specified in process step f1) is 5° C. to 20° C., in particular 10° C. to 18° C.

Furthermore, it is preferably provided that the base is an aqueous base.

Furthermore, it is preferably provided that the aqueous base is a potassium hydroxide or sodium hydroxide solution.

It is also preferably provided that the rearrangement is a Beckmann rearrangement.

Furthermore, it is preferably provided that in the process for producing a 3-caranlactam-enriched mixture, the 3-caranoxime-enriched mixture obtained in process step e) is brought in a further process step f1) to a temperature of 5° to 20° C., in particular 10° to 18° C., and is reacted, with the addition of a, in particular aqueous, base, in particular potassium hydroxide or sodium hydroxide solution, and para-toluenesulfonic acid chloride, with rearrangement, in particular Beckmann rearrangement, to produce a 3-caranlactam-enriched mixture with an isomer ratio of at least 80%, in particular at least 85%, at least 90% or at least 95% 3S- or 3R-caranlactam (based on the total material quantity of caranlactam).

Furthermore, it is preferably provided that in the process for producing a 3-caranlactam-enriched mixture, the 3-caranoxime-enriched mixture obtained in process step e) is brought to a predetermined temperature in a further process step f2) and is reacted, with the addition of a, in particular strong, Lewis acid, with rearrangement, to produce a 3-caranlactam-enriched mixture with an isomer ratio of at least 80%, in particular at least 85%, at least 90% or at least 95% 3S- or 3R-caranlactam (based on the total material quantity of caranlactam).

Furthermore, it is preferably provided that the temperature specified in process step f2) is 15° C. to 100° C., preferably 77° C. to 87° C., particularly preferably 82° C.

It is further preferably provided that the mixture is brought to the boiling temperature of a solvent, the solvent being the solvent in which the 3-caranoxime-enriched mixture obtained in process step e) is dissolved or is present.

It is preferably provided that a solvent in which the 3-caranoxime-enriched mixture obtained in process step e) is dissolved or is present is acetonitrile.

Furthermore, it is preferably provided that the Lewis acid is a strong Lewis acid.

It is also preferably provided that the Lewis acid is $In(ClO_4)_3 \cdot nH_2O$ and/or $Zn(ClO_4)_2 \cdot n$ is $H_2O$.

It is furthermore preferably provided that the Lewis acid is $In(CF_3SO_3)_3$ and/or $Zn(CF_3SO_3)_2$ It is also preferably provided that the rearrangement is a Beckmann rearrangement.

Furthermore, it is preferably provided that in the process for producing a 3-caranlactam-enriched mixture, the 3-caranoxime-enriched mixture obtained in process step e) is brought in a further process step f2) to a temperature of 77° C. to 87° C., in particular 82° C., and is reacted, with the addition of a, especially strong, Lewis acid, such as $In(ClO_4)_3 \cdot nH_2O$ and/or a $Zn(ClO_4)_2 \cdot nH_2O$, with rearrangement, to produce a 3-caranlactam-enriched mixture with an isomer ratio of at least 80%, in particular at least 85%, at least 90% or at least 95% 3S- or 3R-caranlactam (based on the total material quantity of caranlactam), wherein preferably the 3-caranoxime-enriched mixture obtained from process step e) is dissolved or is present in acetonitrile.

According to the invention, the present invention also relates to a process for the preparation of 3S-caranlactam from 3S-caranone, wherein the process comprises process steps e) and f), and wherein in process step e) an isomer-enriched mixture, preferably obtained by process step c), of 3S- and 3R-caranone with an isomer ratio of at least 80%, in particular at least 85%, at least 90% or at least 95% 3S-caranone (based on the total material quantity of caranone) is used and is reacted to produce a 3S-caranoxime-enriched mixture with an isomer ratio of at least 80%, in particular at least 85%, at least 90% or at least 95% 3S-caranoxime (based on the total material quantity of caranoxime), and is reacted in process step f) without removal of the solvent from process step e) and without isolation of the caranoxime to produce a 3S-caranlactam enriched mixture with an isomer ratio of at least 80%, in particular at least 85%, at least 90% or at least 95% 3S-caranlactam (based on the total material quantity of caranlactam), and optionally 3S-caranlactam is obtained in process step g) by crystallization, no alcohol being used as the third organic solvent in process step e).

According to the invention, the present invention also relates to a process for the preparation of 3R-caranlactam from 3R-caranone, wherein the process comprises process steps e) and f) and wherein in process step e) an isomer-enriched mixture, preferably obtained by process step d), of 3S- and 3R-caranone with an isomer ratio of at least 50%, in particular at least 60%, in particular at least 70%, in particular at least 80%, in particular at least 85%, in particular at least 90% or in particular at least 95% 3R-caranone (based on the total material quantity of caranone used) is used, and is reacted to produce a 3R-caranoxime-enriched mixture with an isomer ratio of at least 50%, in particular at least 60%, in particular at least 70%, in particular at least 80%, in particular at least 85%, in particular at least 90% or in particular at least 95% 3R-caranoxime (based on the total material quantity of caranoxime), and is reacted in process step f) without removing the solvent from process step e) and without isolation of the caranoxime to produce a 3R-caranlactam-enriched mixture with an isomer ratio of at least 50%, in particular at least 60%, in particular at least 70%, in particular at least 80%, in particular at least 85%, in particular at least 90% or in particular at least 95% 3R-caranlactam (based on the total material quantity of caranlactam), and optionally 3R-caranlactam is obtained in process step h) after separation of 3S-caranlactam by crystallization in process step f), wherein in process step e) no alcohol is used as the third organic solvent.

According to the invention, the present invention also relates to a process for the preparation of 3S-polycaranamide, 3R-polycaranamide or 3S/3R-co-polycaranamide and the polyamides prepared therewith, wherein, in particular the 3S-caranlactam, 3R-caranlactam obtained according to the invention or a mixture of 3S- and 3R-caranlactam is polymerized to 3S-polycaranamide, 3R-polycaranamide or 3S/3R co-polycaranamide in a process step i), preferably by anionic ring opening polymerization, cationic ring opening polymerization, hydrolytic polymerization or polycondensation.

According to the invention, the present invention also relates to a process for the preparation of 3S-polycaranamide and the polyamides produced therewith, wherein in particular the 3S-caranlactam obtained according to the invention is polymerized to 3S-polycaranamide in a process step i), preferably by anionic ring-opening polymerization, cationic ring-opening polymerization, hydrolytic polymerization or polycondensation.

Accordingly, the present invention also relates to a 3S-polycaranamide.

According to the invention, the present invention also relates to a process for the preparation of 3R-polycaranamide and the polyamides produced therewith, wherein in particular the 3R-caranlactam obtained according to the invention is polymerized to 3R-polycaranamide in a process step i), preferably by anionic ring-opening polymerization, cationic ring-opening polymerization, hydrolytic polymerization or polycondensation.

Accordingly, the present invention also relates to a 3R-polycaranamide.

According to the invention, the present invention also relates to a process for the preparation of 3S/3R-co-polycaranamide and the polyamides produced therewith, wherein a mixture of 3S- and 3R-caranlactam, in particular a mixture of the 3S- and 3R-caranlactams obtained according to the invention, is polymerized to 3S/3R-co-polycaranamide in a process step i), preferably by anionic ring opening polymerization, cationic ring opening polymerization, hydrolytic polymerization or polycondensation.

Accordingly, the present invention also relates to a 3S/3R co-polycaranamide.

According to the invention, the present invention also relates to a process for the preparation of co-polyamides and the co-polyamides produced therewith, wherein the 3S-caranlactam or 3R-caranlactam obtained according to the invention or a mixture of 3S- and 3R-caranlactam is polymerized with a monomer such as laurolactam or caprolactam to a co-polyamide in process step i2), preferably by anionic ring opening polymerization, cationic ring opening polymerization, hydrolytic polymerization or polycondensation—in particular to 3S-caranlactam-laurolactam co-polycaranamide (3S-caranlactam-laurolactam co-polyamide), 3R-caranlactam-laurolactam co-polycaranamide (3R-caranlactam-laurolactam co-polyamide), 3S-caranlactam-3R-caranlactam-laurolactam co-polycaranamide (3S-caranlactam-3R-caranlactam-laurolactam co-polyamide), 3S-caranlactam-caprolactam co-polycaranamide (3S-caranlactam-caprolactam co-polyamide), 3R-caranlactam-caprolactam co-polycaranamide (3R-caranlactam-caprolactam co-polyamide) or 3S-caranlactam-3R-caranlactam-caprolactam co-polycaranamide (3S-caranlactam-3R-caranlactam-caprolactam co-polyamide).

According to the invention, the present invention also relates to a process for the preparation of polymers, in particular polyamides, which contain, completely or as a copolymer or as part of a mixture of different polymers or monomers, the 3-caranlactams according to the invention, in particular 3S-polycaranamide and/or 3R-polycaranamide, in particular 3S-polycaranamide, or their opened amino acids, amino acid esters or amino acid derivatives.

According to the invention, the present invention also relates to a process for the preparation of 3S-caranlactam from 3-carene, wherein the process comprises the process steps a) to c), e), f) and g), in particular a1) to c), e), f) and g) and wherein in process step a) a 3S-carane epoxide, preferably obtained by epoxidation of 3-carene, is used, and in process step c) a 3S-caranone-enriched mixture is obtained with an isomer ratio of at least 80%, in particular at least 85%, at least 90% or at least 95% 3S-caranone (based on the total material quantity of caranone), is reacted in process step e) to produce a 3S-caranoxime-enriched mixture with an isomer ratio of at least 80%, in particular at least 85%, at least 90% or at least 95% 3S-caranoxime (based on the total material quantity of caranoxime), which is reacted in process step f) to produce a 3S-caranlactam mixture with an isomer ratio of at least 80%, in particular at least 85%, at least 90% or at least 95% 3S-caranlactam (based on the total material quantity of caranlactam), and 3S-caranlactam is obtained in process step g) by crystallization.

In a preferred embodiment, in a process step ia), 3S-polycaranamide can then be obtained from 3S-caranlactam by polymerization, preferably by anionic ring-opening polymerization, cationic ring-opening polymerization, hydrolytic polymerization or polycondensation.

According to the invention, the present invention also relates to a process for the preparation of 3R-caranlactam from 3-carene, wherein the process comprises process steps a) to c), e), f) and g), in particular a1) to c), e), f) and g), and wherein in process step a) a 3R-carane epoxide is used, the same preferably obtained by epoxidation of 3-carene, in process step c) a 3R-caranone-enriched mixture with an isomer ratio of at least 80%, in particular at least 85%, at least 90% or at least 95% 3R-caranone (based on the total material quantity of caranone) is obtained, and in process step e) is reacted to a 3R-caranoxime-enriched mixture with an isomer ratio of at least 80%, in particular at least 85%, at least 90% or at least 95% 3R-caranoxime (based on the total material quantity of caranoxime), which is reacted in process step f) to a 3R-caranlactam mixture with an isomer ratio of at least 80%, in particular at least 85%, at least 90% or at least 95% 3R-caranlactam (based on the total material quantity of caranlactam), and 3R-caranlactam is obtained after separation of 3S-caranlactam in process step h).

In a preferred embodiment, 3R-polycaranamide can subsequently be obtained, in a process step ib), from 3R-caranlactam by polymerization, preferably by anionic ring-opening polymerization, cationic ring-opening polymerization, hydrolytic polymerization or polycondensation.

According to the invention, the present invention also relates to a process for the preparation of 3R-caranlactam from 3-carene, wherein the process comprises process steps a) to h), preferably a1) to h) and wherein in process step a) a 3S-carane epoxide is used, the same preferably obtained by epoxidation of 3-carene, in process step c) a 3S-caranone-enriched mixture with an isomer ratio of at least 80%, in particular at least 85%, at least 90% or at least 95% 3S-caranone (based on the total material quantity of caranone) is obtained, this is isomerized in process step d) to a 3R-caranone-enriched mixture with an isomer content of at least 50%, in particular at least 60%, in particular at least 70%, in particular at least 80%, in particular at least 85%, in particular at least 90% or in particular at least 95% 3R-caranone (based on the total material quantity of caranone), is reacted in process step e) to produce a 3R-caranoxime-enriched mixture with an isomer ratio of at least 50%, in particular at least 60%, in particular at least 70%, in particular at least 80%, in particular at least 85%, in particular at least 90% or in particular at least 95% 3R-caranoxime (based on the total material quantity of caranoxime), which is reacted in process step f) to produce a 3R-caranlactam-enriched mixture with an isomer ratio of at least 50%, in particular at least 60%, in particular at least 70%, in particular at least 80%, in particular at least 85%, in particular at least 90% or in particular at least 95% 3R-caranlactam (based on the total material quantity of caranlactam), and after separation of 3S-caranlactam in process step h), 3R-caranlactam is obtained.

In a preferred embodiment, 3R-caranlactam can subsequently be obtained in a process step ib) from 3R-caranlactam by polymerization, preferably by anionic ring-opening polymerization, cationic ring-opening polymerization, hydrolytic polymerization or polycondensation.

According to the invention, the present invention also relates to a 3S-caranone, in particular which is prepared or can be prepared by one of the processes according to the invention, according to the formula:

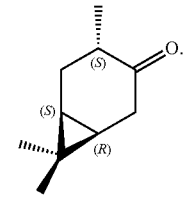

3-3S

According to the invention, the present invention also relates to a 3S-caranoxime, in particular which is prepared or can be prepared by one of the processes according to the invention, according to the formula:

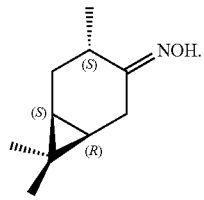

4-3S

According to the invention, the present invention also relates to a 3S-caranlactam, in particular which is prepared or can be prepared by one of the processes according to the invention, according to the formula:

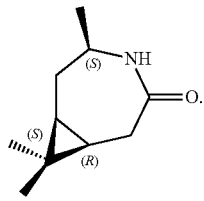

5-3S

In the context of the present invention, the number n is understood to be a natural number, in particular a natural number greater than or equal to 2, preferably a natural number from 2 to 1,000,000, in particular a natural number from 10 to 10,000, particularly preferably a natural number of 75 to 2000, especially from 100 to 1000.

In the context of the present invention, the numbers a, b and c, in particular a and b, are each a natural number, in particular a natural number greater than or equal to 1, preferably a natural number from 1 to 1000, in particular a natural number of 10 to 50.

In the context of the present invention, the number a is understood to be a natural number, in particular a natural number greater than or equal to 1, preferably a natural number from 1 to 1000, particularly preferably a natural number from 10 to 50.

In the context of the present invention, the number b is understood to be a natural number, in particular a natural number greater than or equal to 1, preferably a natural number from 1 to 1000, particularly preferably a natural number from 10 to 50.

In the context of the present invention, the number c is understood to be a natural number, in particular a natural number greater than or equal to 1, preferably a natural number from 1 to 1000, particularly preferably a natural number from 10 to 50.

In the context of the present invention, the natural numbers a and b preferably have a ratio of from 1:100 to 100:1, preferably 1:10 to 10:1, particularly preferably 1:6 to 6:1.

In the context of the present invention, the natural numbers a and c preferably have a ratio of from 1:100 to 100:1, preferably 1:10 to 10:1, particularly preferably 1:6 to 6:1.

In the context of the present invention, the natural numbers b and c preferably have a ratio of from 1:100 to 100:1, preferably 1:10 to 10:1, particularly preferably 1:6 to 6:1.

In a preferred embodiment, the natural numbers n, a, b and c, in particular a, b and c, in particular a and b, can be identical or different from one another. In a preferred embodiment of the present invention, the natural numbers, n, a, b and c are independent of one another.

According to the invention, the present invention also relates to a 3S-polycaranamide, in particular which is prepared or can be prepared by one of the processes according to the invention, according to the formula (with n repeat units):

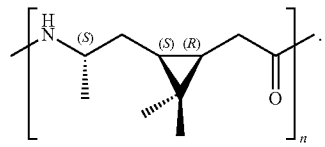

In a preferred embodiment, it is provided that the 3S-polycaranamide according to the invention consists solely of 3S-polycaranamide repeat units according to the following repeat unit:

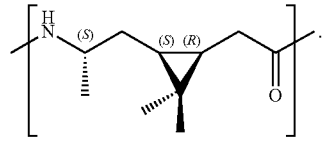

It is further preferably provided that the 3S-polycaranamide according to the invention comprises at least 80%, in particular at least 85%, in particular at least 90%, in particular at least 95%, in particular at least 98%, in particular at least 99%, in particular at least 99.5%, in particular at least 99, 9%, in particular 100% (based on the total number n of repeat units) 3S-polycaranamide repeat units according to the following repeat unit:

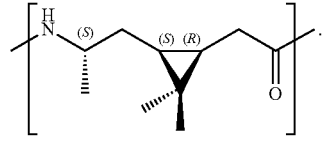

According to the invention, the present invention also relates to a 3R-polycaranamide, in particular which is prepared or can be prepared by one of the processes according to the invention, according to the formula (with n repeat units):

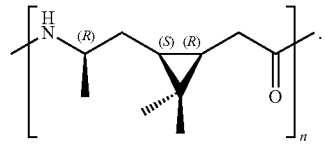

In a preferred embodiment, it is provided that the 3R-polycaranamide according to the invention consists solely of 3R-polycaranamide repeat units according to the following repeat unit:

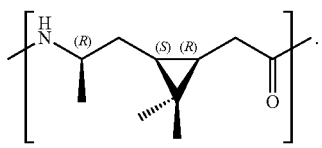

It is further preferably provided that the 3R-polycaranamide according to the invention comprises at least 80%, in particular at least 85%, in particular at least 90%, in particular at least 95%, in particular at least 98%, in particular at least 99%, in particular at least 99.5%, in particular at least 99.9%, in particular 100% (based on the total number n of repeat units) 3R-polycaranamide repeat units according to the following repeat unit:

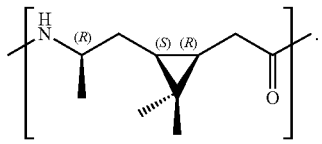

According to the invention, the present invention also relates to a co-polycaranamide which is prepared or can be prepared by a process according to the invention, in particular from 3S-caranlactam, 3R-caranlactam or a mixture of 3S-caranlactam and 3R-caranlactam, containing at least one repeat unit of the following formula

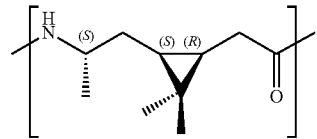

and at least one repeat unit of the following formula

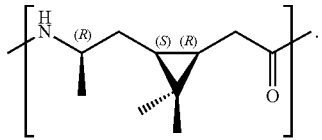

According to the invention, the present invention also relates to a 3S/3R-co-polycaranamide, in particular which is prepared or can be prepared by one of the processes according to the invention, according to the formula (with a, b and n repeat units):

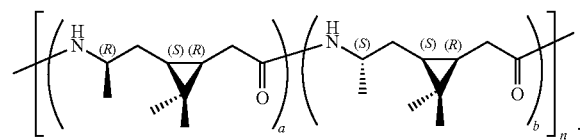

The present invention also relates to a co-polycaranamide, which is prepared or can be prepared by a process according to the invention, in particular from 3S-caranlactam, 3R-caranlactam or a mixture of 3S-caranlactam and 3R-caranlactam, in particular 3S-polycaranamide, with at least one further lactam, wherein the co-polycaranamide contains at least one incorporated lactam, preferably laurolactam and/or caprolactam, and at least one repeat unit of the formula

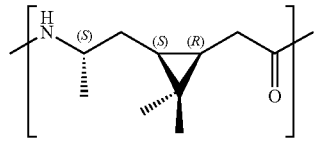

or at least one repeat unit of the formula

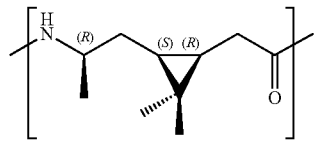

or has both of the aforementioned repeat units.

According to the invention, the present invention also relates to a co-polycaranamide which is prepared or can be prepared by a process according to the invention, in particular from 3S-caranlactam, 3R-caranlactam or a mixture of 3S-caranlactam and 3R-caranlactam, with at least one further lactam, in particular containing at least one of the following repeat units according to one of the following formulas (with a, b and c repeat units):

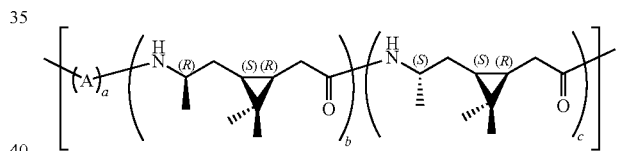

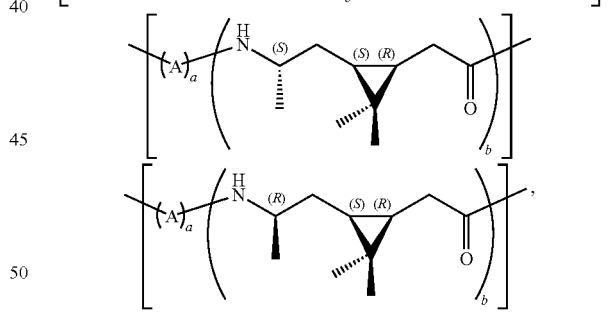

where A is a repeat unit of the further lactam incorporated in the co-polyamide.

It is preferably provided that the lactam is selected from the group consisting of laurolactam, caprolactam and a mixture of the named lactams.

According to the invention, the present invention also relates to a co-polycaranamide which is prepared or can be prepared by a process according to the invention, in particular from 3S-caranlactam or a mixture of 3S-caranlactam and 3R-caranlactam, with at least one further lactam, in particular comprising at least one of the following repeat units in accordance with one of the following formulas (with a, b and c repeat units):

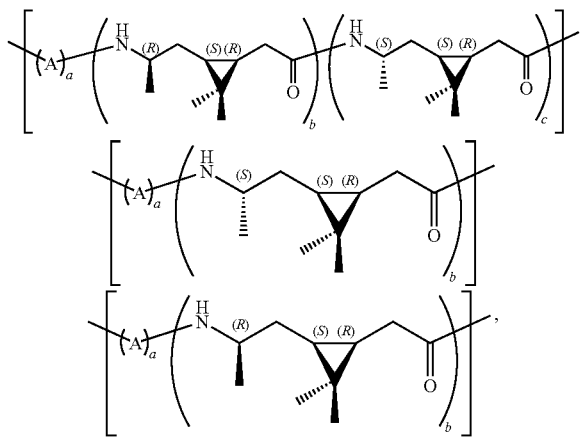

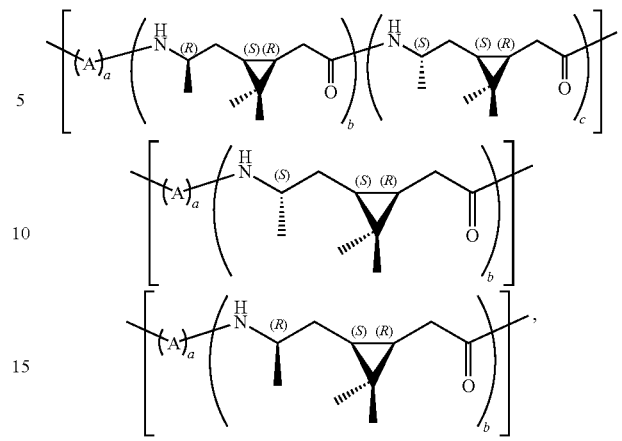

where A is a repeat unit of the further lactam incorporated in the co-polyamide.

It is preferably provided that the lactam is selected from the group consisting of laurolactam, caprolactam and a mixture of the named lactams.

According to the invention, the present invention also relates to a co-polycaranamide which is prepared or can be prepared by a process according to the invention, in particular from 3R-caranlactam or a mixture of 3S-caranlactam and 3R-caranlactam, with at least one further lactam, in particular comprising at least one of the following repeat units in accordance with one of the following formulas (with a, b and c repeat units):

where A is a repeat unit of the further lactam incorporated into the co-polyamide.

It is preferably provided that the lactam is selected from the group consisting of laurolactam, caprolactam and a mixture of the named lactams.

According to the invention, the present invention also relates to a 3S-caranlactam-laurolactam co-polycaranamide (3S-caranlactam-laurolactam co-polyamide), in particular which is prepared or can be prepared by one of the processes of the invention, in particular from 3S-caranlactam and laurolactam, in particular according to of the formula (with a, b and n repeat units):

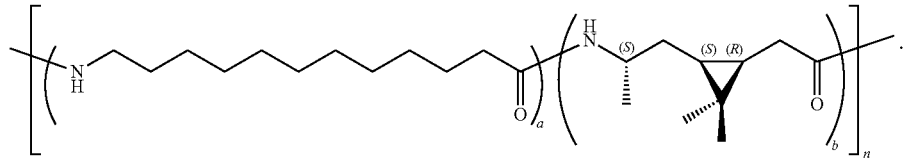

According to the invention, the present invention also relates to a 3S-caranlactam-caprolactam co-polycaranamide (3S-caranlactam-caprolactam co-polyamide), in particular which is prepared or can be prepared by one of the processes according to the invention, in particular from 3S-caranlactam and caprolactam, in particular according to the formula (with a, b and n repeat units):

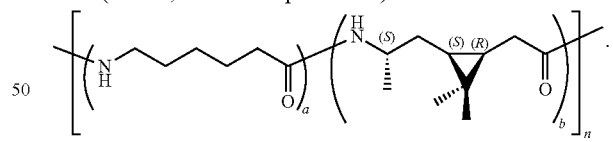

According to the invention, the present invention also relates to a 3R-caranlactam-laurolactam co-polycaranamide (3R-caranlactam-laurolactam co-polyamide), in particular which is prepared or can be prepared by one of the processes of the invention, in particular from 3R-caranlactam and laurolactam, in particular according to of the formula (with a, b and n repeat units):

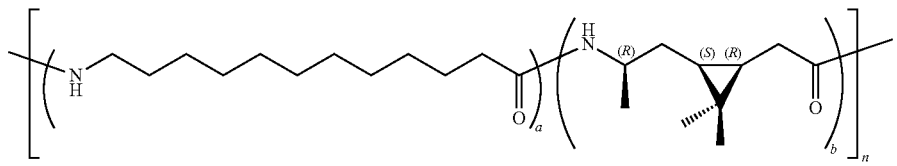

According to the invention, the present invention also relates to a 3R-caranlactam-caprolactam co-polycaranamide (3R-caranlactam-caprolactam co-polyamide), in particular which is prepared or can be prepared by one of the processes according to the invention, in particular from 3R-caranlactam and caprolactam, in particular according to of the formula (with a, b and n repeat units):

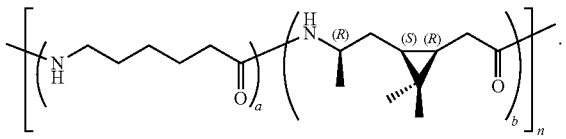

According to the invention, the present invention also relates to a 3S-caranlactam-3R-caranlactam-laurolactam co-polycaranamide (3S-caranlactam-3R-caranlactam-laurolactam co-polyamide), in particular which is prepared or can be prepared by one of the processes according to the invention, in particular from 3S-caranlactam, 3R-caranlactam and laurolactam, especially according to the formula (with a, b, c and n repeat units):

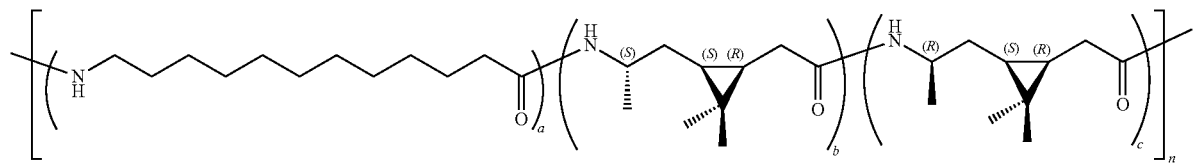

According to the invention, the present invention also relates to a 3S-caranlactam-3R-caranlactam-caprolactam co-polycaranamide (3S-caranlactam-3R-caranlactam-caprolactam co-polyamide), in particular which is prepared or can be prepared by one of the processes of the invention, in particular from 3S-caranlactam, 3R-caranlactam and caprolactam, especially according to the formula (with a, b, c and n repeat units):

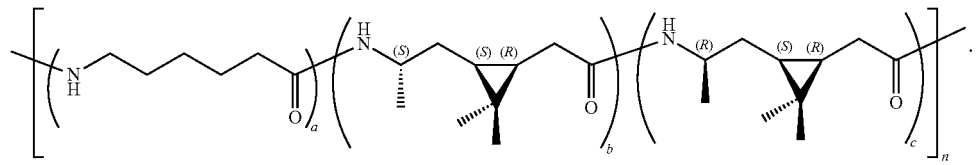

The present invention also relates to products, in particular plastic products containing at least one of the polyamides produced according to the invention, in particular 3S-polycaranamide, 3R-polycaranamide or at least one of the co-polycaranamides provided according to the invention, in particular comprising at least 5 wt. %, at least 10 wt. %, at least 15 wt. %, at least 20 wt. %, at least 30 wt. %, at least 40 wt. %, at least 50 wt. %, at least 60 wt. %, at least 70 wt. %, at least 80 wt. %, at least 90 wt. %, at least 95 wt. % or at least 99 wt. % of the polyamide, in particular consisting of at least one of these polyamides.

In a preferred embodiment, such plastic products are industrial products, medical products or components.

The preferred embodiments for process steps a1) to i2) disclosed in connection with the process according to the invention for the preparation and further reaction of the isomer-enriched mixture of 3S-caranone and 3R-caranone are also preferred according to the invention in process steps a1) to i2) as in the present case for the processes for the preparation of the 3-caranoxime-enriched mixture, the 3-caranlactam-enriched mixture, the 3S-polycaranamide, the 3R-polycaranamide, 3S/3R-co-polycaranamide, the 3S-caranlactam-laurolactamco-polycaranamide (3S-caranlactam-laurolactam co-polyamide), 3R-caranlactam-laurolactam co-polycaranamide (3R-caranlactam-laurolactam co-polyamide), 3S-caranlactam-3R-caranlactam-laurolactam co-polycaranamide (3S-caranlactam-3R-caranlactam-laurolactam co-polyamide), 3S-caranlactam-caprolactam co-polycaranamide (3S-caranlactam-caprolactam co-polyamide), 3R-caranlactam-caprolactam co-polycaranamide (3R-caranlactam-caprolactam co-polyamide), 3S-caranlactam-3R-caranlactam-caprolactam co-polycaranamide (3S-caranlactam-3R-caranlactam-caprolactam co-polyamide), as well as for the 3S-caranoxime, 3S-caranlactam, 3S-polycaranamide, 3R-polycaranamide, 3S/3R-co-polycaranamide, 3S-caranlactam-laurolactam co-polycaranamide (3S-caranlactam-laurolactam co-polyamide), 3R-caranlactam-laurolactam co-polycaranamide (3R-caranlactam-laurolactam co-polyamide), 3S-caranlactam-3R-caranlactam-laurolactam co-polycaranamide (3S-caranlactam-3R-caranlactam-laurolactam co-polyamide), 3S-caranlactam-caprolactam co-polycaranamide (3S-caranlactam-caprolactam co-polyamide), 3R-caranlactam-caprolactam co-polycaranamide (3R-caranlactam-caprolactam co-polyamide), and 3S-caranlactam-3R-caranlactam-caprolactam co-polycaranamide (3S-caranlactam-3R-caranlactam-caprolactam co-polyamide), and polymers, in particular polyamides, which contain, entirely or as copolymer, or as part of a mixture of different polymers or monomers, the 3-caranlactams or their opened amino acids, amino acid esters or amino acid derivatives.

The present invention also relates to polymers, in particular polyamides, which, completely or as a copolymer or as part of a mixture of different polymers or monomers, contain the 3-caranlactams according to the invention, in particular 3S-caranlactam or 3R-caranlactam, in particular 3S-caranlactam, or the opened amino acids, amino acid esters, or amino acid derivatives thereof, preferably according to the formulas shown here for 3S-caranlactam, 3S-polycaranamide, 3R-polycaranamide and 3S/3R-co-polycaranamide.

Further preferred embodiments are particularly found in the dependent claims.

The following examples and the associated figures explain the present invention.

Figure 3:
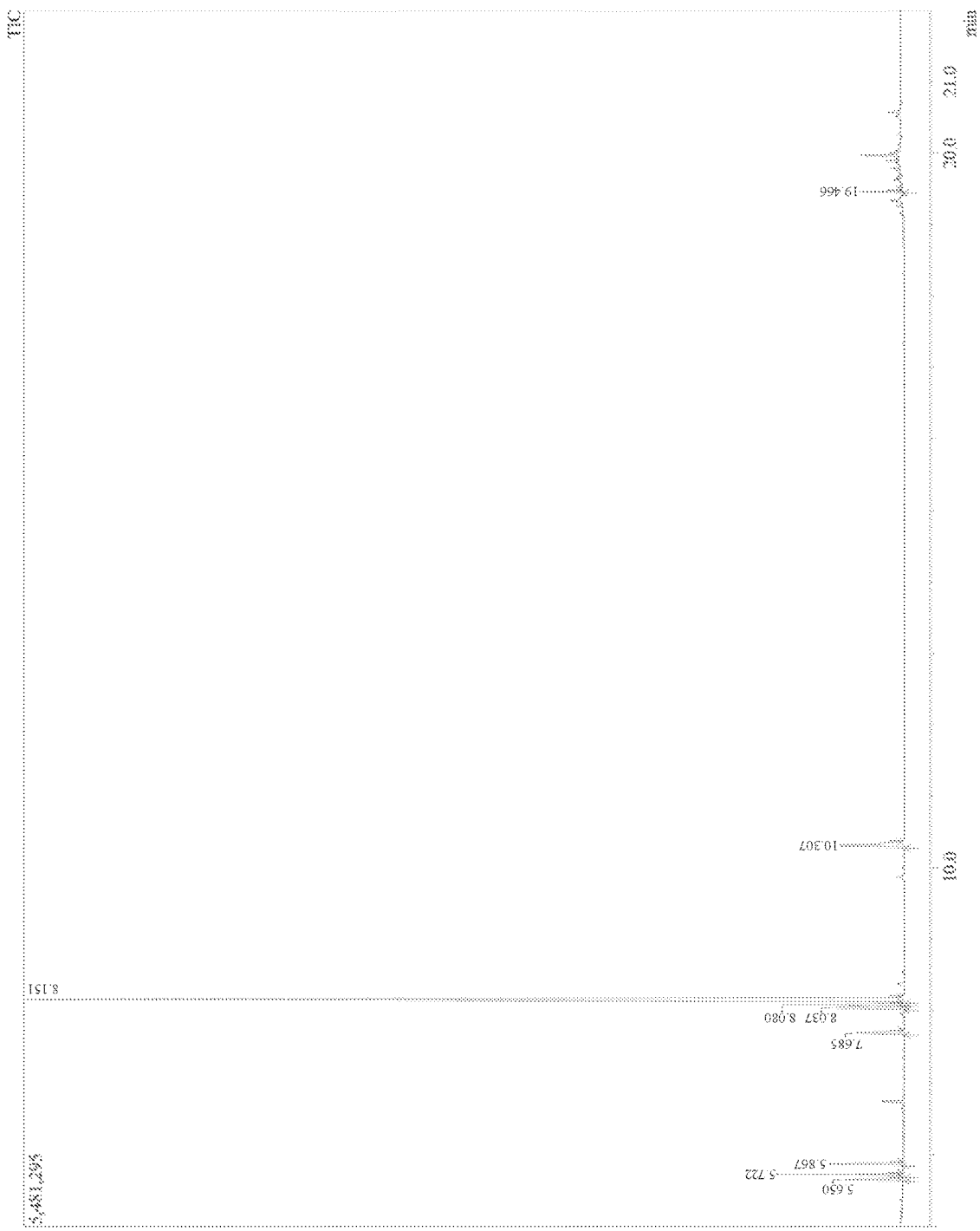
Figure 4:
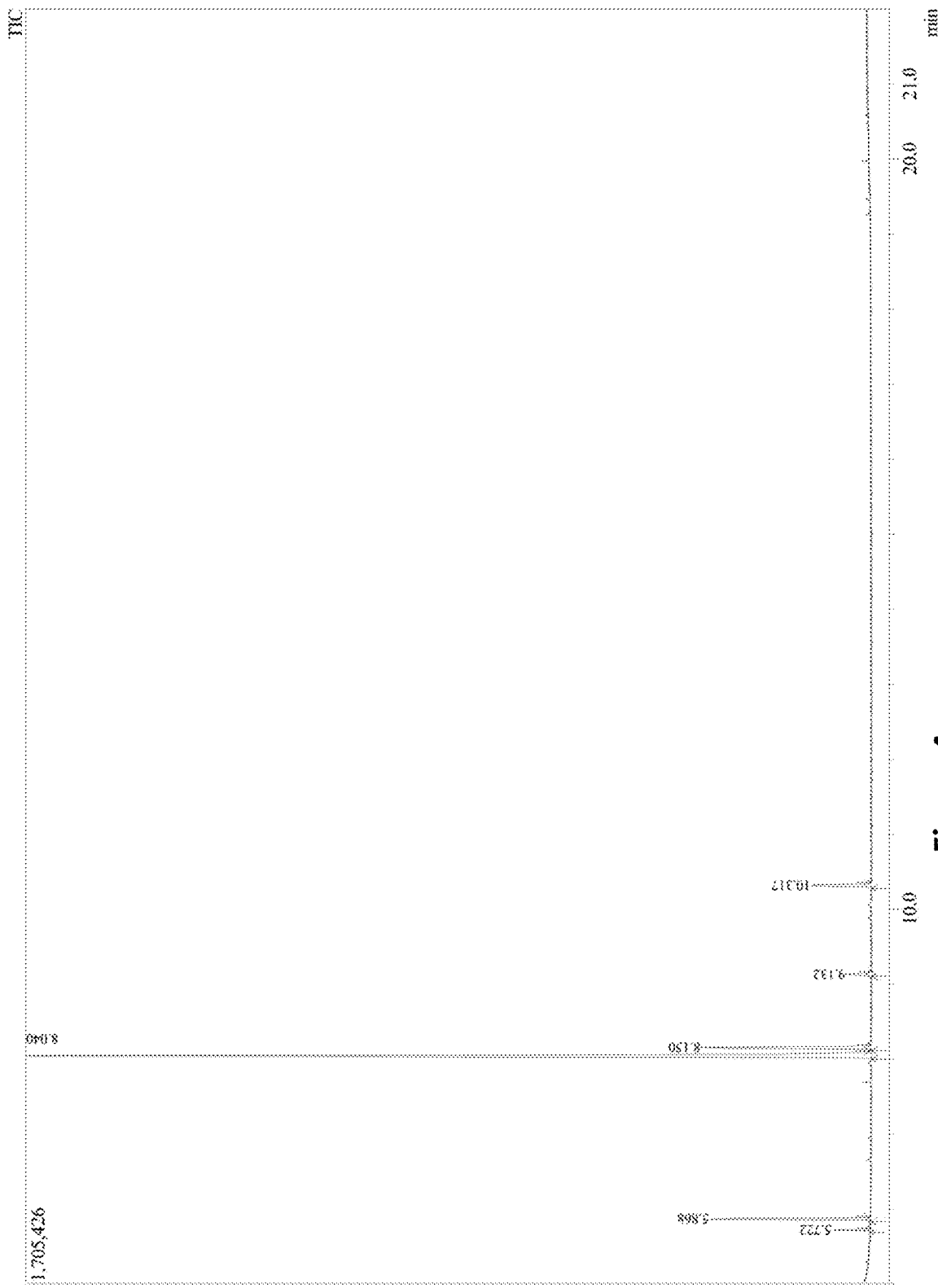
Figure 6:
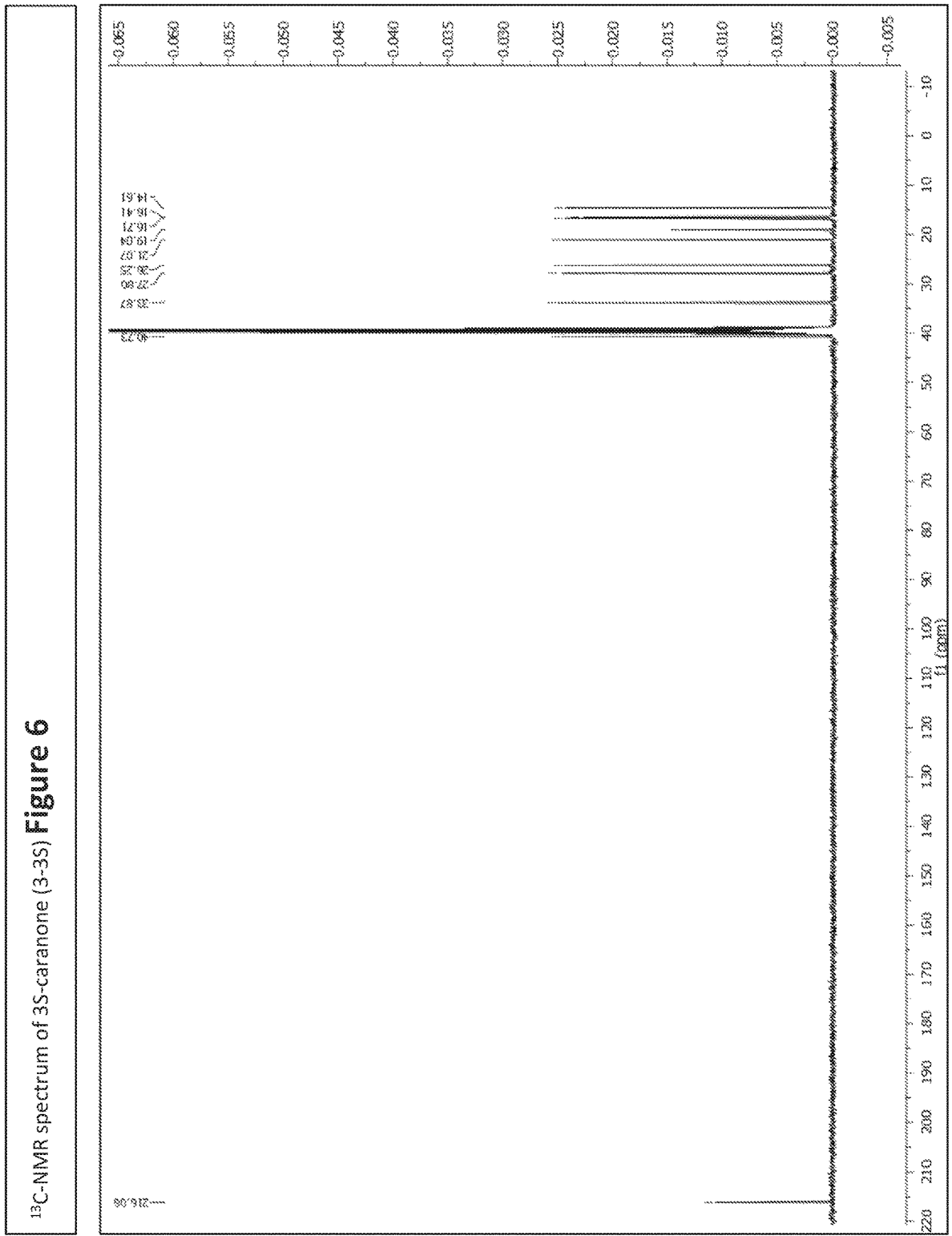
Figure 7:
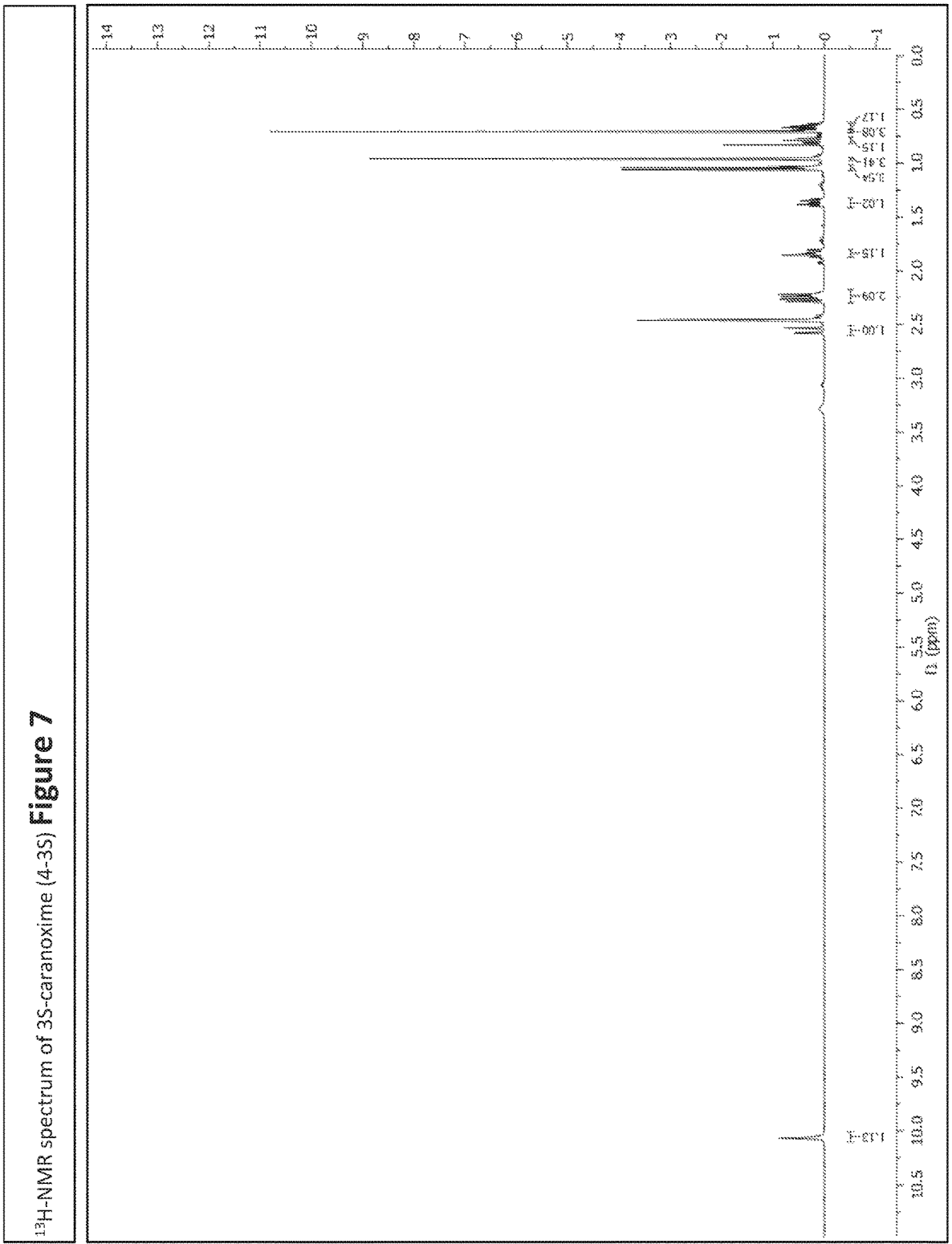
Figure 8:
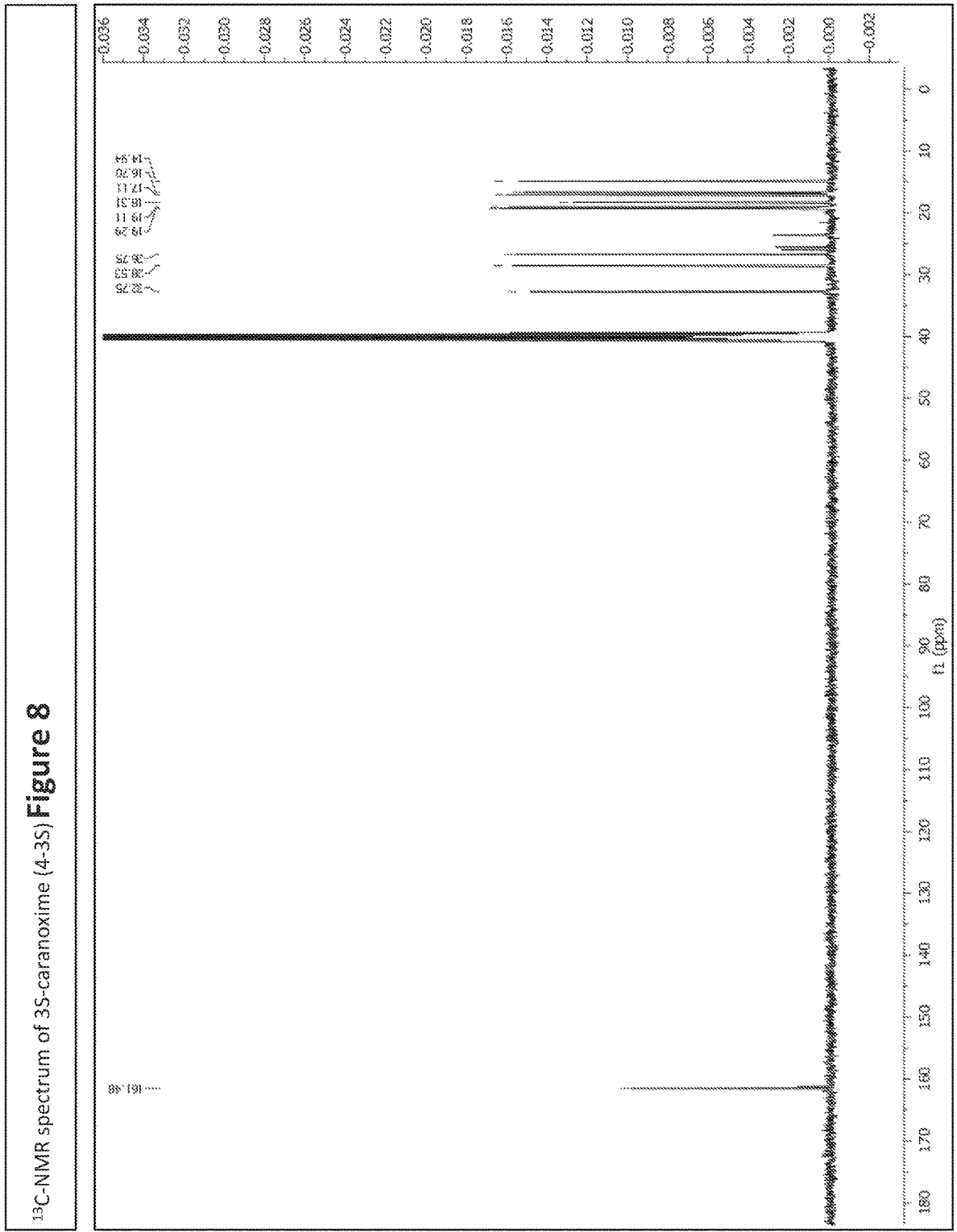
Figure 9:
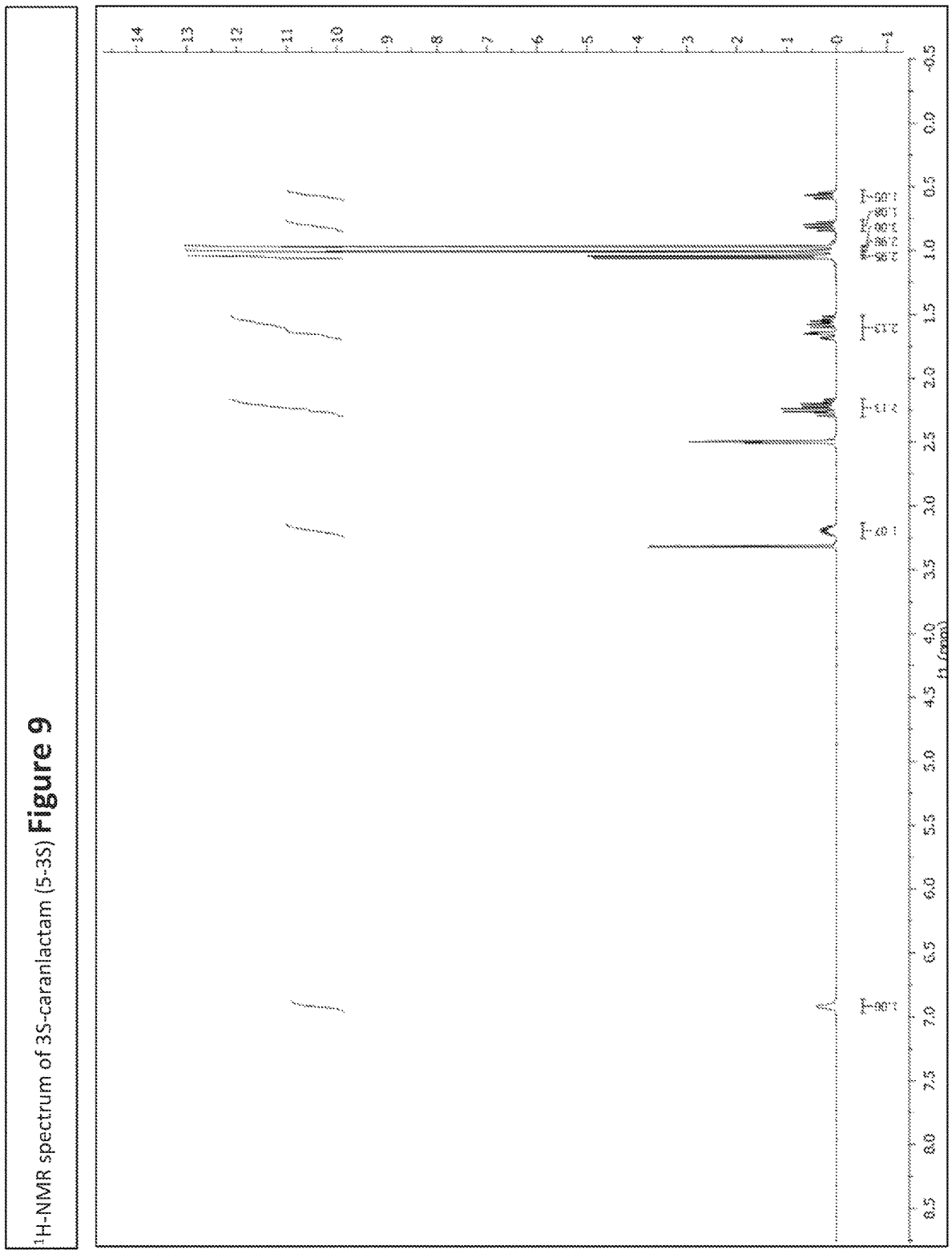
Figure 10:
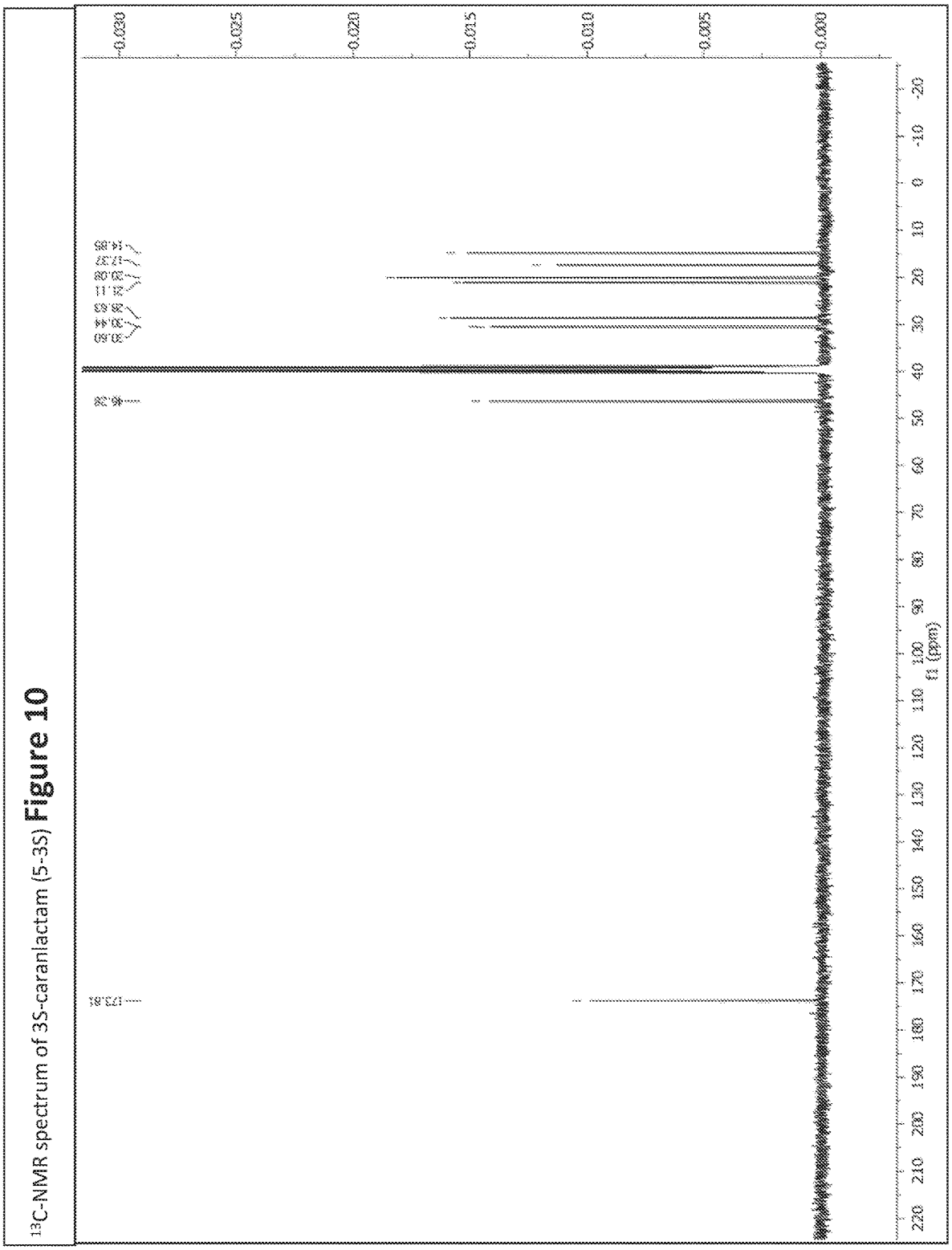
Figure 12:
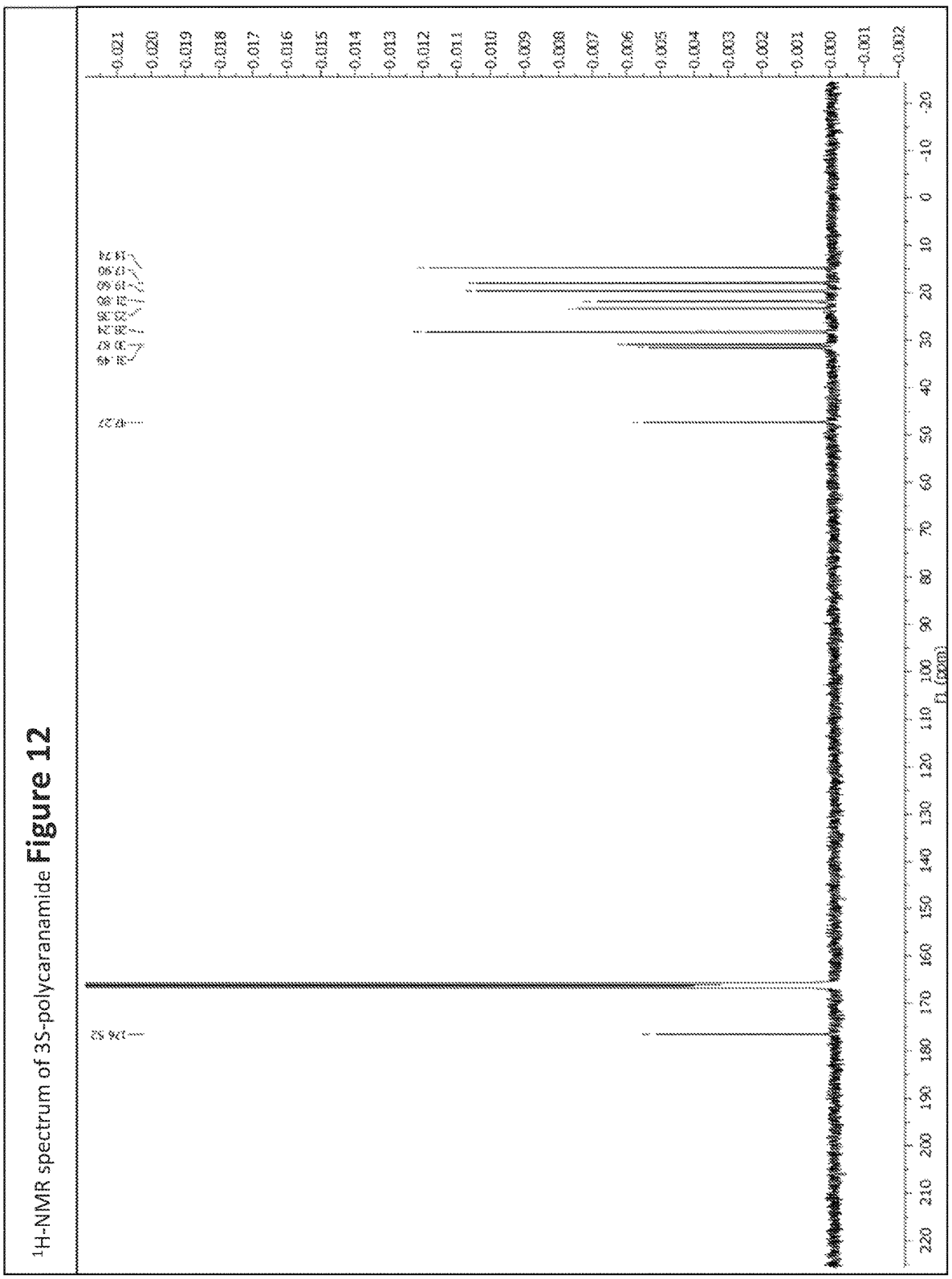
Figure 13:
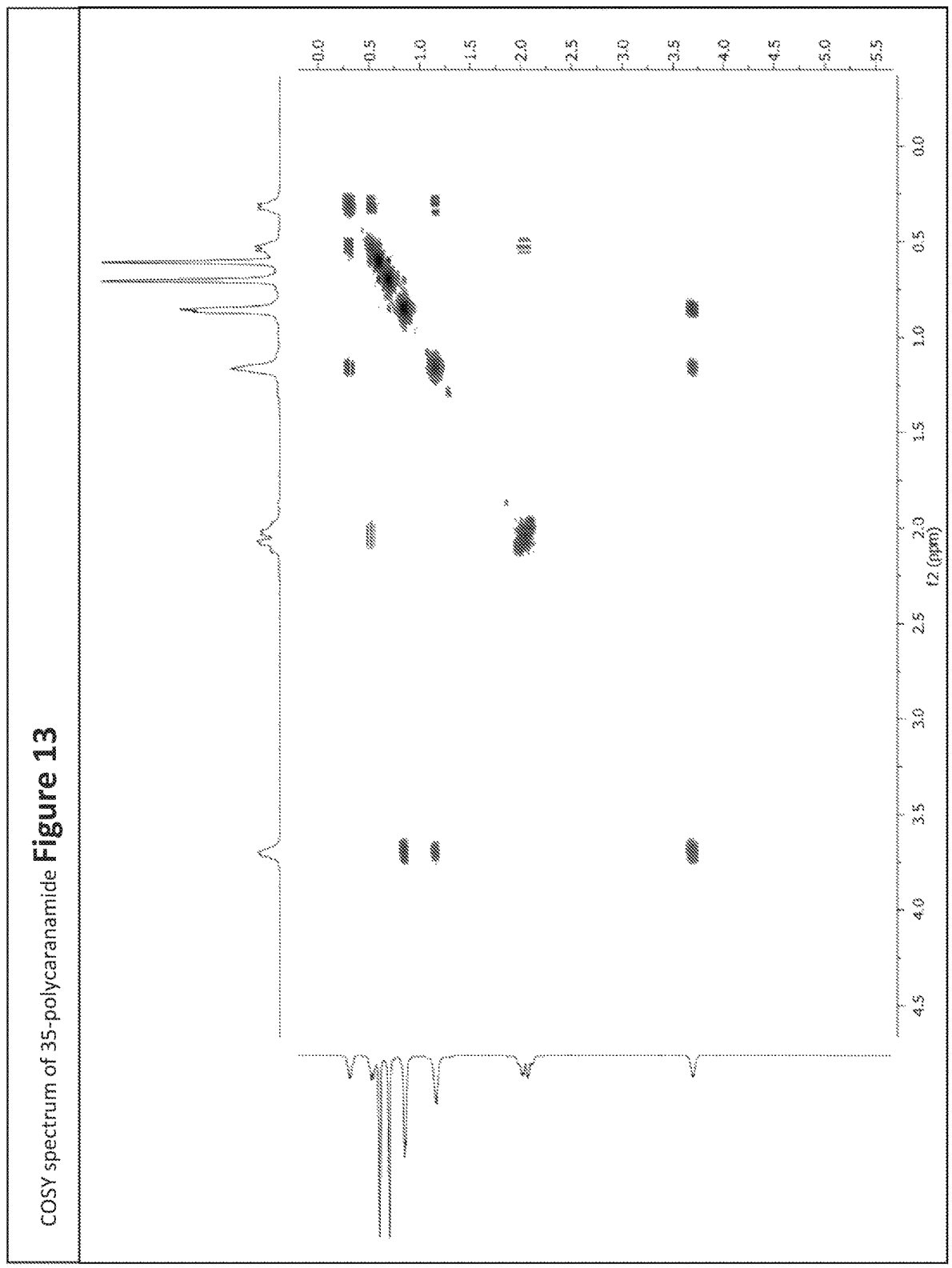
Figure 14:
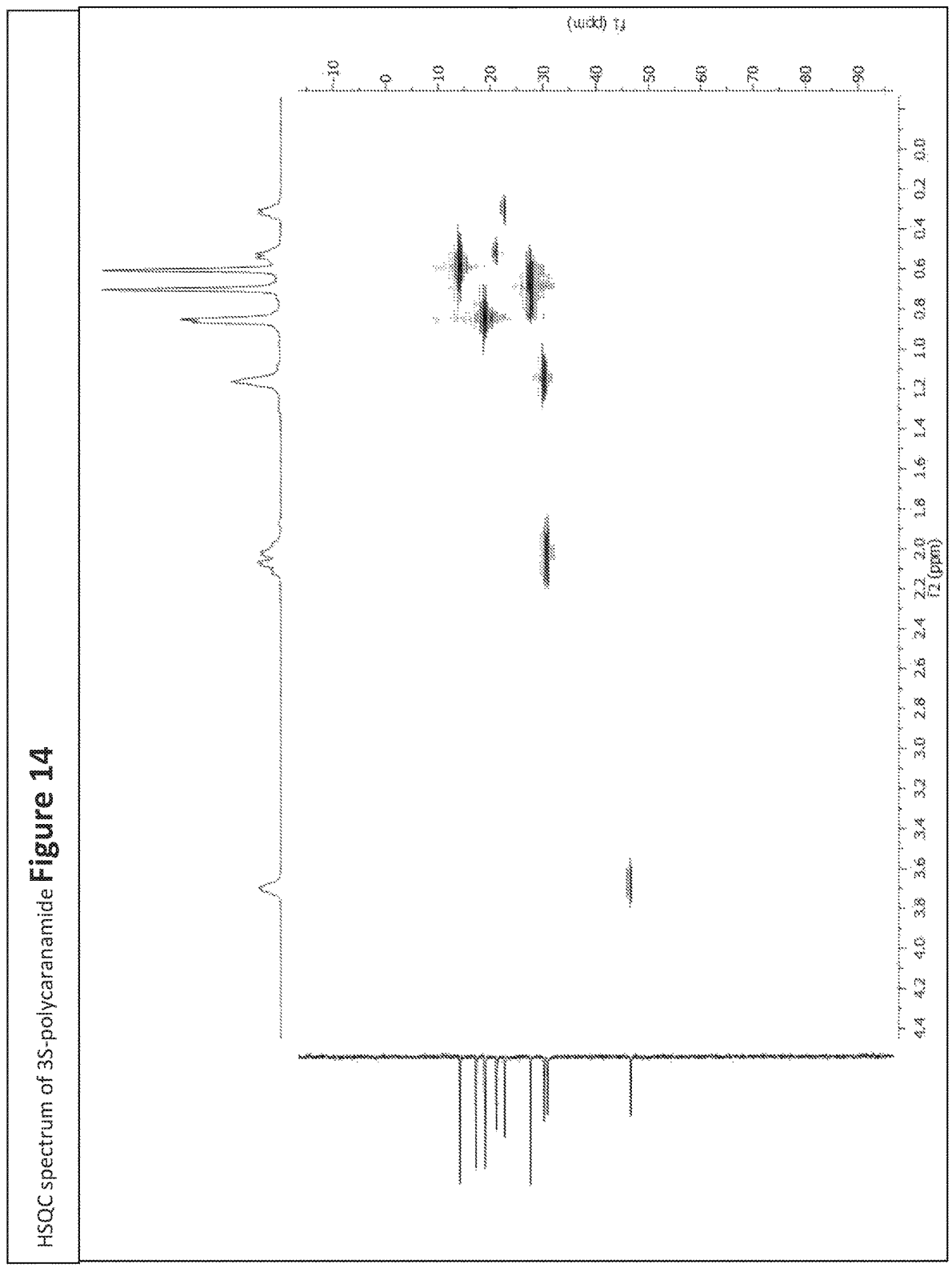
Figure 15:
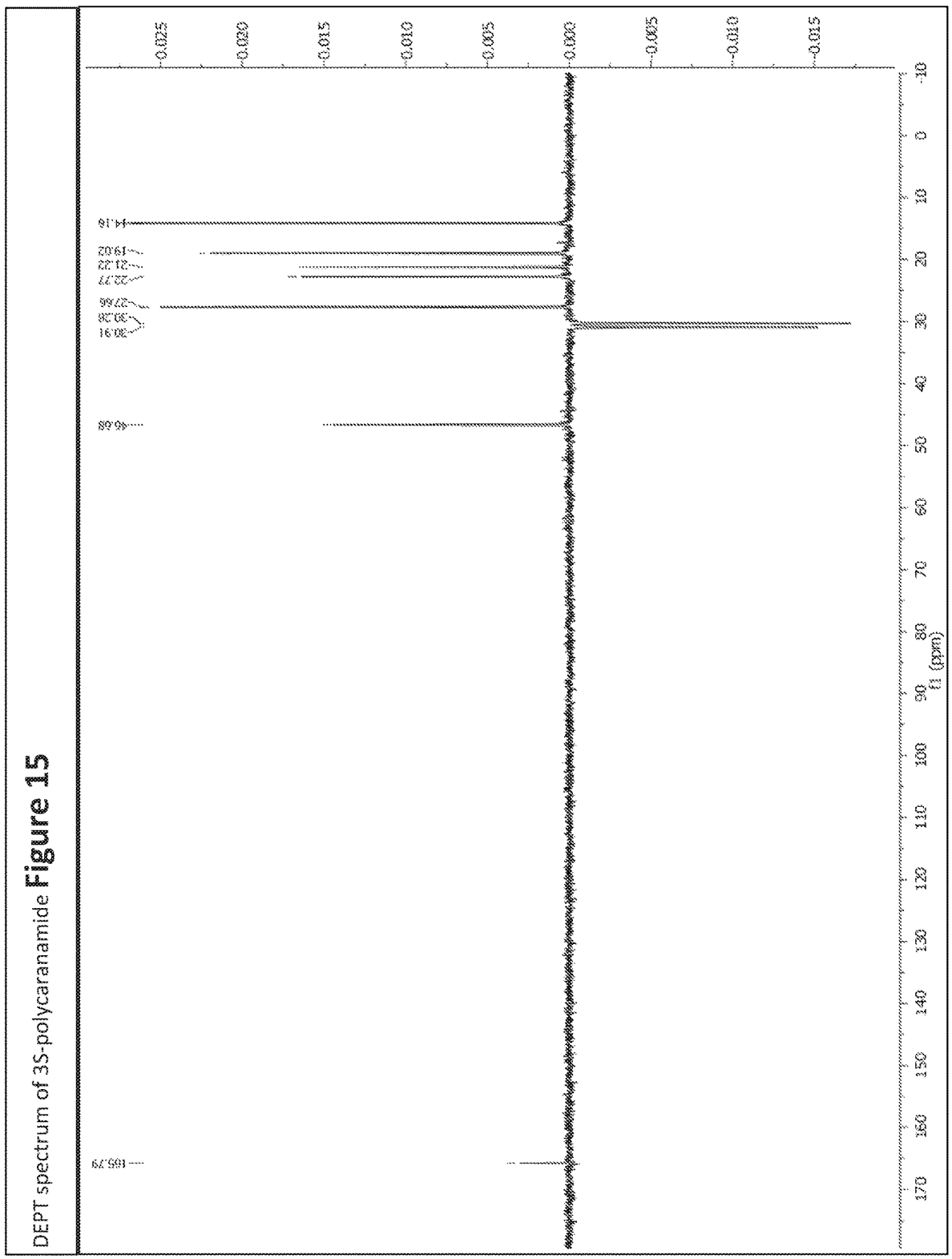
Figure 17:
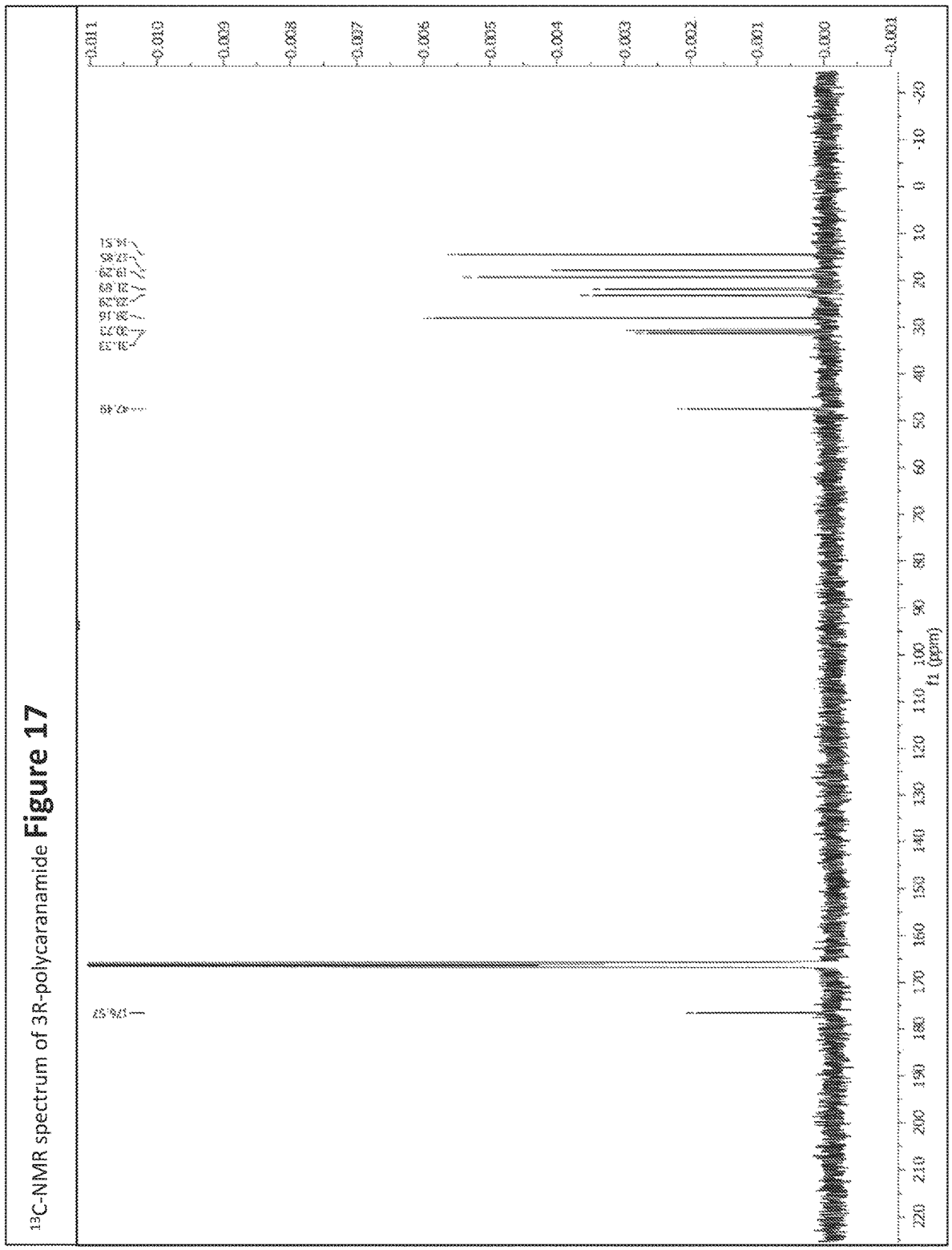
Figure 18:
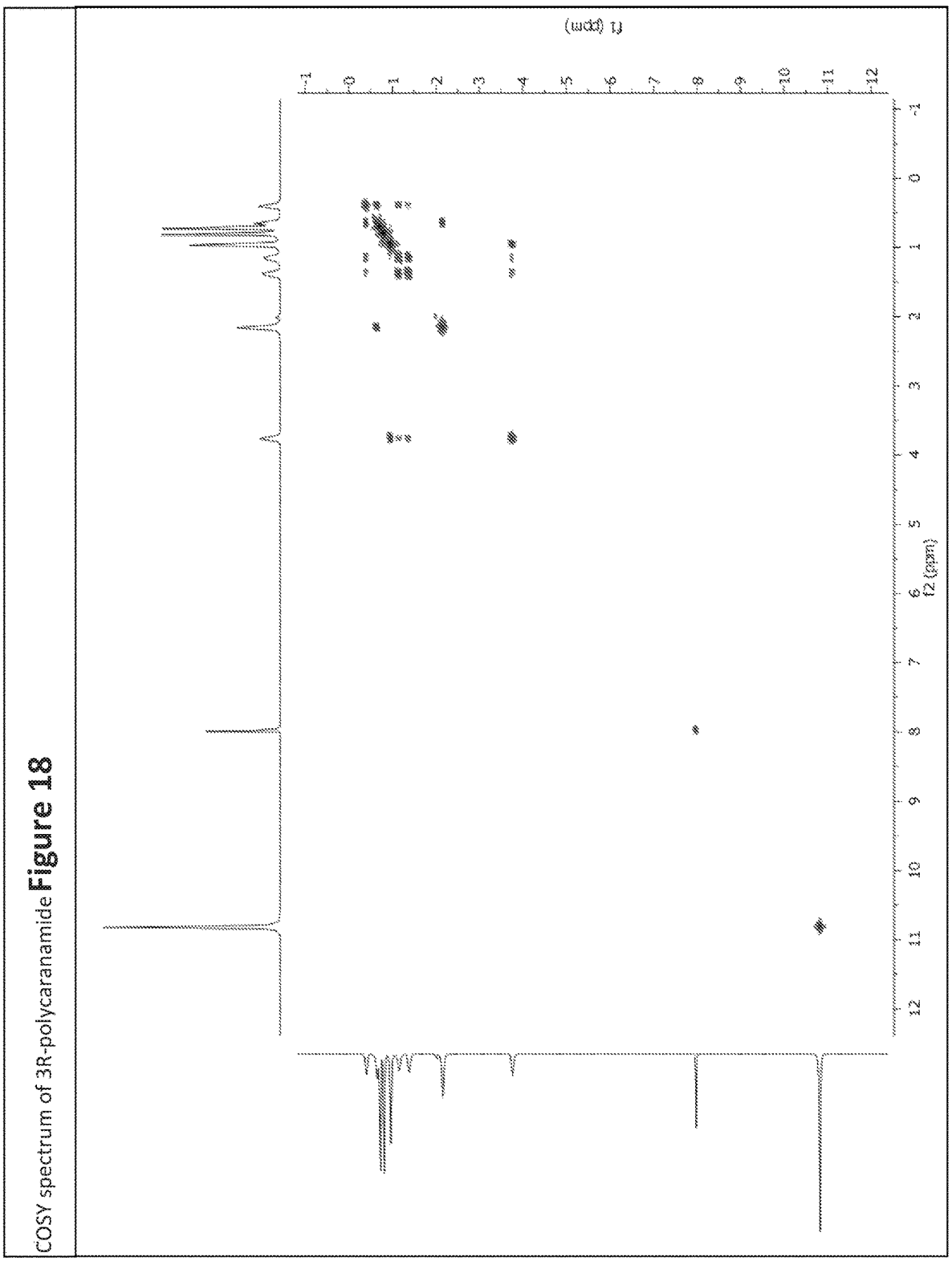
Figure 19:
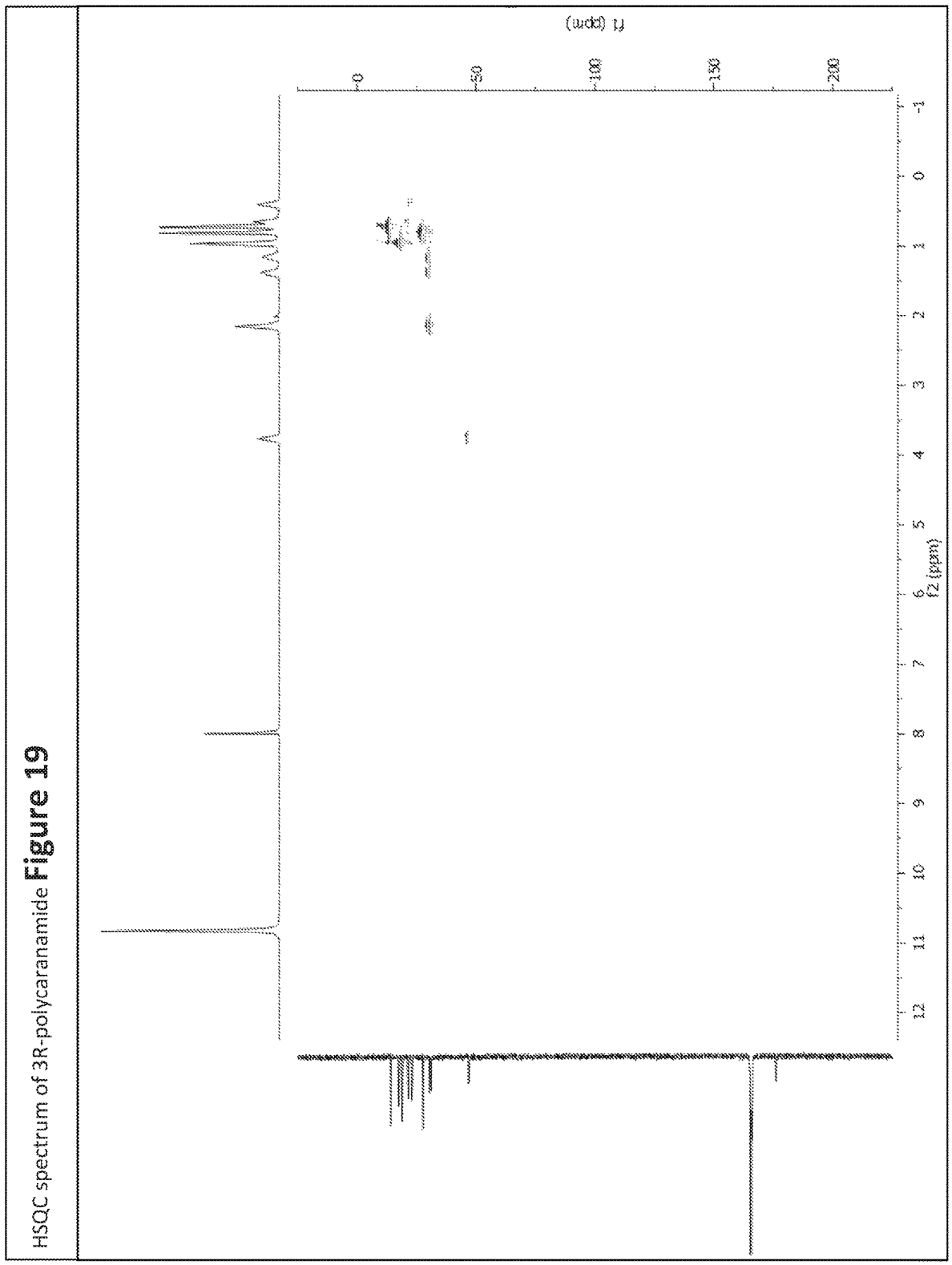
Figure 20:
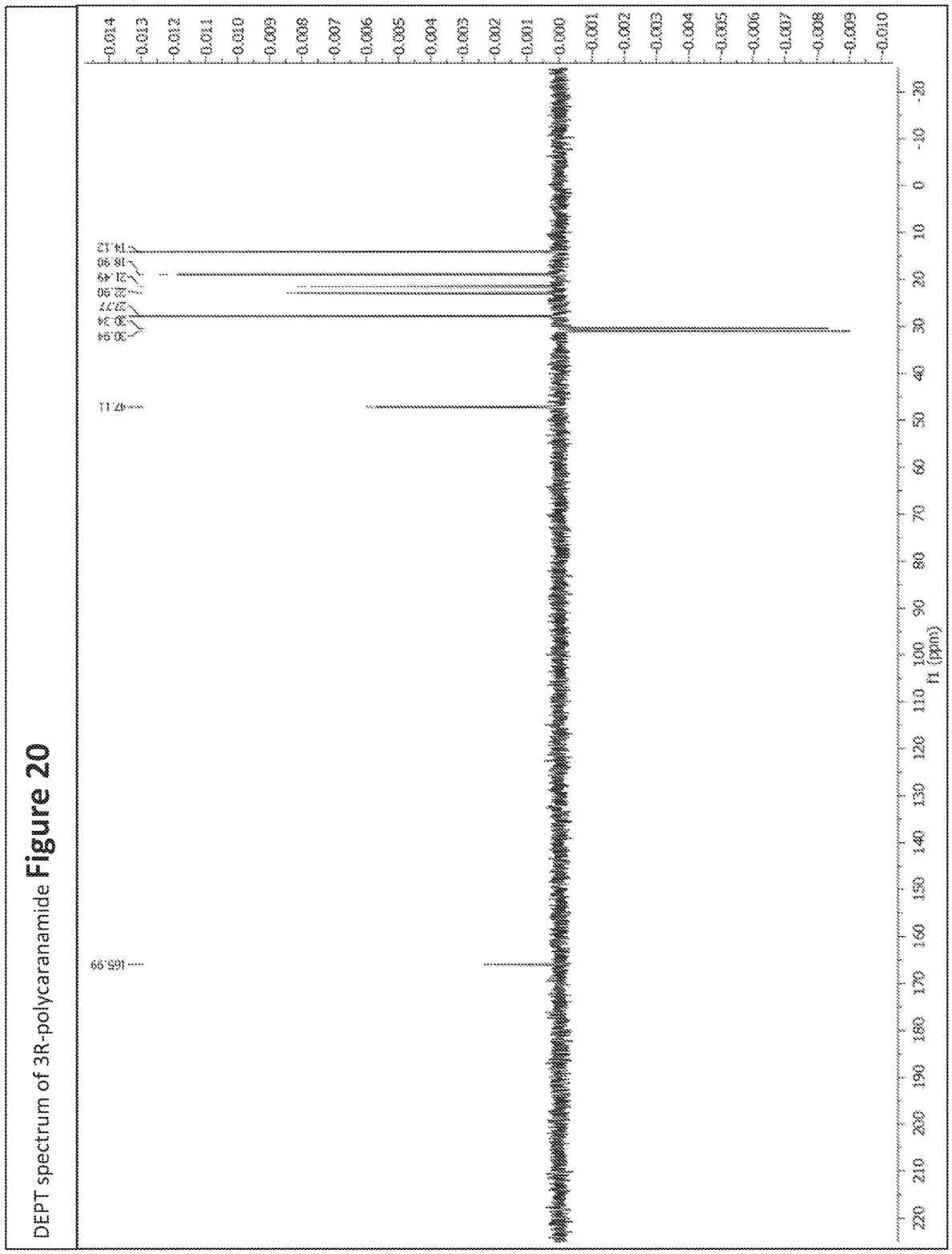
Figure 22:
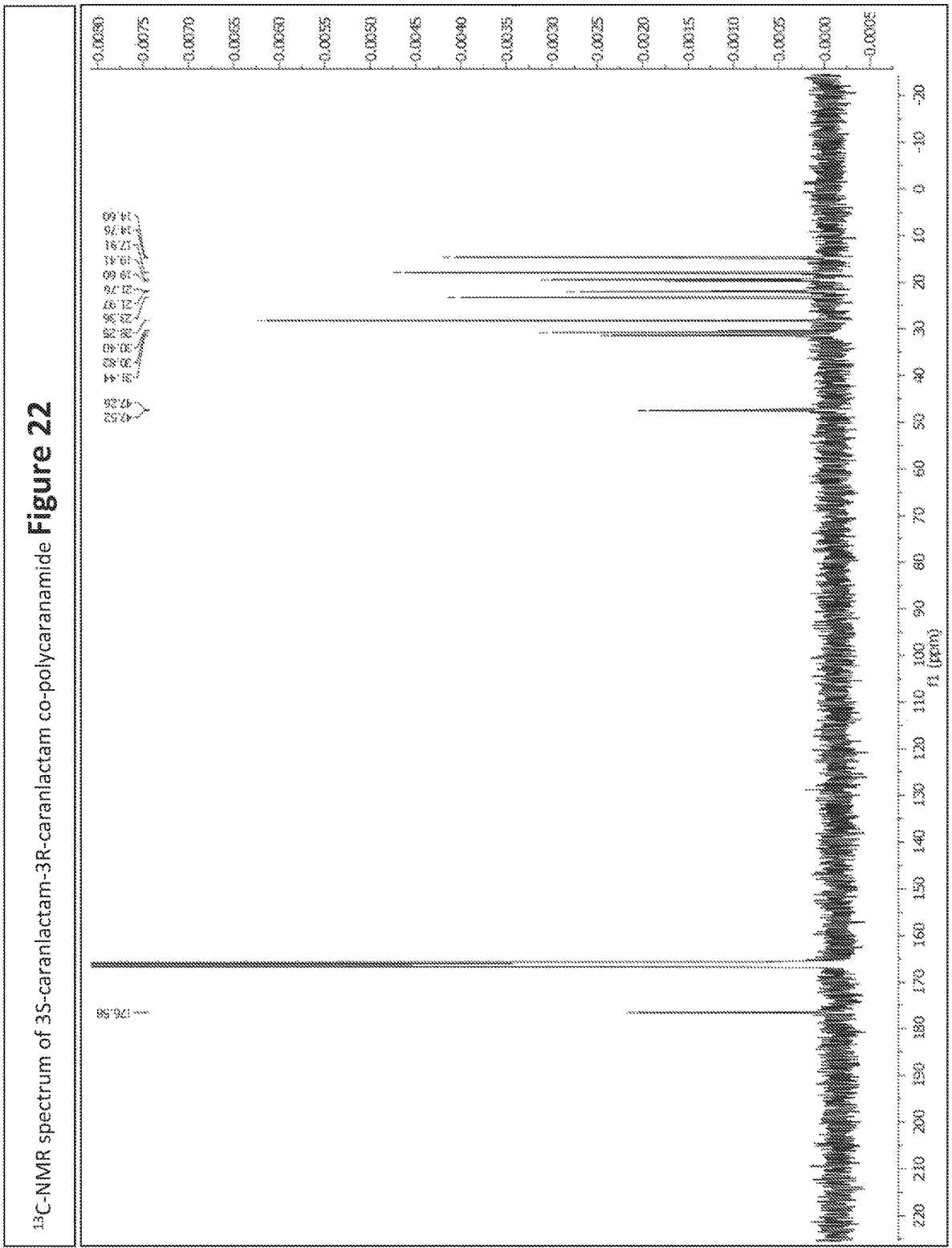
Figure 23:
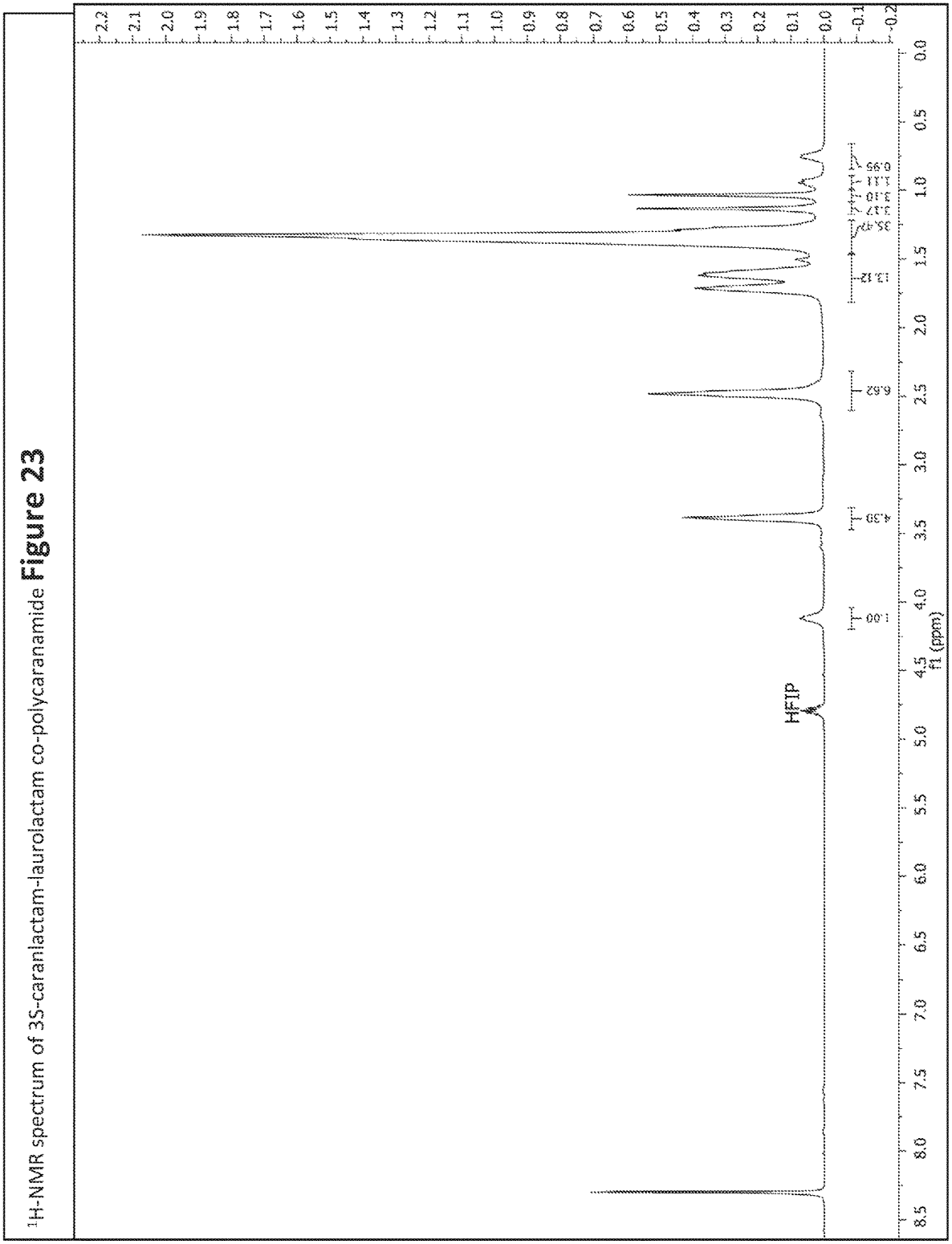
Figure 24:
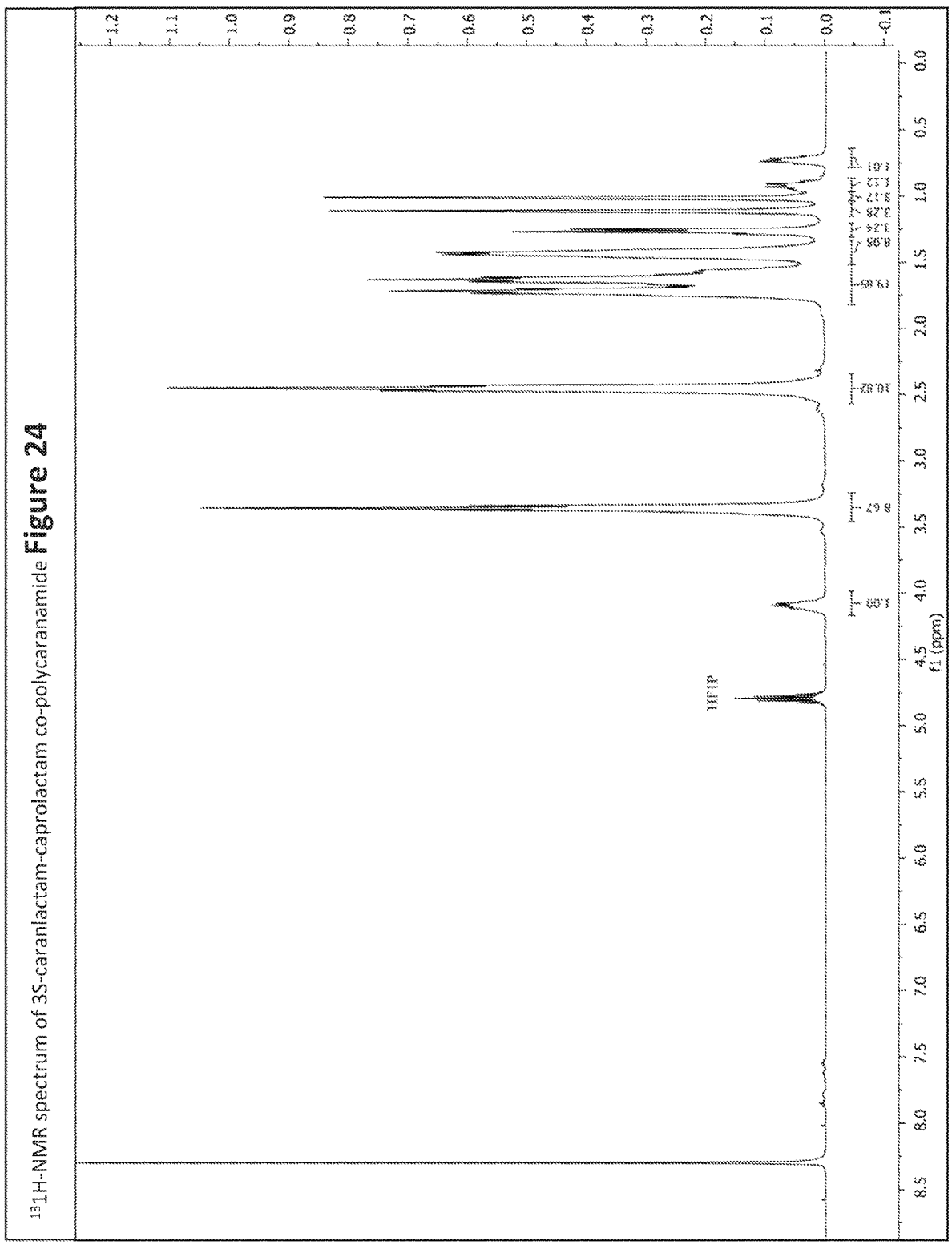
Figure 25:
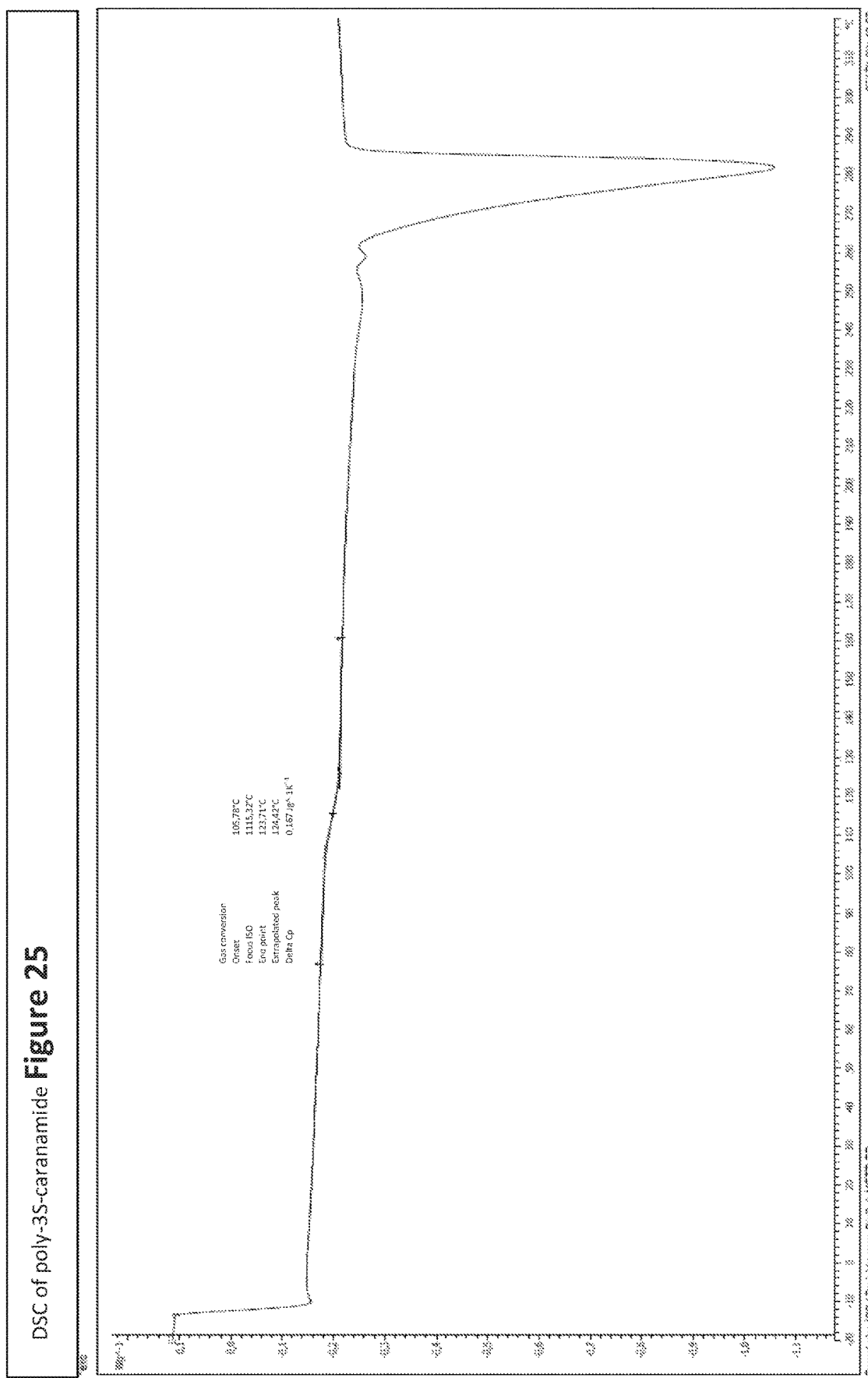
Figure 26:
Figure 27:
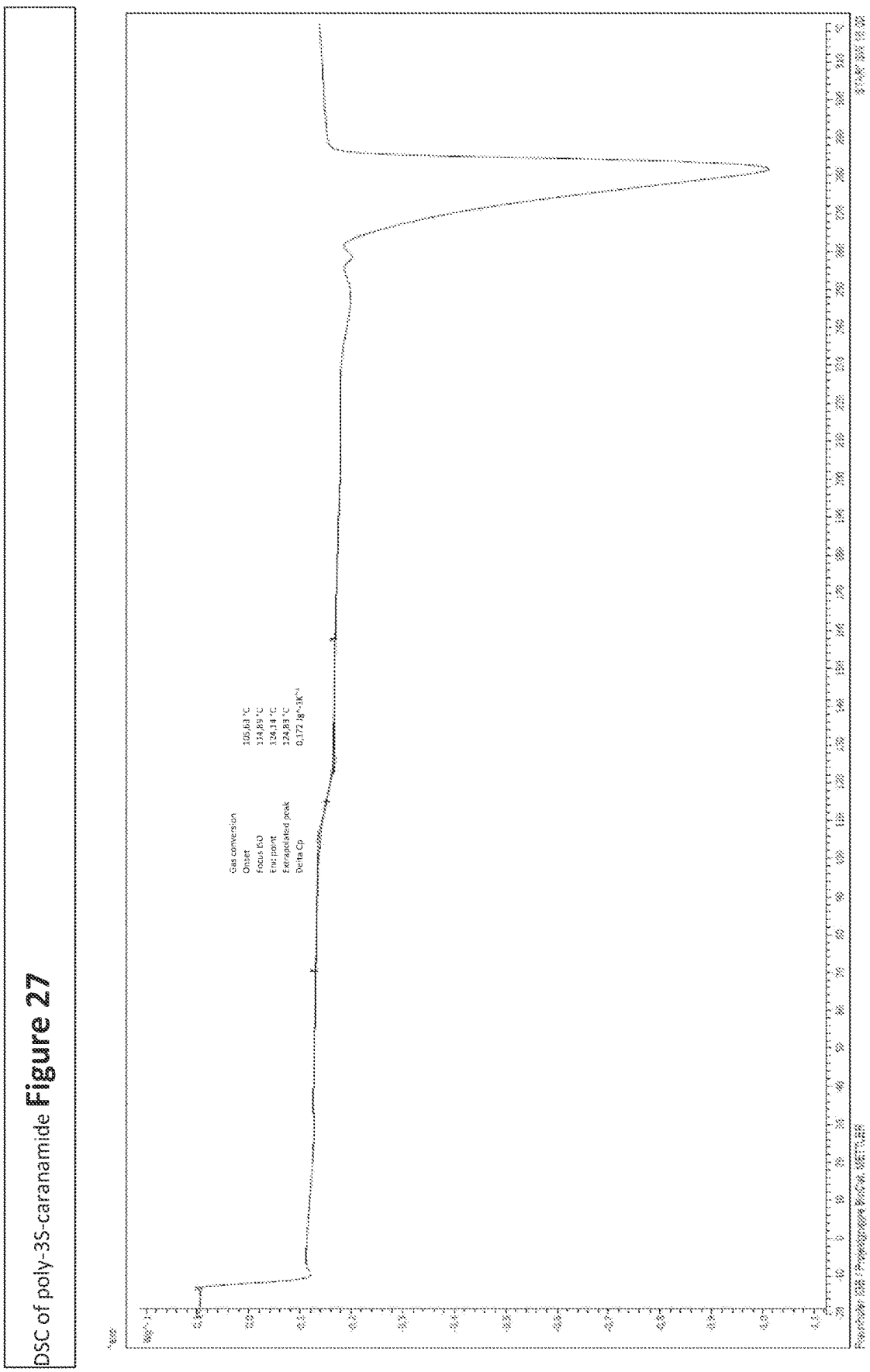
Figure 28:
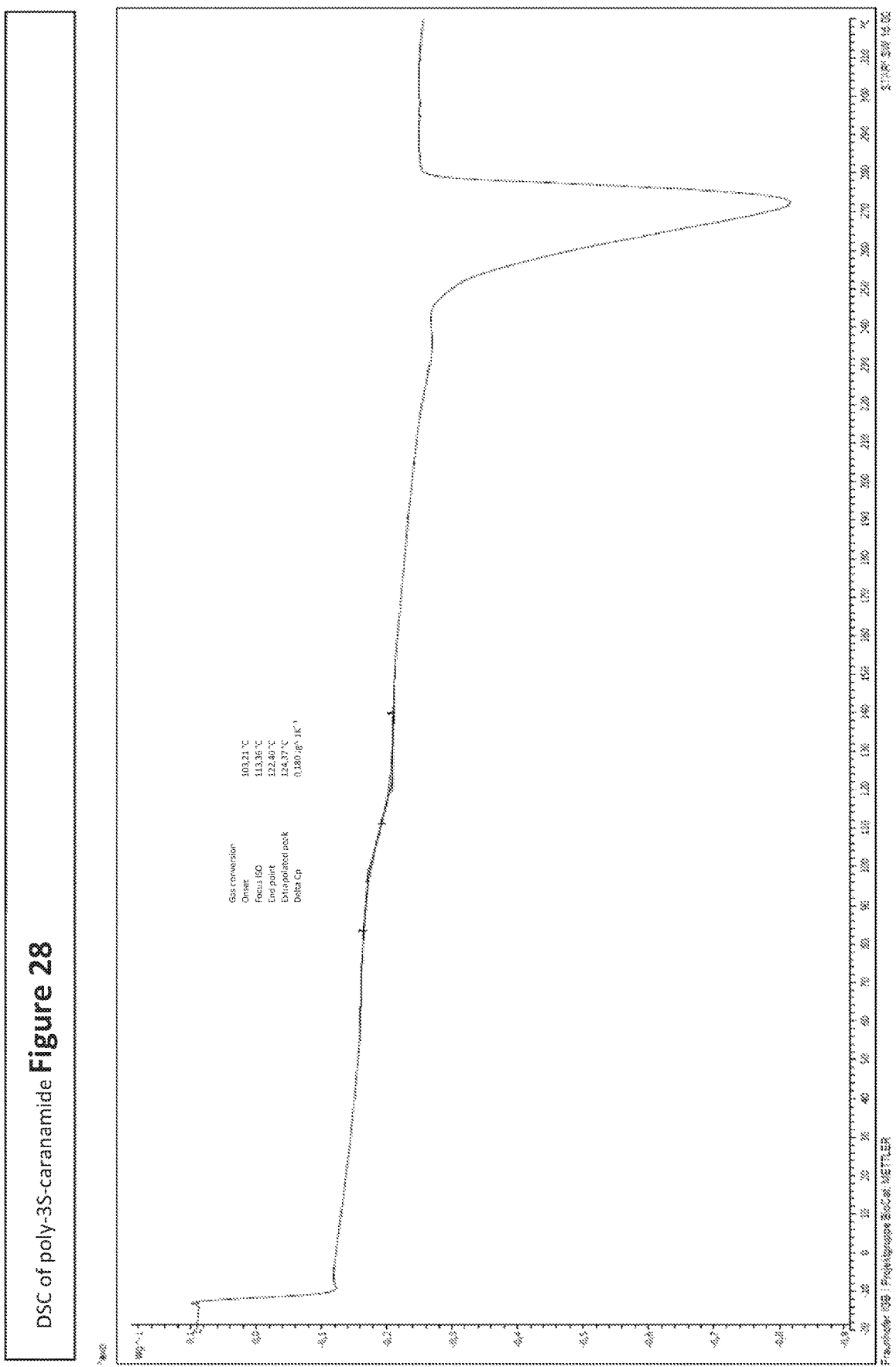
Figure 29:
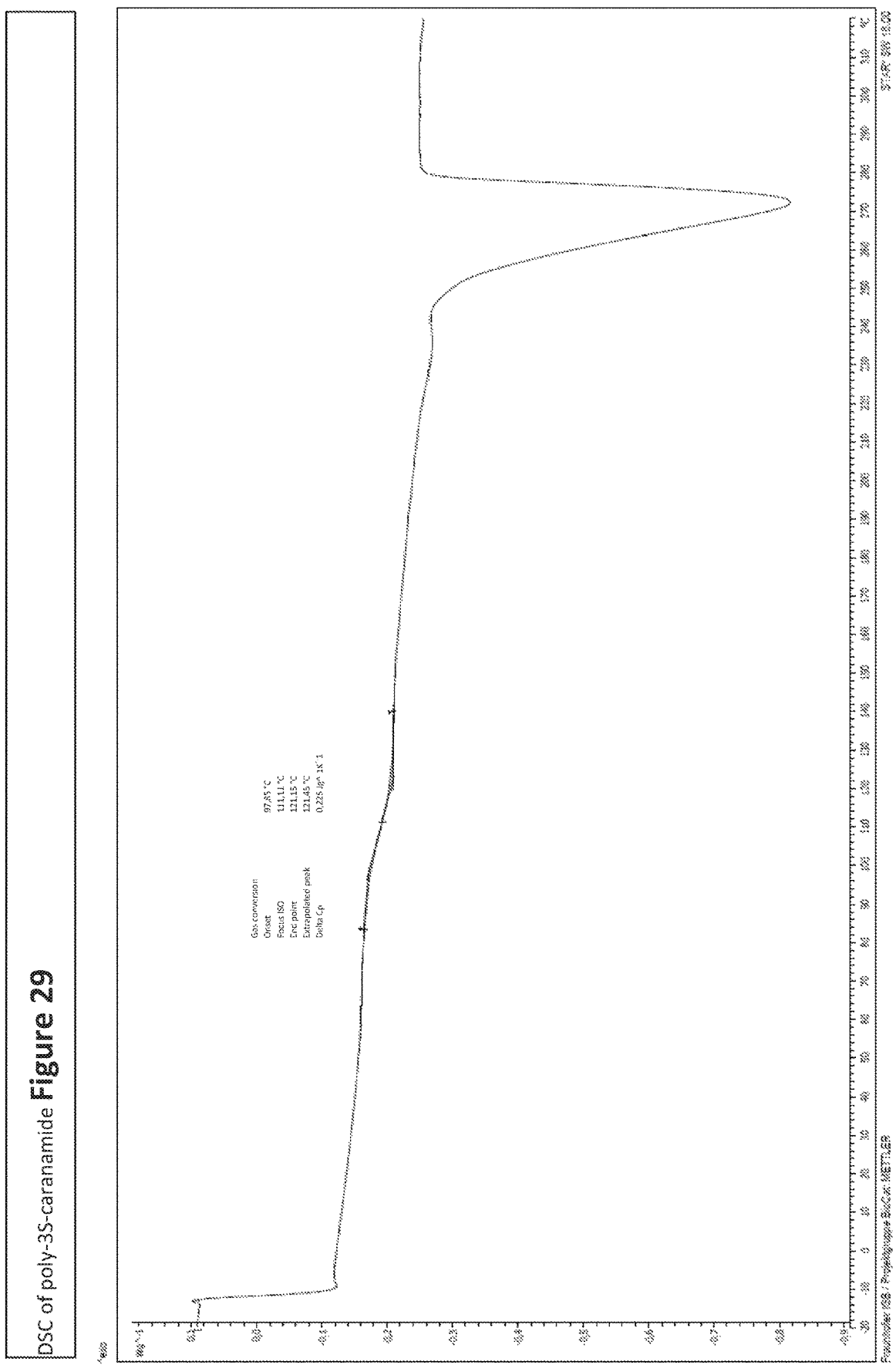
Figure 30:
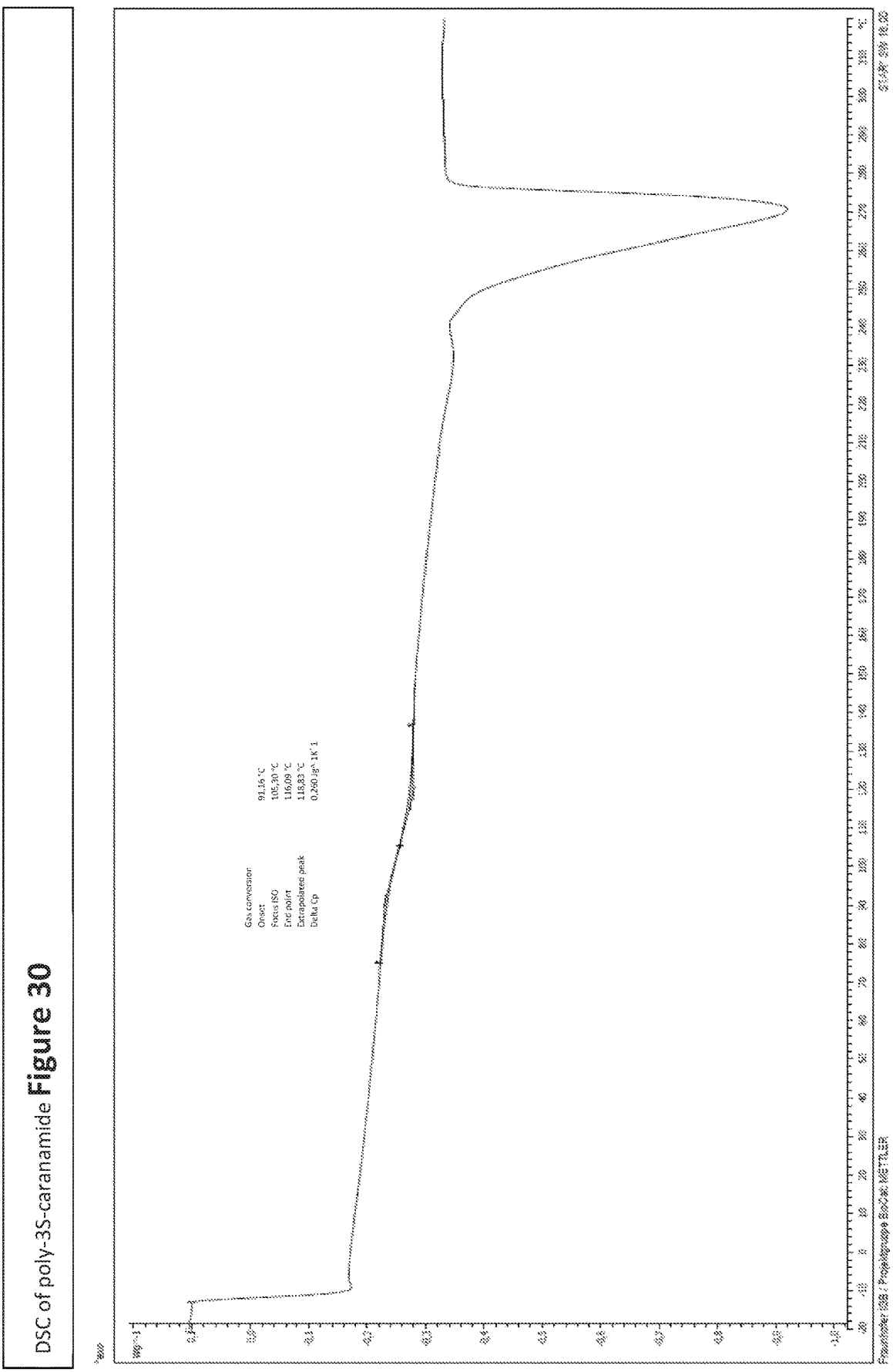
Figure 31:
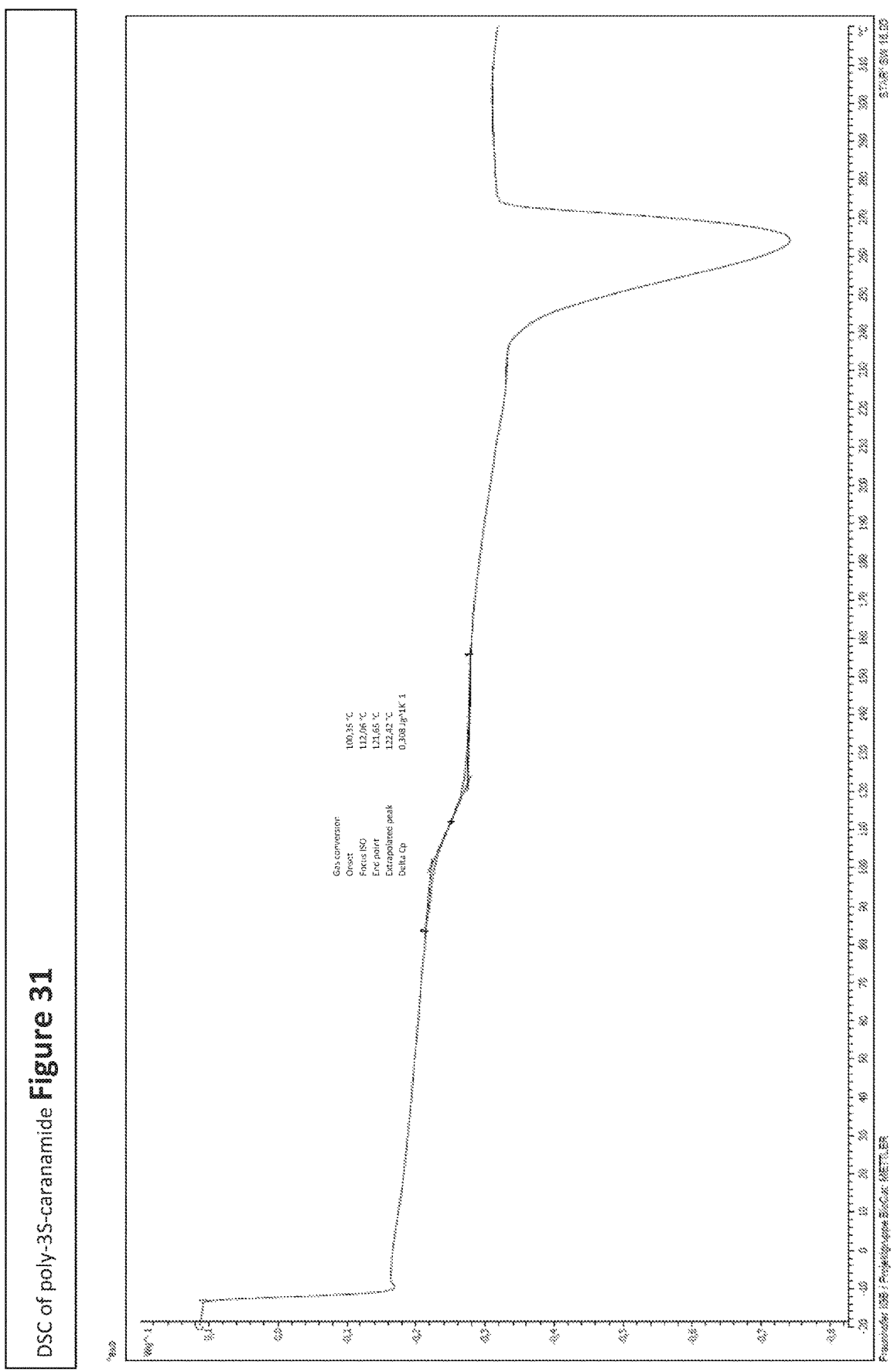
Figure 32:
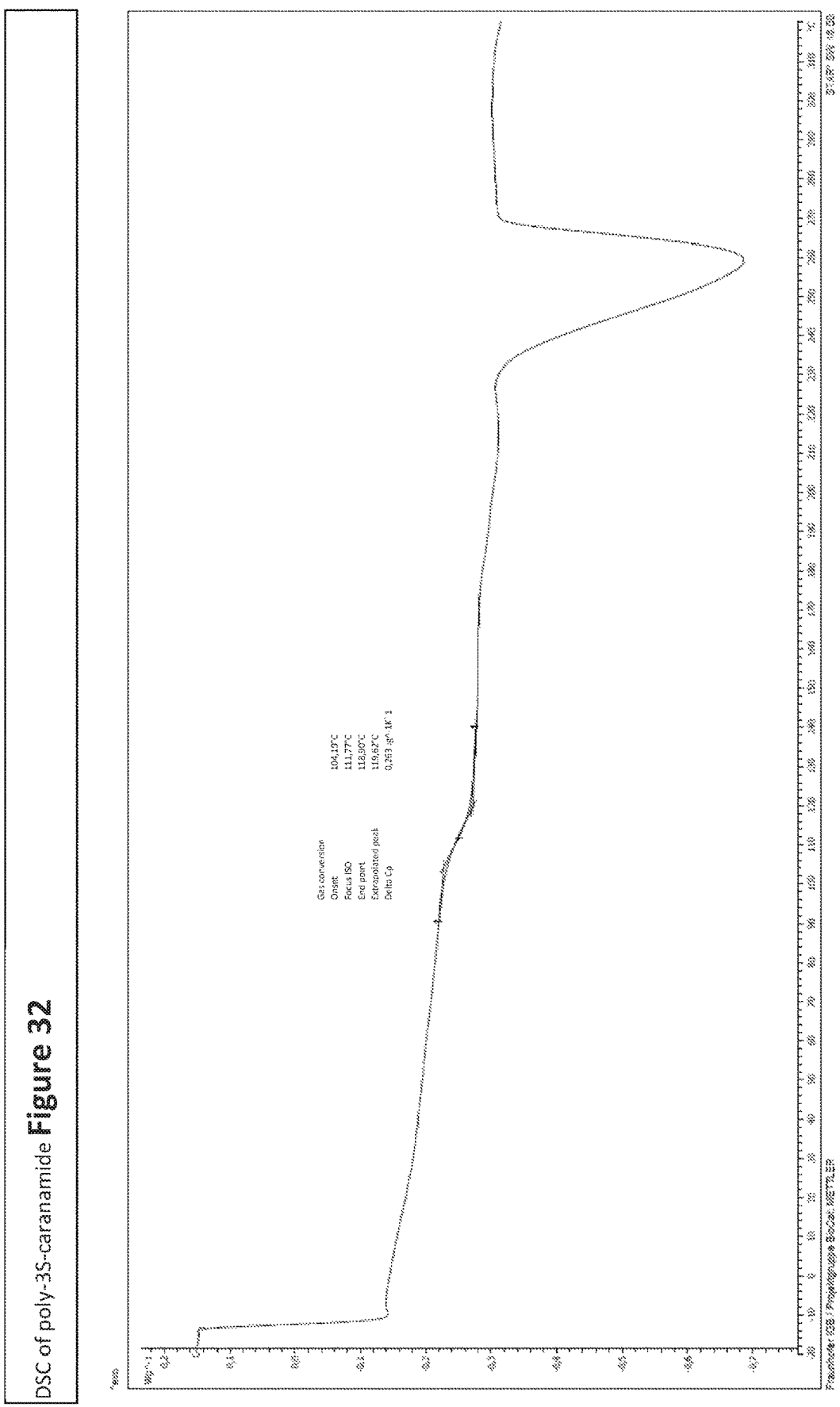
Figure 33:
Figure 34:
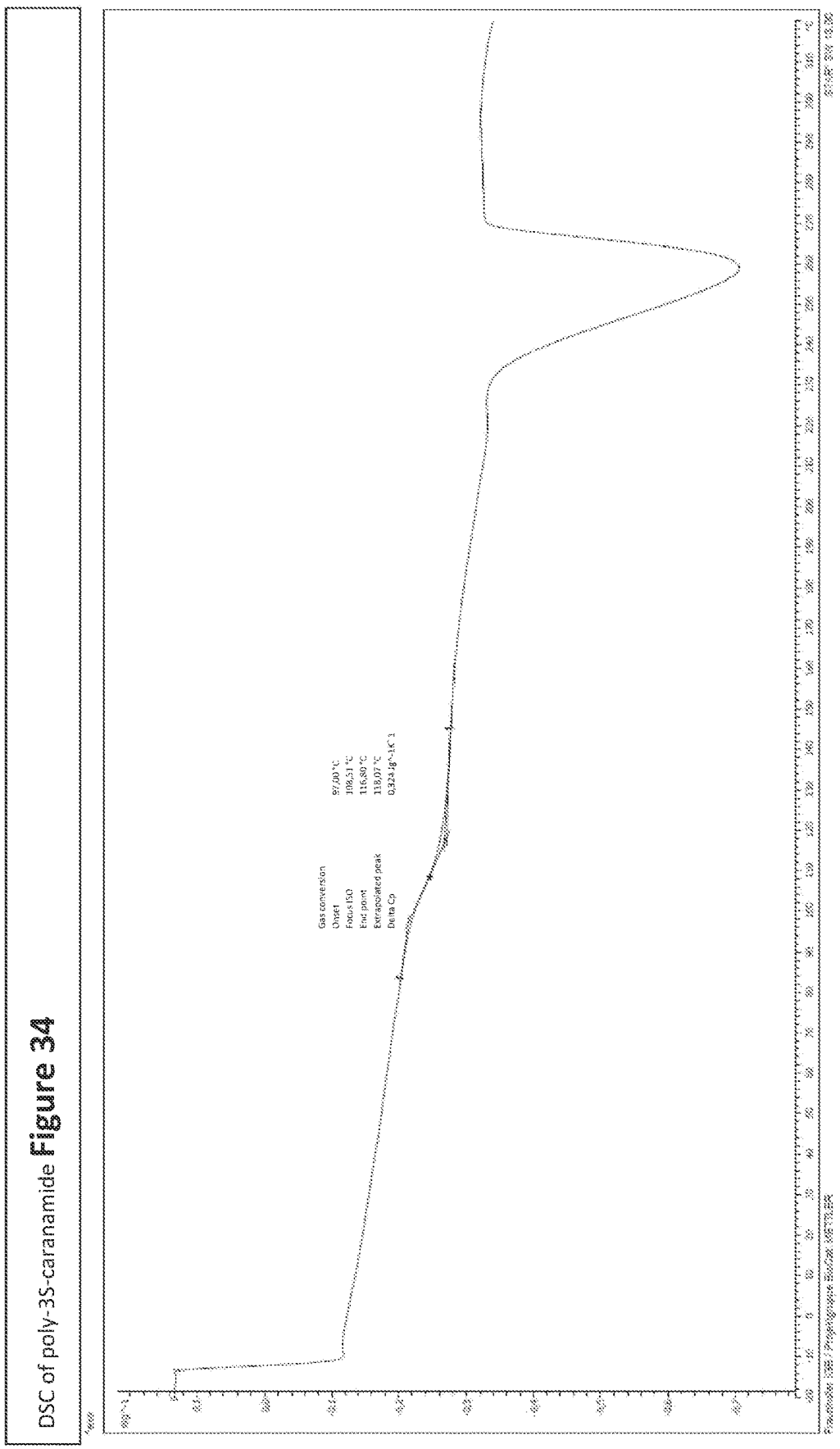
Figure 35:
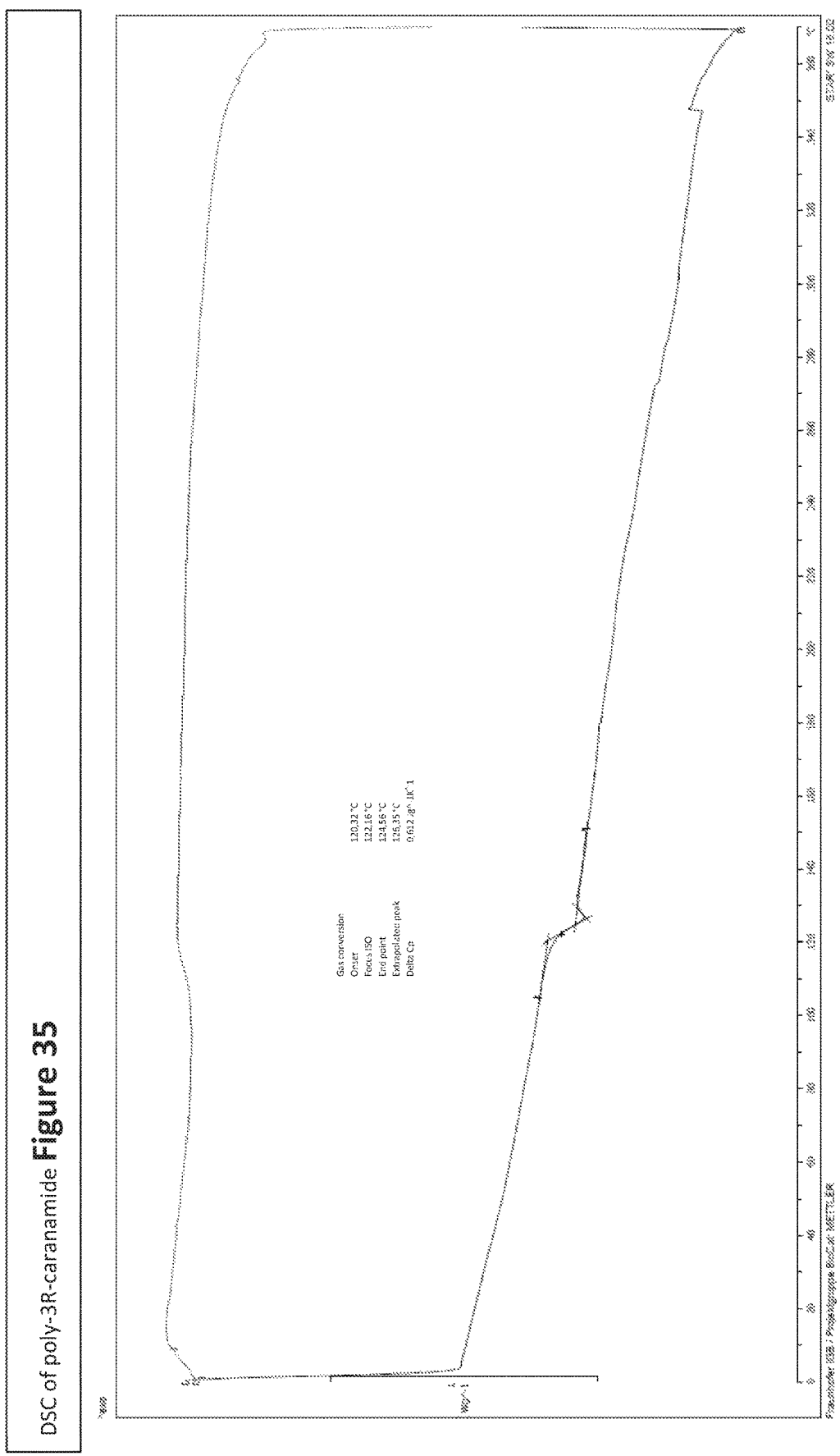
Figure 39:
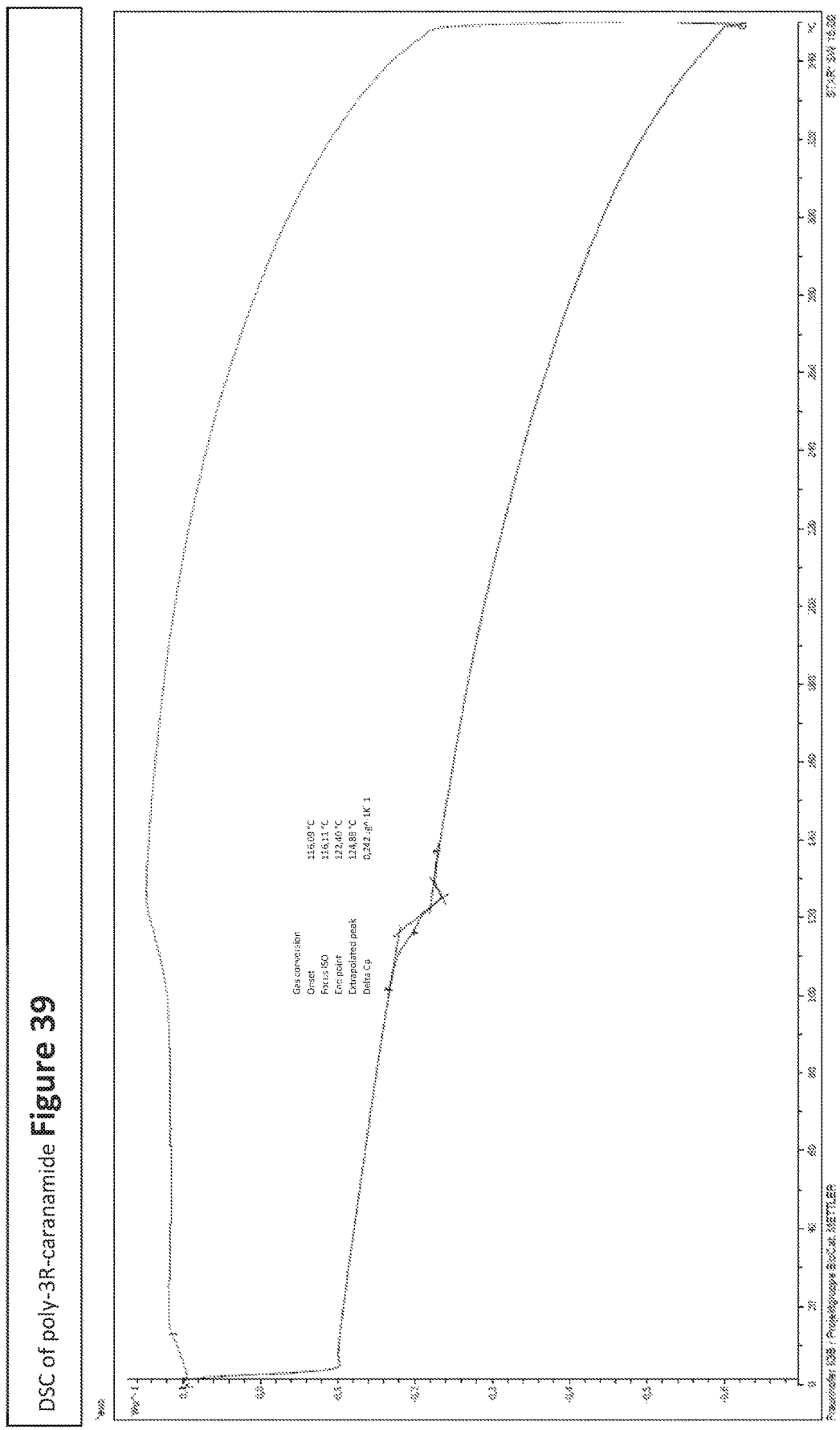
Figure 40:
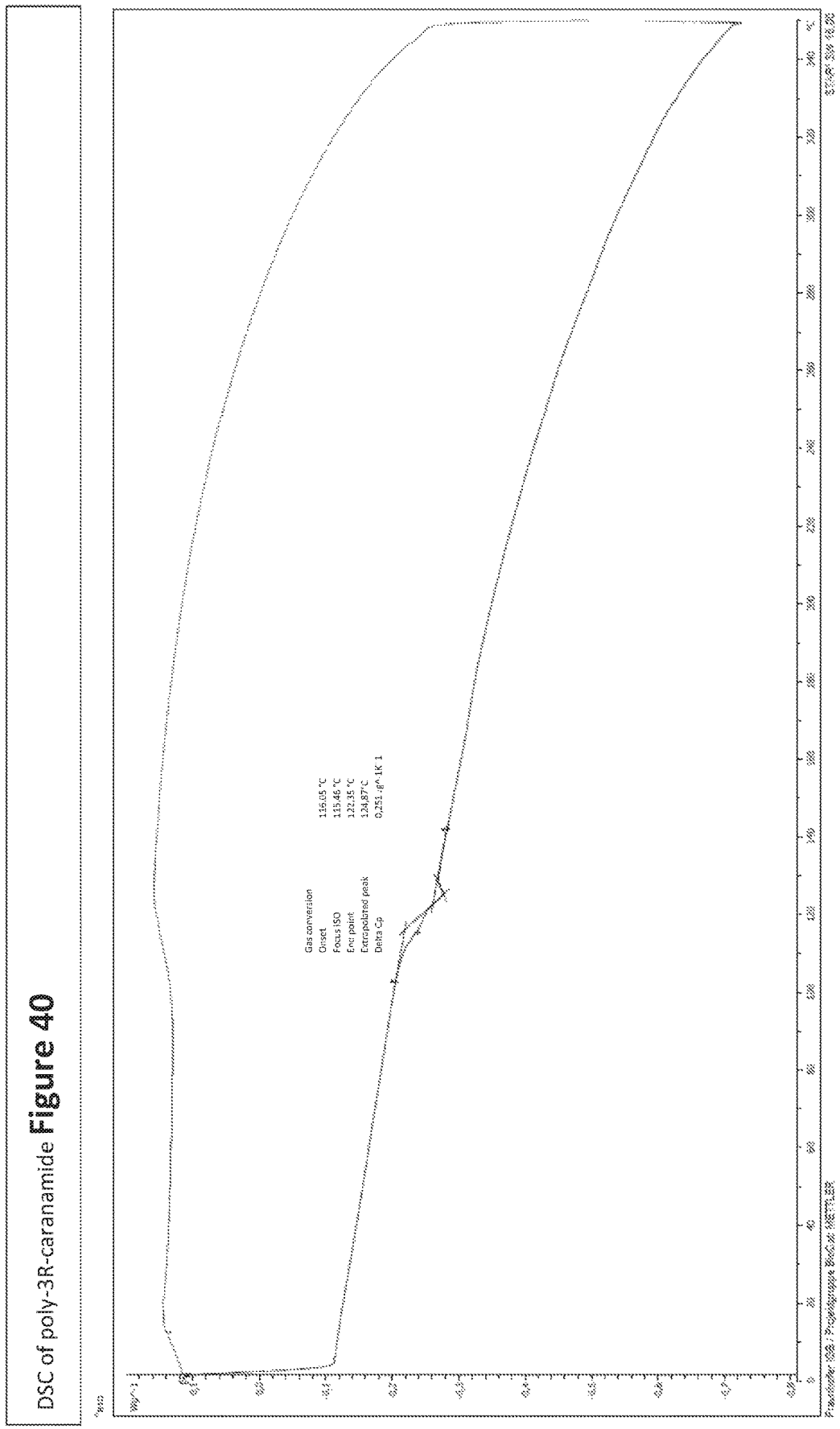
Figure 41:
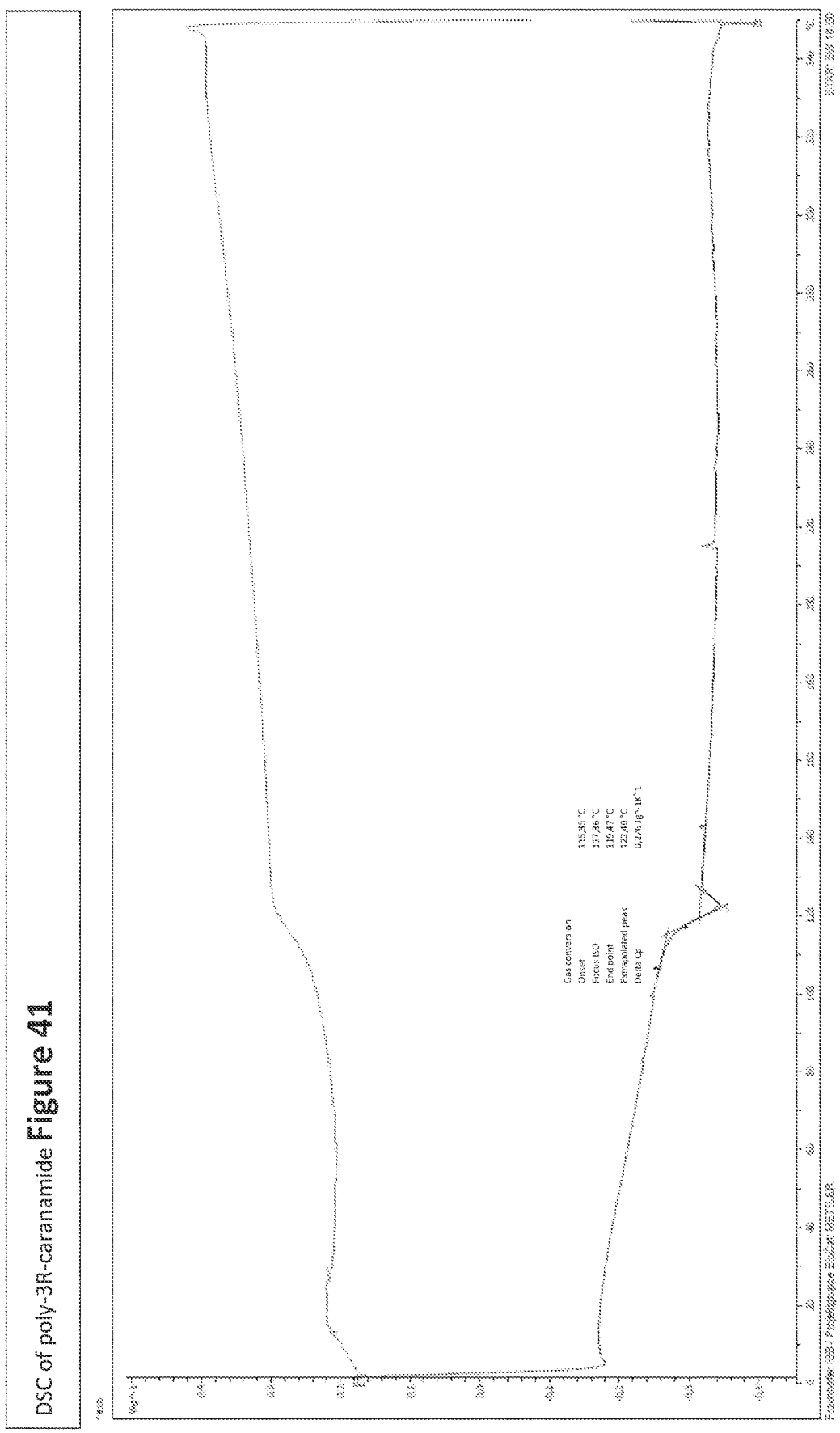
Figure 43:
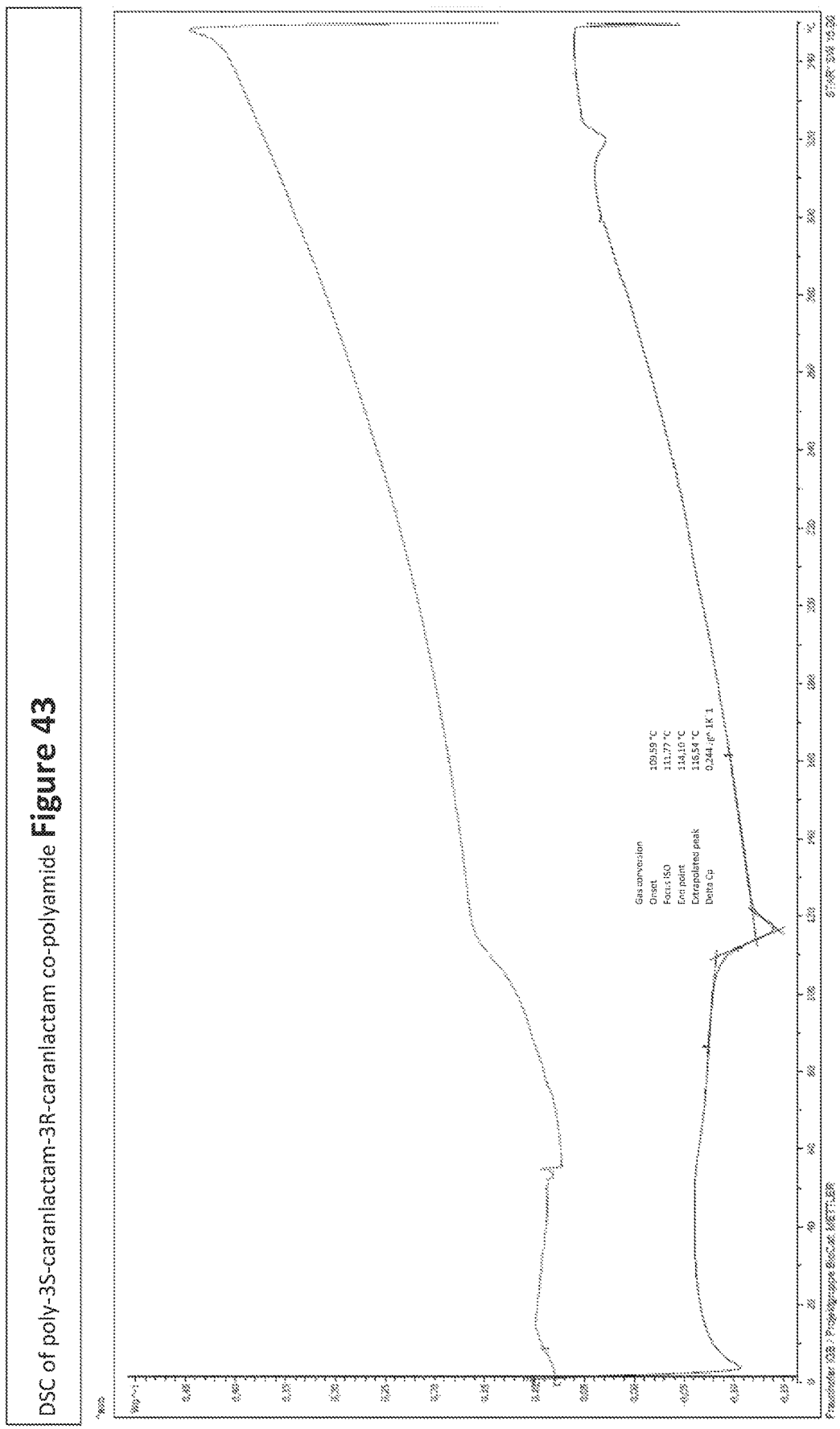
Figure 45:
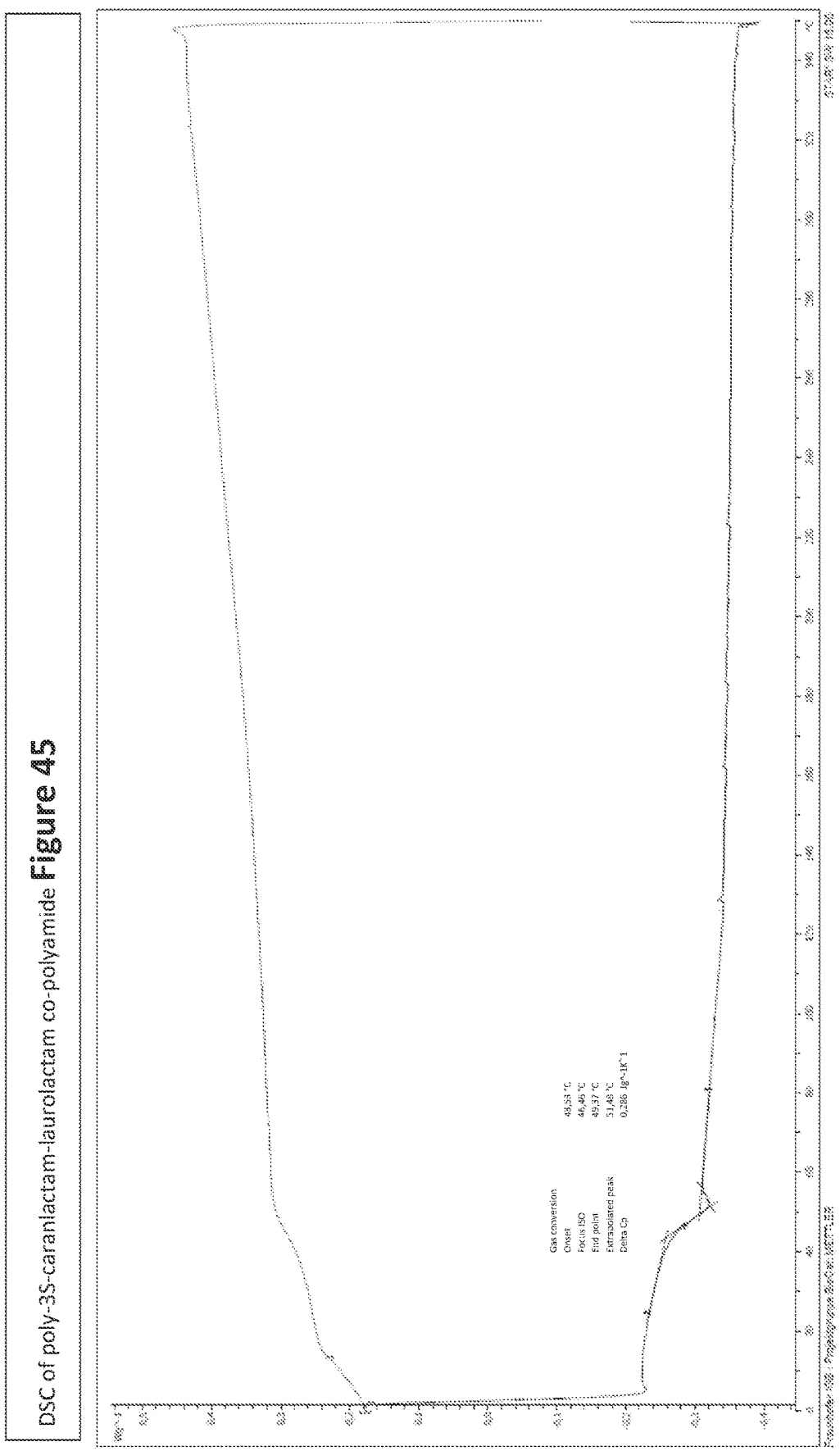

| FIG. | Description |
| --- | --- |
| FIG. 1 | An overview of the individual process steps a1) to f) |
| FIG. 2 | An overview of the individual process steps i) and i2) |
| FIG. 3 | A GC chromatogram of a 3S-caranone isomer-enriched mixture |
| FIG. 4 | A GC chromatogram of a 3R-caranone isomer-enriched mixture |
| FIG. 5 | A 1H NMR of a 3S-caranone |
| FIG. 6 | A 13C NMR of a 3S-caranone |
| FIG. 7 | A 1H NMR of a 3S-caranoxime |
| FIG. 8 | A 13C NMR of a 3S-caranoxime |
| FIG. 9 | A 1H NMR of a 3S-caranlactam |
| FIG. 10 | A 13C NMR of a 3S-caranlactam |
| FIG. 11 | A 1H NMR spectrum of a 3S-polycaranamide |
| FIG. 12 | A 13C NMR spectrum of a 3S-polycaranamide |
| FIG. 13 | A COSY spectrum of a 3S-polycaranamide |
| FIG. 14 | An HSQC spectrum of a 3S-polycaranamide |
| FIG. 15 | A DEPT spectrum of a 3S-polycaranamide |
| FIG. 16 | A 1H NMR spectrum of a 3R-polycaranamide |
| FIG. 17 | A 13C NMR spectrum of a 3R-polycaranamide |
| FIG. 18 | A COSY spectrum of a 3R-polycaranamide |
| FIG. 19 | An HSQC spectrum of a 3R-polycaranamide |
| FIG. 20 | A DEPT spectrum of a 3R-polycaranamide |
| FIG. 21 | A 1H NMR spectrum of a 3S-caranlactam-3R-caranlactam co-polycaranamide |
| FIG. 22 | A 13C-NMR spectrum of a 3S-caranlactam-3R-caranlactam co-polycaranamide |
| FIG. 23 | A 1H-NMR spectrum of a 3S-caranlactam-laurolactam co-polycaranamide |
| FIG. 24 | 1H-NMR spectrum of a 3S-caranlactam-caprolactam co-polycaranamide |
| FIG. 25 | A DSC curve of a 3S-polycaranamide |
| FIG. 26 | A DSC curve of a 3S-polycaranamide |
| FIG. 27 | A DSC curve of a 3S-polycaranamide |
| FIG. 28 | A DSC curve of a 3S-polycaranamide |
| FIG. 29 | A DSC curve of a 3S-polycaranamide |
| FIG. 30 | A DSC curve of a 3S-polycaranamide |
| FIG. 31 | A DSC curve of a 3S-polycaranamide |
| FIG. 32 | A DSC curve of a 3S-polycaranamide |
| FIG. 33 | A DSC curve of a 3S-polycaranamide |
| FIG. 34 | A DSC curve of a 3S-polycaranamide |
| FIG. 35 | A DSC curve of a 3R-polycaranamide |
| FIG. 36 | A DSC curve of a 3R-polycaranamide |
| FIG. 37 | A DSC curve of a 3R-polycaranamide |
| FIG. 38 | A DSC curve of a 3R-polycaranamide |
| FIG. 39 | A DSC curve of a 3R-polycaranamide |
| FIG. 40 | A DSC curve of a 3R-polycaranamide |
| FIG. 41 | A DSC curve of a 3R-polycaranamide |
| FIG. 42 | A DSC curve of a 3R-polycaranamide |
| FIG. 43 | A DSC curve of a 3S-caranlactam-3R-caranlactam co-polycaranamide |
| FIG. 44 | A DSC curve of a 3S-caranlactam-3R-caranlactam co-polycaranamide |
| FIG. 45 | A DSC curve of a 3S-caranlactam-laurolactam co-polycaranamide |
| FIG. 46 | A DSC curve of a 3S-caranlactam-laurolactam co-polycaranamide |
| FIG. 47 | A DSC curve of a 3S-caranlactam-laurolactam co-polycaranamide |
| FIG. 48 | A DSC curve of a 3S-caranlactam-caprolactam co-polycaranamide |
| FIG. 49 | A DSC curve of a 3S-caranlactam-caprolactam co-polycaranamide |
| FIG. 50 | A DSC curve of a 3S-caranlactam-caprolactam co-polycaranamide |
| FIG. 51 | A GPC curve of a 3S-polycaranamide |
| FIG. 52 | A GPC curve of a 3S-polycaranamide |
| FIG. 53 | A GPC curve of a 3S-polycaranamide |
| FIG. 54 | A GPC curve of a 3S-polycaranamide |
| FIG. 55 | A GPC curve of a 3S-polycaranamide |
| FIG. 56 | A GPC curve of a 3S-polycaranamide |
| FIG. 57 | A GPC curve of a 3S-polycaranamide |
| FIG. 58 | A GPC curve of a 3S-polycaranamide |
| FIG. 59 | A GPC curve of a 3S-polycaranamide |
| FIG. 60 | A GPC curve of a 3S-polycaranamide |
| FIG. 61 | A GPC curve of a 3S-polycaranamide |
| FIG. 62 | A GPC curve of a 3R-polycaranamide |
| FIG. 63 | A GPC curve of a 3R-polycaranamide |
| FIG. 64 | A GPC curve of a 3R-polycaranamide |
| FIG. 65 | A GPC curve of a 3R-polycaranamide |
| FIG. 66 | A GPC curve of a 3R-polycaranamide |
| FIG. 67 | A GPC curve of a 3R-polycaranamide |
| FIG. 68 | A GPC curve of a 3R-polycaranamide |
| FIG. 69 | A GPC curve of a 3R-polycaranamide |
| FIG. 70 | A GPC curve of a 3R-polycaranamide |
| FIG. 71 | A GPC curve of a 3R-polycaranamide |
| FIG. 72 | A GPC curve of a 3S-caranlactam-3R-caranlactam co-polycaranamide |
| FIG. 73 | A GPC curve of a 3S-caranlactam-laurolactam co-polycaranamide |
| FIG. 74 | A GPC curve of a 3S-caranlactam-laurolactam co-polycaranamide |
| FIG. 75 | A GPC curve of a 3S-caranlactam-laurolactam co-polycaranamide |
| FIG. 76 | A GPC curve of a 3S-caranlactam-caprolactam co-polycaranamide |
| FIG. 77 | A GPC curve of a 3S-caranlactam-caprolactam co-polycaranamide |
| FIG. 78 | A GPC curve of a 3S-polycaranamide |
| FIG. 79 | A GPC curve of a 3R-polycaranamide |
| FIG. 80 | A GPC curve of a 3S-caranlactam-caprolactam co-polycaranamide |
| FIG. 81 | A DSC curve of a 3S-polycaranamide |
| FIG. 82 | A DSC curve of a 3R-polycaranamide |
| FIG. 83 | A DSC curve of a 3S-caranlactam-3R-caranlactam co-polycaranamide |

Analytical Methods

GCMS Analytical Methods, Method (1) (GCMS Gas Chromatography Mass Spectrometry):

Evaluation of the reaction mixtures by means of gas chromatographic separation with subsequent mass spectrometric analysis Gas chromatography analysis was carried out on a GC-2010 Plus (Shimadzu). The separation was produced by a GC capillary column (BPX 5: 5% phenyl, 95% methylpolysilphenylene/siloxane, SGE). A MS-QP2010 Plus (Shimadzu) with electron ionization (70 eV) was used for mass spectrometry. The software analysis of the measured data was carried out with GC-MS Postrun Analysis (Shimadzu). The data obtained were compared with the National Institute of Standards and Technology database version 08.

TABLE 2

| GC specification | |
| --- | --- |
| Parameter | Values |
| Split rate | 5 |
| Injection temperature | 250° C. |
| Carrier gas | helium |
| Column flow rate | 1.69 ml/min |
| Heating program | 50° C. for 1 min. |
| | 50-120° C., heating at 15° C. per min. |
| | 120-170° C., heating at 15° C. per min. |
| | 170-200° C., heating at 15° C. per min. |
| | 200° C. for 1 min. |
| Column | BPX5 (CS Chromatography), length 30 m, Inner diameter 0.25 µm, diameter 0.25 mm |

Example chromatograms of a3S-caranone isomer-enriched mixture (FIG. 3) and a3R-caranone isomer-enriched mixture (FIG. 4) can be found in the corresponding figures.

Table 3 below shows the retention times of all product-relevant compounds:

TABLE 3

Retention times

| Compound | Retention time [min] |
| --- | --- |
| 3-carene | 5.69 |
| 3S-carane epoxide | 7.25 |
| 3S-caranone | 8.15 |
| 3R-caranone | 8.04 |
| 3R-caranoxime (trans) | 11.11 |
| 3S-caranoxime (trans) | 10.75 |
| 3S-caranlactam | 14.61 |
| 3R-caranlactam | 14.14 |

A percentage isomer ratio between 3S-caranone and 3R-caranone of an isomer-enriched mixture can be determined by a comparison (peak area of the product divided by the total peak area of both products) of the peak areas, in particular the TIC peak areas (total ion current, TIC), of the two products 3S-caranone and 3R-caranone in the retention times according to the table "Retention times of all product-relevant compounds." With the theoretical assumption—without being bound to it—that the two products 3S-caranone and 3R-caranone break down into the same number of fragments and thus cause a corresponding ion current, the numerical ratio of the two peak areas also corresponds—calculated as indicated above—to a numerical substance ratio of the two products 3S-caranone and 3R-caranone. The statements made here with regard to isomer-enriched mixtures of 3S-caranone and 3R-caranone also apply accordingly to 3-caranoxime-enriched mixtures and to 3-caranlactam-enriched mixtures.

NMR Analytical Method, Method (2) (NMR, Nuclear Magnetic Resonance): Evaluation of the Reaction Mixtures Using NMR Spectroscopy All NMR measurements were carried out on a JNM-ECA 400 MHz spectrometer from JEOL using the software JEOL Delta v5.0.4 at 25° C., using the standard pulse programs contained in JEOL Delta v5.0.4. The DEPT135° technique was used to assign the CH2 signals. 2D NMR methods (COSY, HSQC, HMBC) were applied if necessary. Polymers were measured in DCOOD, all other substances in DMSO-d6. The measurements were evaluated with the JEOL Delta v5.0.4 software.

NMR spectra (1H, 13C) of the compounds 3S-caranone (1H: FIG. 5, 13C: FIG. 6), 3S-caranoxime (1H: FIG. 7, 13C: FIG. 8) and 3S-caranlactam (1H: FIG. 9, 13C: FIG. 10) and the polymers 3S-polycaranamide (1H: FIG. 11, 13C: FIG. 12, COSY: FIG. 13, HSQC: FIG. 14, DEPT: FIG. 15), 3R-polycaranamide (1H: FIG. 16, 13C: FIG. 17, COSY: FIG. 18, HSQC: FIG. 19, DEPT: FIG. 20) and 3S/3R-co-polycaranamide (1H: FIG. 21, 13C: FIG. 22), 3S-caranlactam-laurolactam co-polycaranamide (1H: FIG. 23) and 3S-caranlactam-caprolactam co-polycaranamide (1H: FIG. 24) can be found in the corresponding figures.

DSC Analytical Method, Method (3) (DSC, Differential Scanning Calorimetry)

The DSC analysis was carried out on a DSC-One from Mettler Toledo. The measurements were evaluated with the STARe evaluation software (version: 13.00a (Build6917) by Mettler Toledo:

TABLE 4

DSC analysis specification

| c | Values |
| --- | --- |
| Protective gas | nitrogen |
| Heating run I | −20° C. to 350° C. |
| Heating run I | 20K/min |
| Cooling run I | 350° C. to −20° C. |
| Cooling run I | −20K/min |
| Heating run II | −20° C. to 350° C. |
| Heating rate II | 10K/min |
| Sample quantity | 5 mg to 10 mg |

DSC spectra of the polymers 3S-polycaranamide (FIG. 81), 3R-polycaranamide (FIG. 82) and 3S/3R-co-polycaranamide (FIG. 83) can be found in the corresponding figures, and show heating run II.

DSC Analysis, Method (3.1) (DSC, Differential Scanning Calorimetry)

The DSC analysis according to method (3.1) was carried out on a Mettler Toledo DSC 1 with the STARe V. 16.00 software. The samples (5-10 mg) were measured in aluminum crucibles under a nitrogen atmosphere. Method (3.1) was used for analysis of the 3S-polycaranamides. The corresponding FIGS. 35-50 show segment 10.

TABLE 4.1

DSC analysis specification method (3.1)

| Segment | Temperature [° C.] Start/end | Heating rate [K/min] | $N_2$ [mL/min] |
| --- | --- | --- | --- |
| 1 | −20° C., 2 min | isothermal | 50 |
| 2 | −20° C./320° C. | 10 | 50 |
| 3 | 320° C./1 min | isothermal | 50 |
| 4 | 320° C./−20° C. | −10 | 50 |
| 5 | −20° C., 1 min | isothermal | 50 |
| 6 | −20° C./320° C. | 10 | 50 |
| 7 | 320° C./1 min | isothermal | 50 |
| 8 | 320° C./−20° C. | −10 | 50 |
| 9 | −20° C., 1 min | isothermal | |
| 10 | −20° C./320° C. | 10 | |

DSC spectra of 3S-polycaranamide (FIG. 25 through and including FIG. 34) can be found in the correspondingly indicated figures.

DSC Analysis, Method (3.2) (DSC, Differential Scanning Calorimetry)

The DSC analysis according to method (3.2) was carried out on a Mettler Toledo DSC 1 with the STARe V. 16.00 software. The samples (5-10 mg) were measured in aluminum crucibles under a nitrogen atmosphere. Method (3.2) was used for 3R-polycaranamides, 3S-caranlactam-3R-caranlactam co-polycaranamides, 3S-caranlactam-laurolactam co-polyamides and 3S-caranlactam-caprolactam co-polyamides. The corresponding FIGS. 35-50 show segments 6 and 7.

TABLE 4.2

DSC analysis specification method (3.2)

| Segment | Temperature [° C.] Start/end | Heating rate [K/min] | $N_2$ [mL/min] |
| --- | --- | --- | --- |
| 1 | 20/350 | 20 | 50 |
| 2 | 350/20 | −20 | 50 |
| 3 | 20/220 | 10 | 50 |
| 4 | 220 (20 mm) | isothermal | 50 |
| 5 | 220/0 | −10 | 50 |

TABLE 4.2-continued

| DSC analysis specification method (3.2) | | | |
|---|---|---|---|
| Segment | Temperature [° C.] Start/end | Heating rate [K/min] | $N_2$ [mL/min] |
| 6 | 0/370 | 10 | 50 |
| 7 | 370/0 | −10 | 50 |
| 8 | 0/440 | 10 | 50 |

DSC spectra of 3R-polycaranamide (FIG. 35 up to and including FIG. 42) and 3S/3R-co-polycaranamide (FIG. 43 and FIG. 44), 3S-caranlactam-laurolactam co-polycaranamide (FIG. 45, FIG. 46, FIG. 47) and 3S-caranlactam-caprolactam co-polycaranamide (FIG. 48, FIG. 49, FIG. 50) can be found in the correspondingly indicated figures.

GPC Analysis, Method (4.1) (GPC, Gel Permeation Chromatography)

GPC measurements were taken on an Agilent 1200 Series with PMMA calibration. The measurements were evaluated using the ChemStation GPC analysis software (WINGPC Unity, Build 5403).

TABLE 5.1

| GPC specification method (4.1) | |
|---|---|
| Parameter | Values |
| Column | HFIP gel column |
| Eluent | HFIP |
| Temperature | 40° C. |
| Injection volume | 20 μL |
| Flow rate | 0.5 ml/min |
| Concentration | 1 g/L |

GPC spectra of the polymers 3S-polycaranamide (FIG. 78), 3R-polycaranamide (FIG. 79) and 3S-caranlactam-caprolactam co-polycaranamide (FIG. 80) can be found in the correspondingly indicated figures.

GPC Analysis, Method (4.2) (GPC, Gel Permeation Chromatography)

The GPC analysis was carried out with a SECurity GPC with autosampler (1260 Infinity, Agilent Technologies) and a TCC6000 column oven (Polymer Standard Services, PSS). The data were evaluated with PSS WinGPC UniChrom (PSS). PMMA standards were used for the narrow molecular weight calibration. PA6 standards (PSS ready-call-kit, MW/M=31400/17400 Da; 22000/13000 Da; 17200/11300 Da) were used for the broad molecular weight calibration. The lower limit of the molecular weight for evaluation was set to 1.0 kDa.

TABLE 5.2

| GPC analysis specification method (4.2) | |
|---|---|
| Parameter | Values |
| Column temperature | 35° C. |
| Flow | 0.6 mL/min |
| Eluent | 0.05M NaTFA in HFIP |
| Sample concentration | 1.0 mg/mL |
| Injection volume | 50 μL |
| Elution time | 30 min |
| Elution volume | 18.6 mL |
| Column 1 | PSS PFG guard column |
| Column 2 | PSS PFG 100 Å |
| Column 3 | PSS PFG 1000 Å |

GPC spectra of the polymers 3S-polycaranamide (FIG. 51 up to and including FIG. 61), 3R-polycaranamide (FIG. 62 up to and including FIG. 71), 3S/3R-co-polycaranamide (FIG. 72), 3S-caranlactam-laurolactam co-polycaranamide (FIG. 73, FIG. 74 and FIG. 75) and 3S-caranlactam-caprolactam co-polycaranamide (FIG. 76 and FIG. 77) can be found in the correspondingly indicated figures.

Determination of Water Absorption in a Qualitative Comparison to PA6, Method (5)

PA6 was prepared by anionic ring opening polymerization (2.8 mmol caprolactam, 0.1 mmol NaH 60% on paraffin wax, 0.05 mmol $Ac_2O$, 180° C.). Residual monomer was removed by refluxing in water/ethanol. 30-42 mg of PA6 (three samples) and at least two samples of polyamide according to the invention were annealed in the DSC (the same device as described in DSC analytical method (3)) for three minutes at 230° C. In this way, uniform polyamide blocks were made. The masses were determined on an OHAUS Discovery DV215CD balance with a maximum error of 0.01 mg. The samples were then each stirred in water at 25° C. for three days. The samples were then air dried and weighed after 30 minutes and four and a half hours. The samples were then dried at 80° C. for three hours and weighed. The qualitative water absorption compared to PA6 results from a comparison of the masses after a water bath and mass loss after the drying steps.

Determination of Transparency in a Qualitative Comparison with PA6 and PA12, Method (6)

PA6 and PA12 were dissolved in HFIP (25 mg/mL) and transferred to crystallization dishes (diameter 4 to 12 cm) or applied to PTFE film. After evaporating the solvent and drying at 85° C. for at least three hours. White, opaque films were obtained and the qualitative transparency of the polymers according to the invention was determined by visual comparison.

EMBODIMENTS

Embodiment 1 (Process Steps a), b) and c)

Synthesis of 3S-Caranone (Over 85% Isomeric Purity)

1.8 g 3S-carane epoxide (11.8 mmol) were dissolved in 6.7 mL hexane (c=1.5 M) and heated to 60° C. 7.0 mg $Fe(ClO_4)_2 \cdot H_2O$ (0.03 mmol, 0.2 mol %) were added and stirred for 20 min. The reaction mixture was cooled to 25° C. and 2 ml of semi-saturated sodium acetate solution were added. The phases were separated and the solvent was removed by distillation.

GCMS analytics (uncorrected): Total selectivity 80% caranone, ratio: 3S-caranone 85%: 15% 3R-caranone.

Mass Spectrum:

MS (EI, 70 eV): m/z (%)=153.10 (2.77), 152.10 (27.38), 138.10 (1.16), 137.10 (12.12), 135.15 (0.47), 134.10 (2.59), 125.15 (0.48), 124.10 (4.38), 123.10 (4.10), 121.10 (0.54).

MS (EI, 70 eV):% (m/z)=100.00 (67.10), 83.36 (81.10), 69.63 (41.10), 45.24 (39.10), 44.25 (82.10), 33.71 (95.10), 32.68 (109.10), 30.74 (110.10), 27.40 (55.10), 27.38 (152.10).

FIG. 4 shows the GC chromatogram of a 3S-caranone isomer-enriched mixture. FIG. 5 shows the 1H-NMR of 3S-caranone (in pure form) and FIG. 6 shows the 13C-NMR of 3S-caranone (in pure form).

NMR Assignment $^1$H NMR (400 MHz, DMSO-d6): δ/ppm=2.56-2.47 (m, 1H, —CO—CH—CH—, superposition from solvent signal), 2.10 (qdd, J=7.3, 5.0, 2.7 Hz, 1H, —CHCH$_3$—), 2.03-1.90 (m, 2H, —CHCH$_3$—CH$_2$—CH—, —CO—CH—

CH—), 1.70-1.62 (m, 1H, —CHCH$_3$—CH$_2$—CH—), 1.13 (d, J=7.2 Hz, 3H, —CHCH$_3$—), 1.04 (s, 3H, —CCHCH$_3$CH$_3$—), 1.03-0.97 (m, 1H, —CO—CH$_2$—CH—), 0.90 (s, 3H, —CCHCH$_3$CH$_3$—), 0.80 (td, J=8.9, 6.4 Hz, 1H, —CHCH$_3$—CH$_2$—CH—).

$^{13}$C NMR (100 MHz, DMSO-d6): δ/ppm=216.1 (—CO—), 40.7 (—CHCH$_3$—), 33.9 (—CO—CH$_2$—CH—), 27.8 (—CCHCH$_3$CH$_3$—, 26.3 (—CHCH$_3$—CH$_2$—CH—), 21.1 (—CO—CH$_2$—CH—), 19.0 (—CCHCHCH$_3$CH$_3$—), 16.7 (—CHCH$_3$—), 16.4 (—CO—CH$_2$—CH—), 14.6 (—CCHCHCH$_3$CH$_3$—).

Embodiment 1.1: Suitable Solvents

TABLE 6

Influence of solvent polarity on the rearrangement of 3S-carane epoxide to a 3S-caranone and 3R-caranone enriched mixture. All experiments were carried out with a concentration of 1M 3S-carane epoxide at 25° C. and 0.2 mol % Fe(ClO$_4$)$_2$•H$_2$O for 8 h. The conversion of 3S-carane epoxide was 100%. Values refer to the TIC area of the GCMS spectrum (uncorrected values).

| | Solvent | Relative polarity * | Caranone [%] | 3R-caranone [%] | 3S-caranone [%] |
|---|---|---|---|---|---|
| 1 | Cyclohexane | 0.006 | 70 | 11 | 89 |
| 2 | Hexane | 0.009 | 64 | 13 | 87 |
| 3 | Toluene | 0.099 | 71 | 14 | 86 |
| 4 | Heptane | 0.012 | 64 | 13 | 87 |

*Source: Christian Reichardt, Solvents and Solvent Effects in Organic Chemistry, Wiley-VCH Publishers, 3rd Ed., 2003

Embodiment 1.2.1: Comparison of Zinc and Iron Lewis Acids

TABLE 7

Comparison of Fe and Zn Lewis acids at 60° C. in cyclohexane with a concentration of 1M 3S-carane epoxide and 0.2% catalyst (mol %). Values refer to the TIC area of the GCMS spectrum (uncorrected values).

| | Catalyst [0.2%] | Conversion [%] | Caranone [%] | 3R-caranone [%] | 3S-caranone [%] | t [h] |
|---|---|---|---|---|---|---|
| 1 | Zn(OTf)$_2$ | 48 | 70 | 9 | 91 | 40 |
| 2 | Fe(OTf)$_2$ | 91 | 73 | 15 | 85 | 0.5 |
| 3 | Fe(ClO$_4$)$_2$·H$_2$O | 100 | 82 | 15 | 85 | 0.5 |
| 4 | Fe(ClO$_4$)$_3$·H$_2$O | 100 | 81 | 16 | 84 | 0.5 |

Embodiment 1.2.2: Comparison of Different Sulfonic Acids

TABLE 8

Conversion with Meinwald rearrangement of 3S-carane epoxide to a 3S-caranone and 3R-caranone-enriched mixture with various sulfonic acids as acid catalyst. The values in Table 4 refer to the TIC area of the GCMS spectrum (uncorrected values).

| | Catalyst [%] | Solvent | c [M] | T [° C.] | Conversion [%] | Caranone [%] | 3R-caranone [%] | 3S-caranone [%] | t [h] |
|---|---|---|---|---|---|---|---|---|---|
| 1 | CF$_3$SO$_3$H 0.1% | Toluene | 1 | 25 | 100 | 73 | 13 | 87 | 12 |
| 2 | PTSA 1% | Cyclohexane | 1 | 60 | 100 | 69 | 17 | 83 | 12 |

Embodiment 1.3: Suitable Concentrations of Lewis Acid

TABLE 9

Influence of the amount of Fe(ClO$_4$)$_2$•H$_2$O on the rearrangement to the 3R and 3S-caranone isomers. All experiments were carried out with a concentration of 1M 3S-carane epoxide at 25° C. for 5 h. Values refer to the TIC area of the GCMS spectrum (uncorrected values). All experiments were carried out in cyclohexane.

| | Fe(ClO$_4$)$_2$•H$_2$O [mol %] | Conversion [%] | Caranone [%] | 3R-caranone [%] | 3S-caranone [%] |
|---|---|---|---|---|---|
| 1 | 0.1 | 90 | 71 | 20 | 80 |
| 2 | 0.25 | 95 | 69 | 14 | 86 |
| 3 | 0.5 | 98 | 67 | 15 | 85 |
| 4 | 1 | 100 | 63 | 15 | 85 |

Embodiment 1.4: Suitable Concentrations of 3S-Carane Epoxide

TABLE 10

Influence of the concentration of 3S-carane epoxide on the rearrangement of 3S-carane epoxide to a 3S-caranone and 3R-caranone enriched mixture. All experiments were carried out at 25° C. and 0.2% Fe(ClO$_4$)$_2$•H$_2$O for 7 h. Values refer to the TIC area of the GCMS spectrum (uncorrected values). All experiments were carried out in cyclohexane.

| | 3S-carane epoxide [M] | Conversion [%] | Caranone [%] | 3R-caranone [%] | 3S-caranone [%] |
|---|---|---|---|---|---|
| 1 | 0.25 | 8 | 56 | 20 | 80 |
| 2 | 0.5 | 78 | 74 | 13 | 87 |
| 3 | 1.0 | 100 | 70 | 10 | 90 |
| 4 | 2.0 | 100 | 67 | 10 | 90 |
| 5 | 3.0 | 100 | 66 | 10 | 90 |

Embodiment 1.5: Temperature Influence

TABLE 11

Temperature influence of Lewis acids on the Meinwald rearrangement of 3S-carane epoxide.
Values refer to the TIC area of the GCMS spectrum (uncorrected values).

| | Catalyst [%] | Solvent | c [M] | T [° C.] | Conversion [%] | Caranone [%] | 3R-caranone [%] | 3S-caranone [%] | t |
|---|---|---|---|---|---|---|---|---|---|
| 1 | Fe(ClO$_4$)$_2$ · H$_2$O 0.2% | Cyclohexane | 1 | 25 | 100 | 70 | 10 | 90 | 7 h |
| 2 | Fe(ClO$_4$)$_2$ · H$_2$O 0.2% | Cyclohexane | 1 | 60 | 100 | 82 | 15 | 85 | 5 min |

Embodiment 1.6: Non-Iron Based Lewis Acids 15.2 mg 3S-carane epoxide (0.1 mmol) are dissolved in 1 mL toluene. Then 2 mol % of Ni(ClO$_4$)$_2$ solution in ethyl acetate are added and the reaction mixture is heated to 60° C. for 20.5 h. GCMS analysis (uncorrected): Caranone total purity 88.9%, 3S-caranone 92.0%, and 3R-caranone 8.0%.

15.2 mg 3S-carane epoxide (0.1 mmol) are dissolved in 1 mL toluene. Then 2 mol % of Co(ClO$_4$)$_2$ solution in ethyl acetate are added and the reaction mixture is heated to 60° C. for 20.5 h. GCMS analysis (uncorrected): Caranone total purity 89.0%, 3S-caranone 93.3%, and 3R-caranone 6.7%.

152 mg 3S-carane epoxide (0.1 mmol) are dissolved in 1 mL toluene. Then 2 mol % Cu(CO$_4$)$_2$ solution in ethyl acetate are added and the reaction mixture is stirred for 20 h at room temperature. GCMS analysis (uncorrected): Caranone total purity 63.0%, 3S-caranone 85.0%, and 3R-caranone 15.0%.

Embodiment 2.1 (Process Step d)): Isomerization of 3S-Caranone to 3R-Caranone

152 µL of an approximately 80% solution of a 3S-caranone (87%) and 3R-caranone (13%) enriched mixture from embodiment 1 were dissolved in 845 µL MeCN and 5 µL sulfuric acid was added. The reaction mixture was stirred at 60° C. for 5 h. The solvent was removed by distillation.

GCMS analytics (uncorrected): Total selectivity 80% caranone, ratio: 3S-caranone 15%: 85% 3R-caranone. FIG. 4 shows the GC chromatogram of a 3R-caranone isomer-enriched mixture. FIG. 5 shows the 1H-NMR of 3S-caranone (in pure form) and FIG. 6 shows the 13C-NMR of 3S-caranone (in pure form).

Embodiment 2.2 (Process Step d)): Influence of Solvent on the Isomerization of 3S-Caranone to 3R-Caranone (III)

TABLE 12

Influence of the solvent on the isomerization of a 3S-caranone-enriched mixture (purity 79%, 3S-caranone 89%, 3R-caranone 11%).
All experiments were carried out with a concentration of 1M 3S-caranone and 2M HCl solution as an isomerization catalyst. Samples were taken after 6 h at room temperature (a), another 15 h at room temperature (b) and another 48 h at 60° C. (c) stirring. Values refer to the TIC area of the GCMS spectrum (uncorrected values).

| | Solvent | Relative polarity* | Caranone [%] | | | 3S-caranone [%] | | | 3R-caranone [%] | | |
|---|---|---|---|---|---|---|---|---|---|---|---|
| | | | (a) | (b) | (c) | (a) | (b) | (c) | (a) | (b) | (c) |
| 1 | Tetrahydrofuran | 0.207 | 76 | 76 | 73 | 22 | 15 | 22 | 78 | 85 | 78 |
| 2 | Ethyl acetate | 0.228 | 77 | 77 | 73 | 45 | 15 | 22 | 55 | 85 | 78 |
| 3 | Acetone | 0.355 | 78 | 78 | 30 | 15 | 15 | 0 | 85 | 85 | 100 |
| 4 | Acetonitrile | 0.460 | 78 | 78 | 20 | 20 | 18 | 0 | 80 | 82 | 100 |

Embodiment 3.1 (Process Step a1a): Epoxidation of 3-Carene to 3S-Carane Epoxide Using the Enzyme Lipase Cal-B (Over 99%)

10.87 g of 3-carene (80 mmol) were dissolved in 160 ml of ethyl acetate and transferred to a reactor with KPG stirring unit and nylon enzyme bag loaded with 2.5 g of Lipase Cal-B from *Candida antarctica* (immobilized). The mixture was heated to 60° C. and 9.35 g of $H_2O_2$ 35% were added continuously (2 ml/h). After 4 h, the reaction mixture was cooled to room temperature and the enzyme pocket was removed and washed with 2×50 mL NaOH 2 M, 1×50 mL saturated $Na_2SO_3$ solution and 1×50 mL water. The solvent was removed under vacuum.

GCMS analysis (uncorrected): 3S-carane epoxide (2)>99%

Embodiment 3.2 (Process Step a1a)): Epoxidation of 3-Carene with Dilute Peracetic Acid to 3S-Carane Epoxide (Over 99%)

1 eq. NaOAc is dissolved in 12% peracetic acid to c=1M (corresponds to 1.3 eq peracetic acid) and 1 eq at room temperature. 3-carene was added within an hour. The temperature is kept constantly below 40° C.

GCMS analysis (uncorrected): 3S-carane epoxide (2)>99%

Exemplary Embodiment 3.3 (Process Step a1b): Epoxidation of 3-Carene to 3R-Carane Epoxide (Purity Over 85%)

50 g of 3-carene (367 mmol, 1.0 eq.) were dissolved in 200 mL acetone and 200 mL water and brought to 0° C. 72 g of N-bromosuccinimide (404 mmol, 1.1 eq.) were added in portions; the internal temperature was kept below 10° C. It was stirred for 0.5 h at a temperature below 10° C., then stirred at room temperature for a further 2 h. Subsequently, 250 ml of 5M NaOH were added dropwise (5.5 ml/min.) and the mixture was stirred until the 3R-carane epoxide was completely converted (0.5 h). The reaction mixture was mixed with 200 mL hexane and the phases were separated. The aqueous phase was extracted with 200 mL hexane. The combined organic phases were washed with 250 ml of saturated sodium sulfite solution and 250 ml of water. The solvent was then removed at 50° C. under vacuum. 50 g of 3R-carane epoxide (purity above 85%) were obtained (312 mmol, 85%).

Embodiment 4.1 (Process Step e)): Oximation of 3S-Caranone

A 3S-caranone and 3R-caranone-enriched mixture (80% purity, 85% 3S-caranone, 15% 3R-caranone) was dissolved in acetonitrile to c=2 M. Then 1.3 eq NaOAc in water were added in the same volume and stirred for 5 min. 1.1 eq $HONH_2·HCl$ are added and the mixture is stirred at 25° C. for one hour.

GCMS analysis (uncorrected): Total oximes 80%, of which 3S-caranoxime 85%, 3R-caranoxime 15%.

Mass Spectrum:
MS (EI, 70 eV): m/z (%)=168.05 (1.30), 167.00 (11.80), 166.05 (1.66), 153.10 (1.47), 152.05 (15.72), 151.05 (1.69), 150.05 (10.83), 149.05 (1.90), 148.10 (5.97), 139.10 (2.56).

MS (EI, 70 eV):% (m/z)=100.00 (41.05), 51.40 (39.10), 47.59 (67.05), 43.19 (112.10), 42.42 (79.05), 41.89 (107.10), 40.65 (55.10), 39.11 (106.05), 38.33 (43.05), 29.88 (81.05).

NMR Assignment
$^1H$ NMR (400 MHz, DMSO-d6): δ/ppm=10.07 (s, 1H, —NO<u>H</u>), 2.56 (dd, J=18.6, 1.6 Hz, 1H, —CNOH—C<u>H</u>$_2$—CH—), 2.32-2.17 (m, 2H, —C<u>H</u>CH$_3$—, —CNOH—C<u>H</u>$_2$—CH—), 1.90-1.78 (m, J=16.8, 8.1, 3.1 Hz, 1H, —CHC<u>H</u>$_3$—C<u>H</u>$_2$—CH—), 1.37 (dt, J=14.4, 4.9 Hz, 1H, —CHC<u>H</u>$_3$—C<u>H</u>$_2$—CH—), 1.05 (d, J=7.1 Hz, 3H, CH$_2$—CHC<u>H</u>$_3$—CNOH—), 0.96 (s, 3H, —CCHCHC<u>H</u>$_3$CH$_3$—), 0.79 (td, J=8.9, 1.8 Hz, 1H, —CNOH—CH$_2$—C<u>H</u>—) 0.71 (s, 3H, —CCHCHCH$_3$C<u>H</u>$_3$—), 0.69-0.62 (m, 1H, C<u>H</u>CH$_3$—CH$_2$—CH—).

$^{13}C$ NMR (100 MHz, DMSO-d6): δ/ppm=161.5 (—<u>C</u>NOH—), 32.8 (—<u>C</u>HCH$_3$—), 28.5 (—<u>C</u>CHCH$_3$CH$_3$—), 26.8 (—<u>C</u>HCH$_3$—<u>C</u>H$_2$—CH—), 19.3 (CH$_2$—<u>C</u>HCH$_3$—CNOH—), 19.1 (—CNOH—<u>C</u>H$_2$—CH—), 18.3 (<u>C</u>CHCHCH$_3$CH$_3$), 17.1 (—CNOH—CH$_2$—<u>C</u>H—), 16.7 (—CHCH$_3$—CH$_2$—<u>C</u>H—), 14.9 (—CCHCHCH$_3$<u>C</u>H$_3$—).

FIG. 7 shows the 1H-NMR of 3S-caranoxime (in pure form) and FIG. 8 shows the 13C-NMR of 3S-caranoxime (in pure form).

Exemplary Embodiment 4.2 (Process Step e): Oximation of 3R-Caranone 9.00 g of 3R-caranone (58 mmol) are dissolved in 60 mL acetonitrile. 50 ml of water with 10.6 g of sodium acetate trihydrate (75 mmol) and 4.6 g of hydroxylamine hydrochloride (64 mmol) are then added and the mixture is stirred at 60° C. for 20 h. The reaction mixture was washed with sodium hydrogen carbonate solution and water, dried with magnesium sulfate and concentrated under vacuum. 5 g of the crude product were purified via column chromatography (hexane/EtOAc). The yield was 3.6 g (72%) with a purity of 92%. The ratio of the oximes is 3R-caranoxime 85%, 3S-caranoxime 15%.

Embodiment 5.1.1 (Process Step f1)): Beckmann Rearrangement of 3S-Caranoxime The reaction mixture from embodiment 4.1 (process step e)) is cooled to 15° C. and 4 eq NaOH as 10M NaOH are slowly added. After two hours of stirring at 15° C., 1 eq of para-toluenesulfonyl chloride is added in portions and the mixture is stirred for a further two hours at room temperature. The aqueous phase is separated off and extracted with ethyl acetate (twice equal in volume). The organic phases are washed with semi-saturated sodium bicarbonate solution (2×) and then with saturated sodium chloride solution.

GCMS analysis (uncorrected): Caranlactams total purity 62%, 3S-caranlactam 94.9% and 3R-caranlactam 5.1%.

Mass Spectrum
MS (EI, 70 eV): m/z (%)=168.10 (1.05), 167.15 (8.33), 166.25 (0.70), 154.20 (0.30), 153.20 (4.44), 152.20 (44.99), 151.25 (0.22), 150.20 (0.23), 139.20 (1.42), 138.15 (1.09).

MS (EI, 70 eV):% (m/z)=100.00 (44.10), 60.39 (67.10), 44.99 (152.20), 44.18 (81.10), 42.43 (82.10), 37.54 (110.15), 35.25 (41.05), 28.11 (57.10), 19.97 (39.05), 19.46 (55.10).

FIG. 9 shows the 1H-NMR of 3S-caranlactam (in pure form) and FIG. 10 shows the 13C-NMR of 3S-caranlactam (in pure form).

NMR Assignment
$^1H$ NMR (400 MHz, DMSO-d6): δ/ppm=6.92 (s, 1H, —CO—N<u>H</u>—) 3.5-3.14 (m, 1H, —NH—C<u>H</u>CH$_3$—CH$_2$—), 2.31-2.15 (m, 2H, —CO—C<u>H</u>—CH—), 1.71-1.49 (m, 2H, —CH—C<u>H</u>$_2$—CCHCH$_3$—), 1.05 (d, J=6.4 Hz, 3H, —NH—CHCH₃—), 1.01 (s, 3H, —CCHCHCH₃CH₃—), 0.97 (s, 3H, —CCHCHCH₃CH₃—), 0.85-0.76 (m, 1H, —CCHCHCH₃CH₃—), 0.57 (td, J=9.0, 2.1 Hz, 1H, —CCHCHCH₃CH₃—)

¹³C NMR (100 MHz, DMSO-d6): δ/ppm=173.8 (—CO—), 46.3 (—NH—CHCH₃—), 30.6 (—CO—CH₂—CH—), 30.4 (CH—CH₂—CHCH₃—), 28.6 (—CCHCHCH₃CH₃—), 21.11 (—NH—CHCH₃—), 20.1 (CO—CH₂—CH—), 20.1 (—CHCH₃—CH₂—CH—), 17.4 (—CCHCHCH₃CH₃—), 14.9 (—CCHCHCH₃CH₃—).

Embodiment 5.1.2 (Process Step f2): Catalytic Beckmann Rearrangement of 3S-Caranoxime 167 mg of 3S-caranoxime (1.0 mmol) were dissolved in 2 mL MeCN and heated under reflux. Then 7.5 mol % of Zn(ClO₄)₂·6H₂O was added and the mixture was stirred for 48 h. The solvent was removed under vacuum and the residue was dissolved in ethyl acetate and washed several times with semi-saturated sodium hydrogen carbonate solution and water. After crystallization from ethyl acetate, 120 mg of 3S-caranlactam were obtained (72%).

Embodiment 5.2 (Process Steps e) and f)): Oximation and Beckmann Rearrangement in One Step (One-Pot)

35 g of a mixture of 3S-caranone (15%) and 3R-caranone (85%) were dissolved in 280 ml of acetonitrile (MeCN) and mixed with 280 ml of water and 50 g of sodium acetate. Then 19.5 g of hydroxylamine hydrochloride were added and the mixture was stirred at room temperature for 48 h. The phases were separated and 270 ml of 3M NaOH were added in portions to the organic phase while cooling in an ice bath. The reaction mixture was stirred in an ice bath for 2 h and then 53.2 g of tosyl chloride were added in portions. The reaction mixture was stirred for 4 h, then washed with 2M hydrochloric acid, sodium hydrogen carbonate solution and semi-saturated sodium chloride solution. The solvent was removed under vacuum and the obtained crude product was recrystallized several times from ethyl acetate. 7.90 g (20%) of pure 3R-caranlactam were obtained.

Embodiment 6.1 (Process Steps g) and h)): Obtaining Crystalline 3S-Caranlactam The reaction mixture from embodiment 5 (process step f)) is fractionally distilled until the 3S-caranlactam is almost completely crystallized. The remaining portion of 3R-caranlactam cannot crystallize under the reaction conditions and is therefore removed by a further distillation step (process step h)), so that the 3S-caranlactam is obtained. The 3R-caranlactam can be obtained as the distillate from the distillation mentioned.

Exemplary Embodiment 6.2 (Process Steps g) and h)): Obtaining 3R-Caranlactam The 3R-caranlactam was obtainable as a pure product from the mother liquor (remaining solution from embodiment 6.1) of the synthesis of 3S-caranlactam after distillation (bp: 350° C.) and multiple recrystallization (ethyl acetate).

Embodiment 6.3 (Process Steps g) and h)): Obtaining 3R-Caranlactam 3.50 g of 3R-caranoxime (21 mmol) were dissolved in 25 mL acetonitrile and cooled in an ice bath. Then 33 mL NaOH 2M were added in portions and stirred for 2 h. Then 4.50 g of tosyl chloride (23 mmol) were added in portions and the mixture was stirred in an ice bath for 2.5 h.

The reaction mixture was washed with sodium hydrogen carbonate solution and water, dried with magnesium sulfate and concentrated under vacuum. The crude product was recrystallized from ethyl acetate at −20° C. and 2.61 g (75%) of pure 3R-caranlactam were obtained.

Embodiment 7.1 (Process Step i)): Polymerization of 3S-Caranlactam to a 3S-Polycaranamide 300 mg of 3S-caranlactam (1.8 mmol), 10 mg of N-benzoyl-3S-caranlactam (Bz-5, 0.036 mmol) and 0.5 mg of NaH on paraffin (0.02 mmol) were mixed in a vacuum glass vessel and evacuated for 10 min. at 2 mbar. The reaction vessel was transferred to a 180° C. oil bath and stirred. The polymerization was complete after about 20 seconds, the polymer was slowly cooled to room temperature and a partially crystalline 3S-polycaranamide was obtained. According to NMR analysis, the homopolymers are isotactic.

Embodiment 7.1.1 (Process Step i))

Polymerization of 3S-Caranlactam to a 3S-Polycaranamide
300 mg of 3S-caranlactam (1.80 mmol), 10 mg of N-benzoyl-3S-caranlactam (Bz-5, 0.036 mmol) and 0.5 mg of NaH on paraffin (0.01 mmol) were mixed in a vacuum glass vessel and evacuated for 10 min. at 2 mbar. The reaction vessel was transferred to a 180° C. oil bath and stirred. The reaction mixture was kept at temperature for five minutes, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.

DSC method (3.1)
Tg (center point): 115° C.
Tm (range): 260-290° C.
Mn: 10.5 kDa (GPC method 4.2)
Mw: 16.8 kDa (GPC method 4.2)
PD: 1.6
1H (FIG. 11)
13C (FIG. 12)
COSY: (FIG. 13)
HSQC: (FIG. 14)
DEPT: (FIG. 15)
DSC: (FIG. 25)
GPC: (FIG. 51)
Crystallinity: semi-crystalline

Embodiment 7.1.2 (Process Step i))

Polymerization of 3S-Caranlactam to a 3S-Polycaranamide
300 mg of 3S-caranlactam (1.8 mmol), 5.4 mg of N-benzoyl-3S-caranlactam (Bz-5, 0.02 mmol) and 3.5 mg of NaH on paraffin (0.09 mmol) were mixed in a vacuum glass vessel mixed and evacuated for 10 min. at 2 mbar. The reaction vessel was transferred to a 180° C. oil bath and stirred. The reaction mixture was kept at temperature for 1.5 hours, then was cooled in air to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.

DSC method (3.1)
Tg (center point): 115° C.
Tm (range): 250-285° C.
Mn: 10.2 (GPC method 4.2)
Mw: 16.2 (GPC method 4.2)
PD: 1.6
DSC: (FIG. 26)
GPC: (FIG. 52)
Crystallinity: semi-crystalline

Embodiment 7.1.3 (Process Step i))

Polymerization of 3S-Caranlactam to a 3S-Polycaranamide 302 mg 3S-caranlactam (1.81 mmol), 9.8 mg N-benzoyl-3S-caranlactam (Bz-5, 0.036 mmol) and 0.9 mg NaH on paraffin (0.02 mmol) were mixed in a vacuum glass vessel and evacuated for 10 min. at 2 mbar. The reaction vessel was transferred to a 180° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.

DSC process 3.1
Tg (center point): 115° C.
Tm (range): 260-290° C.
Mn: 9.3 kDa (GPC method 4.2)
Mw: 14.5 kDa (GPC method 4.2)
PD: 1.6
DSC: (FIG. 27)
GPC: (FIG. 53)
Crystallinity: semi-crystalline

Embodiment 7.1.4 (Process Step i))

Polymerization of 3S-Caranlactam to a 3S-Polycaranamide 305 mg of 3S-caranlactam (1.84 mmol), 10.7 mg of N-benzoyl-3S-caranlactam (Bz-5, 0.039 mmol) and 1.6 mg of NaH on paraffin (0.04 mmol) were mixed in a vacuum glass vessel and evacuated for 10 min. at 2 mbar. The reaction vessel was transferred to a 180° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.

DSC process 3.1
Tg (center point): 113° C.
Tm (range): 255-285° C.
Mn: 9.1 kDa (GPC method 4.2)
Mw: 14.1 kDa (GPC method 4.2)
PD: 1.3
DSC: (FIG. 28)
GPC: (FIG. 54)
Crystallinity: semi-crystalline

Embodiment 7.1.5 (Process Step i))

Polymerization of 3S-Caranlactam to a 3S-Polycaranamide 308 mg of 3S-caranlactam (1.84 mmol), 20.7 mg of N-benzoyl-3S-caranlactam (Bz-5, 0.076 mmol) and 4.0 mg of NaH on paraffin (0.1 mmol) were mixed in a vacuum glass vessel and evacuated for 10 min. at 2 mbar. The reaction vessel was transferred to a 180° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.

DSC process 3.1
Tg (center point): 111° C.
Tm (range): 245-285° C.
Mn: 6.7 kDa (GPC method 4.2)
Mw: 9.5 kDa (GPC method 4.2)
PD: 1.4
DSC: (FIG. 29)
GPC: (FIG. 55)
Crystallinity: semi-crystalline

Embodiment 7.1.6 (Process Step i))

Polymerization of 3S-Caranlactam to a 3S-Polycaranamide 300 mg of 3S-caranlactam (1.80 mmol), 30.0 mg of N-benzoyl-3S-caranlactam (Bz-5, 0.11 mmol) and 3.9 mg of NaH on paraffin (0.10 mmol) were mixed in a vacuum glass vessel and evacuated for 10 min. at 2 mbar. The reaction vessel was transferred to a 180° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.

DSC process 3.1
Tg (center point): 105
Tm (range): 240-280° C.
Mn: 5.9 kDa (GPC method 4.2)
Mw: 8.3 kDa (GPC method 4.2)
PD: 1.4
DSC: (FIG. 30)
GPC: (FIG. 56)
Crystallinity: semi-crystalline

Embodiment 7.1.7 (Process Step i))

Polymerization of 3S-Caranlactam to a 3S-Polycaranamide 300 mg of 3S-caranlactam (1.8 mmol), 4.9 mg of N-benzoyl-3S-caranlactam (Bz-5, 0.02 mmol) and 4.0 mg of NaH on paraffin (0.1 mmol) were mixed in a vacuum glass vessel and evacuated for 10 min. at 2 mbar. The reaction vessel was transferred to a 220° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.

DSC process 3.1
Tg (center point): 112° C.

Tm (range): 240-275° C.
Mn: 7.5 kDa (GPC method 4.2)
Mw: 9.6 kDa (GPC method 4.2)
PD: 1.3
DSC: (FIG. 31)
GPC: (FIG. 57)
Crystallinity: semi-crystalline Embodiment 7.1.8 (Process Step i))

Polymerization of 3S-Caranlactam to a 3S-Polycaranamide
300 mg of 3S-caranlactam (1.8 mmol), 10.6 mg of N-benzoyl-3S-caranlactam (Bz-5, 0.04 mmol) and 3.8 mg of NaH on paraffin (0.1 mmol) were mixed in a vacuum glass vessel and evacuated for 10 min. at 2 mbar. The reaction vessel was transferred to a 220° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.
DSC process 3.1
Tg (center point): 112° C.
Tm (range): 230-270° C.
Mn: 7.1 kDa (GPC method 4.2)
Mw: 9.0 kDa (GPC method 4.2)
PD: 1.3
DSC: (FIG. 32)
GPC: (FIG. 58)
Crystallinity: semi-crystalline Embodiment 7.1.9 (Process Step i))

Polymerization of 3S-Caranlactam to a 3S-Polycaranamide
309 mg of 3S-caranlactam (1.85 mmol), 19.6 mg of N-benzoyl-3S-caranlactam (Bz-5, 0.07 mmol) and 4.0 mg of NaH on paraffin (0.1 mmol) were mixed in a vacuum glass vessel and evacuated for 10 min. at 2 mbar. The reaction vessel was transferred to a 220° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.
DSC process 3.1
Tg (center point): 110° C.
Tm (range): 240-280
Mn: 6.0 kDa (GPC method 4.2)
Mw: 7.5 kDa (GPC method 4.2)
PD: 1.3
DSC: (FIG. 33)
GPC: (FIG. 59)
Crystallinity: semi-crystalline Embodiment 7.1.10 (Process Step i))

Polymerization of 3S-Caranlactam to a 3S-Polycaranamide
300 mg of 3S-caranlactam (1.83 mmol), 30.0 mg of N-benzoyl-3S-caranlactam (Bz-5, 0.11 mmol) and 3.8 mg of NaH on paraffin (0.1 mmol) were mixed in a vacuum glass vessel and evacuated for 10 min. at 2 mbar. The reaction vessel was transferred to a 220° C. oil bath and stirred. The reaction mixture was kept at temperature for one hour, then slowly cooled to room temperature. The obtained polymer was milled. The residual monomers and soluble oligomers were removed by refluxing in a mixture of water and ethanol (1:1). A partially crystalline 3S-polycaranamide was obtained. According to NMR analysis, the homopolymers are isotactic.
DSC process 3.1
Tg (center point): 109° C.
Tm (range): 230-270
Mn: 5.6 kDa (GPC method 4.2)
Mw: 7.3 kDa (GPC method 4.2)
PD: 1.3
DSC: (FIG. 34)
GPC: (FIG. 60)
Crystallinity: semi-crystalline Embodiment 7.1.11 (Process Step i))

Polymerization of 3S-Caranlactam to a 3S-Polycaranamide
523 mg of 3S-caranlactam (3.1 mmol), 10.4 mg of N-benzoyl-3S-caranlactam (Bz-5, 0.038 mmol) and 3.7 mg of NaH on paraffin (0.09 mmol) were polymerized under nitrogen in a heating block for one hour at 190° C. in a glass reaction. The polymer was dissolved directly in hexafluoroisopropanol (HFIP) and samples were taken for GPC and NMR analysis.
Mn: 8.6 kDa (GPC method 4.2)
Mw: 16.9 kDa (GPC method 4.2)
PD: 2.0
GPC: (FIG. 61)

Embodiment 7.1.12 (Process Step i))

Polymerization of 3S-Caranlactam to a 3S-Polycaranamide
500 mg of 3R-caranlactam (3.0 mmol) were melted under an inert atmosphere at 190° C. in a flask with stirring. Then 5.0 mg NaH on paraffin (0.13 mmol) and 4.5 μL acetic anhydride (0.048 mmol) were added. After the reaction mixture had solidified, it was slowly cooled to room temperature. The obtained polymer was milled. The residual monomers and soluble oligomers were removed by refluxing in a mixture of water and ethanol (1:1). An amorphous poly-3R-caranamide was obtained. According to NMR analysis, the homopolymers are isotactic.
Mn: $1.4 \cdot 10^4$ g/mol (GPC method 4.1)
Mw: $65.2 \cdot 10^5$ g/mol (GPC method 4.1)
Tg: 110-120° C. (DSC process 3)
Tm: 260-290° C. (DSC process 3)
GPC: (FIG. 78)
DSC: (FIG. 81)
Crystallinity: semi-crystalline Embodiment 7.2 (Process Step i)): Polymerization of 3R-Caranlactam to a 3R-Polycaranamide 300 mg of 3R-caranlactam (1.8 mmol), 10 mg of N-benzoyl-3R-caranlactam (0.036 mmol) and 0.5 mg of NaH on paraffin (0.02 mmol) were mixed in a vacuum vessel and evacuated for 10 min. at 2 mbar. The reaction vessel was transferred to a 170° C. oil bath and stirred. After about 20 seconds, the polymerization was complete, the polymer was slowly cooled to room temperature and an amorphous 3R-polycaranamide was obtained. According to NMR analysis, the homopolymers are isotactic.

Embodiment 7.2.1 (Process Step i))

Polymerization of 3R-Caranlactam to a 3R-Polycaranamide 500 mg of 3R-caranlactam (3.0 mmol) were melted under an inert atmosphere at 170° C. in a flask with stirring. Then 3.0 mg NaH on paraffin (0.08 mmol) and 1.5 µL acetic anhydride (0.016 mmol) were added. The reaction mixture was kept at temperature for 20 seconds, then slowly cooled to room temperature. The obtained polymer was milled. The residual monomers and soluble oligomers were removed by refluxing in a mixture of water and ethanol (1:1). An amorphous poly-3R-caranamide was obtained. According to NMR analysis, the homopolymers are isotactic.

Tg (center point): 122° C. (DSC process 3.2)
Tm (range): not available (DSC process 3.2)
Tg: 110-120° C. (DSC process 3)
Tm (area): not available (DSC process 3)
Mn: $1.1 \cdot 10^5$ g/mol (GPC method 4.1)
Mw: $3.0 \cdot 10^5$ g/mol (GPC method 4.1)
Mn: 33.3 kDa (GPC method 4.2)
Mw: 64.7 kDa (GPC method 4.2)
PD: 1.9
1H (FIG. 16)
13C (FIG. 17)
COSY: (FIG. 18)
HSQC: (FIG. 19)
DEPT: (FIG. 20)
DSC: FIG. 82 (DSC process 3)
DSC: FIG. 35 (DSC process 3.2)
GPC: (FIG. 62)
GPC: (FIG. 79)
Crystallinity: amorphous

Embodiment 7.2.2 (Process Step i))

Polymerization of 3R-Caranlactam to a 3R-Polycaranamide 500 mg of 3R-caranlactam (3.0 mmol) were melted under an inert atmosphere at 170° C. in a flask with stirring. Then 5.0 mg NaH on paraffin (0.13 mmol) and 4.5 µL acetic anhydride (0.05 mmol) were added. The reaction mixture was kept at temperature for 30 minutes, then slowly cooled to room temperature. The obtained polymer was milled. The residual monomers and soluble oligomers were removed by refluxing in a mixture of water and ethanol (1:1). An amorphous poly-3R-caranamide was obtained. According to NMR analysis, the homopolymers are isotactic.

Mn: 29.5 kDa (GPC method 4.2)
Mw: 55.2 kDa (GPC method 4.2)
PD: 1.9
GPC: (FIG. 63)

Embodiment 7.2.3 (Process Step i))

Polymerization of 3R-Caranlactam to a 3R-Polycaranamide 1.0 g of 3R-caranlactam (6.0 mmol), 14.6 mg of potassium (0.37 mmol) and 20 µL of benzoyl chloride (0.17 mmol) were polymerized under an inert atmosphere at 150° C. in a flask with stirring. The reaction mixture was kept at temperature for 6 hours, then slowly cooled to room temperature. The obtained polymer was milled. The residual monomers and soluble oligomers were removed by refluxing in a mixture of water and ethanol (1:1). An amorphous poly-3R-caranamide was obtained. According to NMR analysis, the homopolymers are isotactic.

Mn: 22.4 kDa (GPC method 4.2)
Mw: 38.1 kDa (GPC method 4.2)
PD: 1.7
GPC: (FIG. 64)

Embodiment 7.2.4 (Process Step i))

Polymerization of 3R-Caranlactam to a 3R-Polycaranamide 511 mg of 3R-caranlactam (3.1 mmol), 0.6 mg of N-benzoyl-3S-caranlactam (Bz-5, 0.002 mmol) and 3.5 mg of NaH on paraffin (0.09 mmol) were polymerized in a glass reaction vessel under nitrogen in a heating block for one hour at 190° C. The polymer was directly dissolved in hexafluoroisopropanol (HFIP) and samples were taken for GPC and NMR analysis. An amorphous poly-3R-caranamide was obtained. According to NMR analysis, the homopolymers are isotactic.

DSC process 3.2
Tg (center point): 119° C.
Tm (range): not available
Mn: 19.9 kDa (GPC method 4.2)
Mw: 32.9 kDa (GPC method 4.2)
PD: 1.7
DSC: (FIG. 36)
GPC: (FIG. 65)
Crystallinity: amorphous

Embodiment 7.2.5 (Process Step i))

Polymerization of 3R-Caranlactam to a 3R-Polycaranamide 506 mg of 3R-caranlactam (3.0 mmol), 1.03 mg of N-benzoyl-3S-caranlactam (Bz-5, 0.004 mmol) and 3.3 mg of NaH on paraffin (0.08 mmol) were polymerized in a glass reaction vessel under nitrogen in a heating block for one hour at 190° C. The polymer was directly dissolved in hexafluoroisopropanol (HFIP) and samples were taken for GPC and NMR analysis. An amorphous poly-3R-caranamide was obtained. According to NMR analysis, the homopolymers are isotactic.

DSC process 3.2
Tg (center point): 120° C.
Tm (range): not available
Mn: 20.2 kDa (GPC method 4.2)
Mw: 43.8 kDa (GPC method 4.2)
PD: 2.2
DSC: (FIG. 37)
GPC: (FIG. 66)
Crystallinity: amorphous

Embodiment 7.2.6 (Process Step i))

Polymerization of 3R-Caranlactam to a 3R-Polycaranamide 505 mg of 3R-caranlactam (3.0 mmol), 2.45 mg of N-benzoyl-3S-caranlactam (Bz-5, 0.009 mmol) and 3.3 mg of NaH on paraffin (0.08 mmol) were polymerized in a glass reaction vessel under nitrogen in a heating block for one hour at 190° C. The polymer was directly dissolved in hexafluoroisopropanol (HFIP) and samples were taken for GPC and NMR analysis. An amorphous poly-3R-caranamide was obtained. According to NMR analysis, the homopolymers are isotactic.

DSC process 3.2
Tg (center point): 117° C.
Tm (range): not available
Mn: 19.6 kDa (GPC method 4.2)
Mw: 45.6 kDa (GPC method 4.2)
PD: 2.3

DSC: (FIG. 38)
GPC: (FIG. 67)
Crystallinity: amorphous

Embodiment 7.2.7 (Process Step i))

Polymerization of 3R-Caranlactam to a 3R-Polycaranamide
508 mg of 3R-caranlactam (3.0 mmol), 5.13 mg of N-benzoyl-3S-caranlactam (Bz-5, 0.02 mmol) and 3.2 mg of NaH on paraffin (0.08 mmol) were polymerized in a glass reaction vessel under nitrogen in a heating block for one hour at 190° C. The polymer was directly dissolved in hexafluoroisopropanol (HFIP) and samples were taken for GPC and NMR analysis. An amorphous poly-3R-caranamide was obtained. According to NMR analysis, the homopolymers are isotactic.
DSC process 3.2
Tg (center point): 116° C.
Tm (range): not available
Mn: 15.2 kDa (GPC method 4.2)
Mw: 36.3 kDa (GPC method 4.2)
PD: 2.4
DSC: (FIG. 39)
GPC: (FIG. 68)
Crystallinity: amorphous Embodiment 7.2.8 (Process Step i))

Polymerization of 3R-Caranlactam to a 3R-Polycaranamide
513 mg of 3R-caranlactam (3.1 mmol), 7.50 mg of N-benzoyl-3S-caranlactam (Bz-5, 0.03 mmol) and 3.5 mg of NaH on paraffin (0.09 mmol) were polymerized in a glass reaction vessel under nitrogen in a heating block for one hour at 190° C. The polymer was directly dissolved in hexafluoroisopropanol (HFIP) and samples were taken for GPC and NMR analysis. An amorphous poly-3R-caranamide was obtained. According to NMR analysis, the homopolymers are isotactic.
DSC process 3.2
Tg (center point): 115° C.
Tm (range): not available
Mn: 13.5 kDa (GPC method 4.2)
Mw: 31.8 kDa (GPC method 4.2)
PD: 2.3
DSC: (FIG. 40)
GPC: (FIG. 69)
Crystallinity: amorphous Embodiment 7.2.9 (Process Step i))

Polymerization of 3R-Caranlactam to a 3R-Polycaranamide
512 mg of 3R-caranlactam (3.1 mmol), 10.2 mg of N-benzoyl-3S-caranlactam (Bz-5, 0.04 mmol) and 3.4 mg of NaH on paraffin (0.09 mmol) were polymerized in a glass reaction vessel under nitrogen in a heating block for one hour at 190° C. The polymer was directly dissolved in hexafluoroisopropanol (HFIP) and samples were taken for GPC and NMR analysis. An amorphous poly-3R-caranamide was obtained. According to NMR analysis, the homopolymers are isotactic.
DSC process 3.2
Tg (center point): 117° C.
Tm (range): not available
Mn: 13.1 kDa (GPC method 4.2)
Mw: 29.7 kDa (GPC method 4.2)
PD: 2.3
DSC: (FIG. 41)
GPC: (FIG. 70)
Crystallinity: amorphous Embodiment 7.2.10 (Process Step i))

Polymerization of 3R-Caranlactam to a 3R-Polycaranamide
900 mg of 3R-caranlactam (5.39 mmol), 5.5 mg of N-benzoyl-3S-caranlactam (Bz-5, 0.02 mmol) and 7.5 mg of NaH on paraffin (0.19 mmol) were mixed in a vacuum glass vessel and evacuated for 10 min. at 2 mbar. The reaction vessel was transferred to a 170° C. oil bath and stirred. The reaction mixture was kept at temperature for 30 minutes, then slowly cooled to room temperature. The obtained polymer was milled. The residual monomers and soluble oligomers were removed by refluxing in a mixture of water and ethanol (1:1). An amorphous poly-3R-caranamide was obtained. According to NMR analysis, the homopolymers are isotactic.
DSC process 3.2
Tg (center point): 112° C.
Tm (range): not available
Mn: 24.6 kDa (GPC method 4.2)
Mw: 55.5 kDa (GPC method 4.2)
PD: 2.3
DSC: (FIG. 42)
GPC: (FIG. 71)
Crystallinity: amorphous Embodiment 7.3 (Process Step i)): Polymerization of 3S-Caranlactam with 3R-Caranlactam to a 3S/3R-Co-Polycaranamide 150 mg 3R-caranlactam (0.9 mmol), 150 mg 3S-caranlactam (0.9 mmol), 10 mg N-benzoyl-3S-caranlactam (0.036 mmol) and 0.5 mg NaH on paraffin (0.02 mmol) were mixed in a vacuum vessel and evacuated for 10 min. at 2 mbar. The reaction vessel was transferred to an oil bath at 180° C. and stirred. After about 20 seconds, the polymerization was complete, the polymer was slowly cooled to room temperature and an amorphous 3S/3R-polycaranamide was obtained.

Exemplary Embodiment 7.3.1 (Process Step i))

Polymerization of 3S-Caranlactam and 3R-Caranlactam to a 3S-Caranlactam-3R-Caranlactam Co-Polycaranamide
250 mg of 3R-caranlactam (1.5 mmol) and 250 mg of 3S-caranlactam (1.5 mmol) were melted under an inert atmosphere at 190° C. in a flask with stirring. Then 5.0 mg NaH on paraffin (0.13 mmol) and 4.5 µL acetic anhydride (0.048 mmol) were added. The reaction mixture was kept at temperature for 30 minutes, then slowly cooled to room temperature. The obtained polymer was milled. The residual monomers and soluble oligomers were removed by refluxing in a mixture of water and ethanol (1:1). An amorphous 3S-caranlactam-3R-caranlactam-polycaranamide was obtained.
Tg (center): 112° C. (DSC process 3.2)
Tm (range): not available (DSC process 3.2)
Tg: 110-120° C. (DSC process 3)
Tm (area): not available (DSC process 3)
Mn: $3.2 \cdot 10^4$ (GPC method 4.1)
Mw: $1.1 \cdot 10^5$ (GPC method 4.1)
1H (FIG. 21)
13C (FIG. 22)
DSC: (FIG. 43)

DSC: (FIG. 83)
GPC: (FIG. 80)
Crystallinity: amorphous

Embodiment 7.3.2 (Process Step i))

Polymerization of 3S-Caranlactam and 3R-Caranlactam to a 3S-Caranlactam-3R-Caranlactam Co-Polycaranamide 750 mg of 3S-caranlactam (5.5 mmol), 362 mg of caprolactam (0.9 mmol), 20.2 mg of N-benzoyl-3S-caranlactam (Bz-5, 0.07 mmol) and 8.0 mg of NaH Paraffin (0.20 mmol) were polymerized in a glass reaction vessel under nitrogen in a heating block for one hour at 190° C. The obtained polymer was milled. The residual monomers and soluble oligomers were removed by refluxing in a mixture of water and ethanol (1:1). A partially crystalline poly-3S-caranlactam-3R-caranlactam co-polyamide was obtained.
DSC process 3.2
Mn: 10.4 kDa (GPC method 4.2)
Mw: 15.0 kDa (GPC method 4.2)
PD: 1.4
Tg (center): 109° C.
Tm (range): 210-250° C.
DSC: (FIG. 44)
GPC: (FIG. 72)
Crystallinity: semi-crystalline

Embodiment 8 (Process Step i2):
Co-Polymerization of 3S-Caranlactam with Laurolactam 5.00 g of laurolactam (26 mmol) were melted at 190° C. and 2.50 g of 3S-caranlactam (15 mmol) were dissolved therein. Then 75 mg of N-benzoyl-3S-caranlactam (JUPAC: (1R,5S,7S)-4-benzoyl-5,8,8-trimethyl-4-azabicyclo[5.1.0] octan-3-one) and 50 mg NaH 60% on paraffin wax were added. After the polymerization had taken place, the temperature was kept at 190° C. for 30 minutes, then the mixtures was cooled to room temperature without active cooling. The polymer obtained was milled and stirred in an ethanol-water mixture (1:1) for 24 h at reflux temperature. After filtration, the polymer obtained was dried at 120° C. for 16 h.
Glass transition point Tg range: 40-50° C.
Melting point Tm range: Not visible
Crystallinity: amorphous

Embodiment 8.1.1 (Process Step i2))

Polymerization of 3S-Caranlactam and Laurolactam to a 3S-Caranlactam-Laurolactam Co-Polycaranamide
1.0 g laurolactam (5.0 mmol), 500 mg 3S-caranlactam (3.0 mmol), 50 mg N-benzoyl-3S-caranlactam (Bz-5, 0.18 mmol) and 18 mg NaH on paraffin (0.45 mmol) were polymerized in a glass reaction vessel under nitrogen in an oil bath for one hour at 190° C. The residual monomers and oligomers were separated by precipitation of the polymer from HFIP with ethanol. An amorphous 3S-caranlactam-laurolactam co-polycaranamide was obtained.
DSC process 3.2
Tg (center): 46° C.
Tm (range): not available
1H (FIG. 23)
Mn: 12.5 kDa (GPC method 4.2)
Mw: 24.5 kDa (GPC method 4.2)
PD: 2.0

DSC: (FIG. 45)
GPC: (FIG. 73)
Crystallinity: amorphous

Embodiment 8.1.2 (Process Step i2))

Polymerization of 3S-Caranlactam and Laurolactam to a 3S-Caranlactam-Laurolactam Co-Polycaranamide
10 g laurolactam (50 mmol), 5 g 3S-caranlactam (30 mmol), 54 mg N-benzoyl-3S-caranlactam (Bz-5, 0.2 mmol) and 20 mg NaH on paraffin (0.50 mmol) were polymerized in a glass reaction vessel under nitrogen in an oil bath for one hour at 190° C. The residual monomers and oligomers were separated by precipitation of the polymer from HFIP with ethanol. An amorphous 3S-caranlactam-laurolactam co-polycaranamide was obtained.
DSC process 3.2
Mn: 30.2 kDa (GPC method 4.2)
Mw: 60.1 kDa (GPC method 4.2)
PD: 2.0
Tg (center): 49° C.
Tm (range): not available
DSC: (FIG. 46)
GPC: (FIG. 74)
Crystallinity: amorphous

Embodiment 8.1.3 (Process Step i2))

Polymerization of 3S-Caranlactam and Laurolactam to a 3S-Caranlactam-Laurolactam Co-Polycaranamide
411 mg of 3S-caranlactam (2.5 mmol), 486 mg of laurolactam (2.5 mmol), 20.0 mg of N-benzoyl-3S-caranlactam (Bz-5, 0.07 mmol) and 8.0 mg of NaH Paraffin (0.20 mmol) were polymerized in a glass reaction vessel under nitrogen in a heating block at 190° C. for one hour. The obtained polymer was milled. The residual monomers and soluble oligomers were removed by refluxing in a mixture of water and ethanol (1:1). An amorphous 3S-caranlactam-laurolactam co-polyamide was obtained.
DSC process 3.2
Mn: 10.0 kDa (GPC method 4.2)
Mw: 15.6 kDa (GPC method 4.2)
PD: 1.6
Tg (center point): 55° C.
Tm (range): not available
DSC: (FIG. 47)
GPC: (FIG. 75)
Crystallinity: amorphous

Exemplary Embodiment 8.2.1 (Process Step i2)

Polymerization of 3S-Caranlactam and Caprolactam to a 3S-Caranlactam-Caprolactam Co-Polycaranamide
5.0 g caprolactam (44 mmol), 2.5 g 3S-caranlactam (15 mmol), 75 mg N-benzoyl-3S-caranlactam (Bz-5, 0.28 mmol) and 50 mg NaH on paraffin (1, 3 mmol) were polymerized in a glass reaction vessel under nitrogen in an oil bath at 190° C. for one hour. The residual monomers and oligomers were separated by precipitation of the polymer from HFIP with ethanol. A partially crystalline 3S-caranlactam-caprolactam co-polycaranamide was obtained.
DSC process 3.2
Mn: 15.2 kDa (GPC method 4.2)
Mw: 31.1 kDa (GPC method 4.2)
PD: 2.0
Tg (center): 62° C.
Tm (range): 160-190° C.

1H (FIG. 24)
DSC: (FIG. 48)
GPC: (FIG. 76)
Crystallinity: semi-crystalline Exemplary Embodiment 8.2.2 (Process Step i2)

Polymerization of 3S-Caranlactam and Caprolactam to a 3S-Caranlactam-Caprolactam Co-Polycaranamide 537 mg of 3S-caranlactam (3.2 mmol), 362 mg of caprolactam (3.2 mmol), 20.1 mg of N-benzoyl-3S-caranlactam (Bz-5, 0.07 mmol) and 7.9 mg of NaH on paraffin (0.20 mmol) were polymerized in a glass reaction vessel under nitrogen in a heating block at 190° C. for one hour. The obtained polymer was milled. The residual monomers and soluble oligomers were removed by refluxing in a mixture of water and ethanol (1:1). An amorphous 3S-caranlactam-caprolactam co-polycaranamide was obtained.
DSC process 3.2
Mn: 12.1 kDa (GPC method 4.2)
Mw: 17.3 kDa (GPC method 4.2)
PD: 1.4
Tg (center): 88° C.
Tm (range): not available
DSC: (FIG. 49)
GPC: (FIG. 77)
Crystallinity: amorphous Exemplary Embodiment 8.2.3 (Process Step i2)

Polymerization of 3S-Caranlactam and Caprolactam to a 3S-Caranlactam-Caprolactam Co-Polycaranamide 250 mg 3S-caranlactam (1.5 mmol), 57 mg caprolactam (0.5 mmol), 10 mg N-benzoyl-3S-caranlactam (Bz-5, 0.04 mmol) and 1.5 mg NaH on paraffin (0.04 mmol) were polymerized in a glass reaction vessel under nitrogen in a heating block at 175° C. for one hour. The obtained polymer was milled. The residual monomers and oligomers were separated by precipitation of the polymer from HFIP with ethanol. An amorphous poly-3S-caranlactam-caprolactam co-polycaranamide was obtained.
DSC process 3.2
Tg (center): 99° C.
Tm (range): not available
DSC: (FIG. 50)
Crystallinity: amorphous Embodiment 9 (Process Step i2): Co-Polymerization of 3S-Caranlactam with Caprolactam 5.00 g of caprolactam (44 mmol) were melted at 190° C. and 2.50 g of 3S-caranlactam (15 mmol) were dissolved therein. Then 75 mg of N-benzoyl-3S-caranlactam (JUPAC: (1R,5S,7S)-4-benzoyl-5,8,8-trimethyl-4-azabicyclo[5.1.0] octan-3-one) and 50 mg NaH 60% on paraffin wax were added. After the polymerization had taken place, the temperature was kept at 190° C. for 30 minutes, then the mixture was cooled to room temperature without active cooling. The polymer obtained was milled and stirred in an ethanol-water mixture (1:1) for 24 h at reflux temperature. After filtration, the polymer obtained was dried at 120° C. for 16 h.
Glass transition point Tg range: 50-60° C.
Melting point Tm range: 160-200° C.
Crystallinity: semi-crystalline Embodiment 10: Water Absorption of a 3R-Polyamide PA6 was prepared by anionic ring opening polymerization (2.8 mmol caprolactam, 0.1 mmol NaH 60% on paraffin wax, 0.05 mmol $Ac_2O$, 180° C.). Residual monomer was removed by refluxing in water/ethanol. 30-42 mg of PA6 (three samples) and two samples of poly-3R-caranamide were annealed in the DSC (same device as described in DSC analytical method (3)) for three minutes at 230° C., resulting in the production of uniform polyamide blocks. The masses were determined on an OHAUS Discovery DV215CD balance with a maximum error of 0.01 mg. The samples were then each stirred in water at 25° C. for three days. The samples were then air dried and weighed after 30 minutes and four and a half hours. The samples were then dried at 80° C. for three hours and weighed. This time was sufficient for the poly-3R-caranamide samples to dry completely. The overall higher water absorption of PA6 and the longer drying time of PA6 indicate a generally lower water absorption of the aliphatic substituted poly-3R-caranamide compared to PA6.

TABLE 13

Water absorption.

| | | Pretreatments | | | |
|---|---|---|---|---|---|
| | | A | B | C. | D |
| | | Sample weight [mg] | | | |
| Entry | Polyamide | Water absorption [w %] | | | |
| 1 | PA6-1 | 35.66 | 37.45 | 37.01 | 36.05 |
| | | | 5.4 | 4.0 | 1.5 |
| 2 | PA6-2 | 37.78 | 39.57 | 39.36 | 38.16 |
| | | | 4.9 | 4.3 | 1.1 |
| 3 | PA6-3 | 31.86 | 33.67 | 32.58 | 32.2 |
| | | | 5.7 | 2.3 | 1.1 |
| 4 | Poly-3R-caranamide-1 | 40.75 | 41.44 | 40.80 | 40.62 |
| | | | 2.0 | 0.44 | 0 |
| 5 | Poly-3R-caranamide-2 | 30.89 | 31.32 | 30.92 | 30.7 |
| | | | 2.3 | 0.75 | <0.1 |

Pretreatments:
A = polyamide block from the DSC;
B = water bath (3 days) and air drying (30 minutes);
C = air drying (four and a half hours);
D = drying at 80° C. (3.0 hours)

Embodiment 11.1: Qualitative Measurement of the Transparency of 3R-Polyamide Compared to PA6 and PA12

3R-polyamide was dissolved in HFIP (25 mg/mL) and applied to a PTFE film by carefully dropping it on. After evaporation of the solvent and drying for three hours at 85° C., a transparent film with defects due to uneven evaporation and air inclusions was obtained, compared to PA6 and PA12.

Embodiment 11.2: Qualitative Measurement of the Transparency of Amorphous 3S-Caranlactam-Laurolactam Co-Polycaranamide in Comparison to PA6 and PA12

Amorphous 3S-caranlactam-laurolactam co-polycaranamide was dissolved in HFIP (25 mg/mL) and transferred to a crystallizing dish (diameter 9 cm). After evaporation of the solvent and drying for three hours at 85° C., a transparent (transparent) film with defects due to uneven evaporation and air inclusions was obtained, compared to PA6 and PA12.

Embodiment 11.3: Qualitative Measurement of the Transparency of Amorphous 3S-Caranlactam-Caprolactam Co-Polycaranamide in Comparison to PA6 and PA12

Amorphous 3S-caranlactam-caprolactam co-polycaranamide was dissolved in HFIP (25 mg/mL) and applied to a PTFE film by carefully dropping it on. After evaporation of the solvent and drying for three hours at 85° C., a transparent (transparent) film with defects due to uneven evaporation and air inclusions was obtained, compared to PA6 and PA12.

The invention claimed is:

1. A polycaranamide, comprising a 3S-polycaranamide according to the formula:

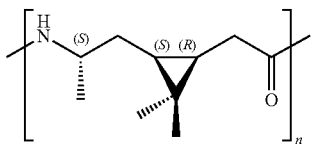

or a 3R-polycaranamide according to the formula:

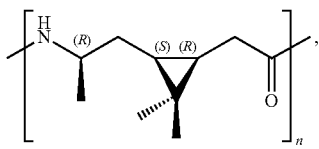

wherein n is a natural number greater than or equal to 2.

2. A polycaranamide, comprising a 3S/3R-co-polycaranamide according to the formula:

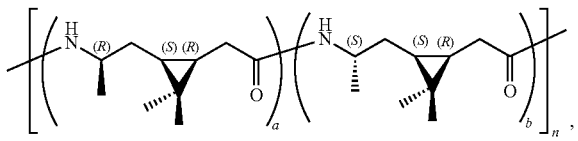

wherein a, b and n each is a natural number and n is greater than or equal to 2.

3. A plastic product comprising the polycaranamide according to claim 1.

4. The plastic product of claim 3, wherein the 3S-polycaranamide or the 3R-polycaranamide constitutes at least 5, 10, 15, 20, 30, 40, 50, 60, 70, 80, 90, 95 or 99 wt. % of the plastic product.

5. A plastic product comprising the polycaranamide according to claim 2.

6. The plastic product of claim 5, wherein the 3S/3R-co-polycaranamide constitutes at least 5, 10, 15, 20, 30, 40, 50, 60, 70, 80, 90, 95 or 99 wt. % of the plastic product.

* * * * *